United States Patent [19]

Hashimoto et al.

[11] Patent Number: 4,539,152
[45] Date of Patent: Sep. 3, 1985

[54] 4-SUBSTITUTED-2-OXOAZETIDINE COMPOUNDS

[75] Inventors: Masashi Hashimoto, Takarazuka; Matsuhiko Aratani, Daitoh; Kozo Sawada, Toyonaka, all of Japan

[73] Assignee: Fujisawa Pharmaceutical Co., Ltd., Osaka, Japan

[21] Appl. No.: 412,263

[22] Filed: Aug. 27, 1982

Related U.S. Application Data

[63] Continuation-in-part of Ser. No. 237,936, Feb. 25, 1981, abandoned, and a continuation-in-part of Ser. No. 296,840, Aug. 27, 1981, Pat. No. 4,383,945.

[30] Foreign Application Priority Data

Feb. 28, 1980 [GB] United Kingdom ................. 8006842

[51] Int. Cl.³ .................... C07D 487/06; A61K 31/40
[52] U.S. Cl. ...................... 260/245.2 T; 260/245.2 R; 260/239 A
[58] Field of Search .................. 260/245.2 T; 424/274

[56] References Cited

FOREIGN PATENT DOCUMENTS 57-116072 7/1982 Japan .

Primary Examiner—Nicholas S. Rizzo
Attorney, Agent, or Firm—Oblon, Fisher, Spivak, McClelland & Maier

[57] ABSTRACT

The present invention relates to novel 4-substituted-2-oxoazetidine compounds and to processes for preparing the same. These compounds are useful intermediates for preparing antibiotics having the basic skeleton of Thienamycin.

4 Claims, No Drawings

4-SUBSTITUTED-2-OXOAZETIDINE COMPOUNDS

This application is continuation-in-part of application Ser. No. 237,936 filed Feb. 25, 1981, now abandoned and a continuation-in-part of application Ser. No. 296,840 filed Aug. 27, 1981, now U.S. Pat. No. 4,383,945.

The present invention relates to novel 4-substituted-2-oxoazetidine compounds and salts thereof. More particularly, it relates to novel 4-substituted-2-oxoazetidine compounds and salts thereof, which are useful intermediates for preparing antibiotics having the fundamental skeleton of Thienamycin and to processes for the preparation thereof.

Accordingly, one object of the present invention is to provide novel 4-substituted-2-oxoazetidine compounds and salts thereof, which are useful intermediates for preparing antibiotics having the fundamental skeleton of Thienamycin, which are highly active against a number of pathogenic microorganisms.

Another object of the present invention is to provide processes for the preparation of 4-substituted-2-oxoazetidine compounds and salts thereof.

The object 4-substituted-2-oxoazetidine compounds can be represented by the following general formula:

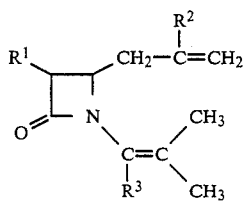
(I)

or a salt thereof,
in which
$R^1$ is hydrogen, halogen, amino, acylamino, isocyano lower alkyl, hydroxy(lower)alkyl, or protected hydroxy(lower)-alkyl,
$R^2$ is hydrogen or an organic group optionally substituted by suitable substituent(s), and
$R^3$ is carboxy or a protected carboxy group.

In the object compounds and the starting compounds in Processes A to Q mentioned below, it is to be understood that there may be one or more stereoisomeric pair(s) such as optical and/or geometrical isomers due to asymmetric carbon atom(s) and double bond(s) in those molecules, and these isomers are also included within the scope of the present invention.

Suitable salts of the object compounds (I) are conventional basic or acidic salts and may include an inorganic basic salt, for example, a metal salt such as an alkali metal salt (e.g. sodium salt, potassium salt, etc.) and an alkaline earth metal salt (e.g. calcium salt, magnesium salt, etc.), and an ammonium salt etc.; an organic basic salt, for example, an organic amine salt [e.g. trimethylamine salt, triethylamine salt, pyridine salt, picoline salt, dicyclohexylamine salt, N,N'-dibenzylethylenediamine salt, N-methylglucamine salt, diethanolamine salt, triethanolamine salt, tris(hydroxymethylamino)methane salt, etc.] etc.; an organic carboxylic or sulfonic acid addition salt (e.g. formate, acetate, maleate, tartrate, methanesulfonate, benzenesulfonate, toluenesulfonate, etc.); an inorganic acid addition salt (e.g. hydrochloride, hydrobromide, sulfate, phosphate, etc.); a salt with a basic or acidic amino acid (e.g. arginine, aspartic acid, glutamic acid, etc.), and the like.

According to the present invention, the object compounds and salts thereof (I) can be prepared by the processes as illustrated by the following reaction schemes.

Process A: (A)

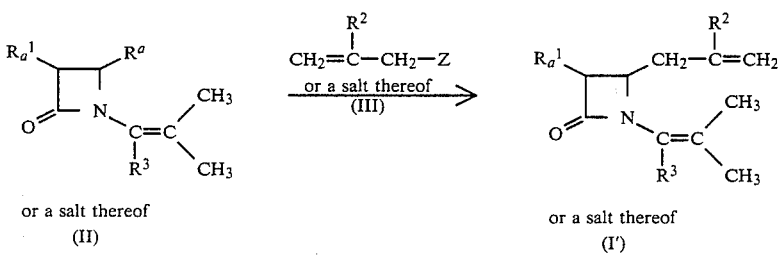

Process B: (B)

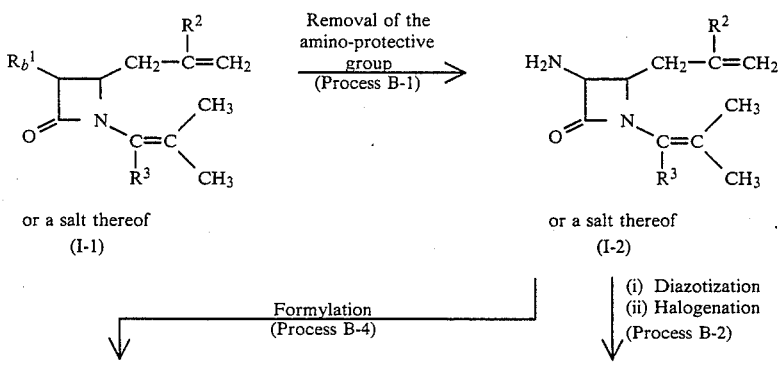

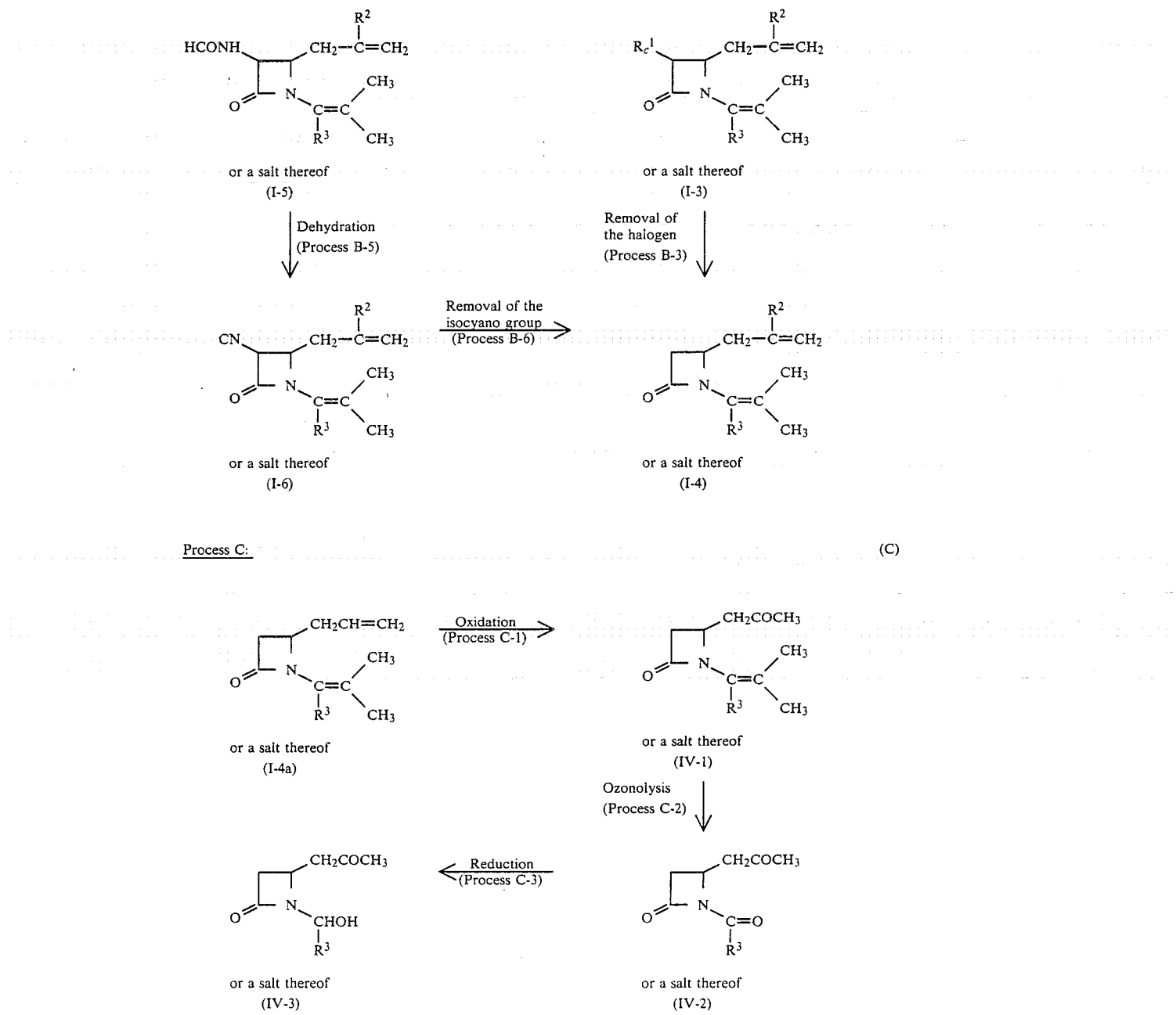
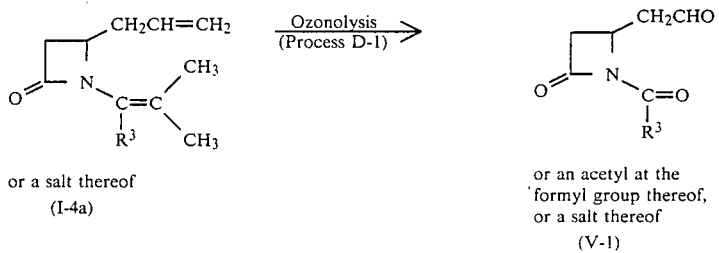

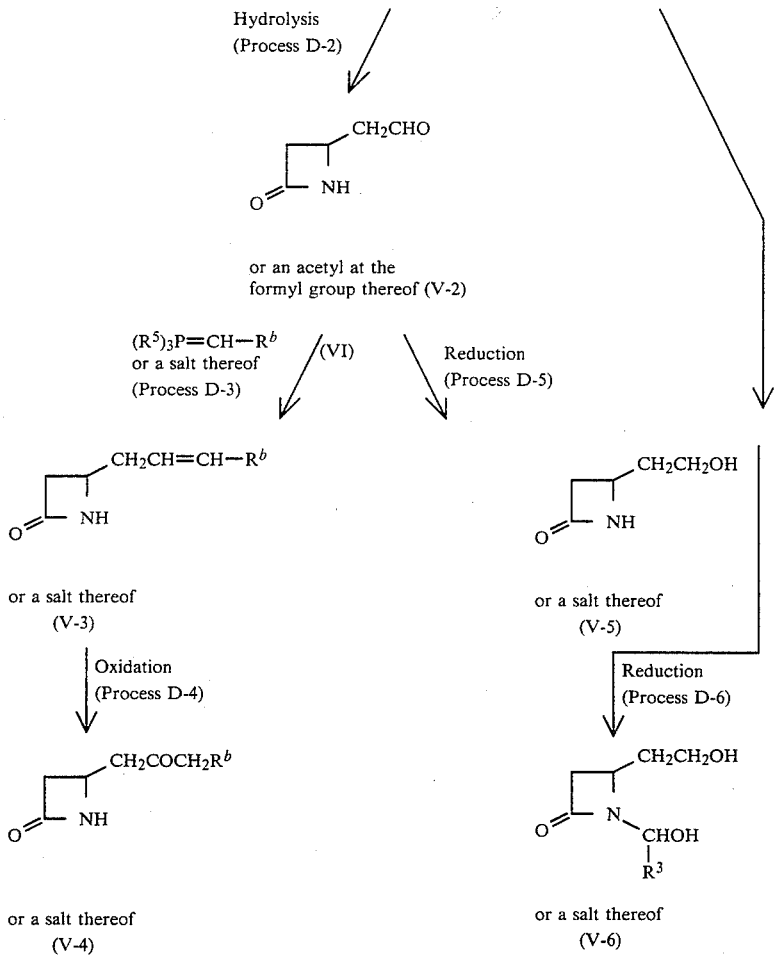
Process E:
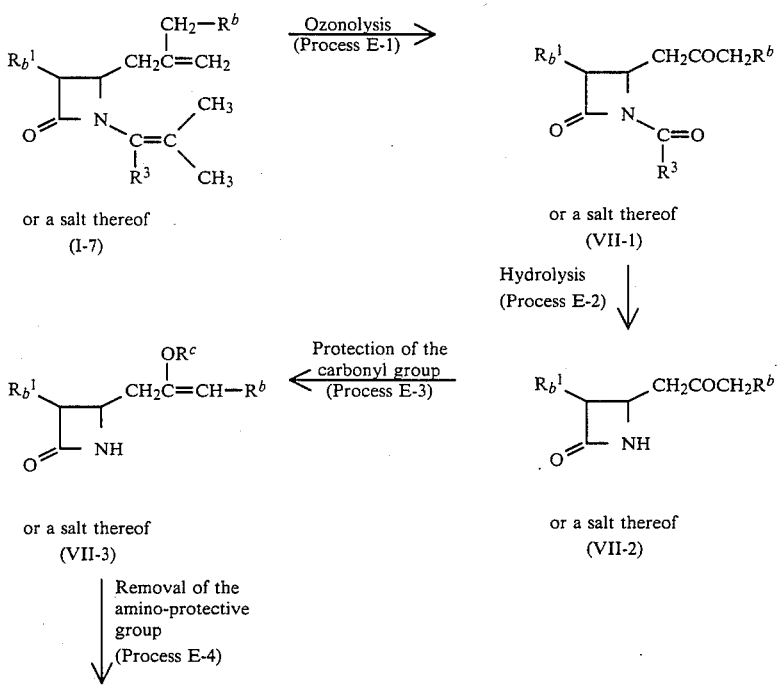

-continued

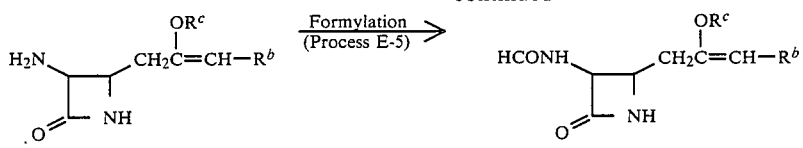

or a salt thereof
(VII-4)

or a salt thereof
(VII-5)

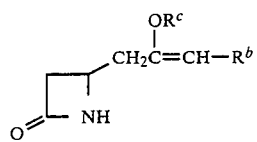

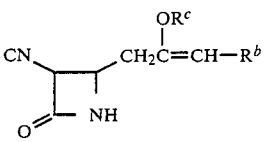

or a salt thereof
(VII-7)

or a salt thereof
(VII-6)

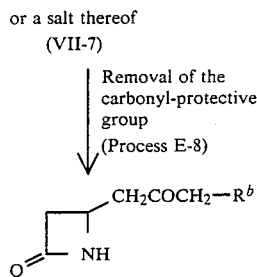

or a salt thereof
(V-4)

Process F:                                                                                  (F)

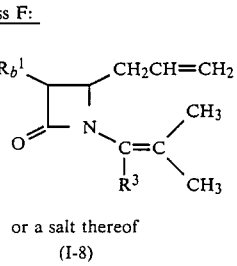

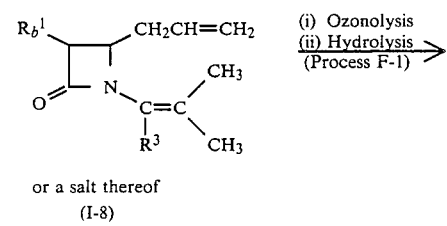

or a salt thereof
(I-8)

or an acetal at the
formyl group thereof or
a hemi-acetal thereof
(VIII-1)

$(R^5)_3P=CH-R^b$
or a salt thereof (VI)
(Process F-2)

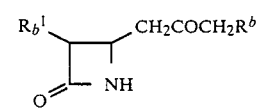

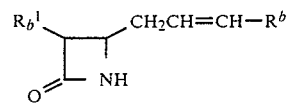

or a salt thereof
(VII-2)

or a salt thereof
(VIII-2)

Removal of the
amino-protective
group
(Process F-4)

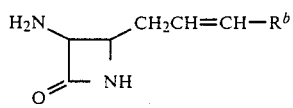

or a salt thereof
(VIII-3)

Process G:                                                                                      (G)
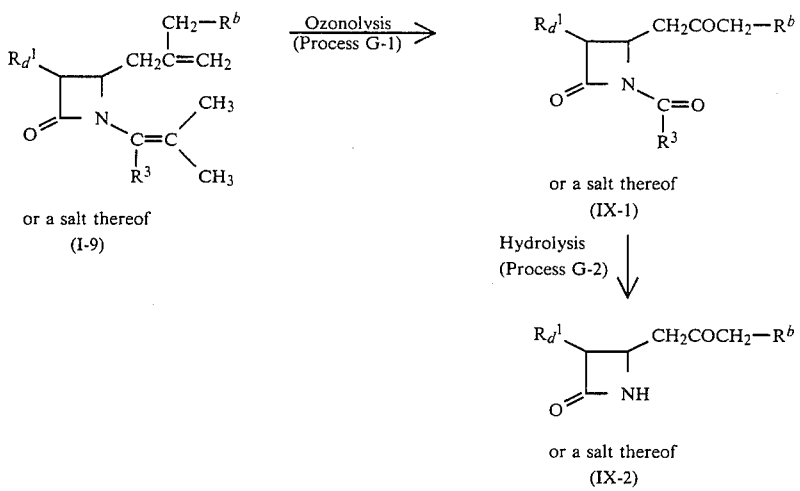
Process H:                                                                                      (H)
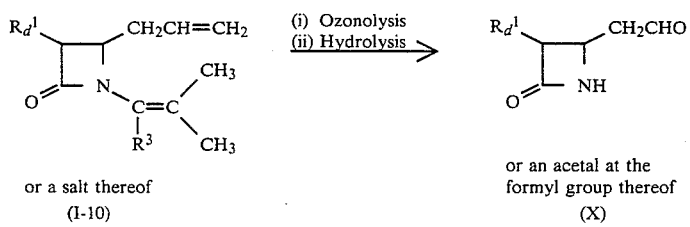
Process I:                                                                                      (I)
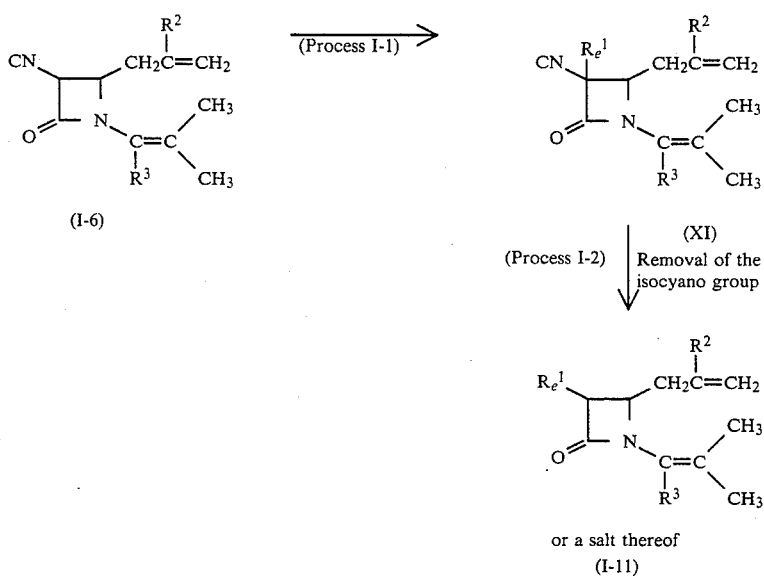
Process J:                                                                                      (J)

-continued

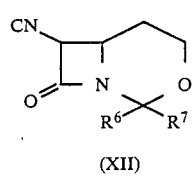
(XII)

(Process J-1) →

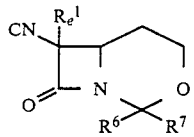
(XIII)

(Process J-2) Removal of the isocyano group ↓

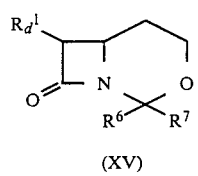
(XV)

← Introduction of the hydroxy-protective group
(Process J-3)

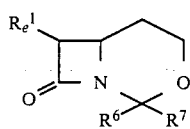
(XIV)

Process K: (K)

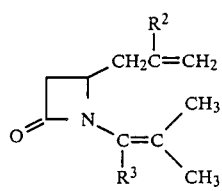
or a salt thereof
(I-4a)

Alkylation →

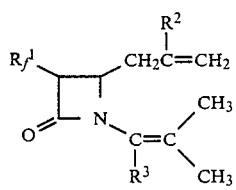
or a salt thereof
(I-12)

Process L: (L)

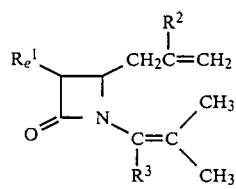
or a salt thereof
(I-11)

Introduction of the hydroxy-protective group →

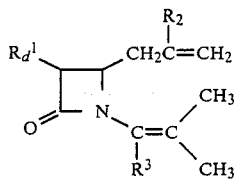
or a salt thereof
(I-13)

Process M: (M)

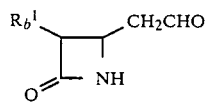
or an acetal at the formyl group thereof or a hemi-acetal thereof
(VIII-1)

reduction
(Process M-1) →

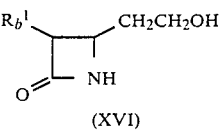
(XVI)

(Process M-2) ↓ $R^6$, $OCH_3$ / C / $R^7$, $OCH_3$

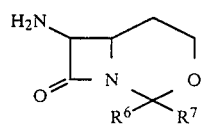
or a salt thereof
(XVIII)

← Removal of the amino-protective group
(Process M-3)

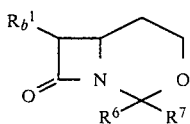
(XVII)

↓ Formylation
(Process M-4)

-continued
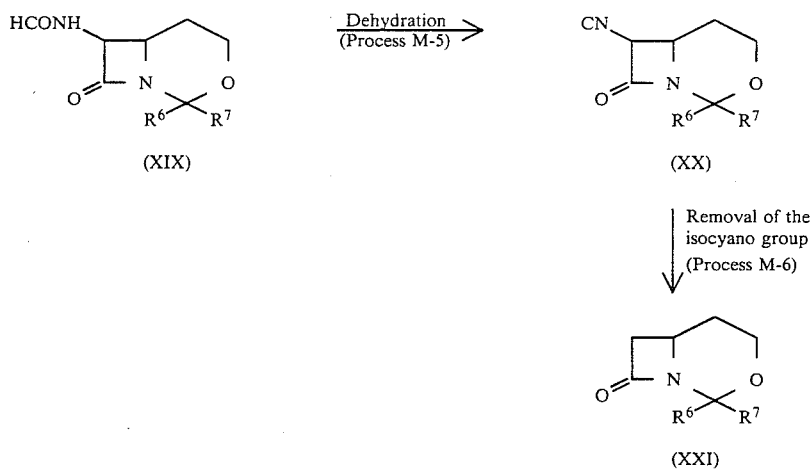
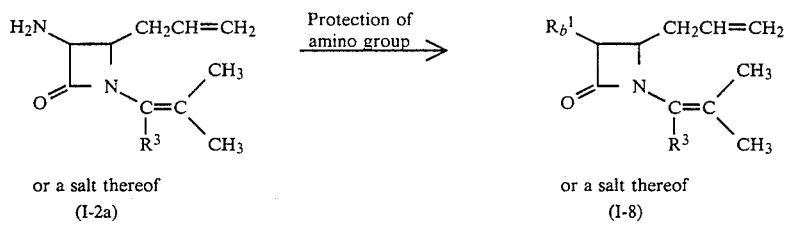
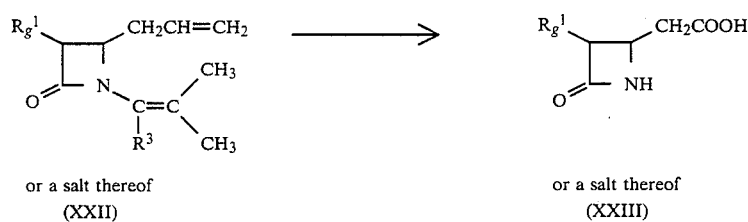
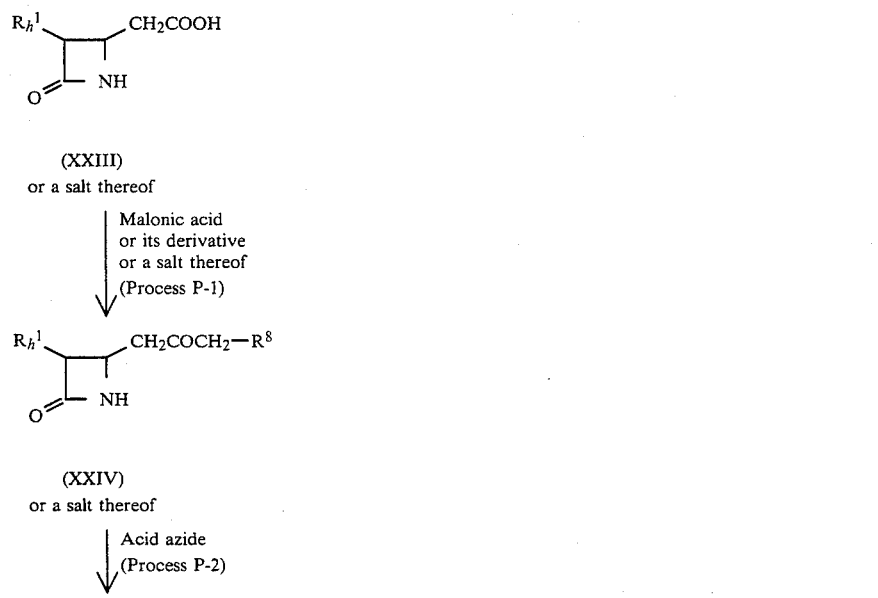

-continued

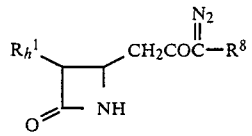

(XXV)
or a salt thereof

↓ Cyclization (Process P-3

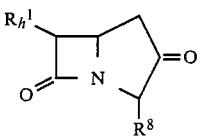

(XXVI)
or a salt thereof

Process Q:  (Q)

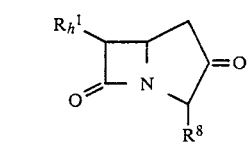 —Acylating agent→ 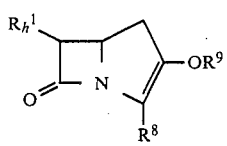

(XXVI)　　　　　　　　　　(XXVII)
or a salt thereof　　　　　　or a salt thereof

↓ R$^{10}$SH or a salt thereof

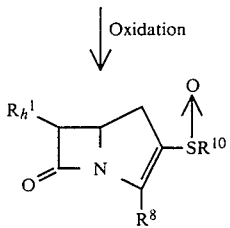

(XXVIII)
or a salt thereof

←Removal of the protective group(s) (If desired)

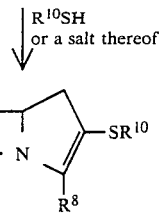

(XXIX)
or a salt thereof

↓ Oxidation (XXX)
or a salt thereof in which

R$^2$ and R$^3$ are each as defined above,

R$_a^1$ is hydrogen, halogen, amino, a protected amino group, isocyano, lower alkyl, hydroxy(lower)alkyl or a protected hydroxy(lower)alkyl, R$_b^1$ is a protected amino group, R$_c^1$ and R$^a$ are each halogen, R$_d^1$ is a protected hydroxy(lower)alkyl, R$_e^1$ is hydroxy(lower)alkyl, R$_f^1$ is lower alkyl or hydroxy(lower)alkyl, R$_g^1$ is hydroxy(lower)alkyl or a protected hydroxy(lower)alkyl, R$_h^1$ is 1-hydroxy-1-methylethyl or 1-protected hydroxy-1-methylethyl, R$^5$ is aryl, lower alkyl or lower alkoxy, R$^b$ is carboxy or a protected carboxy group, R$^c$ is lower alkyl, Z is a group of the formula:

—Si(R$^4$)$_3$ or —Sn(R$^4$)$_3$ wherein

R$^4$ is lower alkyl, aryl, lower alkoxy or halogen,

R$^6$ and R$^7$ are each lower alkyl; or R$^6$ and R$^7$ are linked together to form cycloalkylidene.

R$^8$ is carboxy or a protected carboxy, R$^9$ is acyl, $R^{10}$ is acylamino(lower)alkyl or acylamino(lower)alkenyl, and $R_a{}^{10}$ is amino(lower)alkyl, acylamino(lower)alkyl or acylamino(lower)alkenyl.

Some of the starting compounds (II) and (III) in Process A are novel and can be prepared, for example, from the known compounds by the method in the following reaction schemes or a conventional method thereof.

(A) Preparation A:

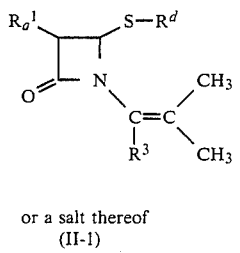

or a salt thereof
(II-1)

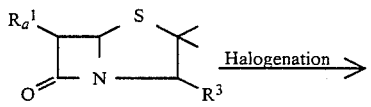

or a salt thereof
(II-2)

(B) Preparation B:

or a salt thereof
(II-3)

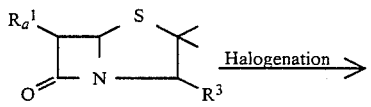

or a salt thereof
(II-2)

(C) Preparation C:

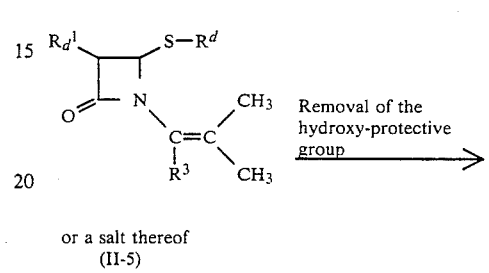

or a salt thereof
(II-4)

-continued

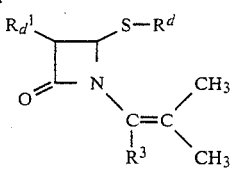

or a salt thereof
(II-5)

(D) Preparation D:

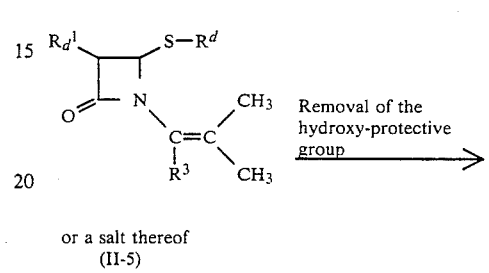

or a salt thereof
(II-5)

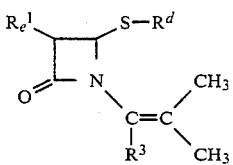

or a salt thereof
(II-4)

(E) Preparation E:

$$CH_2=\underset{R_a{}^2}{\overset{|}{C}}-CH_2-Z \xrightarrow{\text{Introduction of the carboxy-protective group}} CH_2=\underset{R_b{}^2}{\overset{|}{C}}-CH_2-Z$$

or a salt thereof                    (III-2)
(III-1)

in which
$R_a{}^1$, $R_d{}^1$, $R^3$, $R^a$ and Z are each as defined above,
$R_e{}^1$ is hydroxy(lower)alkyl,
$R_a{}^2$ is carboxy(lower)alkyl,
$R_b{}^2$ is protected carboxy(lower)alkyl, and
$R^d$ is lower alkyl.

In the above and subsequent description of the present specification, suitable examples and illustration of the various definitions to be included within the scope thereof are explained in detail as follows.

The term "lower" in the present specification is intended to mean a group having 1 to 6 carbon atom(s), and the term "higher" is intended to mean a group having 7 to 20 carbon atoms, unless otherwise indicated.

Suitable "halogen" may include chlorine, bromine and iodine.

Suitable "a protected amino group" may include an amino group substituted with a suitable protective group which is conventionally used in cephalosporin and penicillin compounds as a protective group of the amino group at their 7th or 6th position, and a suitable "a protected amino group" may include acylamino, mono- or di- or tri-phenyl(lower)alkylamino (e.g. benzylamino, benzhydrylamino, tritylamino, etc.), a group of the formula:

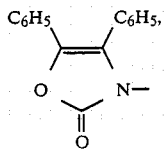

and the like.

Suitable "acyl moiety" in the term "acylamino" may include aliphatic acyl group and acyl group containing an aromatic ring, which is referred to as aromatic acyl, or heterocyclic ring, which is referred to as heterocyclic acyl.

Suitable example of said acyl may be illustrated as follows:

Aliphatic acyl such as lower or higher alkanoyl (e.g. formyl, acetyl, succinyl, hexanoyl, heptanoyl, stearoyl, etc.);

lower or higher alkenoyl (e.g. acryloyl, maleoyl, etc.);

lower or higher alkoxycarbonyl (e.g. methoxycarbonyl, ethoxycarbonyl, t-butoxycarbonyl, t-pentyloxycarbonyl, heptyloxycarbonyl, etc.);

lower or higher alkanesulfonyl (e.g. methanesulfonyl, ethanesulfonyl, etc.); or the like;

Aromatic acyl such as aroyl (e.g. benzoyl, toluoyl, naphthoyl, phthaloyl, etc.) ar(lower)alkanoyl such as phenyl(lower)alkanoyl (e.g. phenylacetyl, phenylpropionyl, etc.);

aryloxycarbonyl (e.g. phenoxycarbonyl, naphthyloxycarbonyl, etc.);

aryloxy(lower)alkanoyl such as phenoxy(lower)alkanoyl (e.g. phenoxyacetyl, phenoxypropionyl, etc.);

arylglyoxyloyl (e.g. phenylglyoxyloyl, naphthylglyoxyloyl, etc.);

arenesulfonyl (e.g. benzenesulfonyl, p-toluenesulfonyl, etc.); or the like;

Heterocyclic acyl such as heterocycliccarbonyl (e.g. thenoyl, furoyl, nicotinoyl, etc.);

heterocyclic(lower)alkanoyl (e.g. thienylacetyl, thiazolylacetyl, tetrazolylacetyl, etc.);

heterocyclicglyoxyloyl (e.g. thiazolylglyoxyloyl, thienylglyoxyloyl, etc.); or the like; in which suitable heterocyclic moiety in the terms "heterocycliccarbonyl", "heterocyclic(lower)alkanoyl" and "heterocyclicglyoxyloyl" as mentioned above means, in more detail, saturated or unsaturated, monocyclic or polycyclic heterocyclic group containing at least one hetero-atom such as an oxygen, sulfur, nitrogen atom and the like.

And, especially preferable heterocyclic group may be heterocyclic group such as unsaturated 3 to 8-membered (more preferably 5 or 6-membered) heteromonocyclic group containing 1 to 4 nitrogen atom(s), for example, pyrrolyl, pyrrolinyl, imidazolyl, pyrazolyl, pyridyl and its N-oxide, dihydropyridyl, pyrimidinyl, pyrazinyl, pyridazinyl, triazolyl (e.g. 4H-1,2,4-triazolyl, 1H-1,2,3-triazolyl, 2H-1,2,3-triazolyl, etc.), tetrazolyl (e.g. 1H-tetrazolyl, 2H-tetrazolyl, etc.) etc.;

saturated 3 to 8-membered (more preferably 5 or 6-membered) heteromonocyclic group containing 1 to 4 nitrogen atom(s), for example, pyrrolidinyl, imidazolidinyl, piperidino, piperazinyl, etc.; unsaturated condensed heterocyclic group containing 1 to 4 nitrogen atom(s), for example, indolyl, isoindolyl, indolizinyl, benzimidazolyl, quinolyl, isoquinolyl, indazolyl, benzotriazolyl, etc.; unsaturated 3 to 8-membered (more preferably 5 or 6-membered) heteromonocyclic group containing 1 to 2 oxygen atom(s) and 1 to 3 nitrogen atom(s), for example, oxazolyl, isoxazolyl, oxadiazolyl (e.g. 1,2,4-oxadiazolyl, 1,3,4-oxadiazolyl, 1,2,5-oxadiazolyl, etc.) etc.;

saturated 3 to 8-membered (more preferably 5 or 6-membered) heteromonocyclic group containing 1 to 2 oxygen atom(s) and 1 to 3 nitrogen atom(s), for example, morpholinyl, sydnonyl, etc.;

unsaturated condensed heterocyclic group containing 1 to 2 oxygen atom(s) and 1 to 3 nitrogen atom(s), for example, benzoxazolyl, benzoxadiazolyl, etc.; unsaturated 3 to 8 membered (more preferably 5 or 6-membered) heteromonocyclic group containing 1 to 2 sulfur atom(s) and 1 to 3 nitrogen atom(s), for example, thiazolyl, isothiazolyl, thiadiazolyl (e.g. 1,2,3-thiadiazolyl, 1,2,4-thiadiazolyl, 1,3,4-thiadiazolyl, 1,2,5-thiadiazolyl, etc.), dihydrothiazinyl, etc.;

saturated 3 to 8-membered (more preferably 5 or 6-membered) heteromonocyclic group containing 1 to 2 sulfur atom(s) and 1 to 3 nitrogen atom(s), for example, thiazolidinyl, etc.;

unsaturated 3 to 8-membered (more preferably 5 or 6-membered) heteromonocyclic group containing 1 to 2 sulfur atom(s), for example, thienyl, dihydrodithiinyl, etc.;

unsaturated condensed heterocyclic group containing 1 to 2 sulfur atom(s) and 1 to 3 nitrogen atom(s), for example, benzothiazolyl, benzothiadiazolyl, etc.; unsaturated 3 to 8-membered (more preferably 5 or 6-membered) heteromonocyclic group containing an oxygen atom, for example, furyl, etc.;

unsaturated 3 to 8-membered (more preferably 5 or 6-membered) heteromonocyclic group containing an oxygen atom and 1 to 2 sulfur atom(s), for example, dihydrooxathiinyl, etc.;

unsaturated condensed heterocyclic group containing 1 to 2 sulfur atom(s), for example, benzothienyl, benzodithiinyl, etc.;

unsaturated condensed heterocyclic group containing an oxygen atom and 1 to 2 sulfur atom(s), for example, benzoxathiinyl, etc. and the like.

The acyl moiety thus defined may optionally be substituted by one to ten, same or different, suitable substituent(s) such as:

lower alkyl (e.g. methyl, ethyl, etc.);

lower alkoxy (e.g. methoxy, ethoxy, propoxy, etc.);

lower alkylthio (e.g. methylthio, ethylthio, etc.);

lower alkylamino (e.g. methylamino, etc.); cyclo(lower)alkyl (e.g. cyclopentyl, cyclohexyl, etc.); cyclo(lower)alkenyl (e.g. cyclohexenyl; cyclohexadienyl, etc.); hydroxy; halogen (e.g. chloro, bromo, etc.); amino; protected amino as aforementioned; cyano; nitro; carboxy; protected carboxy as mentioned below; sulfo; sulfamoyl; imino; oxo; amino(lower)alkyl (e.g. aminomethyl, aminoethyl, etc.).

The preferred embodiment of "acylamino" thus defined may include aroylamino such as phthalimido.

Suitable "protected hydroxy(lower)alkyl" means lower alkyl substituted by a conventional protected hydroxy group and may include acyloxy(lower)alkyl, in which the acyl moiety may include the same as those exemplified above and the lower alkyl moiety may include methyl, ethyl, propyl, isopropyl, butyl, isobutyl, tert-butyl, pentyl, neopentyl, tert-pentyl, hexyl and the like, and the preferred embodiment of "protected hydroxy(lower)alkyl" thus defined may include substituted or unsubstituted ar(lower)alkoxycarbonyloxy(lower)alkyl such as mono- or di- or tri-phenyl(lower)alkoxycarbonyloxy(lower)alkyl optionally substituted by nitro (e.g. benzyloxycarbonyloxymethyl, benzhydryloxycarbonyloxymethyl, trityloxycarbonyloxymethyl, 1- or 2-benzyloxycarbonyloxyethyl, 1- or 2-benzhydryloxycarbonyloxyethyl, p-nitrobenzyloxycarbonyloxymethyl, 1- or 2-p-nitrobenzyloxycarbonyloxyethyl, 1- or 2- or 3-p-nitrobenzyloxycarbonyloxypropyl, etc.).

Suitable "hydroxy(lower)alkyl" may include hydroxymethyl, 1- or 2-hydroxyethyl, 1- or 2- or 3-hydroxypropyl, and the like.

Suitable "a protected carboxy group" may include a carboxy group substituted with a suitable protective group which is conventionally used in cephalosporin and penicillin compounds as the protective group of the carboxy group at their 4th or 3rd position, for example, an esterified carboxy group. And suitable examples of said ester moiety may be the ones such as lower alkyl ester (e.g. methyl ester, ethyl ester, propyl ester, isopropyl ester, butyl ester, isobutyl ester, tert-butyl ester, pentyl ester, tert-pentyl ester, hexyl ester, etc.);
lower cycloalkyl(lower)alkyl ester (e.g. 1-cyclopropylethyl ester, etc.);
lower alkenyl ester (e.g. vinyl ester, allyl ester, etc.);
lower alkynyl ester (e.g. ethynyl ester, propynyl ester, etc.);
lower alkoxyalkyl ester (e.g. methoxymethyl ester, ethoxymethyl ester, isopropoxymethyl ester, 1-methoxyethyl ester, 1-ethoxyethyl ester, etc.);
lower alkylthioalkyl ester (e.g. methylthiomethyl ester, ethylthiomethyl ester, ethylthioethyl ester, isopropylthiomethyl ester, etc.);
mono (or di or tri)-halo(lower)alkyl ester (e.g. 2-iodoethyl ester, 2,2,2-trichloroethyl ester, etc.);
lower alkanoyloxy(lower)alkyl ester (e.g. acetoxymethyl ester, propionyloxymethyl ester, butyryloxymethyl ester, valeryloxymethyl ester, pivaloyloxymethyl ester, hexanoyloxymethyl ester, 2-acetoxyethyl ester, 2-propionyloxyethyl ester, etc.);
lower alkanesulfonyl(lower)alkyl ester (e.g. mesylmethyl ester, 2-mesylethyl ester, etc.);
ar(lower)alkyl ester, for example, phenyl(lower)alkyl ester optionally substituted by one or more suitable substituent(s) such as nitro, hydroxy, lower alkoxy or the like [e.g. benzyl ester, 4-methoxybenzyl ester, 4-nitrobenzyl ester, phenethyl ester, trityl ester, diphenylmethyl ester, bis(methoxyphenyl)methyl ester, 3,4-dimethoxybenzyl ester, 4-hydroxy-3,5-di-t-butylbenzyl ester, etc.];
aryl ester optionally substituted by one or more suitable substituent(s) such as substituted or unsubstituted phenyl ester optionally substituted by halogen, lower alkoxy or the like (e.g. phenyl ester, tolyl ester, t-butylphenyl ester, xylyl ester, mesityl ester, cumenyl ester, 4-chlorophenyl ester, 4-methoxyphenyl ester, etc.); tri(lower)alkyl silyl ester (e.g. trimethylsilyl ester, etc.);
lower alkylthioester (e.g. methylthioester, ethylthioester, etc.) and the like, in which the preferred "esterified carboxy group" may include lower alkoxycarbonyl (e.g methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, tert-pentyloxycarbonyl, hexyloxycarbonyl, etc.) and mono- or di- or triphenyl(lower)alkoxycarbonyl optionally substituted by nitro (e.g. benzyloxycarbonyl, benzhydryloxycarbonyl, trityloxycarbonyl, 4-nitrobenzyloxycarbonyl, etc.).

Suitable "an organic group optionally substituted by suitable substituent(s)" may include lower alkyl (e.g. methyl, ethyl, propyl, isopropyl, butyl, isobutyl, pentyl, isopentyl, neopentyl, hexyl, etc.), aryl (e.g. phenyl, tolyl, xylyl, mesityl, cumenyl, naphthyl, etc.), these groups substituted by one or more suitable substituent(s) such as carboxy, a protected carboxy group mentioned above, lower alkylthio (e.g. methylthio, ethylthio, propylthio, etc.), and the like.

The preferred embodiment of "an organic group substituted by suitable substitutent(s)" may include carboxy(lower)alkyl (e.g. carboxymethyl, 1- or 2-carboxyethyl, 1- or 2- or 3-carboxypropyl, etc.), and protected carboxy(lower)alkyl such as lower alkoxycarbonyl(lower)alkyl (e.g. methoxycarbonylmethyl, ethoxycarbonylmethyl, propoxycarbonylmethyl, 1- or 2-methoxycarbonylethyl, 1- or 2-ethoxycarbonylethyl, etc.), and mono- or di- or tri-phenyl(lower)alkoxycarbonyl(lower)alkyl optionally substituted by nitro (e.g. benzyloxycarbonylmethyl, benzyloxycarbonylethyl, benzyloxycarbonylpropyl, benzhydryloxycarbonylmethyl, trityloxycarbonylmethyl, p-nitrobenzyloxycarbonylmethyl, p-nitrobenzyloxycarbonylethyl, p,p'-dinitrobenzhydryloxycarbonylpropyl, etc.).

Suitable "carboxy(lower)alkyl" and "protected carboxy(lower)alkyl" may include the same as those exemplified above, respectively.

Suitable "lower alkyl" may include methyl, ethyl, propyl, isopropyl, butyl, isobutyl, tert-butyl, pentyl, neopentyl, tert-pentyl, hexyl, and the like, in which the preferred one may include $C_1$–$C_3$alkyl.

Suitable "cycloalkylidene" may include 5–6 membered cycloalkylidene (i.e cyclopentylidene and cyclohexylidene, etc.).

Suitable "lower alkoxy" may include methoxy, ethoxy, propoxy, isopropoxy, butoxy, isobutoxy, tert-butoxy, pentyloxy, hexyloxy, and the like, in which the preferred one may include $C_1$–$C_3$alkoxy.

Suitable "aryl" may include phenyl, tolyl, xylyl, mesityl, cumenyl, naphthyl, and the like.

Suitable "protected hydroxy moiety" in the terms "1-protected hydroxy-1-methylethyl" and "protected hydroxy(lower)alkyl" may include a hydroxy group substituted by a conventional hydroxy-protective group, which is commonly used in β-lactam compounds such as thienamycin or carpetimycin derivatives or its analogue, for example, acyl such as mono(or di or tri)phenyl(lower)alkoxycarbonyl optionally substituted by nitro (e.g. benzyloxycarbonyl, benzhydryloxycarbonyl, trityloxycarbonyl, 4-nitrobenzyloxycarbonyl, etc.), ar(lower)alkyl such as mono(or di- or tri)phenyl(lower)alkyl (e.g. benzyl, benzhydryl, trityl, etc.), trisubstituted silyl such as tri(lower)alkylsilyl (e.g. trimethylsilyl, triethylsilyl, isopropyl-dimethylsilyl, tert-butyldimethylsilyl, diisopropyl-methylsilyl, etc.), triarylsilyl (e.g. triphenylsilyl, etc.) or triar(lower)alkylsilyl (e.g. tribenzylsilyl, etc.), and the like.

Suitable "lower alkyl moiety" in the terms "amino(lower)alkyl" and "acylamino(lower)alkyl" may include methyl, ethyl, propyl, isopropyl, butyl, isobutyl, tert-butyl, pentyl, neopentyl, tert-pentyl, hexyl, and the like, in which the preferred one may include $C_1$–$C_3$alkyl.

Suitable "lower alkenyl moiety" in the term "acylamino(lower)alkenyl" may include vinyl, propenyl and the like.

Suitable "acyl moiety" in the terms "acylamino(lower)alkyl" and "acylamino(lower)alkenyl" may include lower alkanoyl (e.g. formyl, acetyl, etc.), phenyl(lower)alkoxycarbonyl which may have nitro (e.g. benxyloxycarbonyl, 4-nitrobenxyloxycarbonyl, ect.), and the like.

Suitable "acyl" may include a residue of an organic sulfonic or phosphoric acid such as diaryloxyphosphoryl (e.g. diphenoxyphosphoryl etc.). Suitable salts of the compound (I'), (I-2), (II), (II-I) to (II-3), (VII-4), (VIII-3), (XVIII) and (XXIII) to (XXV) are the same as those exemplified for the compound (I).

Suitable salts of the compounds (I-1), (I-3) to (I-10), (I-11), (I-12), (I-4a), (II-4), (II-5), (III), (III-1), (IV-1) to (IV-3), (V-1), (V-3) to (V-6), (VI), (VII-1) to (VII-3), (VII-5) to (VII-7), (VIII-2), (IX-1), (IX-2), (XXII), and (XXVI) to (XXX) are the same as the basic salts as exemplified for the compound (I).

Suitable acetal at the formyl group of the compounds (V-1), (V-2), (VIII-1) and (X) may include di(lower)alkyl acetal such as di(lower)alkoxymethyl (e.g. dimethoxymethyl, diethoxymethyl, dipropoxymethyl, etc.), and the like.

Suitable hemi-acetal at the formyl group of the compound (VIII-1) may include lower alkyl hemi-acetal such as 1-hydroxy-1-(lower)alkoxymethyl (e.g. 1-hydroxy-1-methoxymethyl, 1-hydroxy-1-ethoxymethyl, 1-hydroxy-1-propoxymethyl, etc.), and the like.

The processes for the preparation of the object compounds of the present invention are explained in detail in the following.

Process A: (II)→(I')

The object compound (I') can be prepared by reacting the compound (II) with the compound (III).

This reaction is preferably carried out in the presence of a dehalogenating agent such as silver compounds (e.g. silver tetrafluoroborate, silver perchlorate, etc.), Lewis acids (e.g. titanium tetrachloride, zinc chloride, mercuric chloride, boron trifluoride etherate, etc.), and the like.

Further, this reaction is usually carried out in a conventional solvent which does not adversely influence the reaction such as chloroform, methylene chloride, tetrahydrofuran, benzene, etc., or a mixture thereof.

The reaction temperature is not critical and the reaction is preferably carried out from under cooling to under warming.

This reaction proceeds stereospecifically, and the configuration of the third and fourth positions of the object compound (I') always constitutes a trans form. Accordingly, the compound (I'), for example, having the same configuration as that of the natural Thienamycin can be prepared depending on a selection of the starting compound (II).

Process B-1: (I-1)→(I-2),
Process E-4: (VII-3)→(VII-4),
Process F-4: (VIII-2)→(VIII-3) and
Process M-3: (XVII)→(XVIII)

The object compounds (I-2), (VII-4), (VIII-3) and (XVIII) can be prepared by removing the amino-protective group in $R_b^1$ from the corresponding compounds (I-1), (VII-3), (VIII-2) and (XVIII), respectively.

Suitable method for this removal reaction includes hydrolysis; reduction; a combined method comprising iminohalogenation and iminoetherification, followed by hydrolysis; and the like.

In the above methods, suitable reagents to be used are exemplified as follows.

(i) For hydrolysis which refers to the same meaning as solvolysis including, for example, acidolysis, alcoholysis, aminolysis, hydrazinolysis, etc.:

Hydrolysis is preferably carried out in the presence of an acid or base.

Suitable acid is an inorganic acid (e.g. hydrochloric acid, hydrobromic acid, sulfuric acid, etc.), an organic acid (e.g. formic acid, acetic acid, trifluoroacetic acid, propionic acid, benzenesulfonic acid, p-toluenesulfonic acid, camphorsulfonic acid, etc.), an acidic ion-exchange resin and the like.

Suitable base is an inorganic base such as alkali or alkaline earth metal hydroxide, carbonate or bicarbonate (e.g. sodium hydroxide, potassium carbonate, sodium bicarbonate, calcium hydroxide, magnesium hydroxide, etc.), ammonium hydroxide and the like; an organic base such as an alkoxide or phenoxide of the above metal, (e.g. sodium ethoxide, sodium methoxide, lithium phenoxide), an amine such as mono-, di- or trialkylamine (e.g. methylamine, ethylamine, propylamine, isopropylamine, butylamine, N,N-dimethyl-1,3-propanediamine, trimethylamine, triethylamine, etc.), unsubstituted, mono- or disubstituted arylamine (e.g. aniline, N-methylaniline N,N-dimethylaniline, etc.) or a heterocyclic base (e.g. pyrrolidine, morpholine, N-methylmorpholine, N-methylpiperidine, N,N-dimethylpiperazine, pyridine, etc.), hydrazines (e.g. hydrazine, methylhydrazine, ethylhydrazine, etc.), a basic ion exchange resin and the like.

The hydrolysis is usually carried out in a conventional solvent which does not adversely influence the reaction such as water, methanol, ethanol, propanol, tetrahydrofuran, N,N-dimethylformamide, dioxane, methylene chloride, chloroform, etc., or a mixture thereof.

The reaction temperature of this hydrolysis is not critical and the reaction is preferably carried out from under cooling to under warming.

(ii) For reduction:

Reduction is carried out in a conventional manner, including chemical reduction and catalytic reduction.

Suitable reducing agents to be used in chemical reduction are a combination of a metal (e.g. tin, zinc, iron, etc.) or a metallic compound (e.g. chromium chloride, chromium acetate, etc.) and an organic or inorganic acid (e.g. formic acid, acetic acid, propionic acid, trifluoroacetic acid, p-toluenesulfonic acid, hydrochloric acid, hydrobromic acid, etc.).

The reduction is usually carried out in a conventional solvent which does not adversely influence the reaction such as water, lower alkanol (e.g. methanol, ethanol, propanol, etc.), chloroform, methylene chloride, tetrahydrofuran, N,N-dimethylformamide, benzene, toluene, etc., or a mixture thereof. Additionally, in case that the abovementioned acids to be used in chemical reduction are in liquid, they can also be used as a solvent.

The reaction temperature of this reduction is not critical and the reaction is preferably carried out from under cooling to under warming.

(iii) For combined method:

In this process, when the protected amino group in $R_b^1$ is an organic carboxamide, the carboxamide bond can be more preferably cleaved by the following modified hydrolysis. That is, the compounds (I-1), (VII-3) and (VIII-2) are first subjected to iminohalogenation, iminoetherification, and then hydrolysis.

The first and second steps of this method are preferably carried out in an anhydrous solvent. Suitable solvent for the first step (i.e. iminohalogenation) is an aprotic solvent such as methylene chloride, chloroform, diethyl ether, tetrahydrofuran, dioxane, etc., and for the second step (i.e. iminoetherification) is usually the same as those in the above first step. These two steps and the last step (i.e. hydrolysis step) are most preferably conducted in one-batch system.

Suitable iminohalogenating agent includes a halogenating agent such as phosphorus compound (e.g. phosphorus trichloride, phosphorus pentachloride, phosphorus tribromide, phosphorus pentabromide, phosphorus oxychloride, etc.), thionyl chloride, phosgene, and the like.

Suitable iminoetherifying agent may be an alcohol such as an alkanol (e.g. methanol, ethanol, propanol, isopropanol, butanol, etc.) or the corresponding alkanol having alkoxy (e.g. 2-methoxyethanol, 2-ethoxyethanol, etc.), and alkoxide of metal such as alkali metal, alkaline earth metal (e.g. sodium methoxide, potassium ethoxide, magnesium ethoxide, lithium methoxide, etc.), and the like. Thus obtained reaction product is, if necessary, hydrolyzed in a conventional manner.

The hydrolysis is preferably carried out at ambient temperature or under cooling, and proceeds simply pouring the reaction mixture into water or a hydrophilic solvent such as alcohol (e.g. methanol, ethanol, etc.) moistened or admixed with water, and if necessary, with addition of an acid or base as exemplified in the hydrolysis.

The method for this removal reaction is selected according to a kind of the amino-protective group to be removed.

In addition to the above, in case the protected amino group in $R_b^1$ is a group such as phthalimido, the reaction can also be carried out by reacting the compounds (I-1), (VII-3) and (VIII-2) with a dimetal sulfide (e.g. disodium sulfide, etc.), and then a condensing agent (e.g. N,N'-dicyclohexylcarbodiimide, ethyl chloroformate-triethylamine, trifluoroacetic anhydride, etc.), followed by hydrazine. The present removal reaction is usually carried out in a conventional solvent which does not adversely influence the reaction as aforementioned from under cooling to under warming.

In this reaction, the starting compounds (I-1), (VII-3) and (VIII-2) can be used as a protected form at the first position thereof, and such protected form may be, for example, a silyl derivative formed by the reaction of the starting compounds with a silyl compound such as tetra(lower)alkylsilane (e.g. tert-butyltrimethylsilane, etc.), and the like.

Process B-2: (I-2)→(I-3)

The object compound (I-3) can be prepared by reacting the compound (I-2) with a diazotizing agent and a halogenating agent.

The diazotizing agent used in this reaction may include a conventional one which can be applied to converting amino compounds to diazo compounds such as alkali metal nitrite (e.g. sodium nitrite, etc.), alkyl nitrite (e.g. pentyl nitrite, isopentyl nitrite, etc.), nitrosyl chloride, dinitrogen tetroxide, and the like.

The halogenating agent used in this reaction may include a conventional one which can be applied to converting diazo compounds to halo compounds such as hydrogen halide (e.g. hydrogen chloride, hydrogen bromide, etc.), hydrogen halide with an organic amine, for example, hydrogen halide with trialkylamine (e.g. triethylamine hydrochloride, triethylamine hydrobromide, etc.), and the like.

When hydrogen halide with an organic amine is used as the halogenating agent, the reaction can preferably be carried out in the presence of an acid as those illustrated in Process B-1.

This reaction is usually carried out in a conventional solvent which does not adversely influence the reaction such as water, formic acid, acetic acid, tetrahydrofuran, chloroform, methylene chloride, benzene, etc., or a mixture thereof.

The reaction temperature is not critical and the reaction is preferably carried out from under cooling to under warming.

Process B-3: (I-3)→(I-4)

The object compound (I-4) can be prepared by removing halogen for $R_c^1$ from the compound (I-3).

This reaction is carried out by a conventional method such as reduction and the like.

The method of reduction, and the reaction conditions (e.g. reaction temperature, solvent, etc.) are substantially the same as those illustrated for the removal reaction of the amino-protective group in $R_b^1$ of the compound (I-1) in the Process B-1, and therefore are to be referred to said explanation, and in addition, there may be exemplified by trialkyltin hydride [e.g. tri(n-butyl)tin hydride, etc.] triaryltin hydride (e.g. triphenyltin hydride, etc.) as the reducing agent.

Process B-4: (I-2)→(I-5)
Process E-5: (VII-4)→(VII-5) and
Process M-4: (XVIII)→(XIX)

The object compounds (I-5), (VII-5) and (XVIII) can be prepared by formylating the corresponding compounds (I-2), (VII-4) and (XIX), respectively.

The formylating agent used in this reaction may include formic acid or its salt or its reactive derivative such as formic acid anhydride (e.g. formic anhydride, formic acetic anhydride, etc.), formylimidazole, and the like.

In this reaction, in case that a free formic acid is used as the formylating agent, the reaction is preferably carried out in the presence of a condencing agent such as a carbodiimide compound [e.g., N,N'-dicyclohexylcarbodiimide, N-cyclohexyl-N'-morpholinoethylcarbodiimide, N-cyclohexyl-N'-(4-diethylaminocyclohexyl)-carbodiimide, N,N'-diethylcarbodiimide, N,N'-diisopropylcarbodiimide, N-ethyl-N'-(3-dimethylaminopropyl)carbodiimide, etc.], a ketenimine compound (e.g., N,N'-carbonylbis(2-methylimidazole), pentamethyleneketene-N-cyclohexylimine, diphenylketene-N-cyclohexylimine, etc.); an olefinic or acetylenic ether compounds (e.g., ethoxyacetylene, β-chlorovinylethyl ether), a sulfonic acid ester of N-hydroxybenzotriazole derivative [e.g., 1-(4-chlorobenzenesulfonyloxy)-6-chloro-1H-benzotriazole, etc.], a combination of trialkylphosphite or triphenylphosphine and carbon tetrachloride, disulfide or diazacarboxylate, a phosphorus compound (e.g., ethyl polyphosphate, isopropyl polyphosphate, phosphoryl chloride, phosphorus trichloride, etc.), thionyl chloride, oxalyl chloride, N-ethylbenzisoxazolium salt, N-ethyl-5-phenylisoxazolium-3-sulfonate, a reagent (referred to as so-called "Vilsmeier reagent") formed by the reaction of an amide compound such as dimethylformamide, diethylacetamide, N-methylformamide, etc.

This reaction is usually carried out in a conventional solvent which does not adversely influence the reaction such as methylene chloride, chloroform, benzene, toluene, tetrahydrofuran, dioxane, formic acid, acetic acid, etc., or a mixture thereof.

The reaction temperature is not critical and the reaction is preferably carried out from under cooling to under warming.

Process B-5: (I-5)→(I-6)
Process E-6: (VII-5)→(VII-6) and
Process M-5: (XIX)→(XX)

The object compounds (I-6), (VII-6) and (XX) can be prepared by dehydrating the corresponding compounds (I-5), (VII-5) and (XIX), respectively.

The dehydrating agent used in this reaction may include conventional one such as phosphorus halocompound (e.g. phosphorus trichloride, phosphorus tribromide, phosphorus oxychloride, phosphorus pentachloride, etc.), triphenylphosphine dibromide, phosphorus pentoxide, phosgene, thionyl chloride, trichloromethyl chloroformate, isocyanuric chloride, sulfonyl halide (e.g. benzenesulfonyl chloride, toluenesulfonyl chloride etc.) and the like.

This reaction is preferably carried out in the presence of a base as aforementioned in Process B-1.

Further, this reaction is usually carried out in a conventional solvent which does not adversely influence the reaction such as methylene chloride, chloroform, benzene, toluene, tetrahydrofuran, dioxane and the like.

The reaction temperature is not critical and the reaction is usually carried out under cooling to at ambient temperature.

Process B-6: (I-6)→(I-4)
Process E-7: (VII-6)→(VII-7)
Process I-2: (XI)→(I-11)
Process J-2: (XIII)→(XIV) and
Process M-6: (XX)→(XXI)

The object compounds (I-4), (VII-7), (I-11), (XIV) and (XXI) can be prepared by removing the isocyano group from the corresponding compounds (I-6), (VII-6), (XI), (XIII) and (XX), respectively.

This removal reaction can be carried out in the presence of a reducing agent, and suitable example thereof may include tri- or dialkyltin hydride and tri- or diaryltin hydride as exemplified in Process B-3.

In this process, when a compound (XI) or (XIII) wherein $R_e^1$ is a protected hydroxy(lower)alkyl is used as a starting compound, the corresponding compound (I-11) or (XIV) wherein $R_e^1$ is a protected hydrocy(lower)alkyl can be obtained as a resultant compound. This case may also be included within the scope of this process.

Process C-1: (I-4a)→(IV-1),
Process D-4: (V-3)→(V-4) and
Process F-3: (VIII-2)→(VII-2)

The object compounds (IV-1), (V-4) and (VII-2) can be prepared by oxidizing the corresponding compounds (I-4a), (V-3) and (VIII-2), respectively.

The oxidizing agent used in this reaction may include a conventional one which can be applied to converting an allyl group to an acetyl group such as oxygen, hydrogen peroxide, lower alkyl hydrogen peroxide (e.g. tert-butyl hydrogen peroxide, etc.) in the presence of palladium compound (e.g. palladium chloride, sodium tetrachloropalladate, etc.) optionally in the presence of cupric halide (eg. cupric chloride, etc.) or cuprous halide (e.g. cuprous chloride, etc.), and the like.

This reaction is usually carried out in a conventional solvent which does not adversely influnce the reaction such as water, methanol, ethanol, isopropyl alcohol, N,N-dimethylformamide, N-methylpyrrolidone, acetic acid, etc., or a mixture thereof.

The reaction temperature is not critical and the reaction is preferably carried out from under cooling to under heating.

In this reaction, the starting compounds (I-4a) and (VIII-2) can be used as a protected form at the first position thereof, and such protected form may be, for example, a silyl derivative formed by the reaction of the starting compounds with a silyl compound such as tetraalkylsilane (e.g. tert-butyl-trimethylsilane, etc.), and the like.

Process C-2: (IV-1)→(IV-2),
Process D-1: (I-4a)→(V-1),
Process E-1: (I-7)→(VII-1) and
Process G-1: (I-9)→(IX-1)

The object compounds (IV-2), (V-1), (VII-1) and (IX-1) can be prepared by reacting the corresponding compounds (IV-1), (I-4a), (I-7) and (I-9), respectively with ozone, and then degrading the resultant ozonide in a conventional manner, if necessary.

The ozonide produced by the starting compounds with ozone is usually degraded by redution or heating.

The method of the reduction can be carried out in substantially the same manner as that as explained in Process B-1, and therefore the reaction conditions (e.g. solvent, reaction temperature, etc.) are to be referred to said explanation, and in addition, as suitable reducing agents, there may be exemplified by trialkyl phosphite (e.g. trimethylphosphite, etc.), triphenylphosphine, dimethyl sulfide, sodium bisulfite, sodium sulfite, sodium iodide, stannous chloride, and the like.

In this reaction, in case that lower alkanol is used as the solvent, the acetal or hemi-acetal of the object compounds (V-1) and (IX-1) are occasionally obtained, and this is also included within the scope of this reaction.

Further, in case that the compound (I-4a) is used as the starting compound, and the degradation reaction is carried out by heating, the compound (XI-1) represented by the following formula is also obtained.

In case that the reaction is carried out by heating, the compound (XI-1) can also be prepared, from the ozonide, and this compound can be transformed into the comoound (XI-2) by Hydrolysis in Process D-2 and introduction of the carboxyprotective group in a conventional manner as explained in Preparation E mentioned hereinafter.

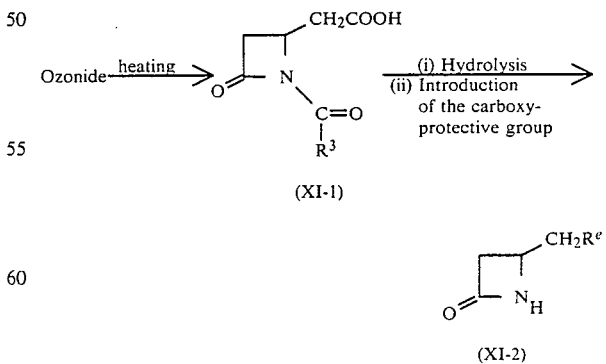

wherein $R^3$ is a protected carboxy such as those exemplified above.

Process C-3: (IV-2)→(IV-3)
Process D-5: (V-2)→(V-5)

Process D-6: (V-1)→(V-6) and
Process M-1: (VIII-1)→(XVI)

The object compounds (IV-3), (V-5), (V-6) and (XVI) can be prepared by reducing the corresponding compounds (IV-2), (V-2), (V-1) and (VIII-1), respectively.

The reducing agent to be used in this reaction may include conventional reducing agent which can reduce an oxo group to a hydroxy group such as those exemplified in Process B-1, and in addition, alkali metal borohydride (e.g. sodium borohydride, sodium cyanoborohydride, etc.), borane complex with amines (e.g. tert-butylamine, N,N-dimethylaniline, lutidine, morpholine, triethylamine, etc.), borane complex with ethers (e.g. tetrahydrofuran, etc.), diborane, alminum-amalgam and the like.

This reaction is usually carried out in a conventional solvent which does not adversely influence the reaction such as water, methylene chloride, methanol ethanol, ethyl acetate, etc., or a mixture thereof.

The reaction temperature is not critical and the reaction is usually carried out from under cooling to under warming.

Process D-2: (V-1)→(V-2),
Process E-2: (VII-1)→(VII-2) and
Process G-2: (IX-1)→(IX-2)

The object compounds (V-2), (VII-2) and (IX-2) can be prepared by hydrolyzing the corresponding compounds (V-1), (VII-1) and (IX-1), respectively.

This reaction can be carried out in substantially the same manner as Hydrolysis as explained in Process B-1, and therefore the reaction conditions (e.g. solvent, reaction temperature, etc.) are to be referred to said explanation.

This reaction is preferably carried out by alcoholysis such as methanolysis.

In this reaction, in case that the object compound (V-2) is obtained as the acetal, it can be transformed into the compound (V-2) having the formyl group in a conventional manner, for example, by treating the acetal with acids as exemplified in Process B-1.

Process D-3: (V-2)→(V-3) and
Process F-2: (VIII-1)→(VIII-2)

The object compounds (V-3) and (VIII-2) can be prepared by reacting the corresponding compounds (V-2) and (VIII-1) with the compound (VI).

The reactive equivalent of the compound (VI) can also be used in this reaction, and such reactive equivalent can be represented by the formula $(R^5O)_2$-$POCH_2R^b$, in which $R^5$ and $R^b$ are each as defined above.

In case that the above reactive equivalent is used in this reaction, the reaction is preferably carried out in the presence of a base as exemplified in Process B-1.

This reaction is usually carried out in a conventional solvent which does not adversely influence the reaction such as methylene chloride, chloroform, benzene, toluene, tetrahydrofuran, dioxane, etc., or a mixture thereof.

The reaction temperature is not critical and the reaction is preferably carried out from under cooling to under heating.

In this reaction, the starting compounds (V-2) and (VIII-1) can be used as a protected form at the first position thereof, and such protected form may be, for example, a silyl derivative formed by the reaction of the starting compounds with a silyl compound such as tetraalkylsilane (e.g. tert-butyl-trimethylsilane, etc.), and the like.

Process F-1: (I-8)→(VIII-1) and
Process H: (I-10)→(X)

The object compounds (VIII-1) and (X) can be prepared by reacting the corresponding compounds (I-8) and (I-10) with ozone, and degrading the resultant ozonide in a conventional manner, if necessary, and then hydrolyzing the resultant compound in a conventional manner.

This reaction can be carried out by substantially the same method as those of Processes C-2 and D-2, and therefore the reaction conditions (e.g. solvent, reaction temperature, etc,) are to be referred to said explanation.

In this reaction, in case that the object compound (VIII-1) is obtained as the acetal form, it can be transformed into the compound (VIII-1) having the formyl group in a conventional manner, for example, by treating the acetal with acids as exemplified in Process B-1.

Process E-3: (VII-2)→(VII-3)

The object compound (VII-3) can be prepared by subjecting the compound (VII-2) to protection reaction of the carbonyl group.

The reagent used in this reaction may include tri(lower)alkyl orthoformate (e.g. trimethyl orthoformate, etc.), O,O-di(lower)alkyl ketone (e.g. O,O-dimethyl acetone, etc.), lower alkanol (e.g. methanol, etc.), and the like.

This reaction is preferably carried out in the presence of an acid such as those exemplified in Hydrolysis in Process B-1.

This reaction is usually carried out in a conventional solvent which does not adversely influence the reaction such as methylene chloride, chloroform, benzene, toluene, tetrahydrofuran, dioxane, etc., or a mixture thereof.

The reaction temperature of this reaction is not critical and the reaction is preferably carried out from under cooling to under heating.

Process E-8: (VII-7)→(V-4)

The object compound (V-4) can be prepared by removing the carbonyl-protective group in the protected carbonyl group from the compound (VII-7).

This reaction can be carried out in the presence of an acid such as those exemplified in Hydrolysis in Process B-1.

This reaction is usually carried out in a conventional solvent which does not adversely influence the reaction such as water, dimethylformamide, etc., or a mixture thereof.

The reaction temperature is not critical and the reaction is preferably carried out from under cooling to under heating.

Process I-1: (I-6)→(XI)
Process J-1: (XII)→(XIII)

The object compounds (XI) and (XIII) can be prepared by reacting the corresponding compounds (I-6) and (XII) with an organo lithium compound, respectively and then reacting the resultant compound with a carbonyl compound.

The organo lithium compound may include alkyl lithium (e.g. n-butyl lithium, etc.), aryl lithium, aralkyl lithium and the like.

The carbonyl compound to be used in this reaction may include oxo(lower)alkane (e.g. acetone, acetaldehyde, etc.) and the like.

This reaction is usually carried out in a conventional solvent which does not adversely influence the reaction such as tetrahydrofuran, dimethoxyethane, ether and the like.

The reaction temperature of this reaction is not critical and the reaction is preferably carried out from under cooling to at ambient temperature.

Process J-3: (XIV)→(XV)
Process L: (I-11)→(I-13)
Process N: (I-2a)→(I-8)

The object compounds (XV), (I-13) and (I-8) can be prepared by subjecting the corresponding compounds (XIV), (I-11) and (I-2a) to introduction reaction of the hydroxy-protective group or the amino-protective group, respectively.

This reaction is substantially the same as Preparation C as mentioned hereinafter, and further, the introducing agent of the amino-protective group is substantially the same as those of hydroxy-protective group.

Therefore the introducing agent of the hydroxy-protective group (or the amino-protective group) and reaction conditions (e.g. reaction temperature, solvent, etc.) are referred to those of the Preparation C.

Process K: (I-4a)→(I-12)

The object compound (I-12) can be prepared by reacting the compound (I-4a) with a metal amide and then reacting the resultant compound with a carbonyl compound or alkyl halide.

The metal amide to be used in this reaction may include an alkali metal amide (e.g. lithium isopropyl cyclohexylamide, etc.) and the like.

The carbonyl compound to be used in this reaction may include oxo(lower)alkane (e.g. acetone, acetaldehyde, etc.) and the like.

The alkyl halide to be used in this reaction may include methyl iodide, ethyl iodide and the like.

This reaction is usually carried out in a conventional solvent which does not adversely influence the reaction such as tetrahydrofuran, dimethoxyethane, ether and the like.

The reaction temperature of this reaction is not critical and the reaction is preferably carried out from under cooling to at ambient temperature.

Process M-2: (XVI)→(XVII)

The object compound (XVII) can be prepared by reacting the compound (XVI) with 2,2-dimethoxyalkane (e.g. 2,2-dimethoxypropane, etc.) or dimethoxycycloalkane in the presence of a Lewis acid.

The Lewis acid may include a conventional one such as boron trifluoride etherate and the like.

This reaction is usually carried out in a conventional solvent which does not adversely influence the reaction such as dichloromethane, ether, benzene, toluene and the like.

The reaction temperature of this reaction is not critical and the reaction is preferably carried out from under cooling to at ambient temperature.

Process O: (XXII)→(XXIII)

The object compound (XXIII) can be prepared by reacting the compound (XXII) with ozone (1st step) and then degrading the resultant ozonide in a conventional manner (2nd step) and then reacting the resultant compound with an oxidizing agent (3rd step) and then treating the resultant compound with an alcohol (4th step) (The First Method); or by reacting the compound (XXII) with an oxidizing agent (The Second Method).

Reaction Conditions of the 1st and 2nd steps of the First Method (Ozonolysis and degradation of ozonide) are substantially the same as those of the Process C-2 as mentioned above and therefore are to be referred to those of the Process C-2. It is to be noted that the 2nd step is not essential for the preparation of the object compound (XXIII) and it is possible that the ozonide obtained by the 1st step can be subjected directly to the 3rd step.

The oxidizing agent to be used in the 3rd step of the First Method may include an organic peracid (e.g. m-chloroperbenzoic acid, peracetic acid, etc.), hydrogen peroxide and the like.

The reaction of the 3rd step is usually carried out in the presence of or absence of a conventional solvent which does not adversely influence the reaction.

The reaction temperature of the 3rd step is not critical and the reaction is preferably carried out from under cooling to under heating.

The alcohol to be used in the 4th step of the First Method may include an alkanol (e.g. methanol, etc.) and the like.

The reaction of the 4th step is usually carried out without solvent at ambient temperature to under heating.

The oxidizing agent to be used in the Second Method may include potassium permanganate, a combination of potassium permanganate and sodium periodate, Ruthenium tetraoxide, a combination of Ruthenium tetraoxide and sodium periodate, and the like.

The reaction of the Second Method is usually carried out in a conventional solvent which does not adversely influence the reaction such as acetone, methyl ethyl ketone, aqueous acetone and the like.

Process P-1: (XXIII')→(XXIV)

The compound (XXIV) or a salt thereof can be prepared by reacting the compound (XXIII') or a salt thereof with malonic acid or its derivative or a salt thereof.

Suitable salt of the malonic acid or its derivative may include the same salt with a base as that for the compound (I).

Suitable derivative of the malonic acid may include mono- or di-ester such as exemplified in the explanation of "protected carboxy group".

The reaction can be carried out in a conventional solvent such as dioxane, tetrahydrofuran, N,N-dimethylformamide or any other organic solvents which do not adversely influence the reaction, or a mixture thereof, in the presence of a condensing agent such as carbodiimide compounds (e.g. N,N'-diethylcarbodiimide, N,N-diisopropylcarbodiimide, N,N'-dicyclohexylcarbodiimide, N-cyclohexyl-N'-morpholinoethylcarbodiimide, N-cyclohexyl-N'-(4-diethylaminocyclohexyl)-carbodiimide, N-ethyl-N'-(3-dimethylaminopropyl)-carbodiimide,); N,N'-carbonylbis-(2-methylimidazole); keteneimine compounds (e.g. pentamethyleneketene-N-cyclohexylimine, diphenylketene-N-cyclohexylimine,); ethoxyacetylene; 1-alkoxy-1-chloroethylene; ethyl polyphosphate; isopropyl polyphosphate; phosphorus oxychloride; phosphorus trichloride; thionyl chloride; oxalyl chloride; a combination of triphenylphosphine with carbon tetrachloride or diazenedicarboxylate; 2-ethyl-7-hydroxybenzisoxazolium salt; 2-ethyl-5-(m-sulfophenyl)isoxazolium hydroxide intra-molecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, phosphorus oxychloride, etc.; or the like.

The reaction temperature is not critical, and the reaction is usually carried out under from cooling to warming.

Process P-2: (XXIV)→(XXV) .

The compound (XXV) or a salt thereof can be prepared by reacting the compound (XXIV) or a salt thereof with acid azide.

Suitable acid azide may include arenesulfonyl azide which may have substituent (e.g. benzenesulfonyl azide, p-toluenesulfonyl azide, p-carboxybenzenesulfonyl azide, etc.), lower alkanesulfonyl azide (e.g. methanesulfonyl azide, ethanesulfonyl azide, etc.), and the like.

The reaction is usually carried out in a conventional solvent such as tetrahydrofuran, dioxane, methylene chloride, acetonitrile, N,N-dimethylformamide or any other organic solvents which do not adversely influence the reaction, or a mixture thereof, in the presence of an inorganic or organic base such as an alkali metal bicarbonate (e.g. sodium bicarbonate, potassium bicarbonate, etc.), alkali metal carbonate (e.g. sodium carbonate, potassium carbonate, etc.), alkaline earth metal carbonate (e.g magnesium carbonate, calcium carbonate, etc.), tri(lower)alkylamine (e.g. trimethylamine, triethylamine, N,N-diisopropyl-N-ethylamine, etc.), pyridine compounds (e.g. pyridine, picoline, lutidine, N,N-di(-lower)alkylaminopyridine such as N,N-dimethylaminopyridine, etc.), quinoline, N-lower alkylmorphorine (e.g. N-methylmorphorine, etc.), N,N-di(-lower)alkylbenzylamine (e.g. N,N-dimethylbenzylamine, etc.), and the like.

The reaction temperature is not critical, and the reaction is usually carried out under from cooling to warming.

Process P-3: (XXV)→(XXVI)

The compound (XXVI) or a salt thereof can be prepared by subjecting the compound (XXV) or a salt thereof to cyclization.

The reagent used in this cyclization reaction may include metal (e.g. cupper, etc.), metallic acetate (e.g. lead acetate, palladium acetate, rhodium acetate, cupric acetate, etc.), metallic sulfate (e.g. cupric sulfate, etc.), and the like.

The reaction is usually carried out in a conventional solvent such as benzene, toluene, tetrahydrofuran, dioxane, acetonitrile or any other organic solvents which do not adversely influence the reaction, or a mixture thereof.

The reaction temperature is not critical, and the reaction is usually carried out from at ambient temperature to heating.

Process Q (XXVI)→(XXVII)→(XXVIII)→(XXIX) or (XXX)

The compound (XXVII) or a salt thereof can be prepared by reacting the compound (XXVI) or a salt thereof with an acylating agent.

The present reaction can be carried out in a conventional acylation manner.

Suitable acylating agents may be organic sulfonic or phosphoric acid or its reactive derivative such as acid halide, acid anhydride, and the like, for example, diarylphosphoryl halide (e.g. diphenylphosphoryl chloride, ditolylphosphoryl chloride, etc.), and the like.

The reaction is usually carried out in a conventional solvent such as water, acetone, dioxane, acetonitrile, chloroform, methylene chloride, hexamethylphosphoramide, ethylene chloride, tetrahydrofuran, ethyl acetate, dimethylsulfoxide, N,N-dimethylformamide, pyridine or any other organic solvents which do not adversely influence the reaction, or a mixture thereof.

When the acylating agent is used in a free acid form or its salt form in this reaction, the reaction is preferably carried out in the presence of a conventional condensing agent as exemplified in the explanation of the process P-1.

The reaction may also be carried out in the presence of an inorganic or organic base as exemplified in the explanation of the process P-2.

The reaction temperature is not critical, and the reaction is usually carried out under from cooling to warming.

The compound (XXVII) or a salt thereof can be isolated in a conventional manner, but can also be used as the starting compound of the Second Step without any isolation.

The compound (XXVIII) or a salt thereof can be prepared by reacting the compound (XXVII) or a salt thereof with a thiol compound of the formula: $R^{10}SH$ ($R^{10}$ is the same as defined above) or a salt thereof.

Suitable salt of the thiol compound may include the same salt with a base as that for the compound (I).

The reaction is usually carried out in a conventional solvent such as those given in the explanation of the First Step.

The reaction may also be carried out in the presence of an inorganic or organic base such as those given in the explanation of the First Step.

The reaction temperature is not critical, and the reaction is usually carried out under from cooling to warming.

The compound (XXIX) or a salt thereof can be prepared by subjecting the compound (XXVIII) or a salt thereof to removal reaction of the protective group(s).

The present reaction is carried out in a conventional method such as hydrolysis, reduction, and the like.

Hydrolysis is preferably carried out in the presence of a base or an acid in a conventional manner.

The reaction temperature is not critical and the reaction is usually carried out under from cooling to warming.

The reduction method applicable for this removal reaction may include, for example, reduction by using a combination of a metal (e.g. zinc, zinc amalgam, etc.) or a salt of chrome compound (e.g. chromous chloride, chromous acetate, etc.) and an organic or inorganic acid (e.g. acetic acid, propionic acid, hydrochloric acid, sulfuric acid, etc.); and conventional catalytic reduction in the presence of a conventional metallic catalyst such as palladium catalysts (e.g. spongy palladium, palladium black, palladium oxide, palladium on carbon, colloidal palladium, palladium on barium sulfate, palladium on barium carbonate, etc.), nickel catalysts (e.g. reduced nickel, nickel oxide, Raney nickel, etc.), platinum catalysts (e.g. platinum plate, spongy platinum, platinum black, colloidal platinum, platinum oxide, platinum wire, etc.), and the like.

The reaction is usually carried out in a conventional solvent such as water, alkanol (e.g. methanol, ethanol, propanol, etc.), dioxane, tetrahydrofuran, acetic acid or any other organic solvents which do not adversely influence the reaction, or a mixture thereof around a neutral condition.

The reaction temperature is not critical, and the reaction is usually carried out under from cooling to warming.

The removal methods can be selected according to the kind of the protective groups to be removed.

The compound (XXX) or a salt thereof can be prepared by oxidizing the compound (XXVIII) or a salt thereof. The present oxidation reaction can be carried out in a similar manner to that in Process O accordingly the reaction condition of present oxidation can be referred to that in Process O.

The Preparations A to E are explained in detail as follows.

Preparation A: (II-1)→(II-2)

The compound (II-2) can be prepared by halogenating the compound (II-1).

The halogenating agent used in this reaction may include conventional one which can be applied to converting a thio group into a halogen atom such as halogen (e.g. chlorine, bromine, etc.), sulfuryl halide (e.g. sulfuryl chloride, etc.), N-halosuccinimide (e.g. N-chlorosuccinimide, N-bromosuccinimide, etc.), and the like.

This reaction is usually carried out in a conventional solvent which does not adversely influence the reaction such as chloroform, methylene chloride, ethylene chloride, carbon tetrachloride, etc., or a mixture thereof.

The reaction temperature is not critical and the reaction is preferably carried out from under cooling to at ambient temperature.

Preparation B: (II-3)→(II-2)

The object compound (II-2) can be prepared by halogenating the compound (II-3).

This reaction is substantially the same as Preparation A, and therefore the halogenating agent, reaction conditions (e.g. reaction temperature, solvent, etc.) are referred to those of Preparation A.

Preparation C: (II-4)→(II-5)

The object compound (II-5) can be prepared by subjecting the compound (II-4) to introduction reaction of the hydroxy-protective group.

The introducing agent of the hydroxy-protective group used in this reaction may include an organic carboxylic, carbonic and sulfonic acid or a reactive derivative thereof.

Suitable reactive derivative of the introducing agent may include, for example, an acid halide, an acid anhydride, an activated amide, an activated ester, and the like, and preferably an acid chloride and acid bromide; a mixed acid anhydride with an acid such as substituted phosphoric acid (e.g., dialkylphosphoric acid, phenylphosphoric acid, diphenylphosphoric acid, dibenzylphosphoric acid, halogenated phosphoric acid, etc.), dialkylphosphorous acid, sulfurous acid, thiosulfuric acid, sulfuric acid, alkyl carbonate (e.g., methyl carbonate, ethyl carbonate, propyl carbonate, etc.), aliphatic carboxylic acid (e.g. pivalic acid, pentanoic acid, isopentanoic acid, 2-ethylbutyric acid, trichloroacetic acid, etc.), aromatic carboxylic acid (e.g., benzoic acid, etc.); a symmetrical acid anhydride; an activated acid amide with a heterocyclic compound containing imino function such as imidazole, 4-substituted imidazole, dimethylpyrazole, triazole or tetrazole; an activated ester (e.g., p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyridyl ester, piperidinyl ester, 8-quinolyl thioester, or an ester with a N-hydroxy compound such as N,N'-dimethylhydroxylamine, 1-hydroxy-2-(1H)pyridone, N-hydroxysuccinimide, N-hydroxyphthalimide, 1-hydroxybenzotriazole, 1-hydroxy-6-chlorobenzotriazole, etc.), and the like.

The suitable reactive derivative can optionally be selected from the above according to the kind of the compound (II-4) to be used preactically.

This introduction reaction is preferably carried out in the presence of an organic or inorganic base such as alkali metal (e.g. lithium, sodium, potassium, etc.), alkaline earth metal (e.g. calcium, magnesium, etc.), alkali metal hydride (e.g. sodium hydride, etc.), alkaline earth metal hydride (e.g. calcium hydride, etc.), alkyl lithium (e.g. butyl lithium, etc.), lithium amide (e.g. lithium diisopropylamide, lithium isopropyl cyclohexylamide, etc.), alkali metal hydroxide (e.g. sodium hydroxide, potassium hydroxide, etc.), alkali metal carbonate (e.g. sodium carbonate, potassium carbonate, etc.), alkali metal bicarbonate (e.g. sodium bicarbonate, potassium bicarbonate, etc.), alkali metal alkoxide (e.g. sodium methoxide, sodium ethoxide, potassium tert-butoxide, etc.), trialkylamine (e.g. triethylamine, etc.), pyridine compound (e.g. pyridine, lutidine, dimethylaminopyridine, picoline, etc.), N-alkylmorpholine (e.g. N-methylmorpholine, etc.), quinoline, and the like.

The reaction is usually carried out in a conventional solvent which does not adversely influence the reaction such as water, acetone, dioxane, acetonitrile, chloroform, benzene, methylene chloride, ethylene chloride, tetrahydrofuran, ethyl acetate, N,N-dimethylformamide, pyridine, hexamethylphosphoramide, etc., or a mixture thereof.

The reaction temperature is not critical and the reaction is usually carried out under cooling to at ambient temperature.

In this reaction, in case that the carboxylic acid or its reactive derivative is used as the introducing agent of the hydroxy-protective group in the presence of diethyl azodicarboxylate, the configuration of the carbon atom on which the protected hydroxy group is often converted to the other configuration, and such a case is also included within the scope of the present invention.

Preparation D: (II-5)→(II-4)

The object compound (II-4) can be prepared by removing the hydroxy-protective group from the compound (II-5).

This removal reaction can be carried out by hydrolysis as explained in Process B-1, and therefore the reaction conditions (e.g. reaction temperature, solvent, etc.) are referred to those of Process B-1.

Preparation E: (III-1)→(III-2)

The object compound (III-2) can be prepared by introducing a carboxy-protective group into the compound (III-1).

The introducing agent of a carboxy-protective group used in this reaction may include a conventional esterifying agent which can convert the carboxy group to the esterified group as exemplified before, for example, alcohol or its reactive equivalent such as halide (e.g. chloride, bromide, iodide), sulfonate, sulfate, diazo compound, and the like.

This reaction is usually carried out in the presence of a base as aforementioned in Preparation C, in a conventional solvent which does not adversely influence the reaction such as N,N-dimethylformamide, tetrahydrofuran or a mixture thereof.

The reaction temperature is not critical and the reaction is carried out under cooling to at ambient temperature.

It is to be noted that, in the aforementioned reactions including the Processes A to O and Preparation A to E and/or the post-treatment of the reaction mixture, in case that the compound possesses optical isomer, it may occasionally be transformed into the other optical isomer and such case is also included within the scope of the present invention.

In case that the object compounds have a free carboxy group, for example, in $R^3$ and/or free amino group, for example, in $R_a{}^1$, it may be transformed into its salts by a conventional method.

The object compounds and salts thereof (I) of the present invention are novel and useful intermediates for preparing antibiotics having the fundamental skeleton of Thienamycin, especially optically active skeleton, which are highly active against a number of pathogenic microorganisms.

For example, the object compounds (I-4), (I-8), (I-11), (I-12), (I-13), (V-4) to (V-6), (IX-2), (X), (XV), (XXI) and (XXIII) in Processes B to E, F, G and I to O can be transformed into useful antibiotics having the fundamental skeleton of Thienamycin by the methods as shown in the following literatures.

H. Onoue, et. al. Tetrahedron Letters No. 40, page 3867 (1979);

A. J. Gilby, et. al. German Offenlegungsschrift No. 28 11 514;

Eiji Oki, et. al. Japan Kokai No. 73656/1980;

David B. R. Johnston, et. al. Journal of the American Chemical Society, Volume 100, Page 313 (1978);

L. D. Cama, et. al. Journal of the American Chemical Society, Volume 102, page 6161 (1980); and L. D. Cama, et. al. Journal of the American Chemical Society, Volume 100, page 8006 (1978).

F. A. Bouffard et.al. Journal of the Organic Chemistry, Volume 45, page 1130 (1980);

S. M. Schmitt et.al. ibid, Volume 45, page 1135 and 1142 (1980);

Japan Kokai No. 5478/81;

T. Kametani et. al. Journal of the Amirican Chemical Society, Volume 102, page 2060 (1980);

D. G. Melillo et.al. Tetrahedron Letters, Volume 21, page 2783 (1980);

T. Kametani et. al. Journal of the Chemical Society, Perkin I page 964 (1981);

T. Kametani et. al. Heterocycles, Volume 14, page 1305 (1980);

T. Kametani et. al. Heterocycles, Volume 14, page 1967 (1980); and Japan Kokai No. 22676/55

Further, the object compounds (XXIII') to (XXVII) or their salts are useful intermediates for preparing a carbapenam compound such as the object compounds (XXVIII), (XXIX) or their salts which have an excellent antimicrobial activity against pathogenic microorganisms and therefore are useful as a therapeutic agent for human or animal infectious diseases.

The following test data show an antimicrobial activity of the representative compound of the carbapenem compounds (XXVIII) and (XXIX).

TEST METHOD

One loopful of an overnight culture of each test strain in Trypticase-soy broth ($10^8$ viable cells per ml.) was streaked on heart infusion agar (HI-agar) containing graded concentrations of antibiotics, and the minimal inhibitory concentration (MIC) was expressed in terms of $\mu$g/ml after incubation at 37° C. for 20 hours.

TEST COMPOUND

Potassium (5R,6R)-3-(2-aminoethylthio)-6-(1-hydroxy-1-methylethyl)-7-oxo-1-azabicyclo[3.2.0]-hept-2-ene-2-carboxylate.

TEST RESULT

| Test organisms | MIC ($\mu$g/ml) |
| --- | --- |
| Staphylococcus aureus 6 | 1.56 |
| Pseudomonas aeruginosa NCTC-10490 | 12.50 |

The following Preparations and Examples are given for the purpose of illustrating this invention.

PREPARATION 1

A solution of benzyl 2-[(3R,4R)-4-methylthio-3-phthalimido-2-oxoazetidin-1-yl]-3-methyl-2-butenoate (2.25 g) in methylene chloride (12 ml) was cooled to −78° C. and a solution of chlorine (390 mg) in carbon tetrachloride (3.4 ml) was added. After stirring for 30 minutes at the same temperature, the mixture was warmed to 0° C. and evaporated to leave an oil (2.52 g). A 2.10 g portion of this oil was chromatographed on silica gel (20 g) eluting with 10% ethyl acetate in methylene chloride to give benzyl 2-[(3R,4S)-4-chloro-3-phthalimido-2-oxoazetidin-1-yl]-3-methyl-2-butenoate (1.80 g) as an oil.

I.R. (CH$_2$Cl$_2$): 1790, 1780 (shoulder), 1725 cm$^{-1}$.

N.M.R. (CDCl$_3$)$\delta$: 2.07 (s, 3H), 2.30 (s, 3H), 5.27 (s, 2H), 5.50 (d, J=1.5 Hz, 1H), 6.17 (d, J=1.5 Hz, 1H).

PREPARATION 2

A solution of benzyl (6S)-6-phthalimidopenitillanate (610 mg) in methylene chloride (5 ml) was cooled to −25° C. and a solution of chlorine (465 mg) in carbon tetrachloride (3 ml) was added. After stirring for 45 minutes at the same temperature, the mixture was warmed to 0° C. and concentrated. The concentrate was poured into a cold, dilute aqueous sodium bicarbonate and extracted with ethyl acetate. The extract was washed with brine, dried over magnesium sulfate and evaporated to leave an oil (700 mg), which was chromatographed on silica gel (10 g) eluting with 10% ethyl acetate in methylene chloride to give benzyl 2-[(3S,4R)-4-chloro-3-phthalimido-2-oxoazetidin-1-yl]-3-methyl-2-butenoate (433 mg) as an oil.

I.R. (CH$_2$Cl$_2$): 1790, 1780 (shoulder), 1725 cm$^{-1}$.

N.M.R. (CDCl$_3$) $\delta$: 2.07 (s, 3H), 2.30 (s, 3H), 5.27 (s, 2H), 5.50 (d, J=1.5 Hz, 1H), 6.17 (d, J=1.5 Hz, 1H).

PREPARATION 3

A solution of methyl (6S)-6-phthalimidopenicillanate (9.01 g) in methylene chloride (50 ml) was cooled to −30° C. and a solution of chlorine (5.33 g) in carbon tetrachloride (30 ml) was added. The mixture was stirred for 40 minutes, during which time the temperature was raised to −10° C. After removal of the solvent by evaporation, the residue was dissolved in ethyl acetate (100 ml) and washed with dilute aqueous sodium bicarbonate and water. Drying over magnesium sulfate and evaporation gave an oil, which was chromatographed on silica gel (100 g) eluting with 10% ethyl acetate in methylene chloride to give methyl 2-[(3S,4R)-4-chloro-3-phthalimido-2-oxoazetidin-1-yl]-3- methyl-2-butenoate (6.55 g) as a crystalline solid. mp. 122°-125° C.

I.R. (CH₂Cl₂): 1785, 1675, 1720 cm⁻¹.

N.M.R. (CDCl₃) δ:2.13 (s, 3H), 2.37 (s, 3H), 3.90 (s, 3H), 5.62 (d, J=15 Hz, 1H), 6.27 (d, J=15 Hz, 1H).

PREPARATION 4

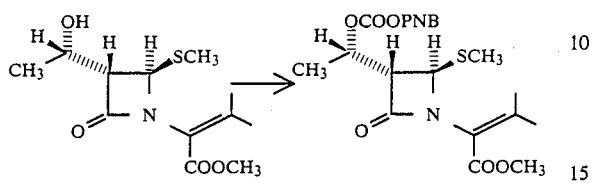

To a solution of methyl 2-[(3S,4R)-3-{(1S)-1-hydroxyethyl}-4-methylthio-2-oxoazetidin-1-yl]-3-methylbut-2-enoate (376 mg) and 4-dimethylaminopyridine (336 mg) in dichloromethane (3 ml) was added p-nitrobenzyl chloroformate (358 mg) at −30° C. under a nitrogen atmosphere. After stirring for one hour at 0° C., the mixture was diluted with ethyl acetate and washed with dilute hydrochloric acid, water, a dilute aqueous sodium bicarbonate, and brine. Drying over magnesium sulfate and the removal of the solvent left an oil (635 mg), which was chromatographed on silica gel (25 g) eluting with 10–25% ethyl acetate in hexane to afford methyl 3-methyl-2-[(3S,4R)-4-methylthio-3-{(1S)-1-(p-nitrobenzyloxycarbonyloxy)ethyl}-2-oxoazetidin-1-yl]-but-2-enoate (566 mg) as an oil.

IR (CH₂Cl₂): 1760, 1725, 1525, 1350 cm⁻¹.

NMR (CDCl₃) δ: 1.50 (d, J=7 Hz, 3H), 2.01 (s, 3H), 2.12 (s, 3H), 2.22 (s, 3H), 3.43 (dd, J=5, 3 Hz, 1H), 3.73 (s, 3H), 4.94 (d, J=3 Hz, 1H), 5.2 (m, 1H), 5.25 (s, 2H), 7.52 (d, J=9 Hz, 2H), 8.17 (d, J=9 Hz, 2H).

PREPARATION 5

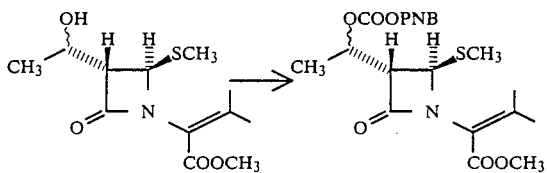

To a solution of a mixture (1:3) of methyl 2-[(3S,4R)-3-{(1RS)-1-hydroxyethyl}-4-methylthio-2-oxoazetidin-1-yl]-3-methylbut-2-enoate (1.84 g) and 4-dimethylaminopyridine (1.23 g) in dichloromethane (20 ml) was added a solution of p-nitrobenzyl chloroformate (1.60 g) in dichloromethane (3 ml) at 0° C. After stirring at 0° C. for 1.5 hours, the mixture was diluted with ethyl acetate (150 ml) and washed with dilute hydrochloric acid, water, a dilute aqueous sodium bicarbonate, and brine. Drying over magnesium sulfate and removal of the solvent left an oil (3.1 g), which was chromatographed on silica gel (90 g) eluting with 10–25% ethyl acetate in hexane to give a mixture (1:3) of methyl 3-methyl-2-[(3S,4R)-4-methylthio-3-{(1RS)-1-(p-nitrobenzyloxycarbonyloxy)ethyl}-2-oxoazetidin-1-yl]-but-2-enoate (2.90 g) as an oil.

IR (CH₂Cl₂): 1755, 1725, 1525, 1350 cm⁻¹.

NMR (CDCl₃) δ: 1.51 (d, J=7 Hz, 1H), 2.01 (s, 3H), 2.12 (s, 3H), 2.23 (s, 3H), 3.29 (dd, J=7, 3 Hz, ¼H), 3.43 (dd, J=5, 3 Hz, ¾H), 3.73 (s, 3H), 4.95 (d, J=3 Hz, ¾H), 5.02 (d, J=3 Hz, ¼H), 5.2 (m, 1H), 5.25 (s, 2H), 7.50 (d, J=9 Hz, 2H), and 8.16 (d, J=9 Hz, 2H)

PREPARATION 6

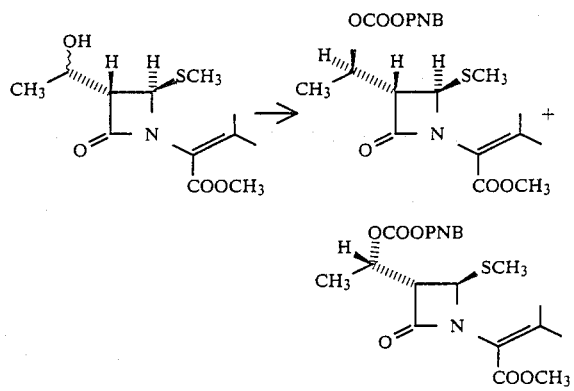

To a solution of a mixture (5:1) of methyl 2-[(3S,4R)-3-{(1RS)-1-hydroxyethyl}-4-methylthio-2-oxoazetidin-1-yl]-3-methylbut-2-enoate (755 mg) and 4-dimethylaminopyridine (440 mg) in dichloromethane (6 ml) was added dropwise a solution of p-nitrobenzyl chloroformate (660 mg) in dichloromethane (4 ml) during three minutes period at 0° C. After 1.5 hours, the solution was concentrated, taken up into ethyl acetate (40 ml), and washed with dilute hydrochloric acid, water and brine. The organic layer was dried over magnesium sulfate and evaporated to leave an oil. Chromatography on silica gel (50 g) eluting with 2–10% ethyl acetate in dichloromethane to give methyl 3-methyl-2-[(3S,4R)-4-methylthio-3-{(1R)-1-(p-nitrobenzyloxycarbonyloxy)ethyl}-2-oxoazetidin-1-yl]but-2-enoate (974 mg).

IR (CH₂Cl₂): 1760, 1720, 1525, 1350 cm⁻¹.

NMR (CDCl₃) δ: 1.50 (d, J=7 Hz, 1H), 2.01 (s, 3H), 2.12 (s, 3H), 2.24 (s, 3H), 3.30 (dd, J=2.5, 7 Hz, 1H), 3.85 (s, 3H), 5.05 (d, J=2.5 Hz, 1H), 5.23 (quinted, J=7Hz, 1H), 5.25 (s, 2H), 7.50 (d, J=9 Hz, 2H), 8.19 (d, J=9 Hz, 2H)

(1S) Isomer of the above compound (165 mg) was also afforded.

PREPARATION 7

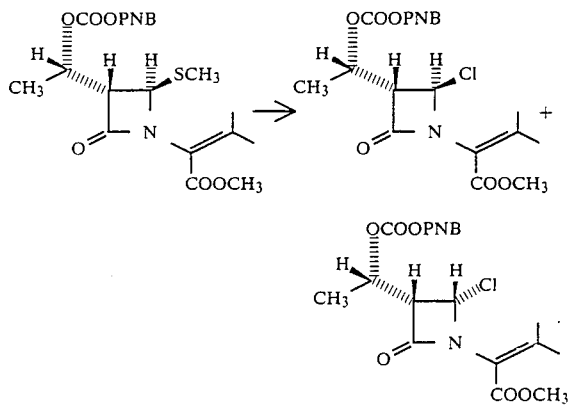

To a solution of methyl 3-methyl-2-[(3S,4R)-4-methylthio-3-{(1S)-1-(p-nitrobenzyloxycarbonyloxy)-ethyl}-2-oxoazetidin-1-yl]but-2-enoate (530 mg) in dichloromethane (6 ml) was added a solution of chlorine (106 mg) in carbon tetrachloride (0.9 ml) at −78° C. The solution was allowed to warm to 0° C. during 30 minutes and cooled again to −78° C. Additional chlorine (59 mg) in carbon tetrachloride (0.5 ml) was added. The solution was allowed to warm to 10° C. during 30 minutes and evaporated in vacuo. The residue was chromatographed on silica gel (18 g) eluting with 10–33% ethyl acetate in hexane to give methyl [(3S,4R)-4-chloro-3-{(1S)-1-(p-nitrobenzyloxycarbonyloxy)ethyl}-2-oxoazetidin-1-yl]-3-methylbut-2-enoate (trans isomer) (215 mg) and methyl[(3S,4S)-4-chloro-3-{(1S)-1-(p-nitrobenzyloxycarbonyloxy)ethyl}-2-oxo-azetidin-1-yl]-3-methylbut-2-enoate (cis isomer) (210 mg).

The Trans isomer:

IR (CH$_2$Cl$_2$): 1780, 1750, 1725, 1525, 1350 cm$^{-1}$.

NMR (CDCl$_3$) δ: 1.53 (d, J=7 Hz, 3H), 2.03 (s, 3H), 2.30 (s, 3H), 3.7 (m, 1H), 3.74 (s, 3H), 5.2 (m, 1H), 5.28 (s, 2H), 5.81 (d, J=1.5 Hz, 1H), 7.54 (d, J=10 Hz, 2H), 8.20 (d, J=10 Hz, 2H).

The cis isomer:

IR (CH$_2$Cl$_2$): 1780, 1750, 1725, 1525, 1350 cm$^{-1}$.

NMR (CDCl$_3$) δ: 1.55 (d, J=7 Hz, 3H), 2.07 (s, 3H), 2.30 (s, 3H), 3.62 (t, J=4.5 Hz, 1H), 3.76 (s, 3H), 5.3 (m, 3H), 5.95 (d, J=4.5 Hz, 1H), 7.48 (d, J=10 Hz, 2H), 8.17 (d, J=10 Hz, 2H).

PREPARATION 8

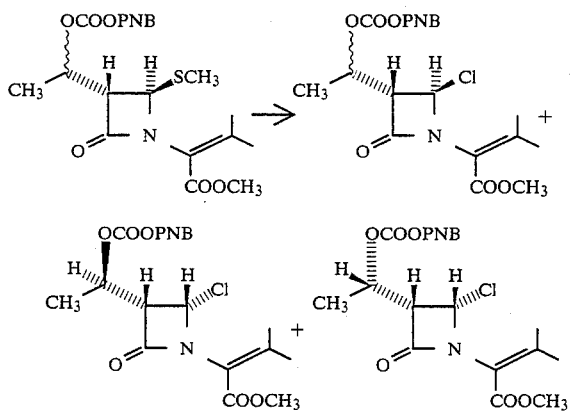

To a solution of a mixture (1:3) of methyl 3-methyl-2-[(3S,4R)-4-methylthio-3-{(1RS)-1-(p-nitrobenzyloxycarbonyloxy)ethyl}-2-oxoazetidin-1-yl]-but-2-enoate (1.30 g) in dichloromethane (13 ml) was added a solution of chlorine (211mg) in carbon tetrachloride (2.2 ml) at −78° C. The solution was allowed to warm to 0° C. during 45 minutes and concentrated. The residue was dissolved in ethyl acetate (30 ml) and washed with a chilled aqueous sodium bicarbonate (2.5 g), water, and brine. Drying over magnesium sulfate and evaporation left an oil (1.30 g), which showed two spots on silica gel thin layer chromatography (1:1 hexane/ethyl acetate). The residue was chromatographed on silica gel (40 g) eluting with 10–30% ethyl acetate in hexane to afford firstly a mixture (5:6:4) of methyl 2-[(3S)-4-chloro-3-{1-(p-nitrobenzyloxycarbonyloxy)ethyl}-2-oxoazetidin-1-yl]-3-methylbutenoate [a mixture (5:6:4) of (1S,4R) isomer, (1R, 4R) isomer and (1R, 4S) isomer] (550 mg).

Further elution with 30% ethyl acetate in hexane and evaporation gave a crystalline solid (407 mg). Crystallization from a mixture of dichloromethane and diethyl ether furnished methyl 2-[(3S,4S)-4-chloro-3-{(1S)-1-(p-nitrobenzyloxycarbonyloxy)ethyl}-2-oxoazetidin-1-yl]-3-methylbut-2-enoate (270 mg), mp 154°–157° C.

IR (nujol): 1770, 1745, 1715 cm$^{-1}$.

NMR (CDCl$_3$-d$_1$) δ: 1.55 (d, J=7 Hz, 3H), 2.07 (s, 3H), 2.29 (s, 3H), 3.65 (t, J=4.5 Hz, 1H), 3.74 (s, 3H), 5.3 (m, 3H), 5.96 (d, J=4.5 Hz, 1H), 7.50 (d, J=10 Hz, 2H), 8.18 (d, J=10 Hz, 2H); Mass spectrum: m/e 442, 440 (M$^+$).

PREPARATION 9

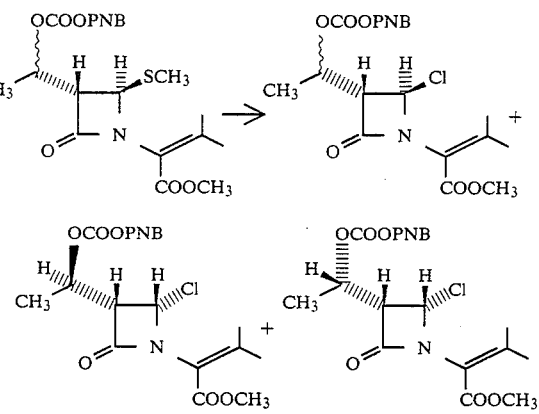

To a solution of a mixture (1:3) of methyl 3-methyl-2-[(3S,4R)-4-methylthio-3-{(1RS)-1-(p-nitrobenzyloxycarbonyloxy)ethyl}-2-oxo-azetidin-1-yl]but-2-enoate (527 mg) in dichloromethane (5.5 ml) was added a solution of chlorine (91 mg) in carbon tetrachloride (1.62 ml) at −78° C. The solution was allowed to warm to 0° C. during one hour and evaporated. In order to remove sulfur derived as by-product, the residue was dissolved in carbon tetrachloride (5 ml) and the solution was evaporated in vacuo. This procedure was repeated once and the residue was pumped to leave the isomeric mixture of chlorides (588 mg) described in Preparation 8.

NMR (CDCl$_3$) δ: 1.5 (m, 3H), 2.02 (s, ~1.5H), 2.07 (s, ~1.5H) 2.29 (s, 3H), 3.7 (m, 4H), 5.3 (m, 3H), 5.81 (d, J=1.5 Hz, ~0.25H), 5.86 (d, J=1.5 Hz, ~0.15H), 5.97 (d, J=4.5 Hz, ~0.6H), 7.5 (m, 2H), 8.21 (d, J=10 Hz, 2H)

The residue (536 mg) was crystallized from diethyl ether to give crude crystals (190 mg). Recrystallization from a mixed solvent of dichloromethane and diethyl ether afforded methyl 2-[(3S,4S)-4-chloro-3-{(1S)-1-(p-nitrobenzyloxycarbonyloxy)ethyl}-2-oxoazetidin-1-yl]-3-methylbut-2-enoate (170 mg). The mother liquors were combined and chromatographed on silica gel (9 g) eluting with 10–30% ethyl acetate in hexane to give a mixture of methyl 2-[(3S)-4-chloro-3-{1-(p-nitrobenzyloxycarbonyloxy)ethyl}-2-oxoazetidin-1-yl]-3-methylbut-2-enoate [a mixture (5:3:2) of (1S,4R) isomer, (1R,4R) isomer and (1R,4S) isomer] (231 mg) as an oil.

IR (CH$_2$Cl$_2$): 1775, 1745, 1725 cm$^{-1}$.

NMR (CDCl$_3$) δ: 1.52 (d, J=7 Hz, 3H), 2.03 (s, 3H), 2.30 (s, 3H), 3.6–3.8 (m, 4H), 5.25 (m, 1H), 5.27 (s, 2H), 5.81 (d, J=1.5 Hz, 0.5H), 5.86 (d, J=1.5 Hz, 0.3H), 5.98 (d, J=4.5 Hz, 0.2H), 7.5 (a pair of d, J=10 Hz, 2H), 8.22 (d, J=10 Hz, 2H).

Further elution with 30% ethyl acetate in hexane recovered methyl 2-[(3S,4S)-4-chloro-3-{(1S)-1-(p-nitrobenzyloxycarbonyloxy)ethyl}-2-oxoazetidin-1-yl]-3-methylbut-2-enoate (43 mg).

PREPARATION 10

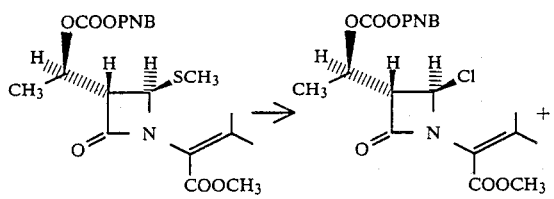

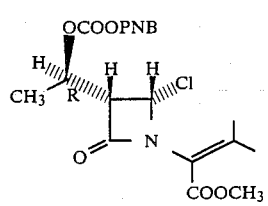

To a solution of methyl 3-methyl-2-[(3S,4R)-4-methylthio-3-{(1R)-1-(p-nitrobenzyloxycarbonyloxy)-ethyl}-2-oxoazetidin-1-yl]but-2-enoate (481 mg) in dichloromethane (5 ml) was added a solution of chlorine (83 mg) in carbon tetrachloride (0.65 ml) at −78° C. The solution was allowed to warm to 0° C. during 45 minutes and evaporated in vacuo. The residue was chromatographed on silica gel (12 g) eluting with 10–33% ethyl acetate in hexane to give methyl 2-[(3S)-4-chloro-3-{(1R)-1-(p-nitrobenzyloxycarbonyloxy)-ethyl}-2-oxoazetidin-1-yl]-3-methylbut-2-enoate [a mixture (55:45) of (4R) isomer and (4S) isomer] (394 mg).

IR (CH$_2$Cl$_2$): 1775, 1745, 1725, 1525, 1350 cm$^{-1}$.

NMR (CDCl$_3$) δ: 1.49 (d, J=7 Hz, 1.65H), 1.58 (d, J=7 Hz, 1.35H), 2.01 (s, 3H), 2.29 (s, 3H), 3.65 (m, 1H), 3.73 (s, 1.65H), 3.75 (s, 1.35H), 5.20 (m, 1H), 5.24 (s, 2H), 5.84 (d, J=1.5 Hz, 0.55H), 5.96 (d, J=4.5 Hz, 0.45H), 7.49 (d, J=9 Hz, 2H), 8.18 (d, J=9 Hz, 2H).

PREPARATION 11

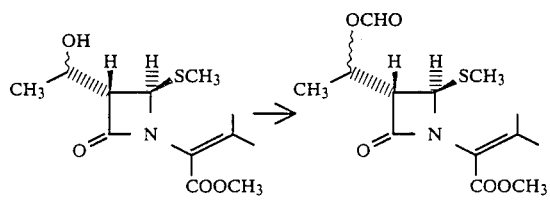

To a solution of triphenylphosphine (1.647 g), formic acid (0.20 ml), and a mixture (1:3) of methyl 2-[(3S,4R)-3-{(1RS)-1-hydroxyethyl}-4-methylthio-2-oxoazetidin-1-yl]-3-methylbut-2-enoate (1.145 g) in tetrahydrofuran (14 ml) was added dropwise diethyl azodicarboxylate (0.83 ml) at 0° C. under a nitrogen atmosphere. After keeping at the same temperature for 15 minutes, the solution was allowed to warm to room temperature and stirred for two hours. The mixture was cooled to 0° C. and additional formic acid (24 μl) and diethyl azodicarboxylate (0.10 ml) were added. After stirring at room temperature for one hour, the solution was concentrated, taken up into ethyl acetate (60 ml) and washed with a chilled dilute aqueous sodium bicarbonate, water, and brine. The organic layer was dried over magnesium sulfate, evaporated and re-dissolved in benzene (20 ml) to result in precipitation of crystals. These crystals were collected and washed with benzene. The combined filtrate and washings were evaporated and chromatographed on silica gel (60 g) eluting with 10–30% ethyl acetate in hexane to give a mixture (5:1) of methyl 2-[(3S,4R)-3-{(1RS)-1-formyloxyethyl}-4-methylthio-2-oxoazetidin-1-yl]-3-methylbut-2-enoate (889 mg).

IR (CH$_2$Cl$_2$): 1758, 1720 cm$^{-1}$.

NMR (CDCl$_3$) δ: 1.48 (d, J=7 Hz, 3H), 2.04 (s, 3H), 2.15 (s, 3H), 2.27 (s, 3H), 3.31 (dd, J=2.5, 7 Hz, 1H), 3.81 (s, 3H), 4.97 (d, J=2.5 Hz, 1/6H), 5.04 (d, J=2.5 Hz, 5/6H), 5.46 (quintet, J=7 Hz, 1H), 8.12 (s, 1H).

PREPARATION 12

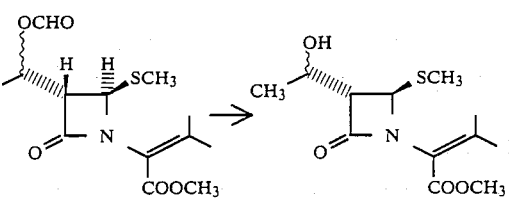

To a solution of a mixture (5:1) of methyl 2-[(3S,4R)-3-{(1RS)-1-formyloxyethyl}-4-methylthio-2-oxoazetidin-1-yl]-3-methylbut-2-enoate (880 mg) in methanol (20 ml) was added a 4.9M solution of sodium methoxide in methanol (0.60 ml) at 0° C. After 30 minutes, acetic acid (0.20 ml) was added and the mixture was evaporated. The residue was taken up into ethyl acetate (30 ml) and washed with a dilute aqueous sodium bicarbonate. Drying over magnesium sulfate and removal of the solvent left an oil, which was chromatographed on silica gel (25 g) eluting with 5–20% acetone in dichloromethane to give a mixture (5:1) of methyl 2-[(3S,4R)-3-}(1RS)-1-hydroxyethyl}-4-methylthio-2-oxoazetidin-1-yl]-3-methylbut-2-enoate (742 mg).

IR (CH$_2$Cl$_2$): 3560, 1750, 1715 cm$^{-1}$.

NMR (CDCl$_3$) δ: 1.34 (d, J=7 Hz, 3H), 2.01 (s, 3H), 2.14 (s, 3H), 2.23 (s, 3H), 2.93 (br d, J=6 Hz, 1H), 3.16 (dd, J=2.5, 7 Hz 1H), 3.77 (s, 3H), 4.22 (quintet, J=7 Hz, 1H), 4.92 (d, J=2.5 Hz, 1/6H), 5.06 (d, J=2.5 Hz, 5/6H).

PREPARATION 13

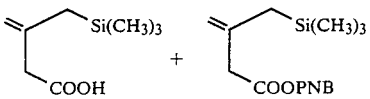

To a solution of 3-(trimethylsilylmethyl)but-3-enoic acid (2.73 g) and triethylamine (2.09 ml) in dimethylformamide (15 ml) was added p-nitrobenzyl bromide (3.24 g) at 0° C. After stirring for four hours at the same temperature, the mixture was poured into chilled dilute hydrochloric acid and extracted with a mixture of diethyl ether and ethyl acetate (1:1, 150 ml). The extract was washed with water, a dilute aqueous sodium bicarbonate, water, and brine. Drying over magnesium sulfate and removal of the solvent left an oil (3.90 g), which was chromatographed on silica gel (100 g) eluting with 20–50% hexane in dichloromethane and then dichloromethane to give an oil (3.50 g). Distillation afforded p-nitrobenzyl 3-(trimethylsilylmethyl)but-3-enoate (3.25 g) bp~160° C. (0.05 Torr).

IR (Film): 1735, 1630, 1605, 1520, 1350 cm$^{-1}$.

NMR (CDCl$_3$) δ: ~0.00 (s, 9H), 1.62 (s, 2H), 3.06 (s, 2H), 4.76 (br s, 2H), 5.22 (s, 2H), 7.50 (d, J=9.5 Hz), 8.22 (d, J=9.5 Hz).

PREPARATION 14

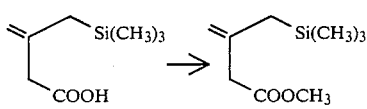

To a solution of 3-(trimethylsilylmethyl)but-3-enoic acid (36.5 g) in diethyl ether (200 ml) at 10°–15° C. was added a solution of diazomethane in diethyl ether (ca 0.6M solution, 400 ml). The excess of diazomethane was decomposed by addition of acetic acid. The resultant solution was concentrated in vacuo to 200 ml and the concentrate was washed with an aqueous sodium bicarbonate and brine. Drying over magnesium sulfate and evaporation of the solvent left a yellow oil, which was distilled in vacuo to give methyl 3-(trimethylsilylmethyl)but-3-enoate (34.74 g) as a colorless oil, bp 74°–75° C. (10 Torr).

IR Film: 1735, 1635 cm$^{-1}$.

NMR (CCl$_4$) δ: 0.00 (s, 9H), 1.56 (s, 2H), 2.84 (s, 2H), 3.57 (s, 3H), 4.60 (d, J=1.5 Hz, 1H), 4.65 (d, J=1.5 Hz, 1H).

PREPARATION 15

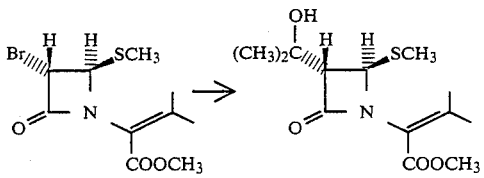

A 0.9M solution of diethylaluminum chloride in hexane (24.4 ml) was added to a suspension of activated zinc powder (4.0 g) in tetrahydrofuran (60 ml). After ten minutes the mixture was cooled to −20° C. A solution of methyl 2-[(3S,4R)-3-bromo-4-methylthio-2-oxoazetidin-1-yl]-3-methylbut-2-enoate (6.16 g) and acetone (1.84 ml) in tetrahydrofuran (45 ml) was added dropwise during 35 minutes at −20° C. under a nitrogen atmosphere. The resulting mixture was stirred at −15° to −10° C. for 1.5 hours and at 0° C. for 30 minutes. The reaction was quenched by addition of pyridine (3 ml). After ten minutes 2N hydrochloric acid (40 ml) and ethyl acetate (100 ml) were added. The mixture was filtered through diatomaceous earth and the filtrate was diluted with 2N hydrochloric acid (40 ml) and ethyl acetate (100 ml). The mixture was shaken and the organic layer was separated. The aqueous layer was extracted with ethyl acetate (50 ml). The combined extracts were washed three times with brine, dried over magnesium sulfate, and evaporated to give an oil (6.0 g). The residue was chromatographed on silica gel (150 g, eluting with 2 to 25% acetone in dichloromethane) to give 3.79 g (66.0%) of methyl 2-[(3S,4R)-3-(1-hydroxy-1-methylethyl)-4-methylthio-2-oxoazetidin-1-yl]-3-methylbut-2-enoate and 1.36 g of impure material. Rechromatography of the impure fraction on silica gel (100 g, eluting with 2 to 25% acetone in dichloromethane) afforded an additional 0.93 g (16.2%) of the desired product: IR(CH$_2$Cl$_2$): 3550, 1745, and 1715 cm$^{-1}$; NMR(CDCl$_3$)δ: 1.34 (s, 3H), 1.41 (s, 3H), 2.00 (s, 3H), 2.13 (s, 3H), 2.21 (s, 3H), 2.56 (s, 1H), 3.14 (d, J=3 Hz, 1H), 3.75 (s, 3H), and 5.01 (d, J=3 Hz, 1H).

PREPARATION 16

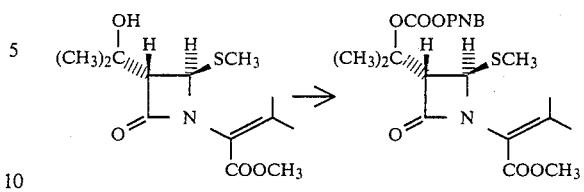

A 1.55N solution of n-butyl lithium in hexane (0.44 ml) was added dropwise to a solution of methyl 2-[(3S,4R)-3-(1-hydroxy-1-methylethyl)-4-methylthio-2-oxoazetidin-1-yl]-3-methylbut-2-enoate (164 mg) in tetrahydrofuran (2 ml) at −78° C. under a nitrogen atmosphere. After five minutes a solution of 4-nitrobenzyl chloroformate (147 mg) in tetrahydrofuran (1.5 ml) was added. The mixture was allowed to warm to 0° C. during 1.5 hours and stirred at the same temperature for 30 minutes. After being left at ambient temperature for 30 minutes, the reaction was quenched by addition of acetic acid (three drops). The mixture was evaporated, and the residue was taken up into ethyl acetate (20 ml) and washed in turn with a dilute aqueous solution of sodium bicarbonate and brine. Drying over magnesium sulfate and removal of the solvent left an oil which was chromatographed on silica gel (6.5 g; eluting with 1 to 2% ethyl acetate in dichloromethane for the desired product followed by 20% acetone in dichloromethane for the starting material) to give 170 mg of the desired product contaminated with some impurities and 52 mg (31.7% recovery) of the starting material. Further purification of the impure product on silica gel plates (20 cm × 20 cm × 2 mm, two pieces; two developments with 2/1 hexane-ethyl acetate) afforded 138 mg (51.8%; ie 83.4% based on consumed starting material) of methyl 3-methyl-2-[(3S,4R)-3-[1-methyl-1-(4-nitrobenzyloxycarbonyloxy)ethyl]-4-methylthio-2-oxoazetidin-1-yl]but-2-enoate: IR(CH$_2$Cl$_2$): 1750, 1720, 1520 and 1350 cm$^{-1}$; NMR (CDCl$_3$) δ; 1.64 (s, 3H), 1.71 (s, 3H), 2.01 (s, 3H), 2.09 (s, 3H), 2.23 (s, 3H), 3.70 (1H, hidden), 3.75 (s, 3H), 5.07 (d, J=3 Hz, 1H), 5.20 (s, 2H), 7.57 (d, J=9 Hz, 2H), and 8.18 (d, J=9 Hz, 2H).

PREPARATION 17

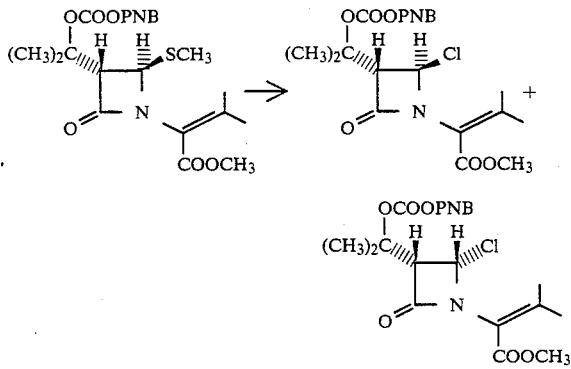

A solution of chlorine (70 mg) in carbon tetrachloride (1.75 ml) was added to a solution of methyl 3-methyl-2-[(3S,4R)-3-[1-methyl-1-(4-nitrobenzyloxycarbonyloxy)ethyl]-4-methylthio-2-oxoazetidin-1-yl]but-2-enoate (386 mg) in dichloromethane (4 ml) at −78° C. The mixture was allowed to warm to 0° C. during 40 minutes and evaporated. The residue was dissolved in carbon tetrachloride (5 ml) and evaporated. This procedure was repeated once and the residue was chromatographed on silica gel (8 g, eluting with 10 to 30% ethyl acetate in hexane) to give a 4:1 mixture of methyl 2-[(3S,4R)-4-chloro-3-[1-methyl-1-(4-nitrobenzyloxycarbonyloxy)ethyl]-2-oxoazetidin-1-yl]-3-methylbut-2-enoate [(3S,4R)-isomer] and its (3S,4S)-isomer: IR (CH₂Cl₂): 1770, 1745, 1720, 1520 and 1350 cm⁻¹; NMR (CDCl₃)δ: 1.67 (s, 2.4H), 1.74 (s, 2.4H), 1.79 (s, 0.6H), 1.82 (s, 0.6H), 2.02 (s, 2.4H), 2.08 (s, 0.6H), 2.30 (s, 3H), 3.74 (s, 2.4H), 3.75 (s, 0.6H), 3.93 (d, J=2 Hz, 0.8H), 4.02 (d, J=4 Hz, 0.6H), 5.21 (s, 2H), 5.91 (d, J=2 Hz, 0.8H), 5.95 (d, partially hidden, 0.2H), 7.53 (d, J=9 Hz, 2H), and 8.22 (d, J=9 Hz, 2H).

PREPARATION 18

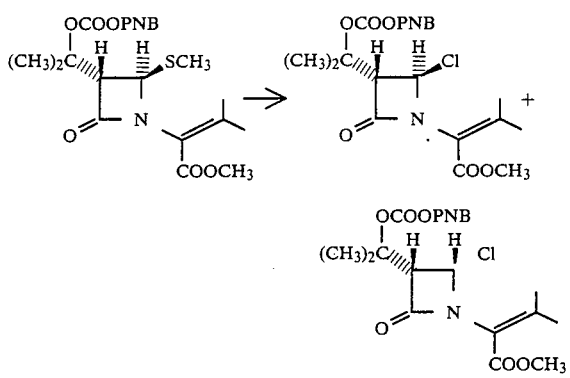

Methyl 3-methyl-2-[(3S,4R)-3-[1-methyl-1-(4-nitrobenzyloxycarbonyloxy)ethyl]-4-methylthio-2-oxoazetidin-1-yl]but-2-enoate (425 mg) was chlorinated in the same manner described above. Chromatography of the product on silica gel (10 g; eluting with 10 to 30% ethyl acetate in hexane) afforded 294 mg (70.9%) of methyl 2-[(3S,4R)-4-chloro-3-[1-methyl-1-(4-nitrobenzyloxycarbonyloxy)ethyl]-2-oxoazetidin-1-yl]-3-methylbut-2-enoate [(3S,4R)-isomer] and 80 mg of the (3S,4S)-isomer contaminated some impurities. Crystallization of the impure (3S,4S)-isomer from ether gave 35 mg of the pure (3S,4S)-isomer.

Spectral Data the (3S,4R)-isomer: IR (CH₂Cl): 1775, 1740, 1720, 1520 and 1350 cm⁻¹; NMR (CDCl₃)δ: 1.66 (s, 3H), 1.71 (s, 3H), 2.02 (s, 3H), 2.30 (s, 3H), 3.74 (s, 3H), 3.93 (d, J=2 Hz, 1H), 5.20 (s, 3H), 5.91 (d, J=2 Hz, 1H), 7.52 (d, J=8 Hz, 2H), and 8.20 (d, J=8 Hz, 2H).

the (3S,4S)-isomer: IR (CH₂Cl₂): 1775, 1740, 1725, 1520, and 1350 cm⁻¹; NMR (CDCl₃)δ: 1.78 (s, 3H), 1.81 (s, 3H), 2.07 (s, 3H), 2.29 (s, 3H), 3.74 (s, 3H), 4.00 (d, J=5 Hz, 1H), 5.18 (s, 2H), 5.93 (d, J=5 Hz, 1H), 7.46 (d, J=9 Hz, 2H), and 8.16 (d, J=9 Hz, 2H).

PREPARATION 19

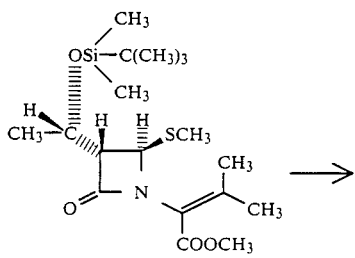

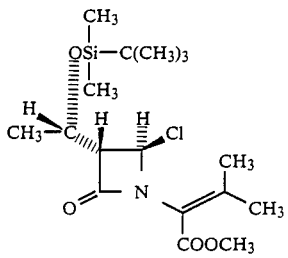

To a solution of methyl 2-[(3S,4R)-3-[(1S)-1-(tert-butyldimethylsilyloxy)ethyl]-4-methylthio-2-oxoazetidin-1-yl]-3-methylbut-2-enoate (60 mg) in dichloromethane (2 ml) was added a solution of chlorine (24 mg) in carbon tetrachloride (0.2 ml) at −50° C. The solution was allowed to warm to −10° C. during 30 minutes and cooled to −50° C. An additional solution of chlorine (12 mg) in carbon tetrachloride (0.1 ml) was added. The solution was allowed to warm to −5° C. and evaporated. The residue was chromatographed on silica gel (1.5 g, eluting with 8–10% ethyl acetate in hexane) to give 21.0 mg (36.1%) of methyl 2-[(3S,4R)-3-[(1S)-1-(tert-butyldimethylsilyloxy)ethyl]-4-chloro-2-oxoazetidin-1-yl]-3-methylbut-2-enoate. NMR (CDCl₃)δ: 0.12 (s, 6H), 0.93 (s, 9H), 1.34 (d, J=6.5 Hz, 3H), 2.01 (s, 3H), 2.29 (s, 3H), 3.56 (dd, J=1.5, 5 Hz, 1H), 3.77 (s, 3H), 4.30 (dq, J=5, 6.5 Hz, 1H), 5.80 (d, J=1.5 Hz, 1H).

EXAMPLE 1

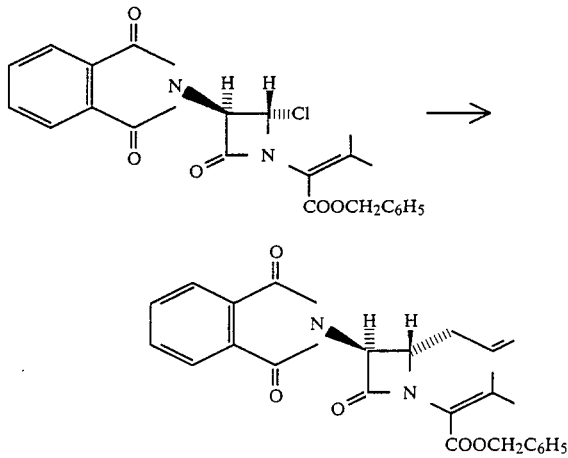

A mixture of benzyl 2-[(3R, 4S)-4-chloro-3-phthalimido-2-oxo-azetidin-1-yl]-3-methyl-2-butenoate (860 mg) and allyltrimethylsilane (0.48 ml) in methylene chloride (6 ml) was cooled to −78° C. and silver tetrafluoroborate (490 mg) was added. The mixture was stirred for 3 hours, during which time the temperature was gradually raised to room temperature. The reaction mixture was diluted with ethyl acetate and filtered by the aid of Celite. The filtrate was washed successively with water, dilute aqueous sodium bicarbonate and brine, dried over magnesium sulfate and evaporated to give an oil (841 mg), which was chromatographed on silica gel (25 g) eluting with 10% ethyl acetate in methylene chloride to give benzyl 2-[(3S,4S)-4-allyl-3-phthalimido-2-oxoazetidin-1-yl]-3-methyl-2-butenoate (445 mg) as an oil.

I.R. (CH$_2$Cl$_2$): 1760, 1720, 1385 cm$^{-1}$.

N.M.R. (CDCl$_3$)δ: 2.10 (s, 3H), 2.25 (s, 3H), 2.43 (m, 2H), 4.38 (ddd, J=3, 6.5 Hz, 1H), 4.8–5.3 (m, 2H), 5.08 (d, J=3 Hz, 1H), 5.33 (s, 2H), 5.56 (m, 1H).

EXAMPLE 2

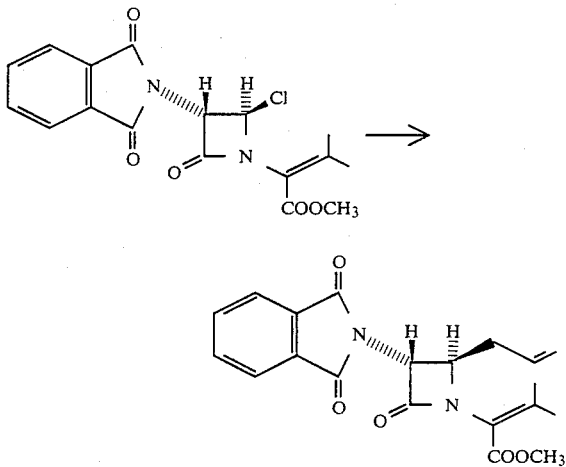

A mixture of methyl 2-[(3S,4R)-4-chloro-3-phthalimido-2-oxoazetidin-1-yl]-3-methyl-2-butenoate (3.55 g) and allyltrimethylsilane (2.26 ml) in methylene chloride (25 ml) was cooled to −78° C., and silver tetrafluoroborate (2.29 g) was added. The mixture was stirred for 2 hours during which time the temperature was gradually raised to 0° C., and the stirring was continued for another 3.5 hours. Saturated aqueous sodium chloride (10 ml) was added to the reaction mixture and the pH value of the aqueous layer was adjusted to pH 7 by adding saturated aqueous sodium bicarbonate. After stirring for 20 minutes at 0° C., the precipitate was filtered off through a pad of Celite and the filtrate was separated into the organic layer and the aqueous layer. The organic layer was washed with brine, dried over magnesium sulfate and evaporated to leave an oil (4.0 g), which was chromatographed on silica gel (50 g) eluting with a mixture of benzene and acetone (10:1) to give methyl 2-[(3R,4R)-4-allyl-3-phthalimido-2-oxoazetidin-1-yl]-3-methyl-2-butenoate (2.74 g) as an oil.

I.R. (CH$_2$Cl$_2$) 1770 (shoulder), 1760, 1720 cm$^{-1}$.

N.M.R. (CDCl$_3$)δ: 2.11 (s, 3H), 2.26 (s, 3H), 2.4–2.6 (m, 2H), 4.40 (m, 1H), 5.0–5.3 (m, 3H), 5.70 (m, 1H).

EXAMPLE 3

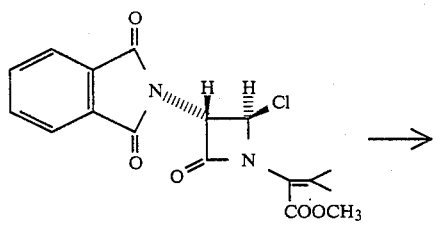

-continued

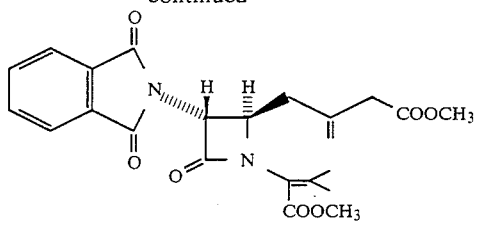

Silver tetrafluoroborate (323 mg) was added to a stirred mixture of methyl 2-[(3S,4R)-4-chloro-2-oxo-3-phthalimidoazetidin-1-yl]-3-methylbut-2-enoate (500 mg) and methyl 3-(trimethylsilylmethyl)-but-3-enoate (460 mg) in dichloromethane (2.5 ml) at −78° C. under a nitrogen atmosphere. The stirring mixture was gradually allowed to warm to 0° C. during one hour and kept at 0° C. for 1.5 hours. A saturated aqueous sodium chloride (2 ml) was added and the heterogeneous mixture was brought to pH 7 with a saturated aqueous sodium bicarbonate. After stirring for 15 minutes, the mixture was diluted with ethyl acetate and filtered through a pad of Celite. The organic layer was separated, washed with brine, dried over magnesium sulfate, and evaporated. The residue was chromatographed on silica gel (10 g) eluting with a mixture of benzene and acetone (5:1). Further purification on a silica gel (10 g) eluting with 10–20% ethyl acetate in dichloromethane) afforded methyl 2-[(3R,4R)-4-[2-(methoxycarbonylmethyl)allyl]-2-oxo-3-phthalimidoazetidin-1-yl]-3-methylbut-2-enoate (483 mg) as an oil.

IR (CH$_2$Cl$_2$): 1780 (sh), 1765, 1730 (sh), 1725 cm$^{-1}$.

NMR (CDCl$_3$)δ: 1.13 (3H, s), 1.27 (3H, s), 2.56 (2H, m), 3.01 (2H, s), 3.62 (3H, s), 3.83 (3H, s), 4.56 (ddd, J=3,6,8 Hz, 1H), 4.96 (2H, br s), 5.10 (d, J=3 Hz, 1H), 7.80 (4H, m).

EXAMPLE 4

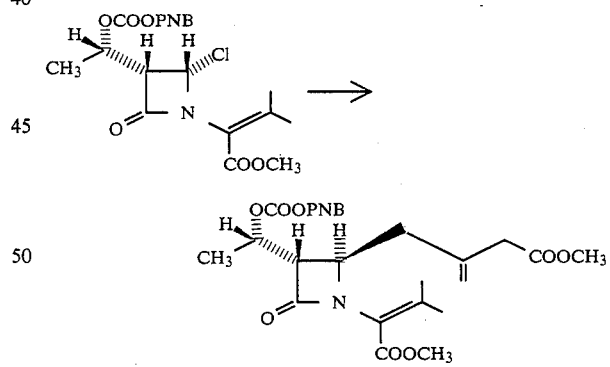

(The symbol of "PNB" means a p-nitrobenzyl group.)

To a solution of methyl 2-[(3S,4S)-4-chloro-3-{(1S)-1-(p-nitrobenzyloxycarbonyloxy)ethyl}-2-oxoazetidin-1-yl]-3-methylbut-2-enoate (222 mg) and methyl 3-(trimethylsilylmethyl)but-3-enoate (190 mg) in dichloromethane (1.7 ml) was added silver tetrafluoroborate (146 mg) at −72° C. under a nitrogen atmosphere. The stirring mixture was gradually allowed to warm to 0° C. during one hour and kept at the same temperature for 30 minutes. The mixture was diluted with ethyl acetate (5 ml). A saturated aqueous sodium chloride (3 ml) was added and the mixture was neutralized with a saturated aqueous sodium bicarbonate. The resultant mixture was filtered through Celite and the solid was washed with ethyl acetate. The organic layer was separated, washed with brine, dried over magnesium sulfate and evaporated. The residue was chromatographed on silica gel (8 g) eluting with 5-10% ethyl acetate in dichloromethane to give an oil (220 mg). Further purification on a silica gel column chromatography (15 g) eluting with 10 to 40% ethyl acetate in hexane afforded methyl 2-[(3S,4R)-4-{2-(methoxycarbonylmethyl)allyl}-3-{(1S)-1-(p-nitrobenzyloxycarbonyloxy)ethyl}-2-oxoazetidin-1-yl]-3-methylbut-2-enoate (190 mg).

IR (CH$_2$Cl$_2$): 1750, 1720 (sh), 1525, 1350 cm$^{-1}$.

NMR (CDCl$_3$)δ: 1.50 (3H, J=6.5 Hz, d), 1.96 (3H, s), 2.20 (3H, s), 2.3–2.7 (2H, m), 3.04 (2H, s), 3.18 (1H, dd, J=2.5, 4.5 Hz), 3.68 (3H, s), 3.74 (3H, s), 4.08 (1H, ddd, J=2.5, 6, 8 Hz), 4.96 (2H, s), 5.14 (1H, dd, J=4.5, 6.5 Hz), 5.25 (2H, s), 7.54 (2H, d, J=10 Hz), 8.18 (2H, d, J=10 Hz).

EXAMPLE 5

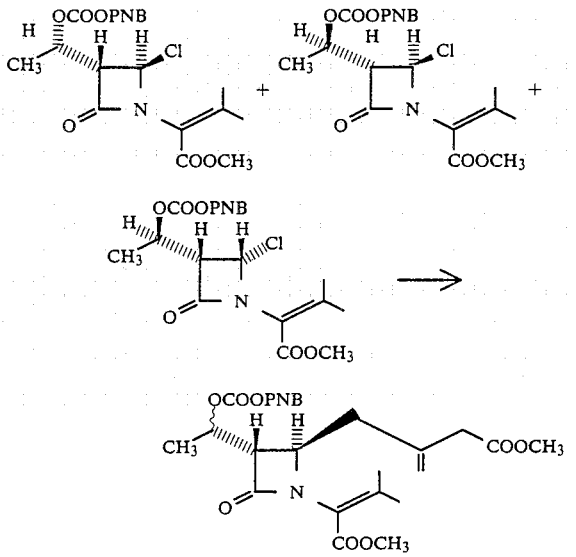

To a solution of a mixture (5:3:2) of methyl 2-[(3S,4R)-4-chloro-3-{(1S)-1-(p-nitrobenzyloxycarbonyloxy)-ethyl}-2-oxoazetidin-1-yl]-3-methylbut-2-enoate[(1S,3s)transisomer] and its (1R,3S-trans)-isomer and (1R,3S,cis)-isomer (191 mg), and methyl 3-(trimethylsilylmethyl)-but-3-enoate (162 mg) in dichloromethane (1.5 ml) was added silver tetrafluoroborate (127 mg) at −78° C. under a nitrogen atmosphere. The stirring mixture was gradually allowed to warm to 0° C. during one hour and kept at the same temperature for 1.5 hours. A saturated aqueous solution of sodium chloride (2 ml) and ethyl acetate (5 ml) were added and the mixture was neutralized with a saturated aqueous solution of sodium bicarbonate. After further dilution with ethyl acetate (15 ml), the mixture was filtered through Celite. The organic layer was separated, washed with brine, dried over magnesium sulfate and evaporated. The residue was chromatographed on silica gel (8 g) eluting with 1-5% acetone in dichloromethane to give an oil (141 mg). Further purification on a silica gel column chromatography (8 g) eluting with 10 to 30% ethyl acetate in hexane afforded a mixture (1:1) of methyl 2-[(3S,4R)-4-{2-(methoxycarbonylmethyl)allyl}-3-{(1RS)-1-(p-nitrobenzyloxycarbonyloxy)ethyl}-2-oxoazetidin-1-yl]-3-methylbut-2-enoate (131 mg).

IR (CH$_2$Cl$_2$): 1750, 1720 (sh), 1525, 1350 cm$^{-1}$.

NMR (acetone-d$_6$) δ: 1.42 (1.5H, d, J=7 Hz), 1.46 (1.5H, d, J=7 Hz), 1.94 (3H, s), 2.14 (3H, s), 2.4–2.6 (2H, m), 3.07 (2H, s), 3.14 (0.5H, dd, J=3, 7 Hz), 3.24 (0.5H, dd, J=3, 5 Hz), 3.62 (3H, s), 3.72 (3H, s), 4.14 (1H, m; t, J=2 Hz upon irradiation at 2.5 ppm), 4.9–5.1 (2H, m), 5.0–5.3 (1H, m), 5.33 (2H, s), 7.69 (2H, brd, J=9 Hz), 8.24 (2H, d, J=9 Hz).

EXAMPLE 6

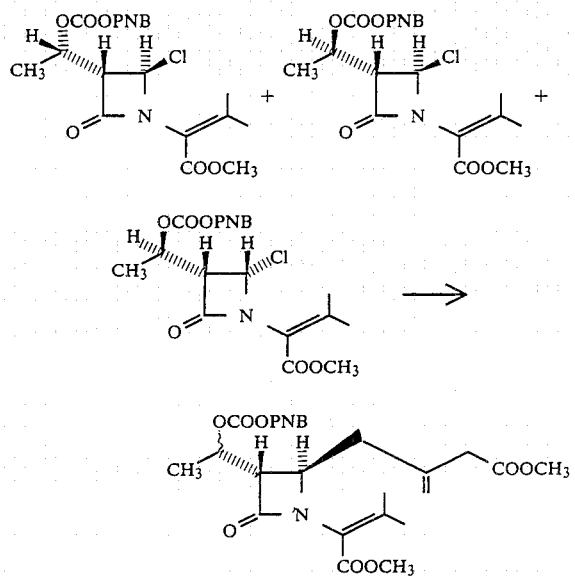

In a similar manner to that described in Example 5, a mixture (5:6:4) of methyl 2-[(3S,4R)-4-chloro-3-{(1S)-1-(p-nitrobenzyloxycarbonyloxy)ethyl}-2-oxoazetidin-1-yl]-3-methylbut-2-enoate[(1S,3S-trans)-isomer], (1R,3S-trans)-isomer and (1R,3S-cis)-isomer (270 mg) afforded a mixture (2:1) of methyl 2-[(3S,4R)-4-{2-(methoxycarbonylmethyl)allyl}-3-{(1RS)-1-(p-nitrobenzyloxycarbonyloxy)ethyl}-2-oxoazetidin-1-yl]-3-methylbut-2-enoate (193 mg).

NMR (acetone-d$_6$)δ: 1.43 (2H, d, J=6.5 Hz), 1.47 (1H, d, J=6.5 Hz), 1.95 (3H, s), 2.15 (3H, s), 2.4–2.6 (2H, m), 3.08 (2H, s), 3.17 ($\frac{2}{3}$H, dd, J=3,7 Hz), 3.26 ($\frac{1}{3}$H, dd, J=3,5 Hz), 3.63 (3H, s), 3.73 (3H, s), 4.15 (1H, m;t, J=2 Hz upon irradiation at 2.5 ppm), 4.9–5.1 (2H, m), 5.13 (~$\frac{2}{3}$H, quintet, J=7 Hz), ~5.1 (~$\frac{1}{3}$H, m), 5.34 (2H, s), 7.67 (2H, br d, J=9 Hz), 8.24 (2H, d, J=9 Hz).

EXAMPLE 7

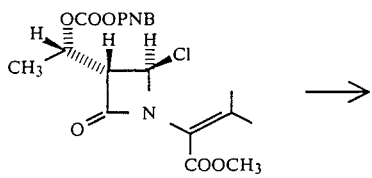

-continued

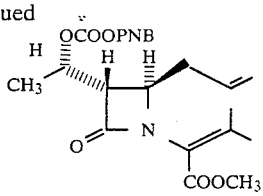

To a solution of methyl 2-[(3S,4R)-4-chloro-3-{(1S)-1-(p-nitrobenzyloxycarbonyloxy)ethyl}-2-oxoazetidin-1-yl]-3-methylbut-2-enoate (180 mg) and allyltrimethylsilane (0.12 ml) in dichloromethane (2 ml) was added silver tetrafluoroborate (240 mg) at −78° C. under a nitrogen atmosphere. The stirring mixture was allowed to warm to 0° C. during 45 minutes and kept at the same temperature for one hour. The mixture was diluted with ethyl acetate (10 ml) and a saturated aqueous sodium chloride was added. The mixture was neutralized with a saturated aqueous sodium bicarbonate, diluted with additional ethyl acetate (20 ml) and filtered through a pad of cellurose powder. The organic layer was separated, washed with brine, dried over magnesium sulfate and evaporated. The residue was chromatographed on silica gel (11 g) eluting with 3–30% ethyl acetate in dichloromethane to give methyl 3-methyl-2-[(3S,4R)-3-{(1S)-1-(p-nitrobenzyloxycarbonyloxy)ethyl}-2-oxo-4-allylazetidin-1-yl]but-2-enoate (47 mg).

IR (CH$_2$Cl$_2$): 1750, 1725, 1525, 1350 cm$^{-1}$.

NMR (CDCl$_3$) δ: 1.49 (3H, d, J=7 Hz), 1.95 (3H, s), 2.19 (3H, s), 2.1–2.6 (2H, m), 3.17 (1H, dd, J=2.5, 5 Hz), 3.73 (3H, s), 3.90 (1H, ddd, J=2.5,6,8 Hz), 4.9–5.3 (3H, m), 5.24 (2H, s), 5.5–5.9 (1H, m), 7.51 (2H, d, J=9 Hz), 8.18 (2H, d, J=9 Hz).

EXAMPLE 8

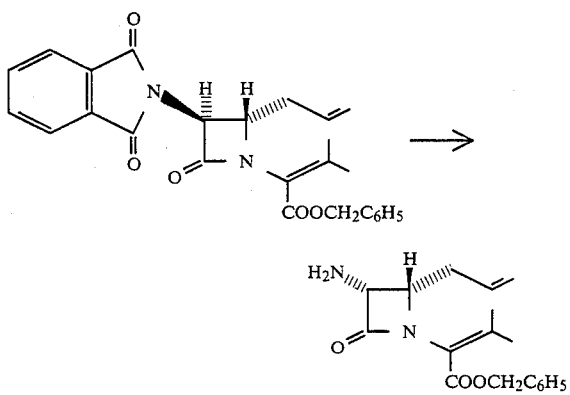

To a solution of benzyl 2-[(3S,4S)-4-allyl-3-phthalimido-2-oxo-azetidin-1-yl]-3-methyl-2-butenoate (340 mg) in a mixture of methylene chloride (5 ml) and methanol (2.5 ml) was added N,N-dimethyl-1,3-propanediamine (0.21 ml) and the mixture was stirred at room temperature for 25 hours. After removal of the solvent by evaporation, the residue was dissolved in ethyl acetate and washed with water. Drying over magnesium sulfate and evaporation gave an oil, which was chromatographed on silica gel (3 g) eluting with a mixture of methylene chloride and acetone (6:1) to give benzyl 2-[(4S)-4-allyl-3-amino-2-oxoazetidin-1-yl]-3-methyl-2-butenoate (155 mg) as an oil.

I.R. (CH$_2$Cl$_2$): 1750, 1710 cm$^{-1}$.

N.M.R. (CDCl$_3$) δ: 1.66 (broad s, 2H), 1.94 (s, 3H), 2.22 (s, 3H), 2.34 (m, 2H), 3.5–3.8 (m, 2H), 4.9–5.3 (m, 4H), 5.62 (m, 1H).

EXAMPLE 9

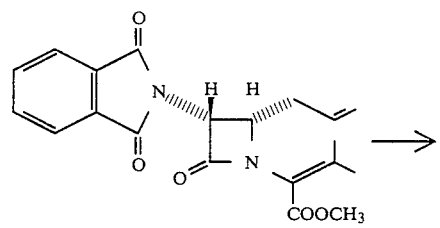

To a solution of methyl 2-[(3R,4R)-4-allyl-3-phthalimido-2-oxoazetidin-1-yl]-3-methyl-2-butenoate (2.64 g) in a mixture of methylene chloride (20 ml) and methanol (10 ml) was added N,N-dimethyl-1,3-propanediamine (1.98 ml) and the mixture was left in a refrigerator for 3 days and at room temperature for 24 hours. The reaction mixture was evaporated and the residue was dissolved in ethyl acetate (50 ml), washed with water, dried over magnesium sulfate and evaporated to give an oil, which was chromatographed on silica gel eluting with a mixture of methylene chloride and acetone (6-5:1) to give methyl 2-[(4R)-3-amino-4-allyl-2-oxoazetidin-1-yl]-3-methyl-2-butenoate (873 mg) as an oil.

IR (CH$_2$Cl$_2$): 1755, 1720 cm$^{-1}$.

EXAMPLE 10

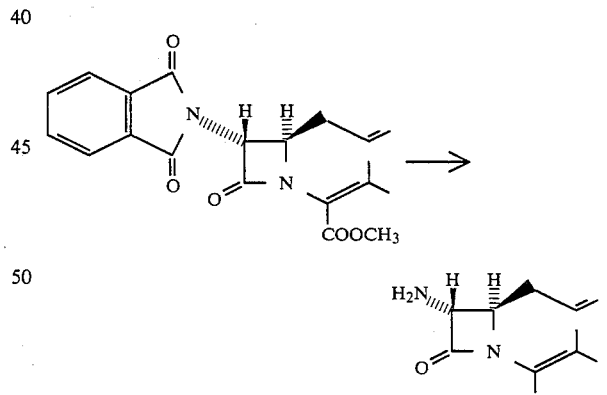

To a solution of methyl 2-[(3R,4R)-4-allyl-3-phthalimido-2-oxoazetidin-1-yl]-3-methylbut-2-enoate (6.78 g) in a mixture of methylene chloride (46 ml) and methanol (23 ml) was added N,N-dimethyl-1,3-propanediamine (6.25 ml) at 0° C. and the mixture was left at room temperature for 5 days. The reaction mixture was evaporated and the residue was chromatographed on silica gel eluting with a mixture of methylene chloride and ethyl acetate (10:1-5) to give methyl 2-[(3R,4R)-3-amino-4-allyl-2-oxoazetidin-1-yl]-3-methylbut-2-enoate (3.70 g) as an oil.

IR (CH$_2$Cl$_2$): 1755, 1720 cm$^{-1}$.

NMR (CD₃COCD₃) δ: 1.92 (3H, s), 1.15 (3H, s), 2.45 (broad t, 2H, J=6.5 Hz), 3.73 (3H, s), 4.13 (d and t, 1H, J=6.5 Hz, 2.5 Hz), 4.58 (1H, d, J=2.5 Hz), 4.9–5.2 (2H, m), 5.5–6.0 (1H, m).

EXAMPLE 11

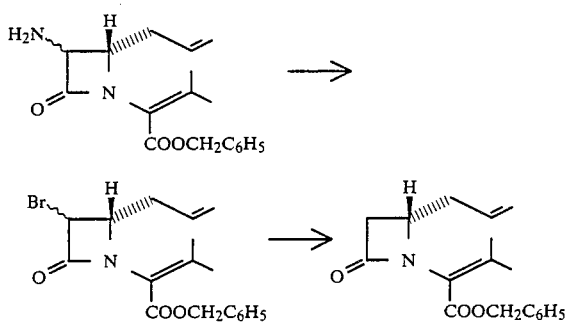

A solution of benzyl 2-[(4S)-4-allyl-3-amino-2-oxoazetidin-1-yl]-3-methyl-2-butenoate (175 mg) in methylene chloride (6 ml) was cooled to 0° C. and triethylamine hydrobromide (404 mg), isopentylnitrite (90 μl) and p-toluenesulfonic acid hydrate (190 mg) were added. After stirring for 30 minutes at the same temperature, the reaction mixture was diluted with ethyl acetate (30 ml) and washed successively with dilute sodium bicarbonate, water and brine. Drying ove magnesium sulfate and evaporation left an oil of benzyl 2-[(4S)-4-allyl-3-bromo-2-oxoazetidin-1-yl]-3-methyl-2-butenoate.

This oil was dissolved in methylene chloride (2 ml) and cooled to 15° C. To this cooled solution were added acetic acid (0.2 ml) and zinc powder (300 mg), and the mixture was stirred for 30 minutes at the same temperature. The reaction mixture was diluted with ethyl acetate (30 ml) and filtered by the aid of Celite. The filtrate was washed successively with dilute aqueous sodium bicarbonate, water and brine. Drying over magnesium sulfate and evaporation gave an oil, which was purified by preparative thin layer chromatography (silica gel plate, developping solvent: 10% ethyl acetate in methylene chloride) to give benzyl 2-[(4S)-4-allyl-2-oxoazetidin-1-yl]-3-methyl-2-butenoate (40 mg) as an oil.

I.R. (CH₂Cl₂): 1750, 1720 cm⁻¹.

N.M.R. (CDCl₃) δ: 1.94 (s, 3H), 1.18 (s, 3H), 2.30 (m, 2H), 2.77 (AB part of an ABX pattern, $J_{AB}$=15 Hz, $J_{AX}$=5 Hz, $J_{BX}$=2 Hz, 2H), 3.90 (m, 1H), 4.92 (m, 1H), 5.04 (m, 1H), 5.16 (ABq, J=12 Hz), 5.56 (m, 1H).

EXAMPLE 12

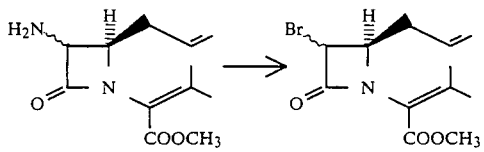

A mixture of methyl 2-[(4R)-3-amino-4-allyl-2-oxoazetidin-1-yl]-3-methyl-2-butenoate (815 mg), triethylamine hydrobromide (2.50 g) and p-toluenesulfonic acid hydrate (1.17 g) in methylene chloride (30 ml) was cooled to 0° C. and isopentyl nitrite (0.54 ml) was added. After stirring for 20 minutes at the same temperature, the mixture was concentrated and the residue was dissolved in ethyl acetate (50 ml). The solution was washed successively with 10% aqueous sodium bisulfite, water and brine, dried over magnesium sulfate and evaporated to give methyl 2-[(4R)-3-bromo-4-allyl-2-oxoazetidin-1-yl]-3-methyl-2-butenoate (840 mg) as a crude oil.

I.R. (CH₂Cl₂): 1770, 1725 cm⁻¹.

EXAMPLE 13

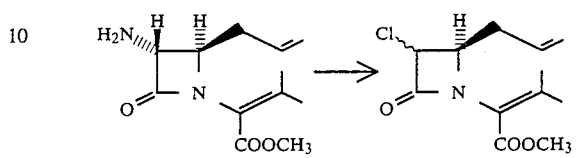

A solution of methyl 2-[(3R,4R)-3-amino-4-allyl-2-oxoazetidin-1-yl]-3-methylbut-2-enoate (1.0 g) in methylene chloride (10 ml) was cooled to −65° C., and isopentylnitrite (1.01 ml) and a solution of hydrogen chloride (524 mg) in ethyl ether (8 ml) were added. The mixture was allowed to warm to 0° C. during a period of 45 minutes and stirred for one hour and half at 0° C. The reaction mixture was poured into a mixture of ethyl acetate (40 ml) and dilute aqueous sodium bicarbonate. The organic layer was separated and washed with brine, dried ove magnesium sulfate and evaporated to leave an oil, which was chromatographed on silica gel (15 g) eluting with a mixture of methylene chloride and acetone (100:2–100:5) to give methyl 2-[(4R)-4-allyl-3-chloro-2-oxoazetidin-1-yl]-3-methylbut-2-enoate (658 mg) as an oil.

IR (CH₂Cl₂): 1775, 1720 cm⁻¹.

NMR (CDCl₃) δ: 2.00 (3H, s), 2.24 (3H, s), 2.2–2.7 (2H, m), 3.78 (a pair of singlets, 3H), 4.0–4.5 (2H, m), 4.9–5.3 (2H, m), 5.5–5.9 (1H, m).

EXAMPLE 14

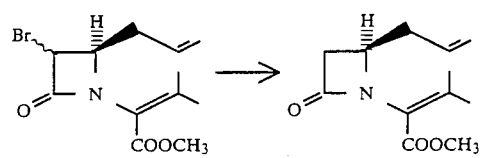

Methyl 2-[(4R)-3-bromo-4-allyl-2-oxoazetidin-1-yl]-3-methyl-2-butenoate (840 mg) was dissolved in methylene chloride (6 ml) and cooled to 5° C. To this cooled solution were added acetic acid (0.5 ml) and zinc powder (0.60 g), and the mixture was allowed to warm to room temperature. After stirring for 30 minutes, the reaction mixture was diluted with ethyl acetate (6 ml) and filtered through a pad of Celite. The filtrate was further diluted with ethyl acetate (50 ml) and washed successively with water, dilute sodium bicarbonate and brine. Drying over magnesium sulfate and evaporation left an oil, which was chromatographed on silica gel (20 g) eluting with a mixture of benzene and acetone (5:1) to give methyl 2-[(4R)-4-allyl-2-oxoazetidin-1-yl]-3-methyl-2-butenoate (174 mg) as an oil.

IR (CH₂Cl₂): 1745, 1720 cm⁻¹.

NMR (CDCl₃) δ: 1.96 (3H, s), 2.18 (3H, s), 2.2–2.5 (2H, m), 2.88 (AB part of a ABA system, $J_{AB}$=16 Hz, $J_{AX}$=2.5 Hz, $J_{BX}$=5 Hz, 2H), 2.75 (3H, s), 3.96 (1H, m), 5.00 (1H, m), 5.14 (1H, m), 5.72 (1H, m).

EXAMPLE 15

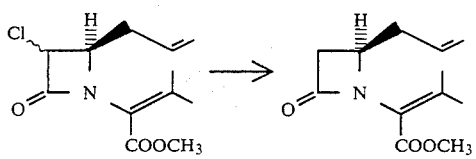

A mixture of methyl 2-[(4R)-4-allyl-3-chloro-2-oxoazetidin-1-yl]-3-methylbut-2-enoate (600 mg), tributyltinhydride (0.97 ml) and 2,2'-azobis-(2-methylpropionitrile) (40 mg) in benzene (16 ml) was refluxed for 1.5 hours. The reaction mixture was poured into a mixture of ethyl acetate (30 ml) and dilute aqueous sodium bicarbonate. The organic layer was separated, and washed with brine, dried over magnesium sulfate and evaporated in vacuo. The oily residue was chromatographed on silica gel (10 g) eluting with a mixture of hexane and ethyl acetate (10:1-10:3) to give methyl 2-[(4R)-4-allyl-2-oxoazetidin-1-yl]-3-methylbut-2-enoate (452 mg) as an oil.

IR (CH$_2$Cl$_2$): 1750, 1720 cm$^{-1}$.

NMR (CDCl$_3$) δ: 1.97 (3H, s), 2.20 (3H, s), 2.3–2.5 (2H, m), 2.63 (dd, 1H, J=3 Hz, 16 Hz), 3.11 (dd, 1H, J=5 Hz, 16 Hz), 3.77 (3H, s), 3.7–4.2 (1H, m), 4.8–5.3 (2H, m), 5.4–6.1 (1H, m).

EXAMPLE 16

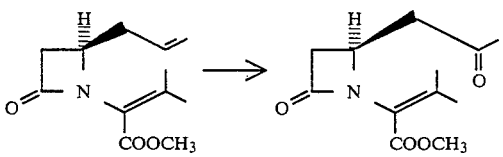

A mixture of methyl 2-[(4R)-4-allyl-2-oxoazetidin-1-yl]-3-methylbut-2-enoate (100 mg), palladium chloride (16 mg) and cuprous chloride (44 mg) in a mixture of dimethylformamide (1 ml) and water (0.12 ml) was stirred under an oxygen atmosphere for 3.5 hours. The reaction mixture was diluted with ethyl acetate (20 ml), and filtered. The filtrate was washed with water and brine. The combined aqueous layer was extracted with ethyl acetate (10 ml×2) and the extract was washed with brine. The organic layers were combined, and dried over magnesium sulfate, and evaporated in vacuo. The oily residue was chromatographed on silica gel (1 g) eluting with methylene chloride and acetone (100:2–100:5) to give methyl 2-[(4R)-4-(2-oxopropyl)-2-oxoazetidin-1-yl]-3-methylbut-2-enoate (89 mg as an oil.

IR (CH$_2$Cl$_2$): 1745, 1710 cm$^{-1}$.

NMR (CDCl$_3$) δ: 1.92 (3H, s), 2.13 (3H, s), 2.18 (3H, s), 2.4–3.4 (4H, m), 3.76 (3H, s), 4.2–4.5 (1H, m).

EXAMPLE 17

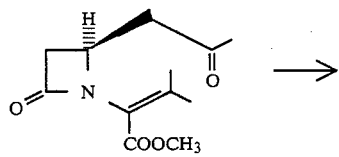

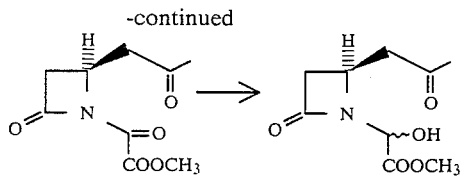

Ozone was bubbled through a solution of methyl 2-[(4R)-4-(2-oxopropyl)-2-oxoazetidin-1-yl]-3-methylbut-2-enoate (580 mg) in ethyl acetate (10 ml) at −65° C. until the color of the mixture turned into blue. The nitrogen was bubbled through the mixture at the same temperature for 15 minutes. The reaction mixture was diluted with ethyl acetate (30 ml) and the solution was treated with brine which contained sodium bicarbonate (1.26 g). The separated water layer was extracted with ethyl acetate (20 ml). The organic layers were combined and dried over magnesium sulfate and evaporated in vacuo to give methyl [(4R)-4-(2-oxopropyl)-2-oxoazetidin-1-yl]-glyoxylate. This product was diluted with methylene chloride (5 ml) and cooled to 0° C., and then zinc powder (1.06 g) and acetic acid (0.5 ml) were added. After stirring for 2 hours at room temperature, zinc powder (580 mg) and acetic acid (0.25 ml) were added and the mixture was stirred for 2 hours at room temperature. The mixture was filtered and the filtrate was evaporated in vacuo. The residue was diluted with methylene chloride, and washed with brine, and the water layer was extracted with ethyl acetate two times. The organic layers were combined, dried over magnesium sulfate and evaporated in vacuo to give methyl 2-hydroxy-2-[(4R)-4-(2-oxopropyl)-2-oxoazetidin-1-yl]acetate (300 mg) as an oil.

IR (CH$_2$Cl$_2$): 1760, 1710 cm$^{-1}$.

NMR (CDCl$_3$) δ: 2.19 (3H, s), 2.2–3.4 (4H, m), 3.80 (3/4H, s), 3.88 (9/4H, s), 4.04–4.4 (1H, m).

EXAMPLE 18

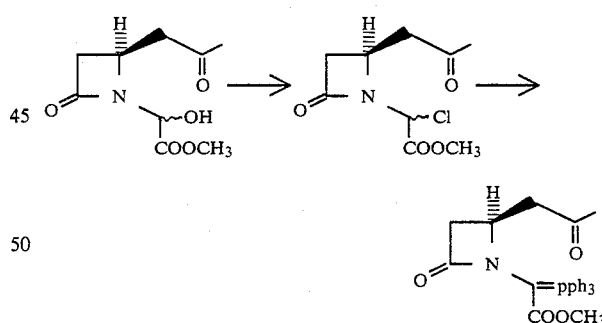

A solution of methyl 2-hydroxy-2-[(4R)-4-(2-oxopropyl)-2-oxoazetidin-1-yl]acetate (268 mg) in tetrahydrofuran (5 ml) was cooled to −40° C. 2,6-Lutidine (0.287 ml) and thionyl chloride (0.18 ml) were added, and the mixture was stirred for one hour, during which time the temperature was allowed to warm to 0° C. The mixture was filtered and the filtrate was concentrated in vacuo to give methyl 2-chloro-2-[(4R)-4-(2-oxopropyl)-2-oxoazetidin-1-yl]acetate. This product was diluted with benzene and concentrated in vacuo again. The residue was diluted with tetrahydrofuran (5 ml), and 2,6-lutidine (0.287 ml) and triphenylphosphine (650 mg) were added at 0° C. The mixture was stirred at room temperature for 15 hours, and filtered. The filtrate was concentrated in vacuo and the residue was chromatographed on silica gel (10 g) eluting with a mixture of ethyl acetate and acetone (10:1-10:5) to give methyl 2-[(4R)-4-(2-oxopropyl)-2-oxoazetidin-1-yl]-2-(triphenylphosphoranylidene)acetate (350 mg) as an oil.

IR (CH$_2$Cl$_2$): 1735, 1705 cm$^{-1}$.

EXAMPLE 19

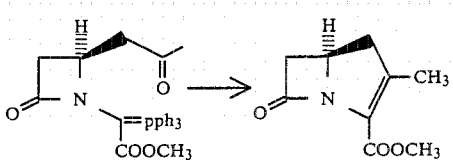

A solution of methyl 2-[(4R)-4-(2-oxopropyl)-2-oxoazetidin-1-yl]-2-(triphenylphospharanylidene)acetate (100 mg) in toluene (3 ml) was stirred at 110° C. for 2 hours. The mixture was concentrated in vacuo and the residue was chromatographed on silica gel (3 g) eluting with a mixture of benzene and acetone (10:1) to give methyl (5R)-3-methyl-7-oxo-1-azabicyclo-[3,2,0]-hept-2-en-2-carboxylate (17 mg).

IR (CHCl$_3$): 1770, 1720 cm$^{-1}$.

NMR (Benzene-d$_6$) δ: 1.7-2.0 (2H, m), 1.85 (3H, s), 2.12 (dd, 1H, J=3 Hz, 15 Hz), 2.66 (dd, 1H, J=7 Hz, 15 Hz), 3.1-3.5 (1H, m), 3.48 (3H, s).

EXAMPLE 20

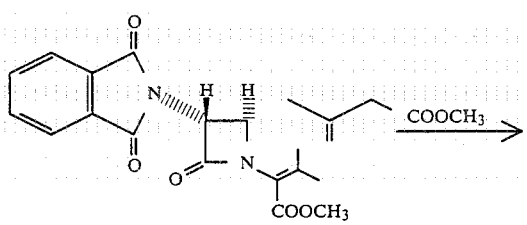

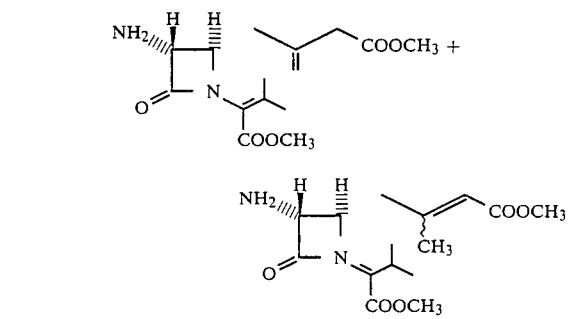

A mixture of methyl 2-[(3R,4R)-4-{2-(methoxycarbonylmethyl)allyl}-2-oxo-3-phthalimidoazetidin-1-yl]-3-methylbut-2-enoate (103 mg) and N,N-dimethyl-1,3-propanediamine (60 μl) in a mixture of dichloromethane (0.7 ml) and methanol (0.7 ml) was stirred at room temperature for 6.5 days. The resultant solution was concentrated in vacuo and the residue was chromatographed on silica gel (1.5 g) eluting with dichloromethane, 30% ethyl acetate in dichloromethane, and 5% methanol in dichloromethane to give an oil (55 mg). Further purification on a silica gel plate (developing solvent: 7% methanol in dichloromethane) afforded a mixture (10:7) of methyl 2-[(3R,4R)-3-amino-4-{2-(methoxycarbonylmethyl)allyl}-2-oxoazetidin-1-yl]-3-methylbut-2-enoate and methyl 2-[(3R,4R)-3-amino-4-{3-(methoxycarbonyl)-2-methylally}-2-oxoazetidin-1-yl]-3-methylbut-2-enoate (47 mg) as an oil.

IR (CH$_2$Cl$_2$): 1750, 1735 (sh), 1720 cm$^{-1}$.

NMR (CDCl$_3$) δ: 5.05 (m, 20/17H), 5.75 (br s 7/17H).

EXAMPLE 21

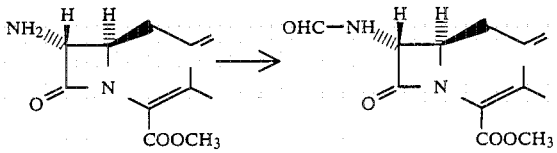

To a solution of methyl 2-[(3R,4R)-3-amino-4-allyl-2-oxoazetidin-1-yl]-3-methylbut-2-enoate (500 mg) in dichloromethane (5 ml) was added acetic formic anhydride (0.34 ml) at 0°. After stirring at the same temperature for one hour, the mixture was diluted with ethyl acetate (35 ml) and washed with a dilute aqueous sodium bicarbonate. The aqueous layer was saturated with sodium chloride and extracted with dichloromethane. The extracts were combined, washed with a saturated aqueous sodium chloride, dried over magnesium sulfate and evaporated. The residue was chromatographed on silica gel (2.5 g) eluting with 10-30% acetone in dichloromethane afforded methyl 2-[(3R,4R)-3-formamido-4-allyl-2-oxoazetidin-1-yl]-3-methylbut-2-enoate (485 mg).

IR (CH$_2$Cl$_2$): 3400, 1760, 1720 (sh), 1695 cm$^{-1}$.

NMR (CDCl$_3$) δ: 1.97 (s, 3H), 2.21 (s, 3H), 2.47 (t, J=7 Hz, 2H), 3.76 (s, 3H), 3.95 (dt, J=3, 7 Hz, 1H), 4.77 (dd, J=3, 7 Hz, 1H), 4.9-5.3 (m, 2H), 5.5-6.0 (m, 1H), 7.15 (brd, J=7 Hz, 1H), 8.19 (s, 1H).

Mass Spectrum: m/e 266 (M$^+$).

EXAMPLE 22

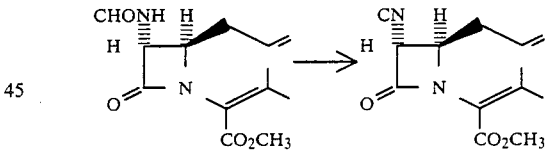

2,6-Lutidine (3.82 ml) and phosphorus oxychloride (1.37 ml) were added to a solution of methyl 2-[(3R,4R)-3-formamido-2-oxo-4-allylazetidin-1yl]-3-methylbut-2-enoate (970 mg) in dichloromethane (10 ml) at 0° C., and the mixture was stirred for three hours at 0° C. Then, the reaction mixture was poured into a mixture of ethyl acetate (100 ml) and brine (50 ml). The organic layer was washed with brine, dried over magnesium sulfate and evaporated in vacuo. The oily residue was chromategraphed on silica gel (15 g) eluting with a mixture of hexane and ethyl acetate (10:1-3:1) to give methyl 2-[(3R,4R)-3-isocyano-2-oxo-4-allylazetidin-1-yl]-3-methylbut-2-enoate (766 mg) as an oil.

I.R. (CH$_2$Cl$_2$): 2145, 1775, 1720 cm$^{-1}$.

N.M.R. (CDCl$_3$) δ: 1.96 (s, 3H), 2.24 (s, 3H) 2.3-2.6 (m, 2H), 3.80 (s, 3H), 4.20 (dt, 1H, J=2.5, 6.5 Hz), 4.98 (d, 1H, J=2.5 Hz), 5.0-5.3 (m, 2H, 5.5-6.0 (m, 1H).

Mass Spectrum: m/e 248 (M$^+$).

EXAMPLE 23

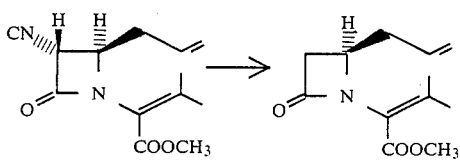

2,2′-Azobis(2-methylpropionitrile) (98 mg) and tributyltin hydride (0.95 ml) were added to a solution of methyl 2-[(3R,4R)-3-isocyano-2-oxo-4-allylazetidin-1-yl]-3-methylbut-2-enoate (740 mg) in benzene (15 ml), and the mixture was refluxed for 20 minutes. The reaction mixture was chromatographed on silica gel (15 g) eluting with a mixture of hexane and ethyl acetate (5:1–3:1) to give methyl 2-[(4R)-2-oxo-4-allylazetidin-1-yl]-3-methylbut-2-enoate (660 mg).

IR($CH_2Cl_2$): 1750, 1720 cm$^{-1}$.

NMR ($CDCl_3$) δ: 1.97 (s, 3H), 2.20 (s, 3H), 2.3–2.5 (m, 2H), 2.63 (dd, 1H, J=3, 16 Hz), 3.11 (dd, 1H, J=5, 16 Hz), 3.77 (s, 3H), 3.7–4.2 (m, 1H), 4.8–5.3 (m, 2H), 5.4–6.1 (m, 1H)

EXAMPLE 24

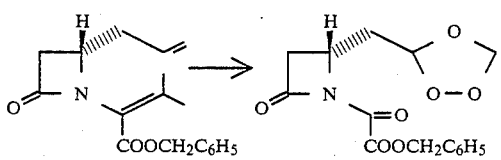

A solution of benzyl 2-[(4S)-4-allyl-2-oxoazetidin-1-yl]-3-methylbut-2-enoate (30 mg) in ethyl acetate (5 ml) was cooled to −78° C. and ozone was bubbled until a blue color appeared. After stirring for 15 minutes at the same temperature, the reaction mixture was purged with nitrogen, poured into dilute aqueous sodium bicarbonate and extracted with ethyl acetate. The extract was washed with water, dried over magnesium sulfate and evaporated to give benzyl [(4S)-4-{(1,2,4-trioxolan-3-yl)methyl}-2-oxoazetidin-1-yl]-glyoxylate (30 mg).

IR ($CH_2Cl_2$): 1805, 1750, 1700 cm$^{-1}$.

EXAMPLE 25

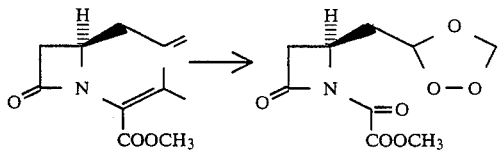

A stream of ozone was bubbled into a solution of methyl 3-methyl-2-[(4R)-2-oxo-4-allylazetidin-1-yl]-but-2-enoate (330 mg) in ethyl acetate (20 ml) at −78° C. until blue color of ozone appeared. The excess of ozone was removed by a stream of nitrogen and the resultant solution was poured into a solution of sodium bisulfite (1.6 g) and sodium sulfite (0.4 g) in dilute aqueous sodium chloride solution. The mixture was shaken and the organic layer was separated. The aqueous layer was extracted three times with dichloromethane. The combined extracts was dried over magnesium sulfate and evaporated to give methyl [(4R)-2-oxo-4-(1,2,4-trioxolan-3-yl-methyl)azetidin-1-yl]glyoxylate (354 mg) as an oil.

IR ($CH_2Cl_2$): 1810, 1755, 1705 cm$^{-1}$.

NMR ($CDCl_3$) δ: 1.9–2.3 (m, 1H), 2.70 (ddd, J=4, 8, 16 Hz, 1H), 3.06 (ddd, J=2.5, 4, 18 Hz, 1H), 3.42 (dd, J=6, 18 Hz, 1H), 3.96 (s, 3H), 4.2–4.6 (m, 1H), 5.15 (~t, J=2 Hz, 2H), 5.44 (m, 1H).

EXAMPLE 26

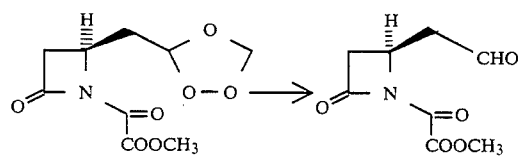

A solution of methyl [(4R)-2-oxo-4-(1,2,4-trioxolan-3-ylmethyl)azetidin-1-yl]glyoxylate (320 mg) and dimethyl sulfide (2 ml) in a mixture of dichloromethane (9 ml) and methanol (10 ml) was stirred at 5° C. for 6 hours and at room temperature for 15 hours. The mixture was then heated at 50° for 4 hours and evaporated to give methyl [(4R)-2-oxo-4-(2-oxoethyl)-azetidin-1-yl]glyoxylate.

IR ($CH_2Cl_2$): 1810, 1755, 1720 (sh), 1700 cm$^{-1}$.

EXAMPLE 27

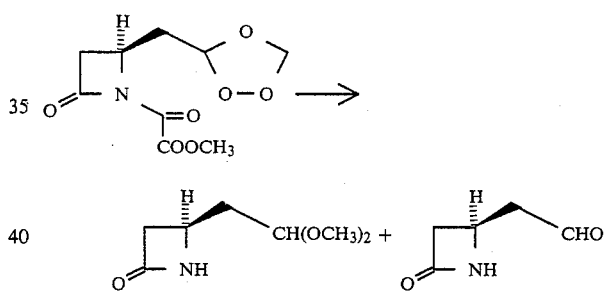

A solution of methyl [(4R)-2-oxo-4-(1,2,4-trioxolan-3-ylmethyl)azetidin-1-yl]glyoxylate (320 mg) and dimethyl sulfide (2 ml) in a mixture of methanol (10 ml) and dichloromethane (9 ml) was stirred at 5° C. for six hours, at room temperature for 15 hours, and at 55° C. for four hours. The resultant solution was concentrated and the residue was dissolved in a mixture of dimethyl sulfide (2 ml) and methanol (15 ml). Silica gel (100 mg) was added and the mixture was stirred at room temperature for four days, at 50° C. for eight hours, and at 60° C. for seven hours. After evaporation of the solvent, the residue was chromatographed on silica gel (7 g) eluting with 2–5% methanol in dichloromethane to give (4R)-4-(2,2-dimethoxyethyl)-2-oxo-azetidine (57 mg) as an impure oil and (4R)-4-(2-oxoethyl)-2-oxoazetidine (31 mg). Further purification of the impure oil on silica gel (4 g) eluting with 0.5–2% methanol in dichloromethane afforded the pure oil (31 mg) of the former compound.

IR ($CH_2Cl_2$): 3400, 1760 cm$^{-1}$.

NMR ($CDCl_3$) δ: 1.8–2.0 (m, 2H), 2.62 (ddd, J=1.5, 2.5, 15 Hz, 1H), 3.10 (ddd, J=2, 5 15 Hz, 1H), 3.37 (s, 6H), 3.6–3.8 (m, 1H), 4.43 (t, J=5.5 Hz, 1H), 6.42 (br s, 1H).

EXAMPLE 28

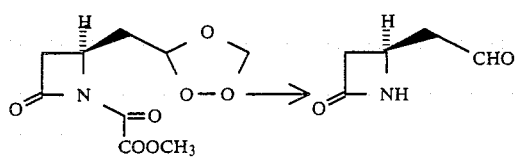

A solution of methyl [(4R)-2-oxo-4-(1,2,4-trioxolan-3-ylmethyl)azetidin-1-yl]glyoxylate (96 mg) and dimethyl sulfide (0.5 ml) in a mixture (1:1) of methanol and dichloromethane (8 ml) was stirred at room temperature for 21 hours and heated at 50° for eight hours. After removal of the solvent, the yellow residue was chromatographed on silica gel (1.5 g) eluting with 3-5% methanol in dichloromethane to give (4R)-4-(2-oxoethyl)-2-oxoazetidine (20 mg).

IR (CH$_2$Cl$_2$): 3400, 1760, 1720 cm$^{-1}$.

EXAMPLE 29

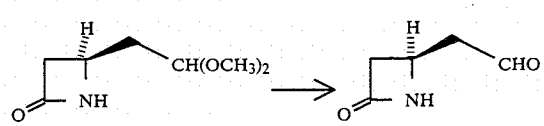

A solution of (4R)-4-(2,2-dimethoxyethyl)-2-oxoazetidine (30 mg) in 80% aqueous acetic acid (1.5 ml) was heated at 62° C. for 2.5 hours under a nitrogen atmosphere. After evaporation of the solvent in vacuo, the residue was chromatographed on silica gel (1.5 g) eluting with 1-3% methanol in dichloromethane to give (4R)-4-(2-oxoethyl)-2-oxoazetidine (5.3 mg).

IR (CH$_2$Cl$_2$): 3400, 1760, 1720 cm$^{-1}$.

NMR (CDCl$_3$) δ: 2.63 (dt, J=~1.5, 16 Hz, 1H), 2.84 (d, J=8 Hz, 1H), 3.20 (ddd, J=3, 6, 16 Hz, 1H), 3.44 (d, J=8 Hz, 1H), 4.0 (m, 1H), 6.2 (br s, 1H), 9.82 (s, 1H).

EXAMPLE 30

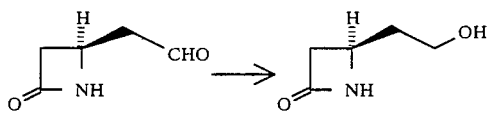

To a solution of (4R)-4-(2-oxoethyl)-2-oxoazetidine (30 mg) in methanol was added sodium borohydride (10 mg) at 0° C. The reaction mixture was stirred at the same temperature for 75 minutes and quenched by addition of acetic acid (three drops). After evaporation of the solvent in vacuo, the residue was chromatographed on silica gel (1.5 g) eluting with 1.5-3% methanol in dichloromethane to give (4R)-4-(2-hydroxyethyl)-2-oxoazetidine (20 mg) as a crystalline solid.

IR (CH$_2$Cl$_2$): 3590, 3390, 1755 cm$^{-1}$.

NMR (CDCl$_3$) δ: 1.7~2.0 (m, 2H), 2.62 (ddd, J=1.5, 3, 14 Hz, 1H), 2.96 (br s, 1H), 3.11 (ddd, J=2, 5, 14 Hz, 1H), 3.75 (t, J=5.5 Hz, 1H), ~3.75 (m, 1H), 6.76 (br s, 1H).

[α]$_D^{126}$= +19.6° (CHCl$_3$, C=0.189).

EXAMPLE 31

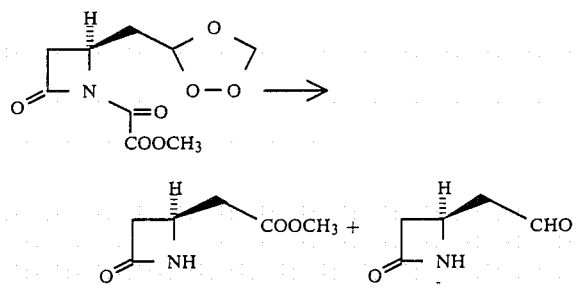

A solution of methyl [(4R)-2-oxo-4-(1,2,4-trioxolan-3-ylmethyl)azetidin-1-yl]glyoxylate (60 mg) in methanol (5 ml) was heated at 65°-70° for two hours. The yellowish solution was cooled to 0° C. and treated with a solution of diazomethane (excess) in diethyl ether. After removal of the solvent, the residue was chromatographed on silica gel (1.5 g) eluting with 20% acetone in dichloromethane to give methyl 2-[(2R)-4-oxoazetidin-2-yl]acetate (6 mg).

IR (CH$_2$Cl$_2$): 3390, 1760, 1730 cm$^{-1}$.

NMR (CDCl$_3$) δ: 2.5-2.8 (m, 3H), 3.16 (ddd, J=2.5, 6, 16 Hz, 1H), 3.74 (s, 3H), 3.8-4.1 (m, 1H), 6.3 (m, 1H).

(4R)-4-(2-Oxoethyl)-2-oxoazetidine (5 mg) was afforded from the subsequent fractions.

EXAMPLE 32

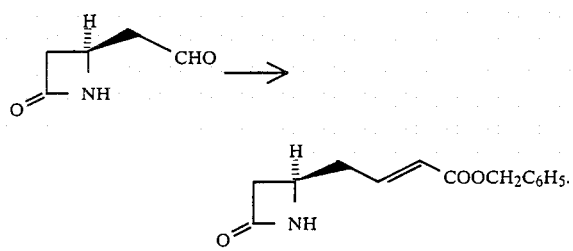

A mixture of (4R)-4-(2-oxoethyl)-2-oxoazetidine (20 mg) and benzyl triphenylphosporanylidene-acetate (80 mg) in dichloromethane (3 ml) was heated under refluxing for 80 minutes. After removal of the solvent, the residue was chromatographed on silica gel (2 g) eluting with 3% methanol in dichloromethane to give an oil (30 mg). Further purification on two silica gel plates (developing solvent: 4% methanol in dichloromethane) afforded crude product (16 mg) of benzyl 4-[(2R)-4-oxoazetidin-2-yl]but-2-enoate.

IR (CH$_2$Cl$_2$): 1765, 1720 cm$^{-1}$.

EXAMPLE 33

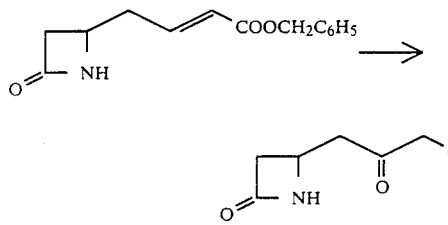

A mixture of benzyl 4-[(2RS)-4-oxoazetidin-2-yl]-but-2-enoate (167 mg), tert-butylhydroperoxide (0.3 ml), and sodium tetrachloropalladate (80 mg) in 67% aqueous acetic acid (2.7 ml) was heated at 50° C. for 8.5 hours. Additional tert-butylhydroperoxide (0.5 ml) and sodium tetrachloropalladate (40 mg) were added. The reaction mixture was stirred at room temperature for three days and heated at 50° C. for 14 hours. After evaporation of the solvent in vacuo, the residue was taken up into ethyl acetate (20 ml) and washed with dilute aqueous sodium chloride. Drying over magnesium sulfate and evaporation left an oil (200 mg), which was chromatographed on silica gel plate (developing solvent: 20% acetone in dichloromethane) afforded benzyl 3-oxo-4-[(2RS)-4-oxoazetidin-2-yl]butanoate (66 mg).

IR (CH$_2$Cl$_2$): 3400, 1760, 1715 cm$^{-1}$.

EXAMPLE 34

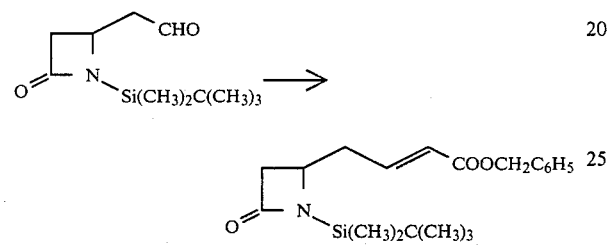

A mixture of (4RS)-1-(tert-butyl-dimethylsilyl)-4-(2-oxoethyl)-2-oxoazetidine (240 mg) and benzyl triphenylphosphoranylidene-acetate (521 mg) in dichloromethane (5 ml) was heated under refluxing for one hour. After removal of the solvent, the residue was chromatographed on silica gel (7 g) eluting with a mixture of dichloromethane and acetone (50:1) to give benzyl 4-[(2RS)-1-(tert-butyl-dimethylsilyl)-4-oxoazetidin-2-yl]but-2-enoate (373 mg) as an oil.

IR (CH$_2$Cl$_2$): 1765, 1720 CM$^{-1}$.

EXAMPLE 35

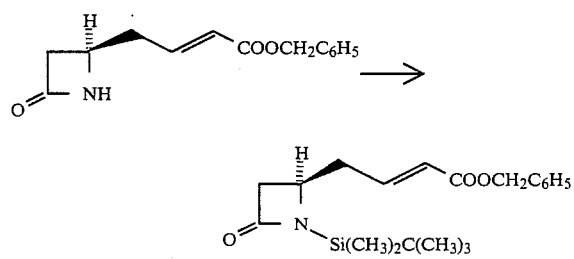

To a mixture of benzyl 4-[(2R)-4-oxoazetidin-2-yl]but-2-enoate (16 mg) and triethylamine (18 μl) in dimethylformamide (0.5 ml) was added tert-butyl-dimethylchlorosilane (15 mg) at 5° C. The mixture was stirred at the same temperature for one hour and at room temperature for 30 minutes. The resultant mixture was diluted with ethyl acetate (20 ml), washed with chilled dilute hydrochloric acid, a dilute aqueous sodium bicarbonate, and brine. Drying over magnesium sulfate and removal of the solvent left an oil (23 mg), which was chromatographed on a silica gel plate (developing solvent: 5% methanol in dichloromethane) to give benzyl 4-[(2R)-1-(tert-butyl-dimethylsilyl)-4-oxoazetidin-2-yl]but-2-enoate (13 mg).

IR (CH$_2$Cl$_2$): 1730, 1720 (sh) cm$^{-1}$.

NMR (CDCl$_3$) δ: 0.21 (s, 3H), 0.23 (s, 3H), 0.93 (s, 9H), 2.1-3.0 (m, 2H), 2.60 (dd, J=3, 16 Hz, 1H), 3.14 (dd, J=5, 16 Hz, 1H), 3.4-3.8 (m, 1H), 5.16 (s, 2H), 5.90 (dt, J=1, 16 Hz, 1H), 6.90 (dt, J=7, 16 Hz, 1H), 7.36 (s, 5H).

EXAMPLE 36

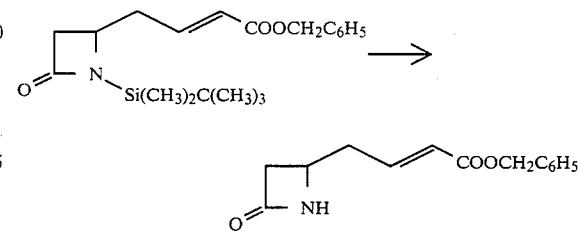

To a solution of benzyl 4-[(2RS)-1-(tert-butyl-dimethylsilyl)-4-oxoazetidin-2-yl]but-2-enoate (45 mg) in methanol was added 1N hydrochloric acid (0.1 ml) at 0°. After stirring at room temperature for 2.5 hours, the reaction mixture was neutralized to pH 7 with saturated aqueous sodium bicarbonate. The resultant solution was concentrated, taken up into ethyl acetate (15 ml), and washed in turn with water and brine. Drying over magnesium sulfate and removal of the solvent left an oil, which was chromatographed on a silica gel plate (developing solvent: 6% methanol in dichloromethane) to give benzyl 4-[(2RS)-4-oxoazetidin-2-yl]but-2-enoate (30 mg) as a crystalline solid.

IR (CH$_2$Cl$_2$): 3390, 1765, 1715, 1655 cm$^{-1}$.

NMR (CDCl$_3$) δ: 2.40-2.80 (m, 3H), 3.10 (ddd, J=3,5,15 Hz, 1H), 3.6-3.9 (m, 1H), 5.18 (s, 2H), 5.93 (br d, J=16 Hz, 1H), 6.50 (br s, 1H), 6.92 (dt, J=7, 16 Hz, 1H), 7.36 (s, 5H).

EXAMPLE 37

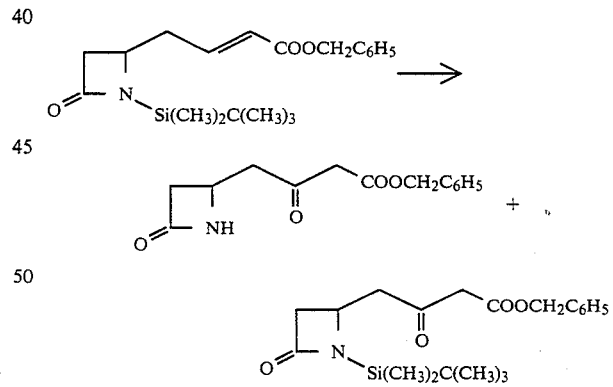

To a solution of benzyl 4-[(2RS)-1-(tert-butyl-dimethylsilyl)-4-oxoazetidin-2-yl]but-2-enoate (50 mg) in 60% aqueous acetic acid (1.5 ml) were added tert-butyl-hydroperoxide (40 μl) and sodium tetrachloropalladate (18 mg). The solution was heated at 55° C. for 5.5 hours. Additional tert-butyl-hydroperoxide (100 μl) and sodium tetrachloropalladate (18 mg) were added and stirring at 50° C. was continued for further 11 hours. After evaporation of the solvent in vacuo, the residue was taken up into ethyl acetate and washed in turn with water (twice) and brine. Drying over magnesium sulfate and removal of the solvent left an oil (30 mg) which was chromatographed on a silica gel plate (developing solvent: 25% acetone in benzene) afforded benzyl 3-oxo-4-[(2RS)-4-oxoazetidin-2-yl]butanoate (13 mg).

IR (CH₂Cl₂): 3400, 1760, 1715 cm⁻¹.

NMR (CDCl₃) δ: 2.54 (ddd, J=1, 3, 15 Hz, 1H), 2.9 (m, 2H), 3.15 (ddd, J=3, 6, 15 Hz, 1H), 3.51 (s, 2H), 3.9 (m, 1H), 5.17 (s, 2H), 6.1 (m, 1H), 7.37 (s, 5H).

Benzyl 4-[(2RS)-1-(tert-butyl-dimethylsilyl)-4-oxoazetidin-2-yl]-3-oxobutanoate (3.5 mg) was afforded from the subsequent fractions.

IR (CH₂Cl₂): 1755, 1735 (sh), 1715 cm⁻¹.

EXAMPLE 38

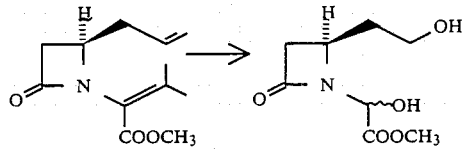

A solution of methyl 2-[(4R)-4-allyl-2-oxoazetidin-1-yl]-3-methylbut-2-enoate (85 mg) in ethyl acetate (7 ml) was cooled to −78° C. and ozone was bubbled until a blue color appeared. After stirring for 10 minutes at the same temperature, the reaction mixture was purged with nitrogen.

To this solution was added sodium borohydride (60 mg) and the mixture was stirred for 30 minutes at −78° C. Acetic acid (0.12 ml) was then added and the mixture was stirred for 2 hours during which time the temperature was gradually raised to 0° C. The reaction mixture was diluted with ethyl acetate (10 ml), washed successively with water, dilute aqueous sodium bicarbonate and brine. Drying over magnesium sulfate and evaporation gave an oil (20 mg), which was chromatographed on silica gel (1 g) eluting with a mixture of methylene chloride and methanol (10:1) to give methyl 2-hydroxy-2-[(4R)-4-(2-hydroxyethyl)-2-oxoazetidin-1-yl]acetate (12 mg).

IR (CH₂Cl₂): 3500, 1765, 1745 (sh) cm⁻¹.

EXAMPLE 39

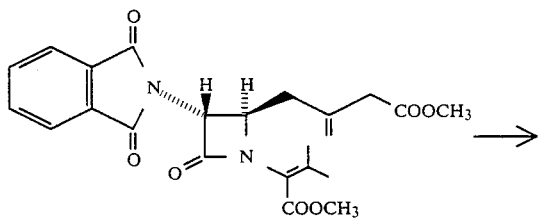

A stream of ozone was bubbled into a solution of methyl 2-[(3R,4R)-4-{2-(methoxycarbonylmethyl)allyl}-2-oxo-3-phthalimidoazetidin-1-yl]-3-methyl-but-2-enoate (180 mg) in ethyl acetate (10 ml) at −78° C. until blue color of ozone appeared. After stirring for 2 minutes at the same temperature, the excess of ozone was removed by a stream of nitrogen. The resultant solution was poured into a chilled dilute aqueous sodium bisulfate and extracted with ethyl acetate (10 ml). The extract was washed twice with brine, dried over magnesium sulfate, and evaporated to afford methyl 4-[(2R,3R)-1-methoxalyl-4-oxo-3-phthalimidoazetidin-2-yl]-3-oxobutanoate (179 mg) as an oil. This material could be crystallized from 7% dichloromethane in methanol, mp 130°–132° C.

IR (nujol): 1800, 1780, 1760, 1735 (sh), 1730 (sh), 1720 cm⁻¹.

NMR (CDCl₃) δ: 3.20 (dd, J=8, 19 Hz, 1H), 3.56 (s, 2H), 3.78 (s, 3H), 3.80 (dd, J=4, 19 Hz, 1H), 4.00 (s, 3H), 4.84 (dt, J=4, 8 Hz, 1H), 5.34 (d, J=4 Hz, 1H), 7.7–8.0 (m, 4H).

EXAMPLE 40

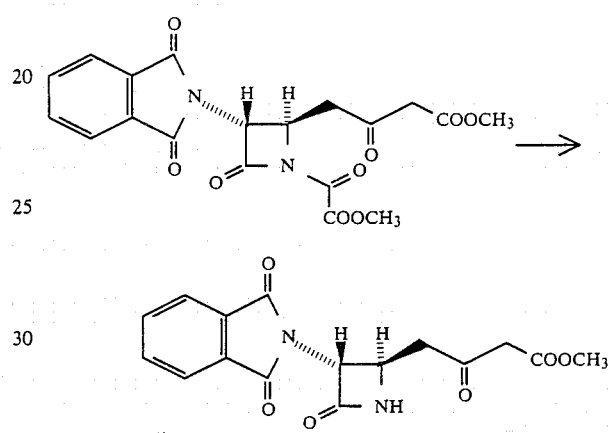

A solution of methyl 4-[(2R,3R)-1-methoxalyl-4-oxo-3-phthalimidoazetidin-2-yl]-3-oxobutanoate (68 mg) in methanol (4 ml) was stirred at room temperature for 16 hours and heated at 55°–60° C. for two hours. The resultant solution was evaporated, and the residue was chromatographed on a silica gel plate (developing solvent: 20% acetone in dichloromethane) to afford methyl 3-oxo-4-[(2R,3R)-4-oxo-3-phthalimidoazetidin-2-yl]butanoate (35 mg) as an amorphous solid. Crystallization from a mixture of ethyl acetate and ether gave crystals (26 mg), mp 120°–124° C.

IR (CH₂Cl₂): 1785, 1770 (sh), 1740 (sh), 1720 cm⁻¹.

NMR (CDCl₃) δ: 3.15 (d, J=6.5 Hz, 1H), 3.52 (s, 2H), 3.73 (s, 3H), 4.40 (dt, J=3, 6.5 Hz, 1H), 5.05 (d, J=3 H, 1H), 6.78 (brs, 1H), 7.6–8.1 (m, 4H).

EXAMPLE 41

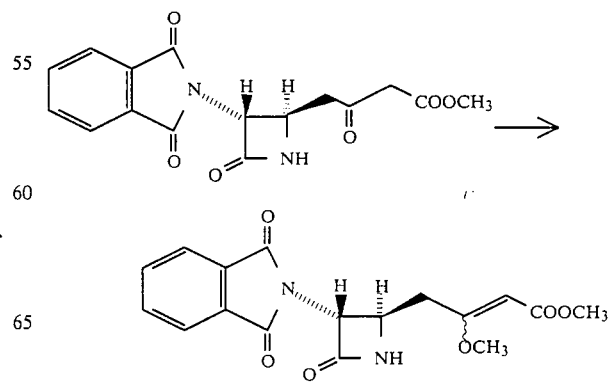

A mixture of methyl 3-oxo-4-[(2R,3R)-4-oxo-3-phthalimidoazetidin-2-yl]butanoate (300 mg), pyridinium p-toluenesulfonate (25 mg), p-toluene-sulfonic acid monohydrate (20 mg), and trimethyl orthoformate (0.6 ml) in a mixture of methanol (3 ml) and dichloromethane (1 ml) was heated to reflux for six hours. Additional trimethyl orthoformate (0.2 ml) was added and the reflux was continued for one hour. After the solution was cooled to room temperature, pyridine (three drops) was added. The resultant solution was evaporated and the residue was dissolved in ethyl acetate (20 ml). The solution was washed in turn with dilute hydrochloric acid, water, and brine, dried over magnesium sulfate and evaporated. The residue was chromatographed on silica gel (8 g) eluting with 5–10% acetone in dichloromethane to give an (E,Z)-isomeric mixture of methyl 3-methoxy-4-[(2R,3R)-4-oxo-3-phthalimidoazetidin-2-yl]but-2-enoate (213 mg) as a crystalline solid, mp 208°–220° C.

IR (CH$_2$Cl$_2$): 3400, 1780, 1770 (sh), 1720, 1630 cm$^{-1}$.

NMR (DMSO-d$_6$) δ: 3.1–3.4 (m, 2H), 3.55 and 3.57 (a pair of singlet, 3H), 3.60 (s, 3H), 4.10 (dt, J=2, 7 Hz, 1H), 5.03 (d, J=2 Hz, 1H), 5.13 (s, 1H), 7.88 (s, 4H), 8.45 and 8.58 (a pair of broad singlet, a ratio of 1:4, 1H).

EXAMPLE 42

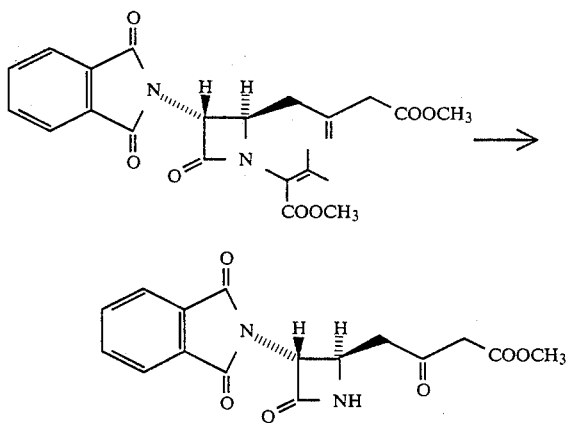

A stream of ozone was bubbled into a solution of methyl 2-[(3R,4R)-4-{2-(methoxycarbonylmethyl)allyl}-2-oxo-3-phthalimidoazetidin-1-yl]-3-methyl-but-2-enoate (4.55 g) in ethyl acetate (80 ml) at −78° C. until blue color of ozone appeared. After the excess of ozone was removed by a stream of nitrogen, the resultant solution was allowed to warm to 0° C. and washed successively with an aqueous sodium bisulfite (10 g) and sodium sulfite (3.5 g), a dilute aqueous sodium chloride, and a saturated aqueous sodium chloride. Drying over magnesium sulfate and evaporation afforded methyl 4-[(2R,3R)-1-methoxalyl-4-oxo-3-phthalimidoazetidin-2-yl]-3-oxo-butanoate as an amorphous solid. This material was suspended in a mixture of methanol (80 ml) and dichloromethane (10 ml), and heated at 60° C. for eight hours. The resultant solution was evaporated and the residue was chromatographed on silica gel (60 g) eluting with 10–25% acetone in dichloromethane to give an amorphous solid (2.405 g). Crystallization from a mixture of ethyl acetate and diethyl ether afforded methyl 3-oxo-4-[(2R,3R)-4-oxo-3-phthalimidoazetidin-2-yl]-butanoate (2.08 g), mp 116°–120° C.

EXAMPLE 43

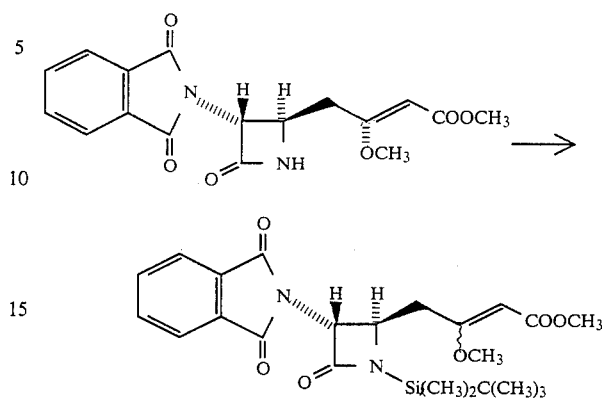

To a mixture of methyl 3-methoxy-4-[(2R,3R)-4-oxo-3-phthalimidoazetidin-2-yl]but-2-enoate[(E,Z)-isomeric mixture] (186 mg) and triethylamine (90 μl) in dimethylformamide (2 ml) was added tert-butyldimethylchlorosilane (96 mg) at 0° C. After the mixture was stirred at 0° C. for 30 minutes and at room temperature for one hour, additional tert-butyl-dimethyl-chlorosilane (32 mg) and triethylamine (30 μl) were added. The mixture was stirred at 0° C. for 30 minutes and at room temperature for 1.5 hours, diluted with ethyl acetate (20 ml), and washed with water (twice), a dilute aqueous sodium bicarbonate solution, and brine. Drying over magnesium sulfate and removal of the solvent afford an oil (280 mg) which was chromatographed on silica gel (6 g) eluting with 10% acetone in benzene to give methyl 4-[(2R,3R)-1-(tert-butyl-dimethylsilyl-4-oxo-3-phthalimidoazetidin-2-yl]-3-methoxybut-2-enoate[-(E,Z)-isomeric mixture](209 mg) as an amorphous solid.

IR (CH$_2$Cl$_2$): 1780 (sh), 1750, 1720, 1625 cm$^{-1}$.

NMR (CDCl$_3$) δ: 0.30 (s, 6H), 0.99 (s, 9H), 2.4–3.2 (m, 2H), 3.46 (s, 3H), 3.62 (s, 3H), 4.1–4.6 (m, 1H) 4.97 (s, 1H), 5.19 (d, J=2.5 Hz, 1H), 7.72 (m, 4H).

EXAMPLE 44

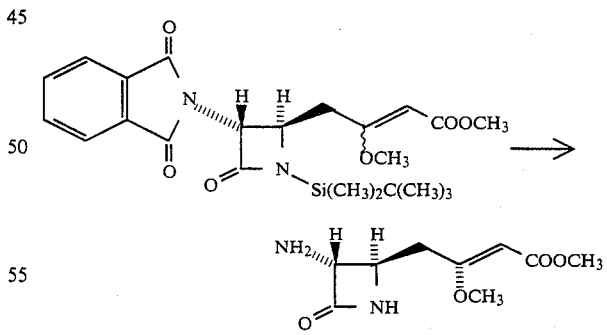

A mixture of methyl 4-[(2R,3R)-1-(tert-butyl-dimethylsilyl)-4-oxo-3-phthalimidoazetidin-2-yl]-3-methoxybut-2-enoate[(E,Z)-isomeric mixture](182 mg) and N,N-dimethyl-1,3-propanediamine (126 μl) in a mixture of methanol (1 ml) and dichloromethane (1 ml) was left at room temperature for four days. After evaporation of the solvent, the residue was chromatographed on silica gel (2.5 g) eluting with 3–5% methanol in dichloromethane to give an oil (36 mg). Further purification on a silica gel plate (developing solvent: 15% methanol in dichloromethane) afforded methyl 4-[(2R,3R)-3-amino-4-oxoazetidin-2-yl]-3-methoxybut-2-enoate[(E,Z)-isomeric mixture](35 mg) as an oil.

IR (CH$_2$Cl$_2$): 3390, 1765, 1710, 1630 cm$^{-1}$.

NMR (CDCl$_3$) δ: 1.82 (brs, 2H), 2.8–3.9 (m, 3H), 3.70 (s, 6H), 3.95 (brs, 1H), 5.15 (s, 1H), 6.45 (brs, 1H).

EXAMPLE 45

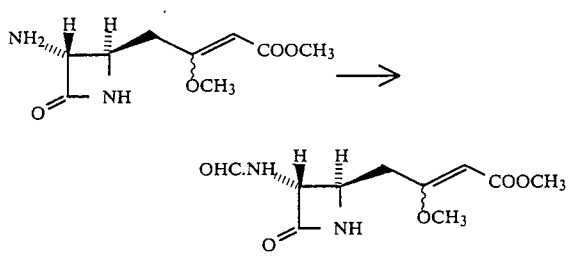

A solution of methyl 4-[(2R,3R)-3-amino-4-oxoazetidin-2-yl]-3-methoxybut-2-enoate[(E,Z)-isomeric mixture](145 mg) in acetic formic anhydride (1 ml) was stirred at 5° C. for one hour. The resultant solution was evaporated in vacuo, and the residue was chromatographed on silica gel (2.5 g) eluting with 3 to 5% methanol in dichloromethane to give methyl 4-[(2R,3R)-3-formamido-4-oxoazetidin-2-yl]-3-methoxybut-2-enoate[-(E,Z)-isomeric mixture](133 mg) as an amorphous solid.

IR (CH$_2$Cl$_2$): 3400, 1770, 1700, 1625 cm$^{-1}$.

NMR (CDCl$_3$) δ: 2.9–3.3 (m, 2H), 3.66 (s, 3H), 3.68 (s, 3H), 3.9 (m, 1H), 4.75 (dd, J=2, 8 Hz, 1H), 5.10 (s, 1H), 7.00 (brs, 1H), 7.48 (brd, J=8 Hz, 1H), 8.15 (s, 1H).

EXAMPLE 46

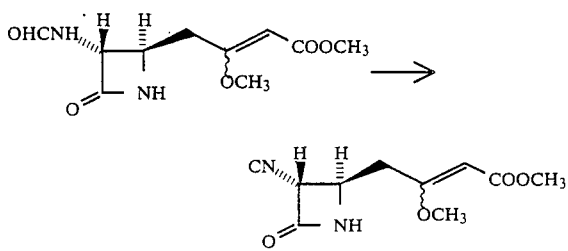

To a solution of methyl 4-[(2R,3R)-3-formamido-4-oxoazetidin-2-yl]-3-methoxybut-2-enoate[(E,Z)-isomeric mixture](133 mg) and 2,6-lutidine (0.96 ml) in dichloromethane (3 ml) was added phosphorus oxychloride (0.15 ml) at 0°. After stirring at the same temperature for four hours, the reaction mixture was diluted with ethyl acetate (20 ml), and washed with a dilute aqueous sodium chloride, dilute phosphoric acid, a dilute aqueous sodium chloride, ice-water, and a saturated aqueous solution of sodium chloride in turn. Drying over magnesium sulfate and removal of the solvent gave a brown oil, which was chromatographed on silica gel (2 g) eluting with 3% methanol in dichloromethane to give methyl 4-[(2R,3R)-3-isocyano-4-oxoazetidin-2-yl]-3-methoxybut-2-enoate[(E,Z)-isomeric mixture](70 mg) as a crystalline solid IR (CH$_2$Cl$_2$): 3380, 2200, 1795, 1705, 1630 cm$^{-1}$.

NMR (CDCl$_3$) δ: 3.1–3.4 (m, 2H), 3.68 (s, 6H), 4.06 (dt. J=2.5, 6 Hz, 1H), 4.60 (m, 1H), 5.23 (s, 1H), 6.52 (brs, 1H).

EXAMPLE 47

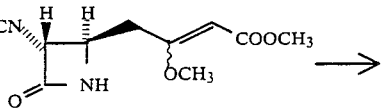

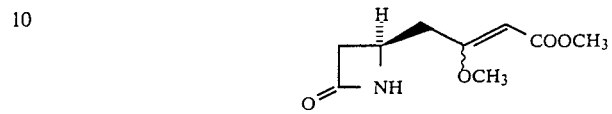

A mixture of methyl 4-[(2R,3R)-3-isocyano-4-oxoazetidin-2-yl]-3-methoxybut-2-enoate[(E,Z)-isomeric mixture](50 mg), tri-n-butyltin hydride (90 μl), and 2,2'-azobis-(2-methylpropionitrile) (5 mg) in benzene (5 ml) was heated to reflux for one hour under a nitrogen atmosphere. The reaction mixture was cooled to room temperature and chromatographed on silica gel (2.5 g) eluting first with dichloromethane and then 4% methanol in dichloromethane to give methyl 3-methoxy-4-[(2R)-4-oxoazetidin-2-yl]but-2-enoate[-(E,Z)-isomeric mixture](35 mg) as a crystalline solid.

IR (CH$_2$Cl$_2$): 3390, 1760, 1710, 1625 cm$^{-1}$.

NMR (CDCl$_3$) δ: 2.6–2.9 (m, 1H), ~3.0 (m, 2H), 3.30 (dd, J=6, 14 Hz, 1H), 3.66 (s, 3H), 3.68 (s, 3H), 3.85 (m, 1H), 5.11 (s, 1H), 6.28 (brs, 1H).

Mass spectrum: m/e 199 (M+), 171, 157, 156, 126, 70.

EXAMPLE 48

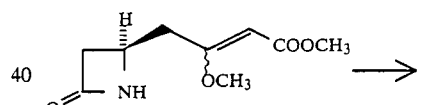

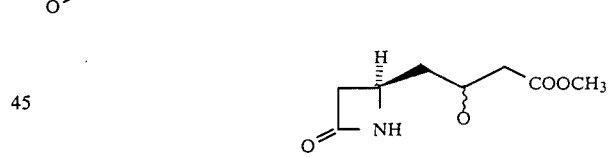

A solution of methyl 3-methoxy-4-[(2R)-4-oxoazetidin-2-yl]but-2-enoate[(E,Z)-isomeric mixture](35 mg) in 1N hydrochloric acid (2 ml) was stirred at 25° C. for two hours. The resultant solution was saturated with sodium chloride and extracted three times with chloroform. The combined extracts were dried over magnesium sulfate and evaporated. The residue (29 mg) was chromatographed on silica gel (1.5 g) eluting with 2% methanol in dichloromethane to give methyl 3-oxo-4-[(2R)-4-oxoazetidin-2-yl]butanoate (28 mg), mp. 45.0°–46.5° C.:

IR (CH$_2$Cl$_2$): 3400, 1760 (br), 1715 cm$^{-1}$.

NMR (CDCl$_3$) δ: 2.4–3.3 (m, 4H), 3.50 (s, 2H), 3.76 (s, 3H), 4.9 (m, 1H), 6.40 (brs, 1H).

Mass spectrum: m/e 185 (m+), 157, 142, 116, 112, 101, 70, 59, and 43.

[α]$_D^{26}$: +61.3° (chloroform, c=0.261).

EXAMPLE 49

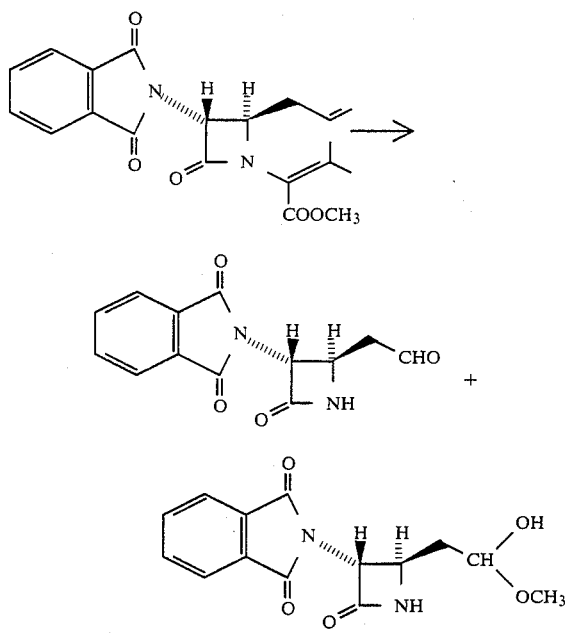

A stream of ozone was bubbled into a solution of methyl 3-methyl-2-[(3R,4R)-2-oxo-3-phthalimido-4-allylazetidin-1-yl]but-2-enoate (5.00 g) in a mixture of ethyl acetate (60 ml) and dichloromethane (30 ml) at −78° until blue color of ozone appeared. After five minutes, the excess of ozone was removed by a stream of nitrogen. The resultant colorless solution was allowed to warm to −20° C., diluted with ethyl acetate (90 ml) and then washed in turn with an aqueous containing sodium bisulfite (6.0 g) and sodium sulfite (2.5 g), and brine. Drying over magnesium sulfate and evaporation gave an amorphous solid (4.90 g). This material was dissolved in a mixture of methanol (50 ml) and dichloromethane (5 ml), and dimethyl sulfide (4 ml) was added. The solution was stirred overnight at room temperature and heated at 50° for seven hours. After evaporation of the solvent, the residue was chromatographed on silica gel (20 g) eluting with 20–33% acetone in dichloromethane to afford an impure material (4 g). Crystallization from ethyl acetate afforded a mixture (1.52 g) of (3R,4R)-2-oxo-4-(2-oxoethyl)-3-phthalimidoazetidine and its methanol-hemiacetal.

IR (Nujol): 3280 (br), 1770 (sh), 1750, 1705 cm$^{-1}$.

NMR (DMSO-d$_6$) δ: 1.7–2.1 (m, ~1H), 2.9–3.5 (m, ~4H), 3.8–4.7 (m, ~1.5H), 5.0 (m, 1H), 6.10 (dd, J=2 and 7 Hz, ~0.5H), 7.95 (s, 4H), 8.47 and 8.55 (a pair of broad singlet, 1H), 9.70 (s, ~0.5H).

EXAMPLE 50

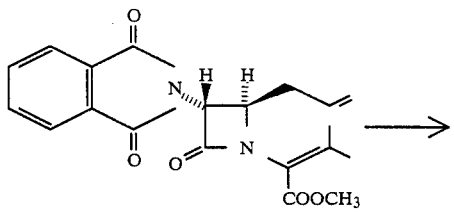

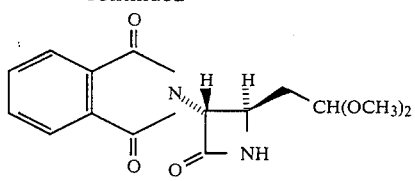

A stream of ozone was bubbled into a solution of methyl 3-methyl-2-[(3R,4R)-2-oxo-3-phthalimido-4-allylazetidin-1-yl]but-2-enoate (250 mg) in a mixture of ethyl acetate (5 ml) and dichloromethane (2 ml) at −78° C. until blue color of ozone appeared. After five minutes, the excess of ozone was removed by a stream of nitrogen at the same temperature. Dimethyl sulfide (0.5 ml) was added. The resultant yellow solution was allowed to warm to −10° C. and kept for one hour at the same temperature. Methanol (2 ml) was added and the solution was stirred at 0° C. for three hours and at room temperature overnight. After concentration of the reaction mixture, the residue was taken up into ethyl acetate and washed with a dilute aqueous sodium bisulfate, water, and brine. Drying over magnesium sulfate and removal of the solvent gave an oil (230 mg) which was dissolved in methanol (8 ml). Dimethyl sulfide (0.5 ml) was added thereto. After heating at 55° C. for three hours and at 65° for two hours, the solution was evaporated. The residue was chromatographed on silica gel (2 g) eluting with 5–17% acetone in dichloromethane to afford (3R,4R)-4-(2,2-dimethoxyethyl)-3-phthalimido-2-oxoazetidine (126 mg) as an amorphous solid.

IR (CH$_2$Cl$_2$): 3410, 1785, 1770 (sh), 1725 cm$^{-1}$.

NMR (CDCl$_3$) δ: ~2.1 (m, 2H), 3.36 (s, 6H), 4.20 (dt, J=3, 7 Hz, 1H), 4.51 (t, J=5 Hz, 1H), 5.07 (d, J=3 Hz, 1H), 6.55 (brs, 1H), 6.5–7.1 (m, 4H).

EXAMPLE 51

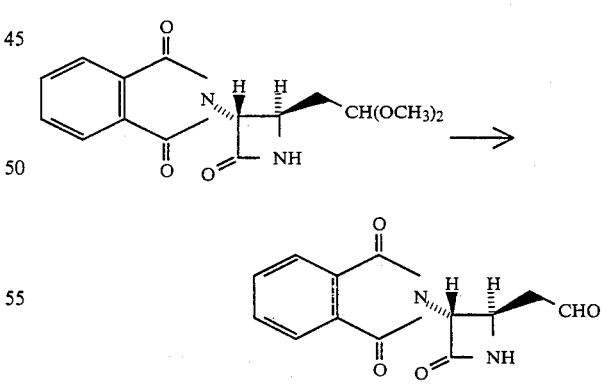

A solution of (3R,4R)-4-(2,2-dimethoxyethyl)-3-phthalimido-2-oxoazetidine (65 mg) in 80% aqueous acetic acid (1.5 ml) was heated at 64° for two hours. After evaporation of the solvent in vacuo, the residue was crystallized from a mixture of diethyl ether and ethyl acetate to afford (3R,4R)-4-(2-oxoethyl)-3-phthalimido-2-oxoazetidine (42 mg).

IR (CH$_2$Cl$_2$): 3400, 1785, 1770, 1720 cm$^{-1}$.

EXAMPLE 52

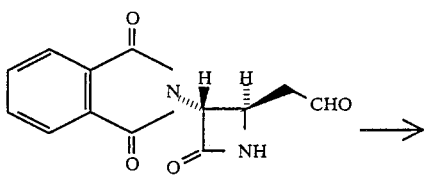

A mixture of (3R,4R)-4-(2-oxoethyl)-3-phthalimido-2-oxoazetidine (a mixture of the free aldehyde and its methanol-hemiacetal) (1.52 g) and benzyl triphenylphosphoranylideneacetate (3.15 g) in dichloromethane (30 ml) was heated under refluxing for 75 minutes in a nitrogen atmosphere. After removal of the solvent, the residue was chromatographed on silica gel (60 g) eluting with 5–10% acetone in dichloromethane to give an oil (1.69 g). Crystallization from diethyl ether afforded benzyl 4-[(2R,3R)-4-oxo-3-phthalimidoazetidin-2-yl]but-2-enoate (1.53 g), mp 115°–120° C.

IR (Nujol): 3280, 1775 (sh), 1765, 1730, 1710 cm$^{-1}$.

NMR (CDCl$_3$) δ: 2.66 (t, J=7 Hz, 2H), 4.17 (dt, J=2.5, 7 Hz, 1H), 5.03 (d, J=2.5 Hz, 1H), 5.15 (s, 2H), 6.00 (d, J=16 Hz, 1H), 6.72 (brs, 1H), 6.97 (dt, J=7, 16 Hz, 1H), 7.35 (s, 5H), 7.8 (m, 4H).

EXAMPLE 53

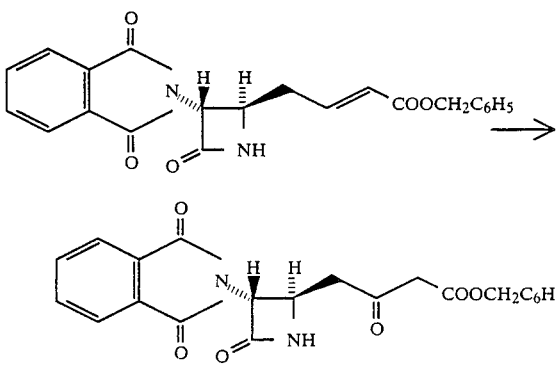

A mixture of benzyl 4-[(2R,3R)-4-oxo-3-phthalimidoazetidin-2-yl]but-2-enoate (35 mg), tert-butylhydroperoxide (20 μl) and sodium tetrachloropalladate (6 mg) in 60% aqueous acetic acid (1 ml) was stirred at room temperature for one hour and then heated at 50° for ten hours, during which time additional sodium tetrachloropalladate (15 mg) and tert-butylhydroperoxide (80 μl) in two portions were added. The resultant solution was evaporated in vacuo. The residue was taken up into ethyl acetate and washed with water and brine. Drying over magnesium sulfate and removal of the solvent gave an oil (40 ml), which was chromatographed on two silica gel plates [developing solvent: a mixture of benzene and acetone (5:2)] to give benzyl 3-oxo-4-[(2R,3R)-4-oxo-3-phthalimidoazetidin-2-yl]butanoate (15 mg) as an oil.

IR (CH$_2$Cl$_2$): 3400, 1785, 1770 (sh), 1720 cm$^{-1}$.

NMR (CDCl$_3$)δ: 3.04 (~d, J=6 Hz, 2H), 3.51 (s, 2H), 4.35 (m, 1H), 4.97 (d, J=3 Hz, 1H), 5.16 (s, 3H), 6.42 (brs, 1H), 7.34 (s, 5H), 7.80 (m, 4H).

EXAMPLE 54

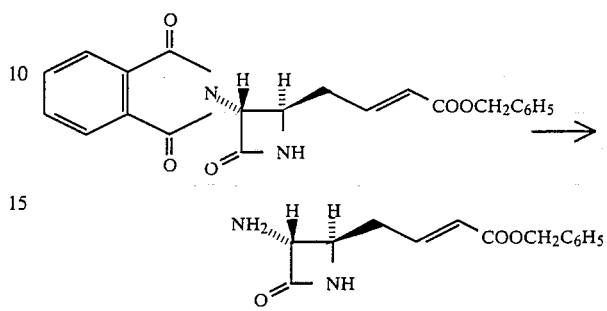

A mixture of benzyl 4-[(2R,3R)-4-oxo-3-phthalimidoazetidin-2-yl]but-2-enoate (960 mg) and N,N-dimethyl-1,3-propanediamine (0.84 ml) in tetrahydrofuran (8 ml) was stirred at room temperature for four days. After evaporation of the solvent, the residue was chromatographed on silica gel (20 g) eluting with 25–50% acetone in benzene to give an oil (250 mg). Further purification on silica gel (8 g) eluting with 3–5% methanol in dichloromethane afforded benzyl 4-[(2R,3R)-3-amino-4-oxoazetidin-2-yl]but-2-enoate (146 mg) as an oil.

IR (CH$_2$Cl$_2$): 3390, 1770, 1720, 1655 cm$^{-1}$.

NMR (CDCl$_3$) δ: 1.80 (s, 2H), 2.4–2.8 (m, 2H), 3.49 (ddd, J=2.5, 6 Hz, 1H), 3.80 (d, J=2 Hz, 1H), 5.20 (s, 2H), 6.00 (dt, J=1.5, 16 Hz, 1H), 6.45 (brs, 1H), 7.00 (dt, J=7, 16 Hz, 1H), 7.38 (s, 5H).

EXAMPLE 55

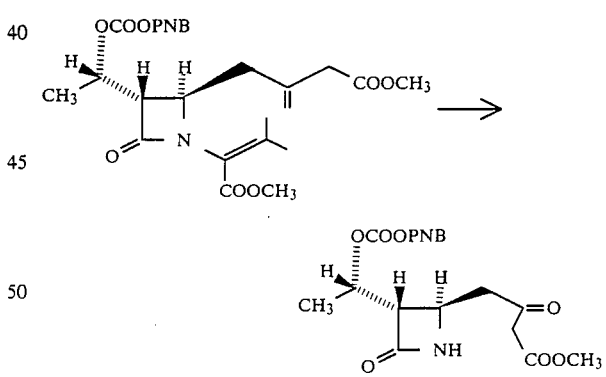

A stream of ozone was bubbled into a solution of methyl 2-[(3S,4R)-4-[2-(methoxycarbonylmethyl)allyl]-3-[(1S)-1-(p-nitrobenzyloxycarbonyloxy)ethyl]-2-oxoazetidin-1-yl]-3-methylbut-2-enoate (190 mg) in ethyl acetate (14 ml) at −78° C. until blue color appeared. After stirring at −78° C. for two minutes, the excess of ozone was removed by a stream of nitrogen. The solution was diluted with ethyl acetate, and washed with a chilled aqueous sodium bisulfite (1.0 g) and brine. Drying over magnesium sulfate and removal of the solvent gave an oil (182 mg). The residue was dissolved in dichloromethane (2.5 ml) and cooled to 0° C. To this solution were added methanol (7.5 ml) and dimethyl sulfide (0.7 ml) and the resultant solution was stirred at 0° for 25 hours. The mixture was then heated to 50° C. for 22 hours and allowed to stand at room temperature for four days. After removal of the solvent, the residue was chromatographed on silica gel (6 g) eluting with 5-20% acetone in dichloromethane to give methyl 4-[(2R,3S)-3-[(1S)-1-(p-nitrobenzyloxycarbonyloxy)ethyl]-4-oxoazetidin-2-yl]-3-oxobutanoate (122 mg).

IR (CH$_2$Cl$_2$): 3380, 1765, 1750, 1715, 1520, 1350 cm$^{-1}$.

NMR (CDCl$_3$)δ: 1.46 (d, J=6.5 Hz, 3H), 2.90–3.05 (m, 2H), 3.10 (dd, J=2.2, 4.5 Hz, 1H), 3.48 (s, 2H), 3.73 (s, 3H), 3.8 (m, 1H), 5.13 (dq, J=4.5, 6.5 Hz, 1H), 5.24 (s, 2H), 6.51 (br s, 1H), 7.53 (d, J=9 Hz, 2H) and 8.18 (d, J=9 Hz, 2H).

EXAMPLE 56

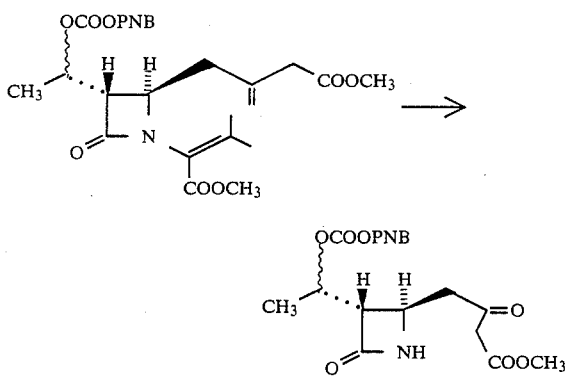

Methyl 4-[(2R,3S)-3-{(1RS)-1-(p-nitrobenzyloxycarbonyloxy)ethyl}-4-oxoazetidin-2-yl]-3-oxobutanoate (61 mg) was afforded from methyl 2-[(3S,4R)-4-{2-(methoxycarbonylmethyl)allyl}-3-[(1RS)-1-(p-nitrobenzyloxycarbonyloxy)ethyl]-2-oxoazetidin-1-yl]-3-methylbut-2-enoate (90 mg) in a similar manner to that of Example 55.

IR (CH$_2$Cl$_2$): 3380, 1765, 1745, 1715, 1520, 1350 cm$^{-1}$.

NMR (acetone-d$_6$) δ: 1.42 (d, J=6.5 Hz, 2H), 1.46 (d, J=6.5 Hz, 1H), 3.0–3.2 (m, 3H), 3.59 (s, 2H), 3.69 (s, 3H), 3.80 (dt, J=2.5, 7 Hz, ⅓H), 3.95 (ddd, J=2.5, 6, 8 Hz, ⅔H, 5.10 (quintet, J=6.5 Hz, ⅔H, 5.15 (m, ⅓H, hidden), 7.15 (brs, ⅓H), 7.23 (brs, ⅔H), 7.66 (d, J=9 Hz, 2H), 8.23 (d, J=9 Hz, 2H).

EXAMPLE 57

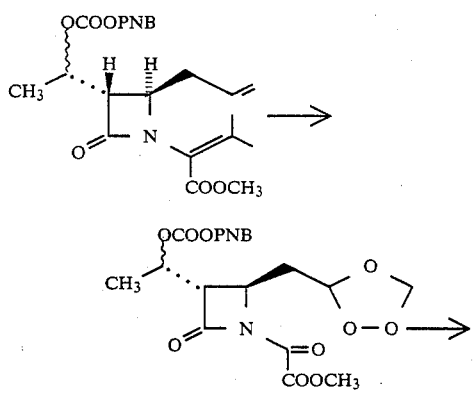

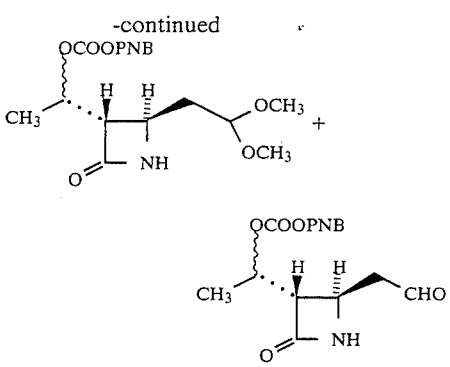

A mixture of methyl 2-[(3S,4R)-3-{(1RS)-1-(p-nitrobenzyloxycarbonyloxy)ethyl}-2-oxo-4-allylazetidin-1-yl]-3-methylbut-2-enoate (62 mg) in ethyl acetate (5 ml) was cooled to −70° C. and ozone was bubbled until a blue color appeared. After stirring for 15 minutes at the same temperature, the reaction mixture was purged with nitrogen and poured into a mixture of ethyl acetate and an aqueous sodium bisulfite and sodium sulfite (4:1). The organic layer was separated and washed with brine. Drying over magnesium sulfate and evaporation gave an oil (56 mg) of methyl[(3S,4R)-3-{(1RS)-1-(p-nitrobenzyloxycarbonyloxy)ethyl}-4-(1,2,4-tri-oxolan-3-ylmethyl)-2-oxoazetidin-1-yl]glyoxylate. This oil was dissolved in a mixture of methanol (4 ml) and methylene chloride (2 ml), and dimethyl sulfide (0.5 ml) was added at 0° C. The mixture was stirred at the same temperature for two hours and at room temperature overnight. After further stirring at 50° C. for 3 hours, the mixture was evaporated. The residue was again dissolved in methanol (14 ml), and dimethyl sulfide (0.5 ml) was added thereto. The mixture was stirred at room temperature overnight and then evaporated. The residue was purified by preparative thin layer chromatography (silica gel) developing with benzene and acetone (1:1) to give a mixture (5 mg) of (3S,4R)-3-[(1RS)-1-(p-nitrobenzyloxycarbonyloxy)ethyl]-4-(2-oxoethyl)-2-oxoazetidine[IR (CH$_2$Cl$_2$): 3375, 1770, 1750, 1720 cm$^{-1}$] and its dimethyl acetal [IR (CH$_2$Cl$_2$): 1760, 1750 cm$^{-1}$.

NMR (CDCl$_3$) δ: 1.45 (d, 3H, 6.5 Hz), 1.94 (dd, 2H, J=6, 5.5 Hz), 3.0–3.2 (m, 1H), 3.32 (s, 3H), 3.5–3.8 (m, 1H), 4.41 (t, 1H, J=5.5 Hz), 4.9–5.3 (m, 1H), 5.24 (s, 2H), 6.12 (broad s, 1H), 7.84 (A$_2$B$_2$, 4H, J=9 Hz).].

EXAMPLE 58

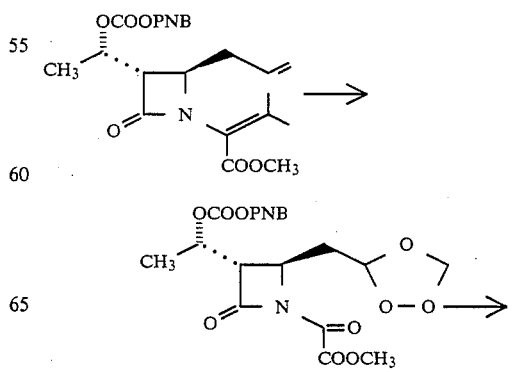

-continued

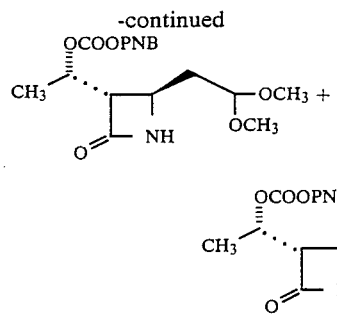

A solution of methyl 3-methyl-2-[(3S,4R)-3-{(1S)-1-(p-nitrobenzyloxycarbonyloxy)ethyl}-2-oxo-4-allylazetidin-1-yl]but-2-enoate (135 mg) in ethyl acetate (10 ml) was cooled to −70° C. and ozone was bubbled until a blue color appeared. After stirring for 15 minutes at the same temperature, the mixture was purged with nitrogen and poured into a mixture of ethyl acetate and an aqueous sodium bisulfite and sodium sulfite (3:1). The organic layer was separated and washed with brine, dried over magnesium sulfate and evaporated to give methyl[(3S,4R)-3-{(1S)-1-(p-nitrobenzyloxycarbonyloxy)ethyl}-2-oxo-4-(1,2,4-tri-oxolan-3-ylmethyl)]-glyoxylate. The product was dissolved in methanol (4 ml) and dimethyl sulfide (1 ml) was added at 0° C. The mixture was stirred at the same temperature for 2 hours and at room temperature for 2 hours. Additional 0.5 ml of dimethyl sulfide was added and the mixture was stirred at 50° C. for 6 hours. After standing overnight at room temperature, the mixture was evaporated and the residue was dissolved in benzene. The solution was evaporated and the residue was chromatographed on silica gel (3 g) eluting with hexane and ethyl acetate (4:1–1:2) to give (3S,4R)-3-[(1S)-1-(p-nitrobenzyloxycarbonyloxy)ethyl]-4-(2-oxoethyl)-2-oxoazetidine (15 mg).

[IR (CH$_2$Cl$_2$): 3375, 1770, 1750, 1720 cm$^{-1}$] and its dimethyl acetal (37 mg).

IR (CH$_2$Cl$_2$): 1760, 1750 cm$^{-1}$.

NMR (CDCl$_3$) δ: 1.45 (d, 3H, J=6.5 Hz), 1.94 (dd, 2H, J=6, 5.5 Hz), 3.10 (dd, 1H, J=5, 2.5 Hz), 3.32 (s, 3H), 3.62 (dt, 1H, J=2.5, 6 Hz), 4.41 (t, 1H, J=5.5 Hz), 4.9–5.3 (m, 1H), 5.24 (s, 2H), 6.28 (broad s, 1H), 7.84 (A$_2$B$_2$, 4H, J=9 Hz).

EXAMPLE 59

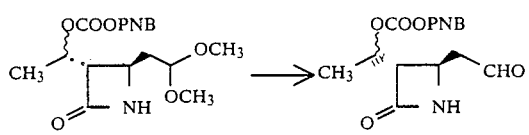

A mixture of (3S,4R)-4-(2,2-dimethoxyethyl)-3-[(1RS)-1-(p-nitrobenzyloxycarbonyloxy)ethyl]-2-oxoazetidine (12 mg) in 80% aqueous acetic acid (1 ml) was stirred at 50° C. for 4 hours. After standing at −20° C. overnight, the mixture was evaporated and the residue was dissolved in ethyl acetate. The solution was washed with aqueous sodium bicarbonate and brine, dried over magnesium sulfate and evaporated to give (3S,4R)-3-[(1RS)-1-(p-nitrobenzyloxycarbonyloxy)ethyl]-2-oxo-4-(2-oxoethyl)]azetidine (8 mg).

IR (CH$_2$Cl$_2$): 3420, 1770, 1750, 1720 cm$^{-1}$.

EXAMPLE 60

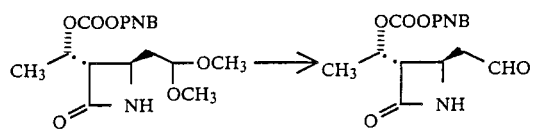

(3S,4R)-3-[(1S)-1-(P-Nitrobenzyloxycarbonyloxy)-ethyl]-2-oxo-4-(2-oxoethyl)azetidine was prepared from (3S,4R)-3-[(1S)-1-(p-nitrobenzyloxycarbonyloxy)ethyl]-4-(2,2-dimethoxyethyl)-2-oxoazetidine in a similar manner to that of Example 59.

IR (CH$_2$Cl$_2$): 3375, 1770, 1750, 1720 cm$^{-1}$.

NMR (CDCl$_3$) δ: 1.48 (d, 3H, J=7 Hz), 2.92 (d, 2H, J=6 Hz), 3.12 (dd, 1H, J=5, 2.5 Hz), 3.86 (dt, 1H, J=2.5, 6 Hz), 5.0–5.3 (m, 1H), 5.25 (s, 2H), 6.48 (s, 1H), 7.84 (A$_2$B$_2$, 4H, J=9 Hz), 9.74 (s, 1H).

EXAMPLE 61

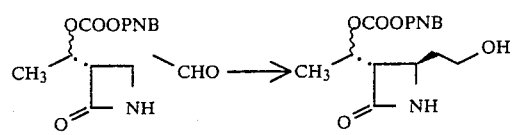

(3S,4R)-3-[(1RS)-1-(p-Nitrobenzyloxycarbonyloxy)ethyl]-2-oxo-4-(2-oxoethyl)azetidine (8 mg) was dissolved in methanol (0.8 ml) and sodium borohydride (2 mg) was added at 0° C. The mixture was then stirred for 30 minutes at the same temperature and acetic acid (3 drops) was added. The mixture was evaporated and the residue was dissolved in ethyl acetate, washed with aqueous sodium bicarbonate, and brine, dried over magnesium sulfate and evaporated. The residue was purified by preparative thin layer chromatography (silica gel) developing with benzene: acetone (1:1) to give (3S,4R)-4-(2-hydroxyethyl)-3-[(1RS)-1-(p-nitrobenzyloxycarbonyloxy)-ethyl]-2-oxoazetidine (5 mg).

IR (CH$_2$Cl$_2$): 3560, 3370, 1760, 1750 cm$^{-1}$.

NMR (CDCl$_3$) δ: 1.47 (d, 3H, J=7 Hz), 1.88 (q, 2H, J=6 Hz), 3.06 and 3.14 (dd, J=7.5, 2.5 Hz, dd, J=5, 2.5 Hz, 1H (1:3)), 3.5–4.0 (m, 3H), 5.0–5.4 (m, 1H), 5.24 (s, 2H), 6.25 (br s, 1H), 7.90 (A$_2$B$_2$, 4H, J=9 Hz).

EXAMPLE 62

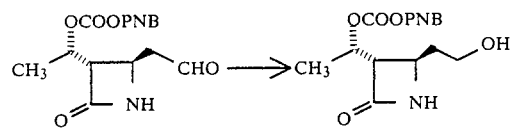

(3S,4R)-4-(2-hydroxyethyl)-3-[(1S)-1-(p-nitrobenzyloxycarbonyloxy)ethyl]-2-oxoazetidine was prepared from (3S,4R)-4-(2-oxoethyl)-3-[(1S)-1-(p-nitrobenzyloxycarbonyloxy)ethyl]-2-oxoazetidine in a similar manner to that of Example 61.

IR (CH$_2$Cl$_2$): 3560, 3370, 1760, 1750 cm$^{-1}$.

NMR (CDCl$_3$) δ: 1.44 (d, 3H, 7 Hz), 1.86 (q, 2H, 6 Hz), 2.12 (broad s, 1H), 3.16 (dd, 1H, J=5, 2.5 Hz), 3.66 (dt, 1H, J=2.5, 6 Hz), 3.76 (t, 2H, J=6 Hz), 5.12 (dq, 1H, J=5, 7 Hz), 5.24 (s, 2H), 6.46 (s, 1H), 7.90 (A$_2$B$_2$, 4H, J=9 Hz).

EXAMPLE 63

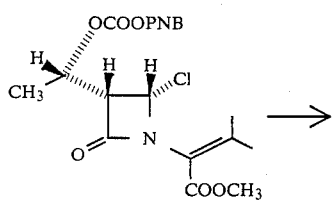

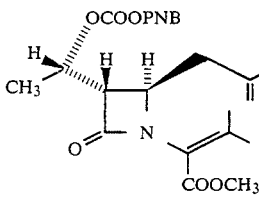

To a solution of methyl 2-[(3S,4S)-4-chloro-3-{(1S)-1-(p-nitrobenzyloxycarbonyloxy)ethyl}-2-oxoazetidin-1-yl]-3-methylbut-2-enoate (200 mg) and p-nitrobenzyl 3-(trimethylsilylmethyl)but-3-enoate (320 mg) in dichloromethane (1.7 ml) was added silver tetrafluoroborate (133 mg) all at once at −78° C. The stirring mixture was gradually allowed to warm to 0° C. during 45 minutes period and kept at the same temperature for 40 minutes. The mixture was diluted with ethyl acetate (5 ml). A saturated aqueous sodium chloride (2 ml) was added and the mixture was brought to pH 7 with a saturated aqueous sodium bicarbonate. After further dilution with ethyl acetate (15 ml), the mixture was filtered through Celite. The organic layer was separated, washed with brine, dried over magnesium sulfate and evaporated to leave an oil, which was chromatographed on silica gel (8 g) eluting with 1 to 5% acetone in dichloromethane to give an oil (215 mg). Further purification by a silica gel column chromatography (8 g) eluting with 10 to 40% ethyl acetate in hexane afforded methyl 3-methyl-2-[(3S,4R)-4-{2-(p-nitrobenzyloxycarbonylmethyl)allyl}3-{(1S)-1-(p-nitrobenzyloxycarbonyloxy)ethyl}-2-oxoazetidin-1-yl]but-2-enoate (200 mg.).

IR (CH$_2$Cl$_2$): 1750, 1725 (sh), 1605, 1525, 1350 cm$^{-1}$.

NMR (CDCl$_3$) δ: 1.50 (d, J=6.5 Hz, 1H), 1.94 (s, 3H), 2.20 (s, 3H), 2.48 (AB part of ABX system, 8 lines, J=6,8, 14 Hz, 2H), 3.15 (s, 2H), 3.19 (dd, J=2.5, 5 Hz, 1H), 3.75 (3H, s), 4.12 (ddd, J=2.5, 6, 8 Hz, 1H), 5.02 (s, 2H), 5.20 (m, hidden, 1H), 5.23 (s, 2H), 5.28 (s, 2H), 7.52 (d, J=9 Hz, 2H), 7.56 (d, J=9 Hz, 2H), 8.23 (d, J=9 Hz, 4H).

EXAMPLE 64

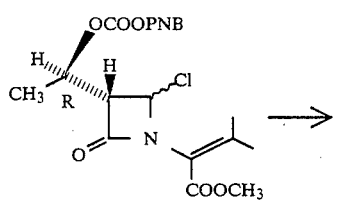

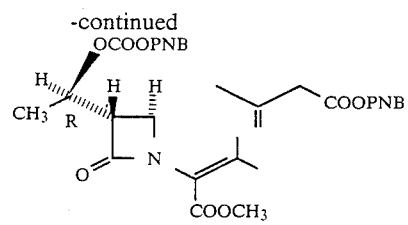

To a solution of a mixture (55:45) of methyl 2-[(3S,4RS)-4-chloro-3-{(1R)-1-(p-nitrobenzyloxycarbonyloxy)ethyl}-2-oxoazetidin-1-yl]-3-methylbut-2-enoate (392 mg) and p-nitrobenzyl 3-(trimethylsilylmethyl)-but-3-enoate (562 mg) in dichloromethane (3.5 ml) was added silver tetrafluoroborate (260 mg) all at once at −78° C. under a nitrogen atmosphere. The stirring mixture was gradually allowed to warm to 0° C. during 45 minutes period and kept at the same temperature for one hour. The mixture was diluted with ethyl acetate (10 ml). A saturated aqueous sodium chloride (3 ml) was added, and the mixture was neutralized to pH 7 with a saturated aqueous sodium bicarbonate. The resultant mixture was filtered through Celite. After further dilution with ethyl acetate (20 ml), the organic layer was separated and washed with brine. Drying over magnesium sulfate and evaporation left an oil, which was chromatographed on silica gel (15 g) eluting with 1-5% acetone in dichloromethane to give an oil (326 mg). Further purification by a silica gel column chromatography (15 g) eluting with 10–40% ethyl acetate in hexane afforded of methyl 3-methyl-2-[(3S,4R)-4-{2-(p-nitrobenzyloxycarbonylmethyl)allyl}-3-{(1R)-1-(p-nitrobenzyloxycarbonyloxy)ethyl}-2-oxoazetidin-1-yl]-but-2-enoate (289 mg).

IR (CH$_2$Cl$_2$): 1750, 1720 (sh), 1525, 1350 cm$^{-1}$.

NMR (CDCl$_3$) δ: 1.46 (d, J=6.5 Hz, 3H), 1.95 (s, 3H), 2.19 (s, 3H), 2.50 (m, 2H), 3.06 (dd, J=2.5, 7 Hz, 1H), 3.13 (s, 2H), 3.74 (s, 3H), 4.10 (ddd, J=2.5, 6, 7.5 Hz, 1H), 5.01 (s, 2H), 5.17 (quintet, partially hidden, J=7 Hz, 1H), 5.20 (s, 2H), 5.25 (s, 2H), 7.48 (d, J=9 Hz, 2H), 7.52 (d, J=9 Hz, 2H), 8.18(d, J=9 Hz, 4H).

[α]$_D^{22}$: −5.65 (c=0.513, CHCl$_3$).

EXAMPLE 65

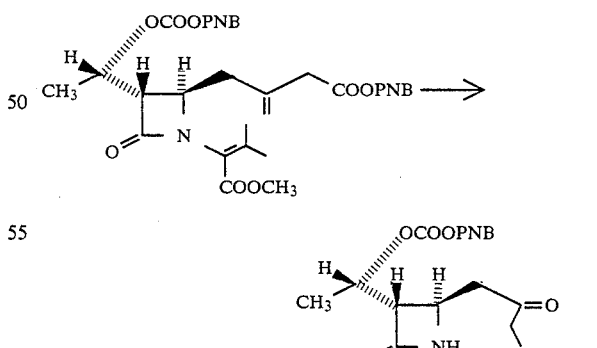

Ozone was bubbled into a solution of methyl 3-methyl-2-[(3S,4R)-4-{2-(p-nitrobenzyloxycarbonylmethyl)-allyl}-3-{(1S)-1-(p-nitrobenzyloxycarbonyloxy)ethyl}-2-oxoazetidin-1-yl]-but-2-enoate (187 mg) in ethyl acetate (8 ml) at −78° C. until blue color appeared. After three minutes, the excess of ozone was removed by a stream of nitrogen. The solution was diluted with ethyl acetate (20 ml) and washed with a chilled aqueous sodium bisulfite (1 g), a dilute aqueous sodium chloride, and a saturated aqueous sodium chloride. The organic layer was dried over magnesium sulfate and evaporated to give an amorphous solid (191 mg). This residue was dissolved in dichloromethane (2.5 ml) containing dimethyl sulfide (0.7 ml) and cooled to 0° C. The solution was stirred at 0° C. for seven hours and at room temperature for 40.5 hours. The resultant solution was heated to 50° C. for 34.5 hours and left at room temperature for two days. The mixture was evaporated and the residue was chromatographed on silica gel (5 g) eluting with 5 to 10% acetone in dichloromethane to afford p-nitrobenzyl 4-[(2R,3S)-3-{(1S)-1-(p-nitrobenzyloxycarbonyloxy)ethyl}-4-oxoazetidin-2-yl]-3-oxobutanoate (124 mg).

IR (CH$_2$Cl$_2$): 3390, 1765, 1745, 1715, 1605, 1525, 1345 cm$^{-1}$.

NMR (CDCl$_3$) δ: 1.46 (d, J=6.5 Hz, 3H), 3.00 (m, 2H), 3.10 (dd, J=2.5, 5 Hz, 1H), 3.60 (s, 3H), 3.85 (m, 1H), 5.16 (m, 1H; d, J=5 Hz upon irradiation at 1.46 ppm), 5.27 (s, 4H), 6.47 (br s, 1H), 7.51 (d, J=9 Hz, 2H), 7.53 (d, J=9 Hz, 2H), 8.18 (d, J=9 Hz, 4H).

[α]$_D^{22}$ +28.13° C. (c=0.736, CHCl$_3$).

EXAMPLE 66

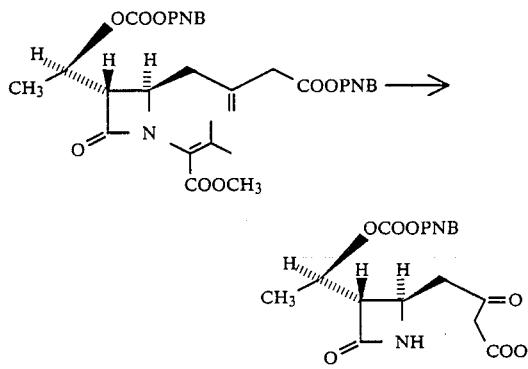

A stream of ozone was bubbled into a solution of methyl 3-methyl-2-[(3S,4R)-4-{2-(p-nitrobenzyloxycarbonylmethyl)allyl}-3-}(1R)-1-(p-nitrobenzyloxycarbonyloxy)ethyl}-2-oxoazetidin-1-yl]but-2-enoate (233 mg) in ethyl acetate (10 ml) at −78° C. until blue color appeared. After three minutes, the excess of ozone was removed by a stream of nitrogen. The solution was diluted with ethyl acetate (20 ml) and washed with a chilled aqueous sodium bisulfite (1.2 g) and brine. The organic layer was dried over magnesium sulfate and evaporated to leave an amorphous solid (240 mg). This residue was dissolved in dichloromethane (3 ml) containing dimethyl sulfide (0.9 ml) and cooled to 0° C. Methanol (9 ml) was added and the solution was stirred at 0° C. for five hours, and at room temperature for nine hours under a nitrogen atmosphere. The mixture was then heated to 55° C. for 31 hours. The resultant solution was evaporated, and the residue was chromatographed on silica gel (6 g) eluting with 5–14% acetone in dichloromethane to give p-nitrobenzyl 4-[(2R,3S)-3-{(1S)-1-(p-nitrobenzyloxycarbonyloxy)-ethyl}-4-oxoazetidin-2-yl]-3-oxobutanoate (145 mg).

IR (CH$_2$Cl$_2$): 3370, 1760, 1745, 1710, 1605, 1520, 1350 cm$^{-1}$.

NMR (CDCl$_3$) δ: 1.42 (d, J=6.5 Hz, 3H), 2.8–3.1 (m, 3H), 3.60 (s, 2H), 3.94 (ddd, J=2.5,5,8 Hz, 1H), 5.11 (quintet, J=7 Hz, 1H), 5.26 (s, 4H), 6.52 (brs, 1H), 7.50 (d, J=9 Hz, 2H), 7.52 (d, J=9 Hz, 2H), 8.17 (d, J=9 Hz, 2H).

[α]$_D^{22}$ +21.83° (c=0.907, CHCl$_3$).

EXAMPLE 67

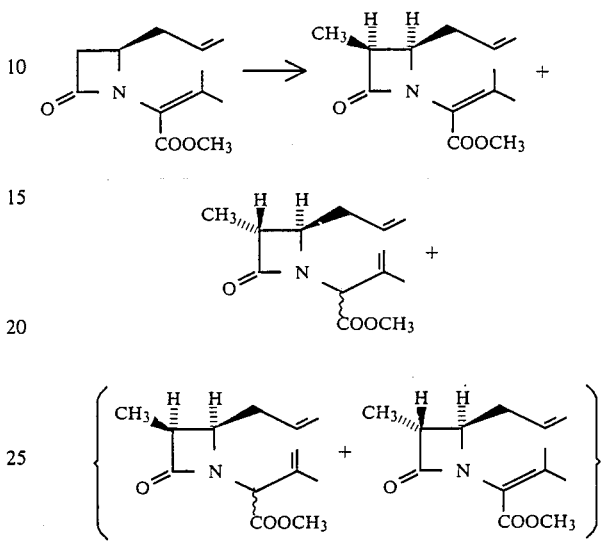

1.55M Butyl lithium-hexane solution (1.66 ml) was added to a solution of N-isopropylcyclohexylamine (0.29 ml) in tetrahydrofuran (3 ml) at −70° C., and the mixture was stirred for 20 minutes at −70° C. and allowed to warm up to 0° C. This mixture was added to a solution of methyl 3-methyl-2-[(4R)-2-oxo-4-allylazetidin-1-yl]but-2-enoate (100 mg) in tetrahydrofuran (3 ml) at −70° C., and the mixture was stirred for 1 hour at −70° C. and allowed to warm up to −30° C. during 30 minutes. 1N Hydrochloric acid (3.6 ml) was added to the reaction mixture at −70° C., and the mixture was diluted with ethyl acetate (30 ml). The solution was washed with water and brine, dried over magnesium sulfate, and evaporated in vacuo. The residue was chromatographed on silica gel eluting with a mixture of hexane and ethyl acetate (5:1–2:1) to give methyl 3-methyl-2-[(3S,4R)-3-methyl-2-oxo-4-allylazetidin-1-yl]but-2-enoate (20 mg); IR (CH$_2$Cl$_2$): 1740, 1715 cm$^{-1}$; NMR (CDCl$_3$) δ: 1.23 (d, 3H, J=8 Hz), 1.95 (s, 3H), 2.19 (s, 3H), 1.36 (t, 2H, J=7 Hz), 3.36 (dq, 1H, J=6, 8 Hz), 3.75 (s, 3H), 4.04 (dt, 1H, J=6, 7 Hz), 4.9–5.2 (m, 2H), 5.4–5.9 (m, 2H); and methyl 3-methyl-2-[(3R,4R)-3-methyl-2-oxo-4-allylazetidin-1-yl]but-3-enoate (28 mg); IR (CH$_2$Cl$_2$): 1740 cm$^{-1}$. NMR (CDCl$_3$) δ: 1.27 and 1.29 (a pair of d, 3H, J=8 Hz), 1.83 (broad s, 3H), 2.1–2.9 (m, 2H), 2.85 (dq, 1H, J=2, 8 Hz), 3.2–3.4 (m, 1H), 3.74 and 3.76 (a pair of s, 3H), 4.8–5.2 (m, 5H), 5.5–6.0 (m, 1H); and a mixture of methyl 3-methyl-2-[(3R,4R)-3-methyl-2-oxo-4-allylazetidin-1-yl]but-2-enoate and methyl 3-methyl-2-[(3S,4R)-3-methyl-2-oxo-4-allylazetidin-1-yl]but-3-enoate (36 mg): IR (CH$_2$Cl$_2$): 1740 cm$^{-1}$.

EXAMPLE 68

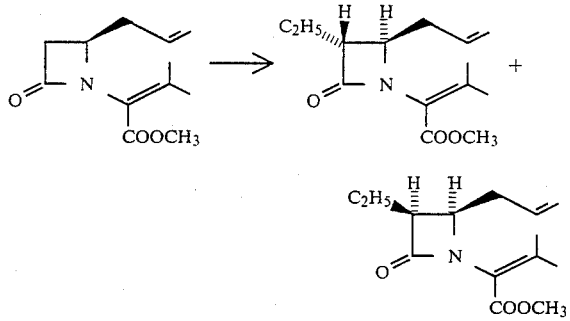

1.55M Butyl lithium-hexane solution (2.97 ml) was added to a solution of N-isopropylcyclohexylamine (0.76 ml) in tetrahydrofuran (6 ml) at −70° C. and the mixture was stirred for 20 minutes at −70° C. This mixture was added to a solution of methyl 3-methyl-2-[(4R)-2-oxo-4-allylazetidin-1-yl]but-2-enoate (210 mg) in tetrahydrofuran (6 ml) during 3 minutes at −70° C., and the mixture was stirred for 1 hour at −70° C. and for 30 minutes at −30° C. Ethyl iodide (0.37 ml) was then added to the reaction mixture at −70° C. and the mixture was stirred for 1 hour at the same temperature and for 30 minutes at −30° C. 1N Hydrochloric acid (10 ml) was added to the reaction mixture at −70° C. and the mixture was diluted with ethyl acetate (120 ml). The solution was washed with water, brine, aqueous sodium bicarbonate and brine, dried over magnesium sulfate and evaporated in vacuo. Triethylamine (0.16 ml) was added to a solution of the residue in dichloromethane (2 ml) at 0° C., and the mixture was stirred overnight at ambient temperature. The reaction mixture was diluted with ethyl acetate (20 ml) and the solution was washed with 0.1N hydrochloric acid, brine, aqueous sodium bicarbonate and brine dried over magnesium sulfate, and evaporated in vacuo. The residue was chromatographed on silica gel (5 g) eluting with a mixture of hexane and ethyl acetate (10:1–2:1) to give 169 mg of a 2.3:1 mixture of methyl 3-methyl-2-[(3R,4R)-3-ethyl-2-oxo-4-allylazetidin-1-yl]but-2-enoate [(3R,4R)-isomer] and its (3S,4R)-isomer: IR (CH$_2$Cl$_2$): 1740, 1720 cm$^{-1}$. NMR (CDCl$_3$) δ: 1.04 and 1.12 (a pair of t, 3H, J=8 Hz), 1.6–2.0 (m, 2H), 1.96 (s, 3H), 2.20 (s, 3H), 2.2–2.61 (m, 2H), 2.80 and 3.14 (a pair of dq, 1H, J=2.5, 7 Hz and J=6, 7.5H (2.3:1), 3.70 and 4.04 (a pair of dt, 1H, J=2.5, 7 Hz and J=6, 7 Hz), 3.76 (s, 3H), 4.9–5.3 (m, 2H), 5.5–6.0 (m, 1H).

EXAMPLE 69

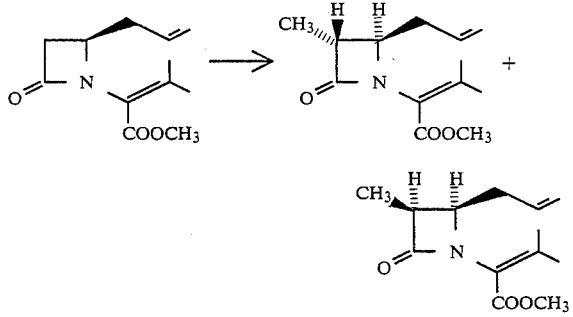

Methyl 3-methyl-2-[(3R,4R)-3-methyl-2-oxo-4-allylazetidin-1-yl]but-2-enoate [(3R,4R)-isomer] and its (3S,4R)-isomer were prepared in a similar manner to that of Example 68.

For the (3R,4R)-isomer: IR (CH$_2$Cl$_2$): 1740, 1710 cm$^{-1}$. NMR (CDCl$_3$) δ: 1.32 (d, 3H, J=7.5 Hz), 1.93 (s, 1H), 1.19 (s, 1H), 2.36 (q, 2H, J=8 Hz), 2.84 (dq, 1H, J=2.5, 7.5 Hz), 3.56 (dt, 1H, J-2.5, 8 Hz), 3.72 (s, 3H), 4.9–6.3 (m, 2H), 5.5–6.0 (m, 1H).

For the (3S,4R)-isomer: IR (CH$_2$Cl$_2$): 1740, 1715 cm$^{-1}$. NMR (CDCl$_3$) δ: 1.23 (d, 3H, J=8 Hz), 1.95 (s, 3H), 2.19 (s, 3H), 1.36 (t, 2H, J=7 Hz), 3.36 (dq, 1H, J=6, 8 Hz), 3.75 (s, 3H), 4.04 (dt, 1H, J=6, 7 Hz), 4.9–5.2 (m, 2H), 5.4–5.9 (m, 2H).

EXAMPLE 70

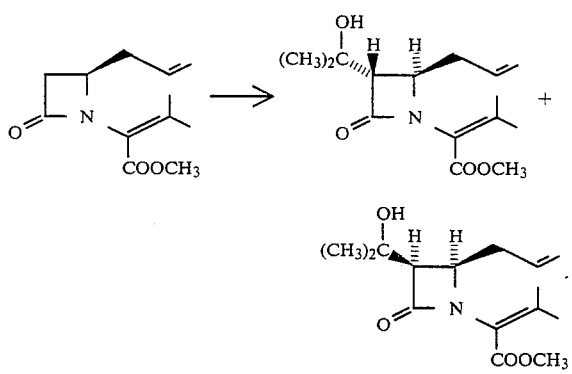

1.55M Butyl lithium-hexane solution (2.82 ml) was added to a solution of N-isopropylcyclohexylamine (0.72 ml) in tetrahydrofuran (6 ml) at −70° C., and the mixture was stirred for 20 minutes at −70° C. This mixture was added to a solution of methyl 3-methyl-2-[(4R)-2-oxo-4-allylazetidin-1-yl]but-2-enoate (247 mg) in tetrahydrofuran (6 ml) at −70° C. and the mixture was stirred for 1 hour at −70° C., and for 30 minutes at −30° C. Acetone (0.12 ml) was added to the reaction mixture at −70° C., and the mixture was stirred for 1 hour at −70° C. and for 30 minutes at −30° C.–15° C. 3N Hydrochloric acid was added to the reaction mixture at −70° C. and the mixture was diluted with ethyl acetate (200 ml). The solution was washed with water, brine, aqueous sodium bicarbonate and brine, dried over magnesium sulfate, and evaporated in vacuo. Triethylamine (0.15 ml) was added to a solution of the residue in dichloromethane (3 ml) at 0° C. and the mixture was stirred overnight at ambient temperature. The reaction mixture was diluted with ethyl acetate (20 ml) and the solution was washed with 0.1N hydrochloric acid (15 ml) brine, aqueous sodium bicarbonate and brine, dried over magnesium sulfate, and evaporated in vacuo. The residue was chromatographed on silica gel (10 g) eluting with a mixture of benzene and acetone (10:1–2:1) to give methyl 3-methyl-2-[(3S, 4R)-3-(1-hydroxy-1-methylethyl)-2-oxo-4-allylazetidin-1-yl]but-2-enoate (100 mg); IR (CH$_2$Cl$_2$): 1740, 1715 cm$^{-1}$. NMR (CDCl$_3$) δ: 1.31 (s, 3H), 1.38 (s, 3H), 1.96 (s, 3H), 2.18 (s, 3H), 2.2–2.5 (m, 3H), 2.90 (d, 1H, J=3 Hz), 3.76 (s, 3H), 3.81 (dt, 1H, J=3, 7 Hz), 4.9–5.2 (m, 2H), 5.5–6.0 (m, 1H) and methyl 3-methyl-2-[(3R,4R)-3-(1-hydroxy-1-methylethyl)-2-oxo-4-allylazetidin-1-yl]but-2-enoate (50 mg).

NMR (CDCl$_3$) δ: 1.39 (s, 3H), 1.52 (s, 3H), 1.99 (s, 3H), 2.19 (s, 3H), 2.21 (broad s, 1H), 2.74 (t, 2H, J=7

Hz), 3.30 (d, 1H, J=6 Hz), 3.74 (s, 3H), 4.12 (dt, 1H, J=6, 7 Hz), 4.9–5.2 (m, 2H), 5.5–5.9 (m, 1H).

EXAMPLE 71

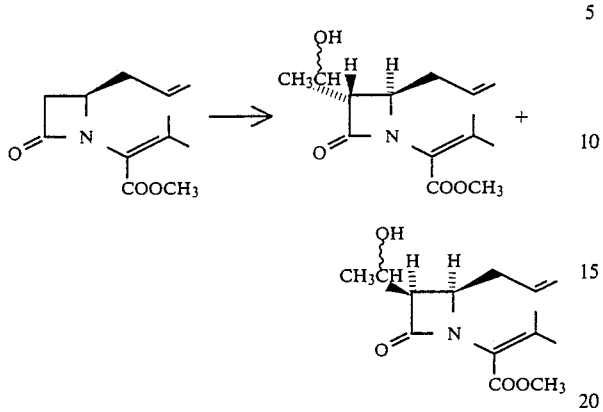

Methyl 3-methyl-2-[(3S,4R)-3-[(1RS)-1-hydroxyethyl]-2-oxo-4-allylazetidin-1-yl]but-2-enoate [(3S,4R)-isomer] and methyl 3-methyl-2-[(3R,4R)-3-[(1RS)-1-hydroxyethyl]-2-oxo-4-allylazetidin-1-yl]but-2-enoate [(3R,4R)-isomer] were prepared in a similar manner to that of Example 70.

For the (3S,4R)-isomer: IR (CH₂Cl₂): 1740, 1720 cm⁻¹. NMR (CDCl₃) δ: 1.32 (d, 3H, J=7 Hz), 1.96 (s, 3H), 2.20 (s, 3H), 2.3–2.5 (m, 2H), 2.6 (broad s, 1H), 2.90 (dd, 1H, J=7, 2.5 Hz), 3.76 (s, 3H), 3.82 (dt, 1H, J=2.5, 6 Hz), 4.0–4.3 (m, 1H), 5.0–5.2 (m, 2H), 5.5–6.0 (m, 1H).

For the (3R,4R)-isomer: IR (CH₂Cl₂): 1740, 1720 cm⁻¹. NMR (CDCl₃) δ: 1.22 (d, 3H, J=5.5 Hz), 2.00 (s, 3H), 2.20 (s, 3H), 2.2–2.8 (m, 3H), 3.24 (dq, 1H, J=4.5, 5.5 Hz), 3.75 (s, 3H), 3.9–4.3 (m, 2H), 4.9–5.2 (m, 2H), 5.5–6.0 (m, 1H).

EXAMPLE 72

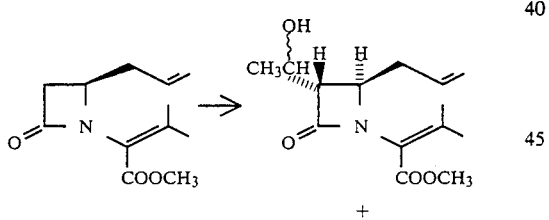

and its other isomers 1.55M Butyl lithium-hexane solution (5.63 ml) was added to a solution of N-isopropylcyclohexylamine (1.44 ml) in tetrahydrofuran (10 ml) at −70° C. The solution was stirred for 20 minutes at −70° C. and allowed to warm up to −20° C. during 5 minutes. This mixture was added to a solution of methyl 3-methyl-2-[(4R)-2-oxo-4-allylazetidin-1-yl]but-2-enoate (650 mg) in tetrahydrofuran (10 ml) during 15 minutes at −70° C., and the mixture was stirred for 1 hour at −70° C. and for 30 minutes at −30° C. A solution of acetaldehyde (187 mg) in tetrahydrofuran (4.4 ml) was added to the reaction mixture at −70° C. The mixture was stirred for 1 hour at −70° C. and for 30 minutes at −30° C. 1N Hydrochloric acid (20 ml) was added to the reaction mixture at −70° C. and the mixture was diluted with ethyl acetate (250 ml). The solution was washed with brine, aqueous sodium bicarbonate and brine, dried over magnesium sulfate and evaporated in vacuo.

The residue was chromatographed on silica gel (20 g) eluting with a mixture of benzene and acetone (10:1–3:1) to give methyl 3-methyl-2-{(3S,4R)-3-[(1RS)-1-hydroxyethyl]-2-oxo-4-allylazetidin-1-yl}but-2-enoate (278 mg) [(3S,4R)-isomer] and its other isomers (257 mg).

For the (3S,4R)-isomer: IR (CH₂Cl₂): 1740, 1720 cm⁻¹. NMR (CDCl₃) δ: 1.32 (d, 3H, J=7 Hz), 1.96 (s, 3H), 2.20 (s, 3H), 2.3–2.5 (m, 2H), 2.6 (broad s, 1H), 2.90 (dd, 1H, J=7, 2.5 Hz), 3.76 (s, 3H), 3.82 (dt, 1H, J=2.5, 6 Hz), 4.0–4.3 (m, 1H), 5.0–5.2 (m, 2H), 5.5–6.0 (m, 1H).

EXAMPLE 73

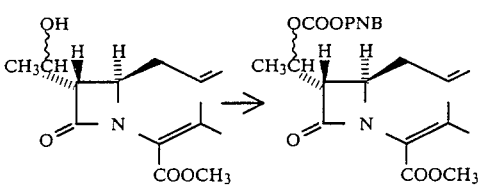

4-Dimethylaminopyridine (79 mg) and 4-nitrobenzyl chloroformate (90 mg) were added to a solution of a 1:3 mixture of methyl 3-methyl-2-[(3S,4R)-3-(1RS)-1-hydroxyethyl)-2-oxo-allylazetidin-1-yl]but-2-enoate (86 mg) in dichloromethane (4 ml) at 0° C. and the mixture was stirred for three hours at 0° C. The reaction mixture was diluted with ethyl acetate (50 ml), and washed in turn with 0.1N hydrochloric acid (20 ml), brine, aqueous sodium bicarbonate and brine. The organic layer was dried over magnesium sulfate and evaporated in vacuo. The residue was chromatographed on silica gel (2 g) eluting with hexane and ethyl acetate (5:1–2:1) to give a 1:3 mixture of methyl 3-methyl-2-{(3S,4R)-3-[(1Rs)-1-(4-nitrobenzyloxycarbonyloxy)ethyl]-2-oxo-4-allylazetidin-1-yl}but-2-enoate (122 mg) as an oil.

IR (CH₂Cl₂): 1745, 1715, 1520 cm⁻¹. NMR (CDCl₃) δ: 1.48 (d, 3H, J=7 Hz), 1.96 (s, 3H), 1.20 (s, 3H), 2.2–2.6 (m, 2H), 3.03 and 3.18 (dd, J=7.5, 2.5 Hz and dd, J=5, 2.5 Hz, 1H (1:3)), 3.75 (s, 3H), 3.8–4.0 (m, 1H), 5.0–5.3 (m, 2H), 5.27 (s, 2H), 5.5–5.9 (m, 1H), 7.89 (A₂B₂, 4H, J=8.5 Hz).

EXAMPLE 74

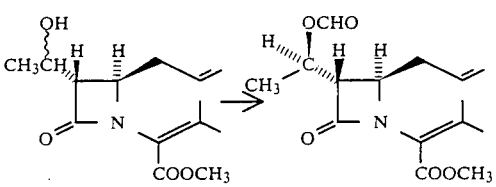

A 1:3 mixture of methyl 3-methyl-2-[(3S,4R)-3-[(1RS)-1-hydroxyethyl]-2-oxo-4-allylazetidin-1-yl]but-2-enoate (55 mg) was dissolved in tetrahydrofuran (2 ml) and triphenylphosphine (135 mg) and formic acid (19.4 μl) were added to the mixture. This mixture was cooled to 0° C. and a solution of diethyl azodicarboxylate (81 μl) in tetrahydrofuran (1 ml) was added. After stirring at the same temperature overnight, the mixture was diluted with ethyl acetate (30 ml), washed with aqueous sodium bicarbonate and brine, dried over magnesium sulfate and evaporated. The residue was chromatographed on silica gel (5 g) eluting with hexane and ethyl acetate (10:1–2:1) to give 25 mg of methyl 3-methyl-2-[(3S,4R)-3-[(1R)-1-formyloxyethyl]-2-oxo-4-allylazetidin-1-yl]-but-2-enoate.

IR (CH$_2$Cl$_2$): 1745, 1720 cm$^{-1}$. NMR (CDCl$_3$) δ: 1.42 (d, 3H, J=6 Hz), 1.96 (s, 3H), 2.20 (s, 3H), 2.38 (q, 2H, J=6 Hz), 3.00 (dd, 1H, J=7.5, 2.5 Hz), 3.76 (s, 3H), 3.7–4.0 (m, 1H), 4.9–5.2 (m, 2H), 5.3–5.9 (m, 2H), 8.00 (s, 1H).

EXAMPLE 75

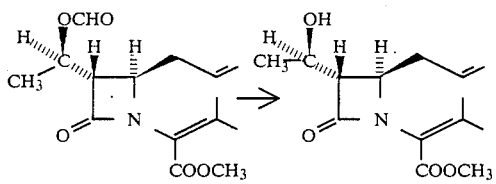

Methyl 3-methyl-2-[(3S,4R)-3-[(1R)-1-formyloxyethyl]-2-oxo-4-allylazetidin-1-yl]but-2-enoate (23 mg) was dissolved in methanol (1 ml) and cooled to 0° C. To this solution was added a solution of sodium methoxide in methanol (0.49M, 0.16 ml) and the mixture was stirred for 1 hour at the same temperature. An additional 0.08 ml of the sodium methoxide solution was added and the mixture was stirred for 30 minutes at the same temperature. Acetic acid (2 drops) was then added and the mixture was evaporated. The residue was dissolved in ethyl acetate, washed with aqueous sodium bicarbonate and brine, dried over magnesium sulfate and evaporated. The residue was purified by preparative thin layer chromatography (silica gel) developing with methylene chloride and ethyl acetate (2:1) to give methyl 3-methyl-2-[(3S,4R)-3-(1R)-1-hydroxyethyl)-2-oxo-4-allylazetidin-1-yl]but-2-enoate (20 mg), IR (CH$_2$Cl$_2$): 3550, 1740, 1710 cm$^{-1}$. NMR (CDCl$_3$) δ: 1.32 (d, 3H, J=7 Hz), 1.96 (s, 3H), 2.20 (s, 3H), 2.3–2.6 (m, 2H), 2.90 (dd, 1H, J=7, 2.5 Hz), 3.76 (s, 3H), 4.00 (dt, 1H, J=2.5, 6.5 Hz), 4.1–4.4 (m, 1H), 5.0–5.3 (m, 2H), 5.5–6.0 (m, 1H).

EXAMPLE 76

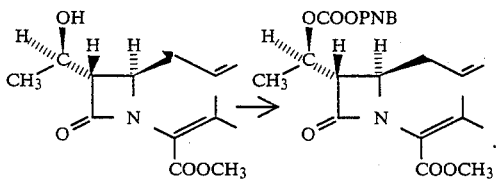

Methyl 3-methyl-2-[(3S,4R)-3-[(1R)-1-(4-nitrobenzyloxycarbonyloxy)ethyl]-2-oxo-4-allylazetidin-1-yl]but-2-enoate was prepared in a similar manner to that of Example 73.

IR (CH$_2$Cl$_2$) δ: 1745, 1715, 1520 cm$^{-1}$. NMR (CDCl$_3$) δ: 1.45 (d, 3H, J=6 Hz), 1.94 (s, 3H), 2.19 (s, 3H), 2.37 (q, 2H, J=6 Hz), 3.01 (dd, 1H, J=7.5, 2.5 Hz), 3.76 (s, 3H), 3.92 (dt, 1H, J=2.5 6 Hz), 4.9–5.3 (m, 3H), 5.4–5.8 (m, 1H), 7.83 (A$_2$B$_2$, 4H, J=9 Hz).

EXAMPLE 77

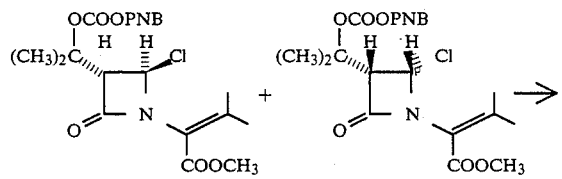

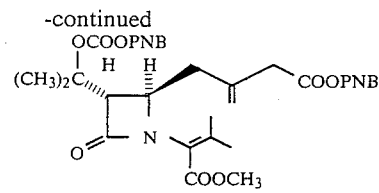

Silver tetrafluoroborate (205 mg) was added to a stirred solution of 4-nitrobenzyl 3-(trimethylsilylmethyl)but-3-enoate (422 mg) and a 4:1 mixture of methyl 2-[(3S,4R)-4-chloro-3-[1-methyl-1-(4-nitrobenzyloxycarbonyloxy)ethyl]-2-oxoazetidin-1-yl]-3-methylbut-2-enoate and its (3S,4S)-isomer (305 mg) in dichloromethane (3 ml) at −78° C. under a nitrogen atmosphere. The mixture was gradually allowed to warm to 0° C. during 40 minutes and kept at the same temperature for one hour. The resulting mixture was diluted with dichloromethane (1 ml) and stirred at 0° C. for 30 minutes and at room temperature for 30 minutes. The mixture was diluted with ethyl acetate (10 ml) and a saturated aqueous solution of sodium chloride (4 ml) was added. The mixture was brought to pH 7 with a saturated aqueous solution of sodium bicarbonate and filtered through diatomaceous earth. The filtrate was diluted with ethyl acetate (30 ml). The organic layer was separated, washed with brine, dried over magnesium sulfate, and evaporated. The residue was chromatographed on silica gel (12 g, eluting with 1 to 5% acetone in dichloromethane) to give 120 mg of the desired product contaminated with some impurities. Further purification on a TLC plate (20 cm×20 cm×2 mm, 1:1 hexane-ethyl acetate) afforded 100 mg (22.8%) of methyl 3-methyl-2-[(3S,4R)-3-[1-methyl-1-(4-nitrobenzyloxycarbonyloxy)ethyl]-4-[2-(4-nitrobenzyloxycarbonyl-methyl)allyl]-2-oxoazetidin-1-yl]but-2-enoate: IR (CH$_2$Cl$_2$): 1740, 1720(sh), 1520, and 1350 cm$^{-1}$; NMR (CDCl$_3$), δ: 1.65 (s, 3H), 1.69 (s, 3H), 1.98 (s, 3H), 2.19 (s, 3H), 2.48 (brd, J=7 Hz, 2H), 3.13 (s, 2H), 3.44 (d, J=2.5 Hz, 1H), 3.76 (s, 3H), 4.24 (dt, J=2.5 and 7 Hz, 1H), 5.01 (m, 2H), 5.19 (s, 2H), 5.22 (s, 2H), 7.52 (d, J=9 Hz, 2H), 7.56 (d, J=9 Hz, 2H), and 8.22 (d, J=9 Hz, 4H).

EXAMPLE 78

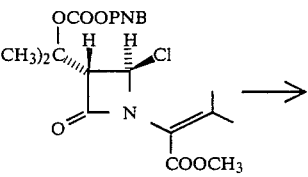

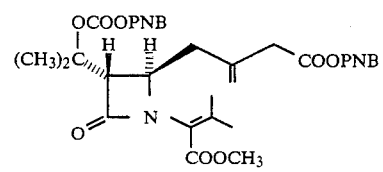

In a manner similar to that of Example 77, 258 mg of methyl 2-[(3S,4R)-4-chloro-3-[1-methyl-1-(4-nitrobenzyloxycarbonyloxy)ethyl]-2-oxoazetidin-1-yl]-3-methylbut-2-enoate afforded 70.0 mg (18.9%) of methyl 3-methyl-2-[(3S,4R)-3-[1-methyl-1-(4-nitrobenzyloxycarbonyloxy)ethyl]-4-[2-(4-nitrobenzyloxycarbonyl-methyl)allyl]-2-oxoazetidine-1-yl]but-2-enoate.

EXAMPLE 79

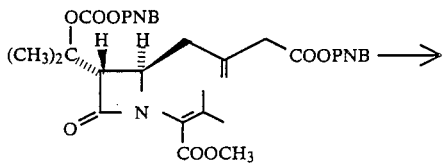

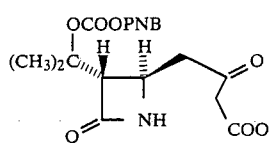

A stream of ozone was bubbled into a solution of methyl 3-methyl-2-[(3S,4R)-3-[1-methyl-1-(4-nitrobenzyloxycarbonyloxy)ethyl]-4-[2-(4-nitrobenzyloxycarbonylmethyl)allyl]-2-oxoazetidin-1-yl]but-2-enoate (163 mg) in ethyl acetate (10 ml) at −78° C. until a permanent blue color developed. After three minutes the excess ozone was removed by bubbling nitrogen. The solution was warmed and poured into a mixture of ethyl acetate (10 ml) and a dilute aqueous solution of sodium bisulfite (900 mg). The mixture was shaken and the organic layer was separated. The solution was washed with brine, dried over magnesium sulfate and evaporated to leave 158 mg of an amorphous solid. This residue was dissolved in dichloromethane (2.5 ml) and cooled to 0° C. Dimethyl sulfide (0.7 ml) and methanol (7.5 ml) were added. The solution was stirred at 0° C. for 8 hours and left at ambient temperature for 15 hours under a nitrogen atmosphere. The mixture was then heated to 55° C. for 26 hours and evaporated. The residue was chromatographed on a TLC plate (20 cm×20 cm×2 mm, 10% acetone in dichloromethane) to give 79 mg (58.3%) of 4-nitrobenzyl 4-[(2R,3S)-3-[1-methyl-1-(4-nitrobenzyloxycarbonyloxy)ethyl]-4-oxoazetidin-2-yl]-3-oxobutanoate: IR (CH$_2$Cl$_2$): 3370, 1760, 1740, 1710, 1520, and 1345 cm$^{-1}$; NMR (CDCl$_3$) δ: 1.57 (s, 3H), 1.62 (s, 3H), 2.4–3.2 (m, small signals), 2.9 (m, 1.5H), 3.34 (d, J=3 Hz, 1H), 3.56 (s, 2H), 3.96 (m, 1H), 5.15 (s, 2H), 5.24 (s, 2H), 6.42 (brs, 1H), 7.50 (d, J=9 Hz, 4H), and 8.16 (d, J=9 Hz, 4H).

(The product may exist as a equilibrium mixture of the keto- and enol-form.)

EXAMPLE 80

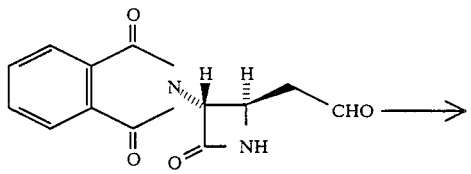

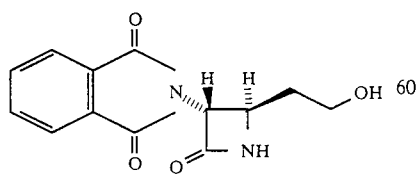

To a solution of (3R,4R)-4-(2-oxoethyl)-3-phthalimidoazetidin-2-one (52 mg) in a mixture of methanol (3ml) and dichloromethane (1 ml) was added a solution of sodium borohydride (8 mg) in methanol (2 ml) at 0° C. during one hour. The reaction was quenched by addition of acetic acid (two drops). After evaporation in vacuo, the residue was chromatographed on silica gel (1.6 g; eluting with 3 to 5% methanol in dichloromethane) to give 32 mg of crude crystals. Crystallization from a mixture of methanol and ether afforded 27 mg(51.5%) of (3R,4R)-4-(2-hydroxyethyl)-3-phthalimidoazetidin-2-one. IR (Nujol): 3350(br), 3250, 1750, and 1705 cm$^{-1}$; NMR (DMSO-d$_6$) δ: 1.79 (q, J=6 Hz, 2H), 3.46 (m, 2H), 3.97 (dt, J=2.5 and 6 Hz, 1H), 4.47 (brs, 1H), 4.89 (d, J=2.5 Hz, 1H), 7.86 (s, 4H), and 8.42 (brs, 1H).

EXAMPLE 81

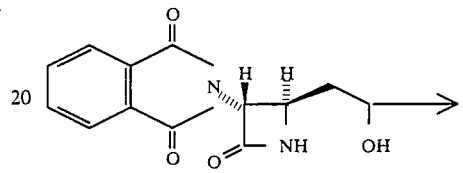

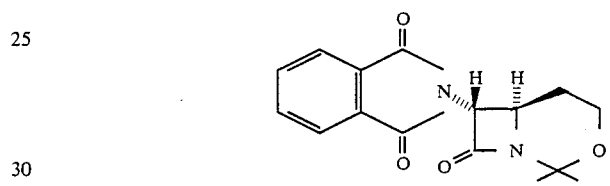

Boron trifluoride etherate (5 μl) was added to a suspension of (3R,4R)-4-(2-hydroxyethyl)-3-phthalimidoazetidin-2-one (126 mg) and 2,2-dimethoxypropane (74 μl) in dichloromethane (3 ml) at ambient temperature. The mixture was stirred for two hours. Additional dimethoxypropane (50 μl) was added and the mixture was stirred for an additional 1.5 hours. The resulting solution was poured into a saturated aqueous solution of sodium chloride and sodium bicarbonate and extracted twice with dichloromethane. The combined extracts were dried over magnesium sulfate and evaporated to give a crystalline solid. Chromatography on silica gel (4 g; eluting with 3% acetone in dichloromethane) and washing the crystals with ether afforded 100 mg of (6R,7R)-2,2-dimethyl-7-phthalimido-1-aza-3-oxabicyclo[4.2.0]-octan-8-one: IR (CH$_2$Cl$_2$): 1770 and 1720 cm$^{-1}$; NMR (CDCl$_3$) δ: 1.56 (s, 3H), 1.81 (s, 3H), 1.7–2.0 (m, 2H), 3.7–4.1 (m, 3H), 5.01 (d, J=2 Hz, 1H), and 7.5–7.9 (m, 4H).

EXAMPLE 82

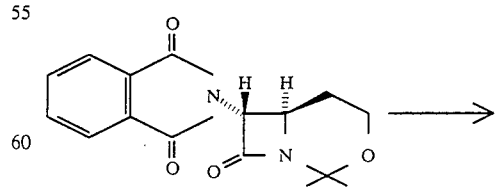

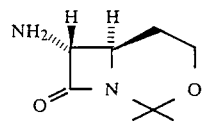

N,N-Dimethylaminopropylamine (91 μl) was added to a solution of (6R,7R)-2,2-dimethyl-7-phthalimido-1-aza-3-oxabicyclo[4.2.0]octan-8-one (80 mg) in a mixture of methanol (1.4 ml) and dichloromethane (0.7 ml) at 0° C. under a nitrogen atmosphere. The solution was stirred at the same temperature for two hours and left at ambient temperature for 24 hours. The mixture was evaporated and the residue was chromatographed on silica gel (1.5 g; eluting with 3 to 5% methanol in dichloromethane) to give 27 mg (59.5%) of (6R,7R)-7-amino-2,2-dimethyl-1-aza-3-oxabicyclo[4.2.0]octan-8-one: IR (CH$_2$Cl$_2$): 3100–3600 (broad) and 1735 cm$^{-1}$; NMR (CDCl$_3$) δ: 1.41 (s, 3H), 1.72 (s, 3H), 1.5–2.1 (m, 4H), 3.34 (ddd, J=2, 5 and 10 Hz, 1H), and 3.7–3.9 (m, 3H).

EXAMPLE 83

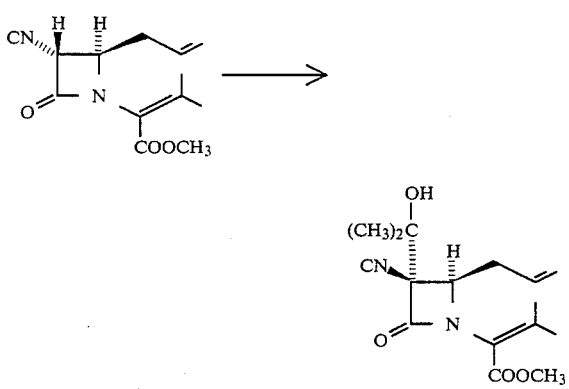

To a solution of methyl 2-[(3R,4R)-3-isocyano-2-oxo-4-allylazetidin-1-yl]-3-methylbut-2-enoate (106.9 mg) in tetrahydrofuran (2.1 ml) was added dropwise a solution of n-butyl lithium (0.375 ml of 1.38M solution in hexane) at −78° C. After stirring for 15 minutes at −78° C., the reaction mixture was added with a solution of acetone (0.0385 ml) in tetrahydrofuran (0.3465 ml) at −78° C. After stirring for 25 minutes at −78° C., the reaction mixture was added with acetic acid (0.0493 ml) at −78° C., diluted with ethyl acetate (30 ml), and washed with chilled brine (10 ml), aqueous sodium bicarbonate (10 ml), brine (10 ml), and saturated aqueous sodium chloride (10 ml). After drying over magnesium sulfate, the ethyl acetate extract was filtered and evaporated in vacuo. The residual oil was chromatographed on silica gel (1.2 g) eluting with a mixture of ethyl acetate and hexane (1:5–1:3) to give methyl 2-[(3R,4R)-3-(1-hydroxy-1-methylethyl)-3-isocyano-2-oxo-4-allylazetidin-1-yl]-3-methylbut-2-enoate (96.5 mg) as an oil.

IR (CH$_2$Cl$_2$): 2115, 1770, 1720 cm$^{-1}$. NMR (CDCl$_3$) δ: 1.40 (s, 3H), 1.53 (s, 3H), 1.97 (s, 3H), 2.23 (s, 3H), 2.39 (s, 1H), 2.53 (t, 2H, J=7 Hz), 3.76 (s, 3H), 4.24 (t, 1H), J=7 Hz), 5.0–5.3 (m, 2H), 5.5–5.9 (m, 1H).

EXAMPLE 84

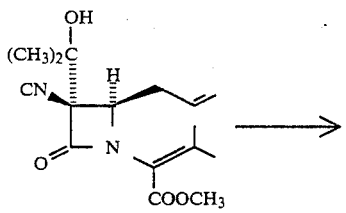

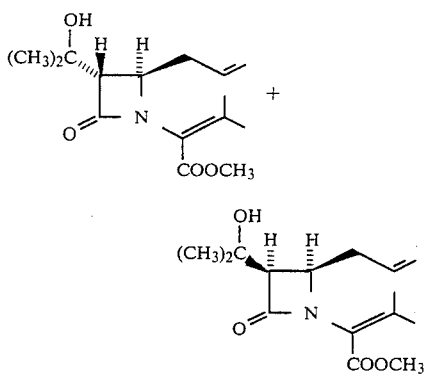

Tributyltin hydride (0.707 ml) was added to a mixture of methyl 2-[(3R,4R)-3-(1-hydroxy-1-methylethyl)-3-isocyano-2-oxo-4-allylazetidin-1-yl]-3-methylbut-2-enoate (630 mg) and azobisisobutyronitrile (34 mg) in benzene (6 ml) at room temperature, and the mixture was refluxed for 15 minutes. The reaction mixture was cooled and chromatographed on silica gel (20 g) eluting with a mixture of hexane and ethyl acetate (3:1–1:1) to give a 3:1 mixture (559 mg) of methyl 2-[(3S,4R)-3-(1-hydroxy-1-methylethyl)-2-oxo-4-allylazetidin-1-yl]-3-methylbut-2-enoate and its (3R,4R)-isomer.

IR (CH$_2$Cl$_2$): 1740, 1715 cm$^{-1}$. NMR (CDCl$_3$) δ: 1.31 (s, 3H×¾), 1.38 (s, 3H), 1.52 (s, 3H×¼), 1.96 (s, 3H×¾), 1.99 (s, 3H×¼), 2.18 (s, 3H), 2.1–2.8 (m, 2H), 2.90 (d, 1H×¾, J=3 Hz), 3.30 (d, 1H×¼, J=6 Hz), 3.74 (s, 3H×¼), 3.76 (s, 3H×¾), 3.8–4.2 (m, 1H), 4.9–5.2 (m, 2H), 5.5–5.9 (m, 1H).

EXAMPLE 85

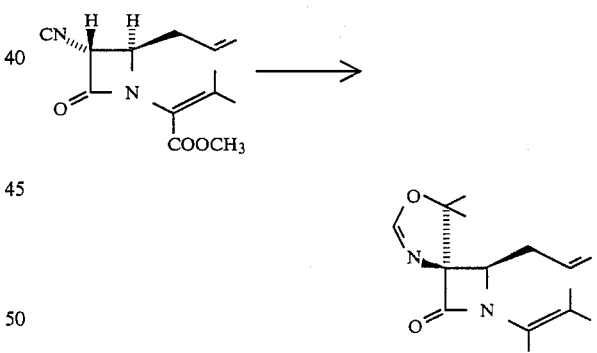

Potassium carbonate (113 mg) was added to a solution of methyl 2-[(3R,4R)-3-isocyano-2-oxo-4-allylazetidin-1-yl]-3-methylbut-2-enoate (203 mg) in acetone (2 ml) at 0° C., and the mixture was stirred for 20 hours at ambient temperature.

Potassium carbonate (210 mg) and acetone (1.5 ml) were added to the reaction mixture at ambient temperature, and the mixture was stirred for 18 hours at ambient temperature. The reaction mixture was diluted with dichloromethane (3 ml) and filtered. The filtrate was evaporated in vacuo, and the residue was chromatographed on silica gel (2 g) eluting with a mixture of hexane and ethyl acetate (3:1) to give methyl 2-[(3R,4R)-3-allyl-5,5-dimethyl-1-oxo-2,8-diaza-6-oxaspiro[3,4]oct-5-en-2-yl]-3-methylbut-2-enoate (120 mg).

IR (CH$_2$Cl$_2$): 1755, 1715, 1610 cm$^{-1}$.

NMR (CDCl$_3$) δ: 1.40 (s, 3H), 1.64 (s, 3H), 2.01 (s, 3H), 2.23 (s, 3H), 2.3–2.6 (m, 2H), 3.77 (s, 3H), 4.11 (t, 1H, J=7 Hz), 4.9–5.2 (m, 2H), 5.4–5.8 (m, 1H), 6.94 (s, 1H).

EXAMPLE 86

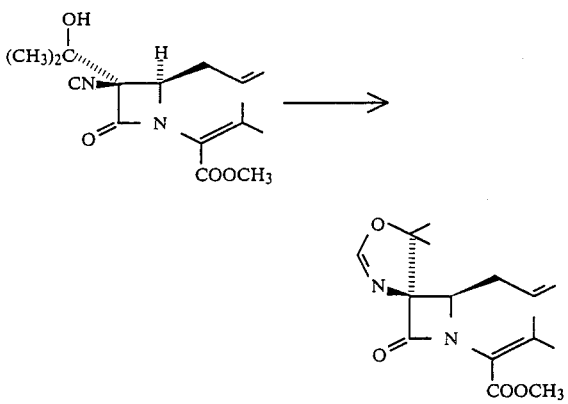

A solution of 1,8-diazabicyclo[5.4.0]undec-7-ene (17 μl) in methylene chloride (0.1 ml) was added to a solution of methyl 2-[(3R,4R)-3-(1-hydroxy-1-methylethyl)-3-isocyano-2-oxo-4-allylazetidin-1-yl]-3-methylbut-2-enoate (17 mg) in methylene chloride (1 ml) and acetone (1 ml) at 0° C., and the mixture was stirred for 20 hours at ambient temperature. Acetic acid (2 drops) was added to the reaction mixture at 0° C., and the mixture was evaporated in vacuo. The residue was dissolved in ethyl acetate (20 ml), and the solution was washed with 10% aqueous phosphoric acid, brine, phosphate buffer (pH 6.9), aqueous sodium bicarbonate and brine, dried over magnesium sulfate and evaporated in vacuo to give methyl 2-[(3R,4R)-3-allyl-5,5-dimethyl-1-oxo-2,8-diaza-6-oxaspiro[3,4]oct-7-en-2-yl]-3-methylbut-2-enoate (19 mg) as crude crystals.

EXAMPLE 87

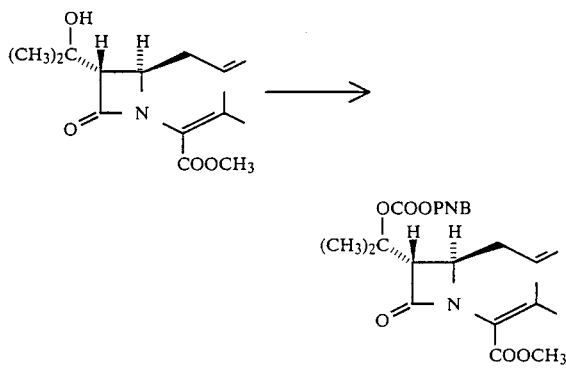

A solution of n-butyl lithium (0.42 ml of 1.55M solution in hexane) was added to a solution of methyl 2-[(3S,4R)-3-(1-hydroxy-1-methylethyl)-2-oxo-4-allylazetidin-1-yl]-3-methylbut-2-enoate (150 mg) in tetrahydrofuran (3 ml) during 3 minutes at −70° C. and the mixture was stirred for 5 minutes at −70° C. A solution of p-nitrobenzyl chloroformate (161 mg) in tetrahydrofuran (1.6 ml) was added to the mixture during 5 minutes at −70° C. and the mixture was stirred for 15 minutes at −70° C. The mixture was allowed to warm to 0° C. during 30 minutes and stirred for 2 hours at 0° C. Acetic acid (0.037 ml) was added to the mixture at 0° C. and the mixture was evaporated in vacuo. The residue was dissolved in ethyl acetate (50 ml), and was washed with water (10 ml), 10% phosphoric acid (10 ml), phosphate buffer (pH 7.0) (10 ml×2), aqueous sodium bicarbonate and brine. The organic layer was dried over magnesium sulfate and evaporated in vacuo. The residue was chromatographed on silica gel (10 g) eluting with a mixture of hexane and ethyl acetate (5:1–1:1) to give methyl 3-methyl-2-[(3S,4R)-3-[1-methyl-1-(4-nitrobenzyloxycarbonyloxy)ethyl]-2-oxo-4-allylazetidin-1-yl]but-2-enoate (135 mg) as an oil.

IR (CH$_2$Cl$_2$): 1740, 1710, 1520, 1345 cm$^{-1}$.

NMR (CDCl$_3$) δ: 1.66 (s, 3H), 1.69 (s, 3H), 1.97 (s, 3H), 2.19 (s, 3H), 2.2–2.5 (m, 2H), 3.40 (d, 1H), J=2.5 Hz), 3.71 (s, 3H), 4.03 (dt, 1H, J=2.5, 6.5 Hz), 4.9–5.2 (m, 2H), 5.19 (s, 2H), 5.5–5.9 (m, 1H), 7.90 (A$_2$B$_2$, 4H, J=9 Hz).

EXAMPLE 88

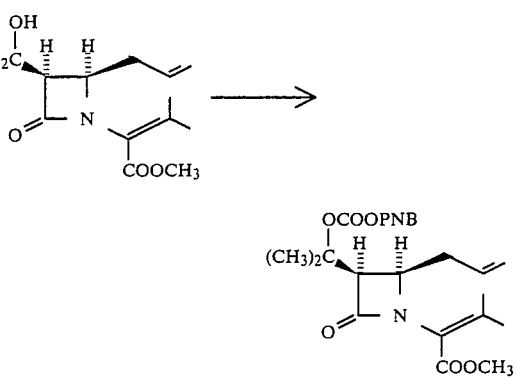

A solution of n-butyl lithium (0.46 ml) of 1.38M solution in hexane) was added to a solution of methyl 2-[3R,4R)-3-(1-hydroxy-1-methylethyl)-2-oxo-4-allylazetidin-1-yl]-3-methylbut-2-enoate (150 mg) in tetrahydrofuran (3 ml) at −70° C. and the mixture was stirred for 15 minutes at −70° C. A solution of p-nitrobenzyl chloroformate (161 mg) in tetrahydrofuran (3.2 ml) was added to the reaction mixture at −70° C. and the mixture was stirred for 10 minutes at −70° C. The mixture was allowed to warm to 0° C. during 30 minutes and stirred at 0° C. for 1.5 hours. Acetic acid (0.043 ml) was added to the mixture at 0° C. and the mixture was evaporated in vacuo. The residue was dissolved in ethyl acetate (30 ml) and the solution was washed with brine, aqueous sodium bicarbonate, and brine. The organic layer was dried over magnesium sulfate and evaporated in vacuo. The residue was chromatographed on silica gel (10 g) eluting with a mixture of hexane and ethyl acetate (10:1–3:1) to give methyl 3-methyl-2-[(3R,4R)-3-[1-methyl-1-(4-nitrobenzyloxycarbonyloxy)ethyl]-2-oxo-4-allylazetidin-1-yl]but-2-enoate (123 mg) as an oil.

IR (CH$_2$Cl$_2$): 1745, 1720, 1520, 1350 cm$^{-1}$.

NMR (CDCl$_3$) δ: 1.70 (s, 3H), 1.81 (s, 3H), 2.01 (s, 3H), 2.10 (s, 3H), 2.64 (t, 2H), J=7 Hz), 3.59 (d, 1H, J=5 Hz), 3.74 (s, 3H), 4.17 (dt, 1H, J=5,7 Hz), 4.9–5.3 (m, 2H), 5.21 (s, 2H), 5.5–5.9 (m, 1H), 7.87 (A$_2$B$_2$, 4H, J=9 Hz).

EXAMPLE 89

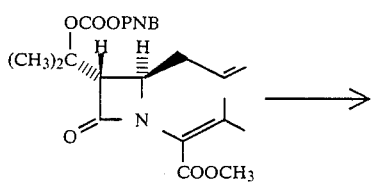

Ozone was bubbled into a solution of methyl 3-methyl-2-[(3S,4R)-3-[1-methyl-1-(4-nitrobenzyloxycarbonyloxy)ethyl]-2-oxo-4-allylazetidin-1-yl]but-2-enoate (50 mg) in ethyl acetate (3 ml) at −70° C. until a blue color appeared. After stirring for 15 minutes at the same temperature, the mixture was purged with nitrogen. The reaction mixture was diluted with ethyl acetate (20 ml) and the solution was washed with an aqueous solution of sodium bisulfite and sodium sulfite (2:1), and brine. The organic layer was dried over magnesium sulfate and evaporated in vacuo.

The residue was dissolved in methylene chloride (3 ml) and m-chloroperbenzoic acid (48 mg) was added to the solution at 0° C. The mixture was stirred for 24 hours at ambient temperature. Additional m-chloroperbenzoic acid (48 mg) was added, and the mixture was stirred for 24 hours at ambient temperature. The mixture was evaporated in vacuo. The residue was dissolved in methanol (3 ml) and the mixture was heated for 24 hours at 50° C. The mixture was evaporated in vacuo and the residue was chromatographed on silica gel (4 g) eluting with a mixture of methylene chloride and methanol (20:1–5:1) to give {(2R,3S)-3-[1-methyl-1-(4-nitrobenzoyloxycarbonyloxy)ethyl]-4-oxoazetidin-2-yl}acetic acid (43 mg) as an oil.

IR ($CH_2Cl_2$): 1740, 1520, 1350 cm$^{-1}$.

NMR (CDCl$_3$) δ: 1.60 (broad s, 6H), 2.3–2.8 (m, 2H), 3.36 (broad s, 1H), 3.7–4.0 (m, 1H), 5.16 (s, 2H), 7.1–7.3 (broad, 1H), 7.84 ($A_2B_2$, 4H, J=8 Hz), 9.1–9.6 (broad, 1H).

EXAMPLE 90

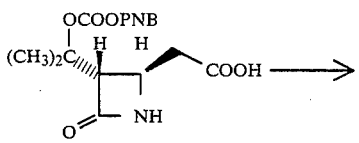

A solution of diazomethane in ether (1 ml) was added to a solution of [(2R,3S)-3-[1-methyl-1-(4-nitrobenzyloxycarbonyloxy)ethyl]-4-oxoazetidin-2-yl]-acetic acid (29 mg) in a mixture of methylene chloride (1 ml) and methanol (1 ml) at 0° C. and the mixture was stirred for 15 minutes at 0° C. Acetic acid (1 drop) was added to the mixture at 0° C. and the mixture was evaporated in vacuo. The residue was chromatographed on silica gel (1 g) eluting with a mixture of methylene chloride and ethyl acetate (10:1) to give methyl [(2R,3S)-3-[1-methyl-1-(4-nitrobenzyloxycarbonyloxy)ethyl]-4-oxoazetidin-2-yl]acetate (31 mg).

IR ($CH_2Cl_2$): 1760, 1740, 1520, 1350 cm$^{-1}$.

NMR (CDCl$_3$) δ: 1.61(s, 3H), 1.65 (s, 3H), 2.4–2.6 (m, 2H), 3.36 (d, 1H, J=3 Hz), 3.69 (s, 3H), 3.8–4.0 (m, 1H), 5.17 (s, 2H), 6.40 (s, 1H), 7.87 ($A_2B_2$, 4H, J=9 Hz).

EXAMPLE 91

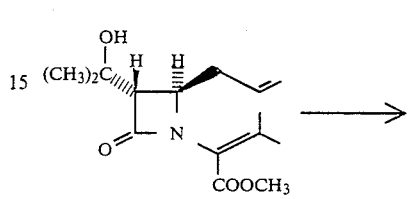

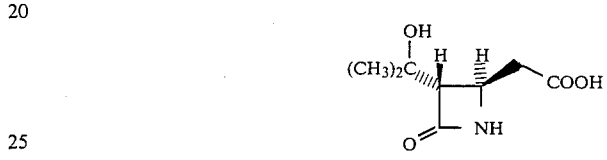

Ozone was bubbled into a solution of methyl 2-[(3S,4R)-3-(1-hydroxy-1-methylethyl)-2-oxo-4-allylazetidin-1-yl]-3-methylbut-2-enoate (159 mg) in ethyl acetate (5 ml) at −70° C. until a blue color appeared. After stirring for 15 minutes at same temperature, the mixture was purged with nitrogen. The mixture was diluted with ethyl acetate (30 ml) and the solution was washed with an aqueous solution of sodium bisulfite and sodium sulfite (2:1). The aqueous layer was extracted with ethyl acetate (10 ml). The combined organic layers were washed with brine, dried over magnesium sulfate, and evaporated in vacuo.

The residue was dissolved in methylene chloride (3 ml) and m-chloroperbenzoic acid (244 mg) was added at ambient temperature. The mixture was refluxed for 24 hours and evaporated in vacuo. The residue was dissolved in methanol (3 ml) and m-chloroperbenzoic acid (244 mg) was added. The mixture was heated at 50° C. for 20 hours and evaporated in vacuo. The residue was chromatographed on silica gel (3 g) eluting with a mixture of methylene chloride and methanol (9:1–2:1) to give [(2R,3S)-3-(1-hydroxy-1-methylethyl)-4-oxoazetidin-2-yl]acetic acid (25 mg).

IR ($CH_2Cl_2$): 1750, 1730, 1710 cm$^{-1}$.

NMR (CD$_3$OD) δ: 1.28 (s, 3H), 1.32 (s, 3H), 2.5–2.7 (m, 2H), 2.90 (d, 1H, J=2.5 Hz), 3.8–4.0 (m, 1H).

EXAMPLE 92

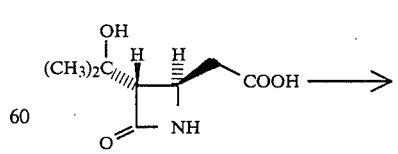

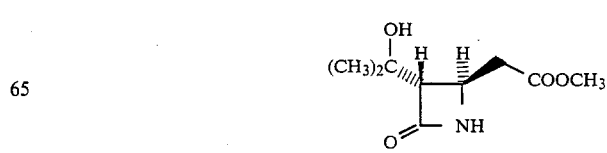

A solution of diazomethane in ether (2 ml) was added to a solution of [(2R,3S)-3-(1-hydroxy-1-methylethyl)-4-oxoazetidin-2-yl]acetic acid (23 mg) in methanol (3 ml) at 0° C. and the mixture was stirred for an hour at 0° C. Acetic acid (2 drops) was added to the mixture at 0° C. and the mixture was evaporated in vacuo to give methyl [(2R,3S)-3-(1-hydroxy-1-methylethyl)-4-oxoazetidin-2-yl]acetate (25 mg).

IR (CH$_2$Cl$_2$): 1760, 1735 cm$^{-1}$.

NMR (CD$_3$OD) δ: 1.28 (s, 3H), 1.34 (s, 3H), 2.6-2.8 (m, 2H), 2.89 (d, 1H, J=2.5 Hz), 3.70 (s, 3H), 3.8-4.0 (m, 1H).

EXAMPLE 93

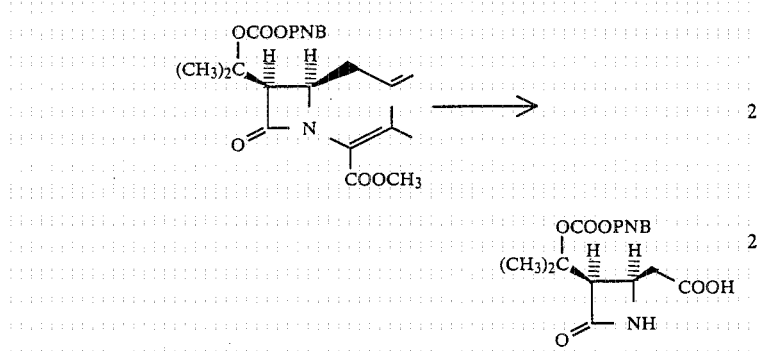

Ozone was bubbled into a solution of methyl 3-methyl-2-[(3R,4R)-3-[1-methyl-1-(4-nitrobenzyloxycarbonyloxy)ethyl]-2-oxo-4-allylazetidin-1-yl]but-2-enoate (120 mg) in ethyl acetate (5 ml) at −70° C. until a blue color appeared. After stirring for 15 minutes at the same temperature, the mixture was purged with nitrogen. The reaction mixture was diluted with ethyl acetate (30 ml) and the solution was washed with an aqueous solution of sodium bisulfite and sodium sulfite (2:1), and brine. The organic layer was dried over magnesium sulfate and evaporated in vacuo. The residue was dissolved in methylene chloride (3 ml) and m-chloroperbenzoic acid (112 mg) was added at 0° C. The mixture was stirred for 24 hours at ambient temperature, and evaporated in vacuo. The residue was dissolved in methanol (5 ml) and m-chloroperbenzoic acid (112 mg) was added. The mixture was heated at 50° C. for 2 days and evaporated in vacuo. The residue was chromatographed on silica gel (6 g) eluting with a mixture of methylene chloride and methanol (20:1-5:1) to give [(2R,3R)-3-[1-methyl-1-(4-nitrobenzyloxycarbonyloxy)ethyl]-4-oxoazetidin-2-yl]acetic acid (43 mg) as an oil.

IR (CH$_2$Cl$_2$): 1735, 1520, 1350 cm$^{-1}$.

NMR (CDCl$_3$) δ: 1.60 (s, 3H), 1.72 (s, 3H), 2.5-3.2 (m, 2H), 3.4-3.7 (m, 1H), 3.9-4.2 (m, 1H), 5.18 (s, 2H), 7.82 (A$_2$B$_2$, 4H, J=9 Hz), 8.4-9.1 (broad, 1H).

EXAMPLE 94

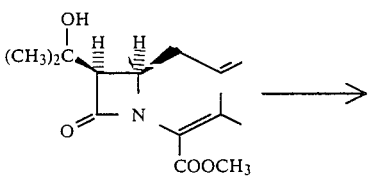

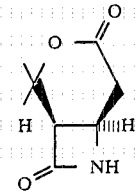

Ozone was bubbled into a solution of methyl 2-[(3R,4R)-3-(1-hydroxy-1-methylethyl)-2-oxo-4-allylazetidin-1-yl]-3-methylbut-2-enoate (240 mg) in ethyl acetate (5 ml) at −70° C. until a blue color appeared. After stirring for 15 minutes at −70° C. The mixture was purged with nitrogen. The mixture was diluted with ethyl acetate (30 ml) and the solution was washed with aqueous saturated sodium bisulfite. The aqueous layer was extracted with chloroform (10 ml). The combined organic layer was dried over magnesium sulfate and evaporated in vacuo. The residue was dissolved in methylene chloride (3 ml) and m-chloroperbenzoic acid (368 mg) was added at ambient temperature. After stirring for 20 hours at ambient temperature, the mixture was evaporated in vacuo. The residue was dissolved in methanol (5 ml) and m-chloroperbenzoic acid (368 mg) was added. The mixture was heated at 50° C. for 2 days, left for a day at room temperature, and evaporated in vacuo. The residue was chromatographed on silica gel (3 g) eluting with a mixture of methylene chloride and methanol (10:1-2:1) to give (1R,6R)-2,2-dimethyl-4,8-dioxo-7-aza-3-oxabicyclo[4.2.0]octane (48 mg).

m.p. 180°-182° C.

IR (CH$_2$Cl$_2$): 1775, 1740 cm$^{-1}$.

NMR (CD$_3$OD) δ: 1.46 (s, 3H), 1.60 (s, 3H), 2.82 (dd, 1H, J=17 Hz, 2 Hz), 2.96 (dd, 1H, J=17 Hz, 4 Hz), 3.50 (d, 1H, J=5 Hz), 4.18 (ddd, 1H, J=5 Hz, 4 Hz, 2 Hz), 4.62 (s, 3H).

Elemental Analysis: C 56.42%, H 6.26%, N 8.24%. Calcd for C$_8$H$_{11}$NO$_3$: C 56.80%, H 6.55%, N 8.28%.

EXAMPLE 95

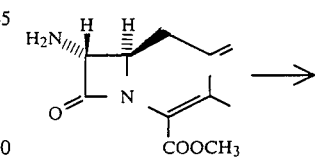

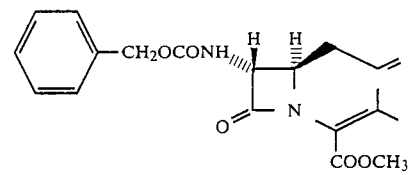

To a solution of methyl [(3R,4R)-3-amino-4-allyl-2-oxoazetidin-1-yl]-3-methylbut-2-enoate (7.0 g) in methylene chloride (110 ml) were added 2,6-lutidine (4.11 ml) and benzyl chloroformate (5.03 ml) at 0° C. and the mixture was stirred for 30 minutes at 0° C. The reaction mixture was diluted with ethyl acetate (800 ml) and the solution was washed with diluted hydrochloric acid, brine, aqueous saturated sodium bicarbonate, and brine. The organic layer was dried over magnesium sulfate and evaporated in vacuo. The residue was chromatographed on silica gel (200 g) eluting with a mixture of methylene chloride and ethyl acetate (20:1-4:1) to give methyl [(3R,4R)-3-benzyloxycarbonylamino-4-allyl-2-oxoazetidin-1-yl]-3-methylbut-2-enoate (10.7 g) as an oil.

IR (CH$_2$Cl$_2$): 3380, 1750, 1720 cm$^{-1}$.

NMR (CD$_3$OD) δ: 1.95 (s, 3H), 2.17 (s, 3H), 2.44 (t, 2H, J=7 Hz), 3.73 (s, 3H), 4.06 (dt, 1H, J=2.5, 7 Hz), 4.44 (d, 1H, J=2.5 Hz), 4.9-5.2 (m, 2H), 5.10 (s, 2H), 5.5-6.0 (m, 1H), 7.34 (s, 5H).

EXAMPLE 96

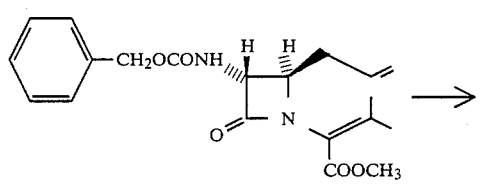

Ozone was bubbled into a solution of methyl [(3R,4R)-3-benzyloxycarbonylamino-4-allyl-2-oxoazetidin-1-yl]-3-methylbut-2-enoate (5 g) in methanol (100 ml) at −60° C. until a blue color was appeared. After stirring for 10 minutes at −60° C., the mixture was purged with nitrogen. Dimethyl sulfide (5 ml) was added to the mixture at −60° C. and the mixture was allowed to warm to 0° C. during 15 minutes. After stirring for an hour at 0° C., the mixture was left for 20 hours at ambient temperature. Dimethyl sulfide (2 ml), trimethyl orthoformate (5 ml), and p-toluenesulfonic acid monohydrate (150 mg) were added to the mixture and the mixture was heated at 50° C. for 6 hours. Pyridine (0.076 ml) was added to the reaction mixture at ambient temperature and the mixture was evaporated in vacuo. The residue was dissolved in ethyl acetate and the solution was washed with water, dilute hydrochloric acid, brine, aqueous sodium bicarbonate, and brine.

The organic layer was dried over magnesium sulfate, and evaporated in vacuo. The residue was dissolved in methanol (100 ml), and the solution was heated at 50° C. for 3 hours and left at ambient temperature for 2 days. The mixture was evaporated in vacuo and the residue was chromatographed on silica gel (100 g) eluting with a mixture of methylene chloride and acetone (10:1-2:1) to give (3R,4R)-3-benzyloxycarbonylamino-4-(2,2-dimethoxyethyl)azetidin-2-one (2.83 g) as an oil.

IR (CH$_2$Cl$_2$): 1770, 1720 cm$^{-1}$.

NMR (acetone-d$_6$) δ: 1.8-2.2 (m, 2H), 3.30 (s, 6H), 3.66 (dt, 1H, J=3, 7 Hz), 4.42 (dd, 1H, J=3, 9 Hz), 4.51 (t, 1H, J=5.5 Hz), 5.12 (s, 2H), 7.0 (brs, 1H), 7.2 (m, 1H), 7.40 (s, 5H).

EXAMPLE 97

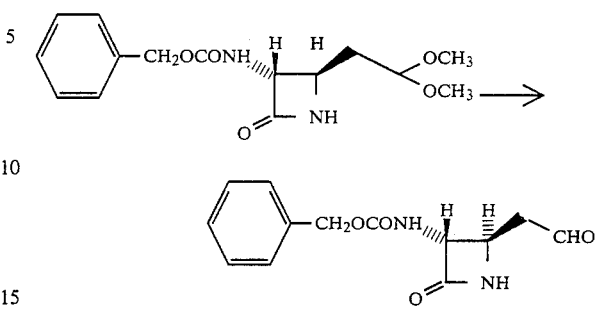

To a solution of (3R,4R)-3-benzyloxycarbonylamino-4-(2,2-dimethoxyethyl)azetidin-2-one (2.15 g) in acetic acid (35.2 ml) were added dimethylsulfide (2 ml) and water (8.8 ml) at ambient temperature and the mixture was heated at 50° C. for 4.5 hours. The reaction mixture was evaporated in vacuo and the residue was dissolved in xylene (40 ml). The mixture was evaporated in vacuo and the residue was chromatographed on silica gel (10 g) eluting with a mixture of methylene chloride and acetone (5:1-2:1) to give a crystalline solid. This crude crystals were washed with ether and dried over phosphorous pentoxide to give (3R,4R)-3-benzyloxycarbonylamino-4-(2-oxoethyl)azetidin-2-one (863 mg).

IR (CH$_2$Cl$_2$): 1780, 1720 cm$^{-1}$.

NMR (acetone-d$_6$) δ: 2.7-3.1 (m, 2H), 3.8-4.0 (m, 1H), 4.43 (dd, 1H, J=2, 8 Hz), 5.07 (s, 2H), 6.9-7.2 (broad, 1H), 7.30 (s, 5H), 9.69 (s, 1H).

EXAMPLE 98

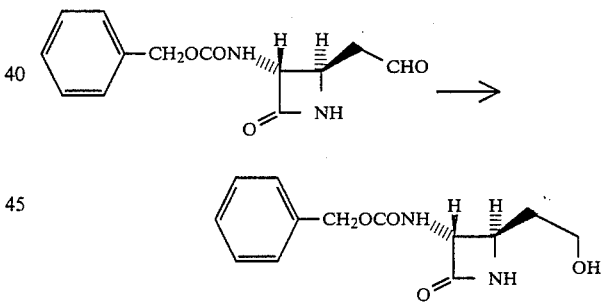

To a solution of (3R,4R)-3-benzyloxycarbonylamino-4-(2-oxoethyl)azetidin-2-one (850 mg) in methanol (17 ml) was added sodium borohydride (123 mg) at 0° C. and the mixture was stirred for 15 minutes at 0° C. Acetic acid (0.37 ml) was added to the mixture at 0° C. After stirring for 15 minutes at 0° C., the mixture was evaporated in vacuo. The residue was chromatographed on silica gel (17 g) eluting with a mixture of methylene chloride and methanol (20:1-10:1) to give a crystalline solid. This crude crystals were washed with ether and dried over phosphorous pentoxide to give (3R,4R)-3-benzyloxycarbonylamino-4-(2-hydroxyethyl)azetidin-2-one (748 mg).

mp. 120°-121° C.

IR (CH$_2$Cl$_2$): 1770, 1720 cm$^{-1}$.

NMR (acetone-d$_6$) δ: 1.7-2.11 (m, 2H), 2.82 (s, 1H), 3.5-3.8 (m, 3H), 4.39 (dd, 1H, J=3, 8 Hz), 5.05 (s, 2H), 6.9-7.3 (broad, 2H), 7.30 (s, 5H).

EXAMPLE 99

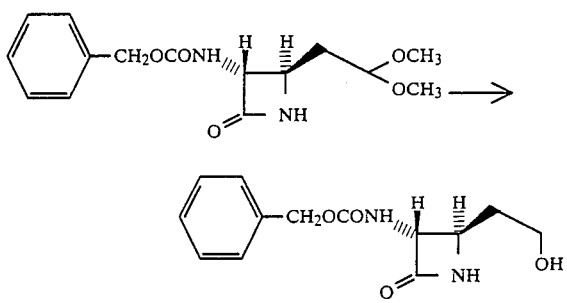

A solution of (3R,4R)-3-benzyloxycarbonylamino-4-(2,2-dimethoxyethyl)azetidin-2-one (0.60 g) in a mixture of tetrahydrofuran (10 ml) and 0.5N hydrochloric acid (2 ml) was heated at 50° C. for 1 hour. The mixture was cooled to 0° C. and 1N aqueous sodium bicarbonate (1.2 ml) was added to the mixture at 0° C. After stirring for 5 minutes at 0° C., sodium borohydride (0.10 g) was added to the mixture at 0° C. After stirring for 15 minutes at 0° C., acetone (0.77 ml) and acetic acid (0.30 ml) were added to the mixture at 0° C. The mixture was evaporated in vacuo and the residue was dissolved in methylene chloride (60 ml). The solution was dried over magnesium sulfate and evaporated in vacuo. The residue was dissolved in xylene (20 ml) and the solution was evaporated in vacuo. The residue was chromatographed on silica gel (12 g) eluting with a mixture of methylene chloride and methanol (20:1–10:1) to give (3R,4R)-3-benzyloxycarbonylamino-4-(2-hydroxyethyl)azetidin-2-one (314 mg) as a crystalline solid.

EXAMPLE 100

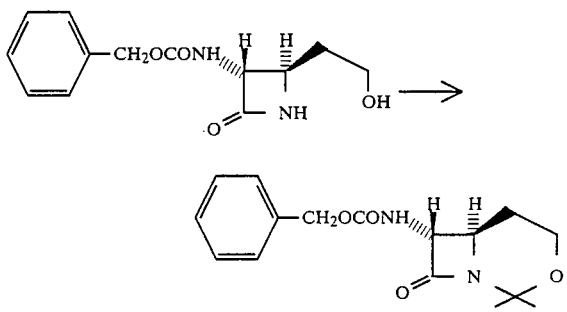

To a suspension of (3R,4R)-3-benzyloxycarbonylamino-4-(2-hydroxyethyl)azetidin-2-one (735 mg) in methylene chloride (30 ml) were added 2,2-dimethoxypropane (0.513 ml) and boron trifluoride etherate (0.026 ml) at 0° C. The mixture was stirred for 10 minutes at 0° C. and for 5 hours at ambient temperature. The reaction mixture was poured into a mixture of methylene chloride (30 ml) and aqueous sodium bicarbonate and sodium chloride (1:1). The organic layer was separated and the aqueous layer was extracted with methylene chloride (20 ml). The combined organic layers were washed with brine, dried over magnesium sulfate, and evaporated in vacuo. The residue was chromatographed on silica gel (16 g) eluting with a mixture of methylene chloride and acetone (10:1–5:1) to give (6R,7R)-7-benzyloxycarbonylamino-2,2-dimethyl-1-aza-3-oxabicyclo-[4.2.0]octan-8-one (753 mg) as an oil.

IR (CH$_2$Cl$_2$): 1760, 1725 cm$^{-1}$.

NMR (acetone-d$_6$) δ: 1.36 (s, 3H), 1.61 (s, 3H), 1.4–2.1 (m, 2H), 3.5–3.9 (m, 3H), 4.38 (dd, 1H, J=2, 8 Hz), 5.08 (s, 2H), 7.0 (broad, 1H), 7.35 (s, 5H).

EXAMPLE 101

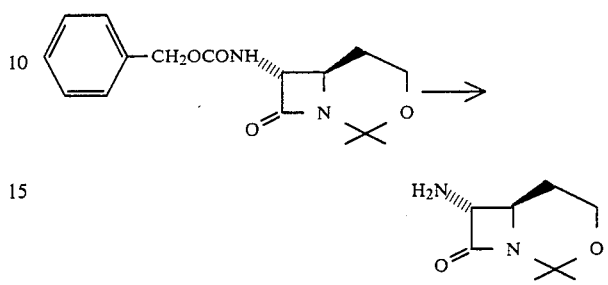

A mixture of (6R,7R)-7-benzyloxycarbonylamino-2,2-dimethyl-1-aza-3-oxabicyclo[4.2.0]octan-8-one (748 mg) and 10% palladium charcoal (180 mg) in ethyl acetate (15 ml) was stirred under a hydrogen atmosphere for 1.5 hours at ambient temperature. The mixture was filtered and the filtrate was evaporated in vacuo to give (6R,7R)-7-amino-2,2-dimethyl-1-aza-3-oxabicyclo[4.2.0]octan-8-one (382 mg) as a crystalline solid.

IR (CH$_2$Cl$_2$): 1740 cm$^{-1}$.

NMR (CDCl$_3$) δ: 1.42 (s, 3H), 1.72 (s, 3H), 1.5–2.1 (m, 2H), 1.86 (s, 2H), 3.34 (ddd, 1H, J=2, 5, 10 Hz), 3.6–3.9 (m, 3H).

EXAMPLE 102

To a solution of (6R,7R)-7-amino-2,2-dimethyl-1-aza-3-oxabicyclo[4.2.0]octan-8-one (300 mg) were added pyridine (0.25 ml) and freshly prepared acetic formic anhydride (0.38 ml) at 0° C. After stirring for 45 minutes at 0° C., the reaction mixture was evaporated in vacuo. The residue was dissolved in xylene and the solution was evaporated in vacuo. The residue was chromatographed on silica gel (6 g) eluting with a mixture of methylene chloride and methanol (25:1–10:1) to give (6R,7R)-2,2-dimethyl-7-formamido-1-aza-3-oxabicyclo[4.2.0]octan-8-one (378 mg) as an oil.

IR (CH$_2$Cl$_2$): 1755, 1685 cm$^{-1}$.

NMR (CDCl$_3$) δ: 1.43 (s, 3H), 1.72 (s, 3H), 1.8–2.1 (m, 2H), 3.56 (ddd, 1H, J=2, 5, 10 Hz), 3.7–3.9 (m, 2H), 4.37 (dd, 1H, J=2, 8 Hz), 7.33 (broad d, 1H, J=8 Hz), 8.11 (s, 1H).

EXAMPLE 103

To a solution of (6R,7R)-2,2-dimethyl-7-formamido-1-aza-3-oxabicyclo[4.2.0]octan-8-one (345 mg) were added 2,6-lutidine (2.05 ml) and phosphorus oxychloride (0.52 ml) at 0° C. After stirring for 3 hours at 0° C., the mixture was poured into a mixture of ethyl acetate (80 ml) and ice-water. The organic layer was separated, washed in turn with 10% phosphoric acid, water, brine, an aqueous mixture of sodium bicarbonate and sodium chloride (1:1), and brine, dried over magnesium sulfate, and evaporated in vacuo. The crystalline residue was washed with a mixture of petroleum ether and ether (1:1) and dried over phosphorus pentoxide to give (6R,7R)-2,2-dimethyl-7-isocyano-1-aza-3-oxabicyclo[4.2.0]octan-8-one (205 mg).

IR (CH$_2$Cl$_2$): 2140, 1770 cm$^{-1}$.

NMR (CDCl$_3$) δ: 1.45 (s, 3H), 1.72 (s, 3H), 1.4–2.1 (m, 2H), 3.7–3.9 (m, 3H), 4.30 (d, 1H, J=2 Hz).

EXAMPLE 104

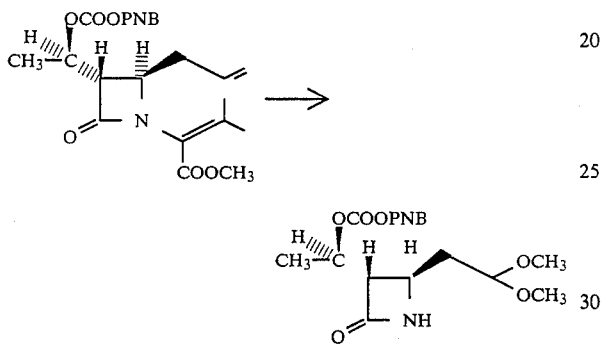

Ozone was passed into a solution of methyl 2-{(3S,4R)-3-[(1R)-1-(4-nitrobenzyloxycarbonyloxy)ethyl]-2-oxo-4-allylazetidin-1-yl}-3-methylbut-2-enoate (100 mg) in methanol (3 ml) at −70° C. until a blue color was appeared. In the course of the reaction, white crystals were precipitated from the reaction mixture. After stirring for 10 minutes at −70° C., the mixture was purged with nitrogen. Cold methylene chloride (2 ml) and dimethyl sulfide (0.6 ml) were added to the mixture at −70° C. and the mixture was warm to 0° C. during 1 hour. Then the mixture was left at 0° C. for 3 hours and at ambient temperature for 12 hours. The mixture was evaporated in vacuo and the residue was dissolved in methanol (5 ml). Dimethyl sulfide (0.3 ml), trimethyl orthoformate (0.5 ml) and p-toluenesulfonic acid monohydrate (4.3 mg) were added to the solution and the mixture was heated for an hour at 58°–55° C. Pyridine (2 drops) was added to the mixture at ambient temperature and the mixture was evaporated in vacuo. The residue was dissolved with ethyl acetate (30 ml) and the solution was washed in turn with water, brine containing 0.1N hydrochloric acid, brine, an aqueous saturated sodium bicarbonate containing sodium chloride, and brine, dried over magnesium sulfate, and evaporated in vacuo. The residue was dissolved in methanol (5 ml) and the solution was left for 15 hours at ambient temperature. The mixture was evaporated in vacuo and the residue was chromatographed on silica gel (2 g) eluting with a mixture of methylene chloride and acetone (20:1–5:1) to give (3S,4R)-4-(2,2-dimethoxyethyl)-3-[(1R)-1-(4-nitrobenzyloxycarbonyloxy)-ethyl]azetidin-2-one (75 mg) as an oil.

IR (CH$_2$Cl$_2$): 1760, 1730, 1520, 1350 cm$^{-1}$.

NMR (CDCl$_3$) δ: 1.44 (d, 3H, J=7 Hz), 1.94 (t, 2H, J=6 Hz), 3.03 (dd, 1H, J=2, 5 Hz), 3.32 (s, 6H), 3.70 (dt, 1H, J=2, 6 Hz), 4.43 (t, 1H, J=6 Hz), 5.0–5.3 (m, 1H), 5.24 (s, 2H), 6.65 (s, 1H), 7.86 (A$_2$B$_2$, 4H, J=9 Hz).

EXAMPLE 105

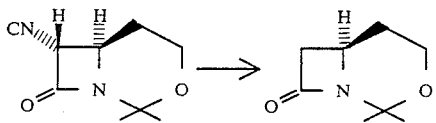

A mixture of (6R,7R)-2,2-dimethyl-7-isocyano-1-aza-3-oxabicyclo[4.2.0]octan-8-one (150 mg), tributyltinhydride (0.263 ml), and azobisisobutyronitrile (14 mg) in benzene (4.5 ml) was refluxed for 15 minutes. The resulting solution was chromatographed on silica gel (4.5 g) eluting with a mixture of benzene and acetone (15:1–16:1) to give the crude product (140 mg) as an oil, which was purified by silica gel (5 g) chromatography (eluate: a mixture of methylene chloride and ethyl acetate 30:1–5:1) to give (6R)-2,2-dimethyl-1-aza-3-oxabicycle[4.2.0]-octan-8-one (98 mg) as an oil.

IR (CH$_2$Cl$_2$): 1740 cm$^{-1}$.

NMR (CDCl$_3$) δ: 1.42 (s, 3H), 1.77 (s, 3H), 1.4–2.1 (m, 2H), 2.56 (dd, 1H, J=2.5, 14.5 Hz), 3.08 (dd, 1H, J=5, 14.5 Hz), 3.5–3.7 (m, 1H), 3.87 (dd, 2H, J=2.5, 8 Hz).

EXAMPLE 106

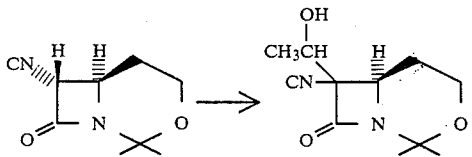

To a solution of (6R,7R)-2,2-dimethyl-7-isocyano-1-aza-3-oxabicycle[4.2.0]octan-8-one (200 mg) in tetrahydrofuran (4 ml) was added a solution of n-butyllithium in hexane (0.93 ml of 1.55M solution) at −70° C. and the mixture was stirred at −70° C. for 15 minutes. A solution of acetaldehyde (73 mg) in tetrahydrofuran (0.8 ml) was added to the mixture at −70° C. and the mixture was stirred at −70° C. for 30 minutes. Acetic acid (0.19 ml) was added to the mixture at −70° C. and the mixture was poured into a mixture of ethyl acetate (100 ml) and aqueous sodium bicarbonate containing a small amount of sodium chloride. The aqueous layer was separated and extracted with ethyl acetate (20 ml). The combined organic layers were washed with brine, dried over magnesium sulfate, and evaporated in vacuo. The residue was chromatographed on silica gel (3 g) eluting with a mixture methylene chloride and ethyl acetate (20:1–5:1) to give a mixture of (6R,7R)-2,2-dimethyl-7-[(1S)-1-hydroxyethyl]-7-isocyano-1-aza-3-oxabicycle[4.2.0]octan-8-one, its (1R,6R,7R) isomer, its (1R,6R,7S) isomer, and its (1S,6R,7S) isomer as a solid (230 mg).

IR (CH$_2$Cl$_2$): 3600, 2140, 1770 cm$^{-1}$.

NMR (CDCl$_3$) δ: 1.3–1.6 (m, 3H), 1.44 (s, 3H), 1.76 (s, 3H), 1.6–2.2 (m, 3H), 2.8–3.1 (m, 1H), 3.7–4.1 (m, 2H), 4.0–4.4 (m, 1H).

EXAMPLE 107

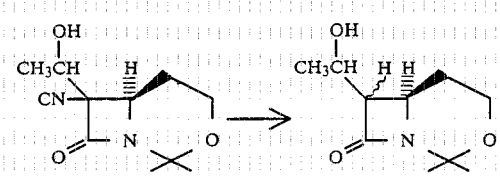

To a mixture of (6R,7R)-2,2-dimethyl-7-[(1S)-1-hydroxyethyl]-7-isocyano-1-aza-3-oxabicycle[4.2.0]-octan-8-one, its (1R,6R,7R) isomer, its (1R,6R,7S) isomer, and its (1S,6R,7S) isomer (210 mg) in benzene (10 ml) were added tributyltinhydride (0.297 ml) and azobisisobutyronitrile (15 mg) at ambient temperature and the mixture was refluxed for 30 minutes. The resulting solution weas chromatographed on silica gel (7.5 g) eluting with a mixture of methylene chloride and acetone (10:1–5:1) to give the crude product, which was purified by silica gel (10 g) chromatography (a mixture of hexane and ethyl acetate 5:1–1:5) to give a mixture of (6R,7R)-2,2-dimethyl-7-[(1S)-1-hydroxyethyl]-1-aza-3-oxabicyclo[4.2.0]octan-8-one, its (1R,6R,7R) isomer, its (1R,6R,7S) isomer, and its (1S,6R,7S) isomer as an oil (157 mg).

IR (CH$_2$Cl$_2$): 3400, 1740 cm$^{-1}$.

NMR (CDCl$_3$) δ: 1.1–1.4 (m, 3H), 1.43 (2,3H), 1.76 (s, 3H), 1.6–2.2 (m, 3H), 2.2–3.0 (m, 1H), 3.0–3.2 (m, 1H), 3.6–4.0 (m, 2H), 4.0–4.4 (m, 1H).

EXAMPLE 108

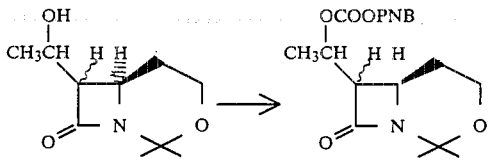

A solution of p-nitrobenzyl chloroformate (251 mg) in methylene chloride (2.5 ml) was added to a mixture of (6R,7R)-2,2-dimethyl-7-[(1S)-1-hydroxyethyl]-1-aza-3-oxabicyclo[4.2.0]octan-8-one, its (1R,6R,7R) isomer, its (1R,6R,7S) isomer, its (1S,6R,7S) isomer, and 4-(dimethylamino)pyridine (143 mg) in methylene chloride (3 ml) at 0° C. After stirring at 0° C. for 30 minutes, the mixture was allowed to warm to ambient temperature during 45 minutes and stirred at ambient temperature for 1.5 hours. A solution of p-nitrobenzyl chloroformate (100 mg) in methylene chloride (1 ml) and 4-(dimethylamino)pyridine (58 mg) were added to the mixture at 0° C. and the mixture was stirred at ambient temperature for 1.5 hours.

3-Dimethylaminopropylamine (0.158 ml) was added to the mixture at 0° C. and the mixture was stirred at 0° C. for 15 minutes. The mixture was poured into a mixture of ethyl acetate (70 ml) and dilute hydrochloric acid. The organic layer was separated, washed with brine, aqueous sodium bicarbonate, and brine, dried over magnesium sulfate, and evaporated in vacuo. The residue was chromatographed on silica gel (10 g) eluting with a mixture of methylene chloride and ethyl acetate (10:1–2:1) to give a 9:11:4:1 mixture of (6R,7R)-2,2-dimethyl-7-[(1S)-1-(4-nitrobenzyloxycarbonyoxy)ethyl]-1-aza-3-oxabicyclo-[4.2.0]octan-8-one, its (1R,6R,7R) isomer, its (1R,6R,7S) isomer, and its (1S,6R,7S) isomer as an oil (167 mg).

The residue was chromatographed on silica gel (15 g) eluting with a mixture of cyclohexane and ethyl acetate (5:1→1:1) to give 70 mg of the (1S,6R,7R)-isomer and 60 mg of the (1R,6R,7R)-isomer, and 10 mg of the (1R,6R,7S)-isomers.

Deta for the (1S,6R,7R)-isomer: IR (CH$_2$Cl$_2$): 1745, 1525, 1350 cm$^{-1}$; NMR (CDCl$_3$) δ: 1.2–2.0 (m, 2H), 1.50 (d, 3H, J=6 Hz), 1.74 (s, 3H), 3.42 (dd, 1H, J=5, 11 Hz), 3.6–4.0 (m, 1H), 5.22 (dq, 1H, J=11, 6 Hz), 5.30 (s, 2H), 7.94 (A$_2$B$_2$, 4H, J=9 Hz).

Deta for the (1R,6R,7R)-isomer: IR (CH$_2$Cl$_2$): 1745, 1525, 1350 cm$^{-1}$; NMR (CDCl$_3$) δ: 1.3–2.0 (m, 2H), 1.4 (d, 3H, partially hidden), 1.44 (s, 3H), 1.75 (s, 3H), 3.39 (dd, 1H, J=5.5, 9 Hz), 3.7–4.1 (m, 3H), 5.1–5.4 (m, 1H), 5.34 (s, 2H), 7.98 (A$_2$B$_2$, 4H, J=9 Hz).

Date for the (1R,6R,7S)-isomer: IR (CH$_2$Cl$_2$): 1745, 1525, 1350 cm$^{-1}$; NMR (CDCl$_3$) δ: 1.3–2.0 (m, 2H), 1.42 (s, 3H), 1.47 (d, 3H, J=6 Hz), 1.76 (s, 3H), 3.00 (dd, 1H, J=2, 8 Hz), 3.5–4.0 (m, 3H), 5.1 (m, 1H), 5.30 (s, 2H), 7.96 (A$_2$B$_2$, 4H, J=9 Hz).

EXAMPLE 109

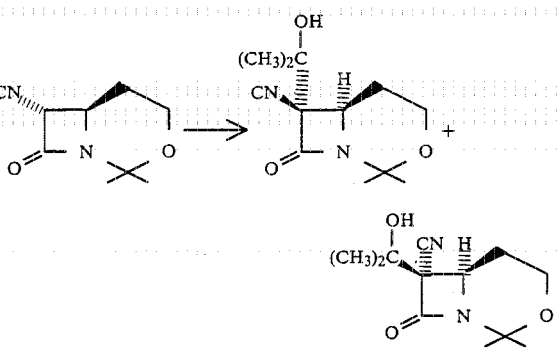

To a solution of (6R,7R)-2,2-dimethyl-7-isocyano-1-aza-3-oxabicyclo[4.2.0]octan-8-one (500 mg) in tetrahydrofuran (15 ml) was added a solution of n-butyllithium in hexane (2.33 ml of 1.55M solution) at −70° C. and the mixture was stirred at −70° C. for 15 minutes. A solution of acetone (0.265 ml) in tetrahydrofuran (2.4 ml) was added to the reaction mixture at −70° C. and the mixture was stirred at −70° C. for 25 minutes. Acetic acid (0.477 ml) was added to the mixture at −70° C. After stirring at −70° C. for 20 minutes, the mixture was evaporated in vacuo. The residue was dissolved in ethyl acetate (80 ml) and the solution was washed with aqueous sodium bicarbonate. The aqueous layer was separated and extracted with ethyl acetate (20 ml). The combined organic layers were washed with brine, dried over magnesium sulfate, and evaporated in vacuo. The crystalline residue was washed with isopropyl ether and filtered to give (6R,7R)-2,2-dimethyl-7-(1-hydroxy-1-methylethyl)-7-isocyano-1-aza-3-oxabicyclo[4.2.0]octan-8-one (460 mg).

The mother liquor was chromatographed on silica gel (5 g) eluting with a mixture of hexane and ethyl acetate (20:1–1:1) to give additional (6R,7R)-2,2-dimethyl-7-(1-hydroxy-1-methylethyl)-7-isocyano-1-aza-3-oxabicyclo[4.2.0]octan-8-one (65 mg) [(6R,7R)-isomer] and its (6R,7S)-isomer (103 mg).

For (6R,7R)-isomer: IR (CH$_2$Cl$_2$): 2125, 1765 cm$^{-1}$. NMR (CDCL$_3$) δ: 1.38 (s, 3H), 1.43 (s, 3H), 1.50 (s, 3H), 1.74 (s, 3H), 1.5-2.2 (m, 2H), 2.10 (s, 1H), 3.7-4.0 (m, 3H).

For (6R,7S)-isomer: IR (CH$_2$Cl$_2$): 2125, 1765 cm$^{-1}$. NMR (CDCl$_3$) δ: 1.40 (s, 3H), 1.48 (s, 3H), 1.63 (s, 3H), 1.74 (s, 3H), 1.5-1.9 (m, 1H), 2.21 (s, 1H), 2.6-3.0 (m, 1H), 3.7-4.0 (m, 3H).

EXAMPLE 110

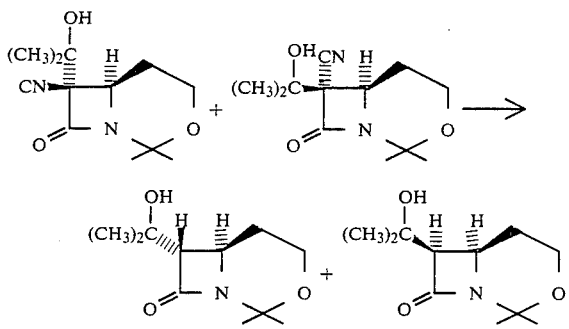

To a mixture of (6R,7R)-2,2-dimethyl-7-(1-hydroxy-1-methylethyl)-7-isocyano-1-aza-3-oxabicyclo[4.2.0]octan-8-one and its (6R,7S)-isomer (2.5 g) in benzene (75 ml) were added tributyltinhydride (3.07 ml) and azobisisobutyronitrile (170 mg) at ambient temperature and the mixture was refluxed for 30 minutes. The reaction mixture was chromatographed on silica gel (65 g) eluting with a mixture of methylene chloride and acetone (10:1-2:1) to give a crude product, which was purified by silica gel (75 g) chromatography (hexane and ethyl acetate) to give (6R,7S)-2,2-dimethyl-7-(1-hydroxy-1-methylethyl)-1-aza-3-oxabicyclo[4,2,0]-octan-8-one (0.545 g) [(6R,7S)-isomer] and its (6R,7R)-isomer (1.406 g).

For (6R,7S)-isomer: IR (CH$_2$Cl$_2$): 1735 cm$^{-1}$. NMR (CDCl$_3$) δ: 1.29 (s, 3H), 1.36 (s, 3H), 1.42 (s, 3H), 1.74 (s, 3H), 1.5-2.0 (m, 2H), 1.96 (s, 1H), 2.81 (d, 1H, J=2 Hz), 3.52 (ddd, 1H, J=2, 5.5, 11 Hz), 3.83 (dd, 2H, J=3, 8.5 Hz).

For (6R,7R)-isomer: IR (CH$_2$Cl$_2$): 1735 cm$^{-1}$. NMR (CDCl$_3$) δ: 1.28 (s, 3H), 1.40 (s, 3H), 1.47 (s, 3H), 1.74 (s, 3H), 1.5-2.0 (m, 1H), 1.98 (s, 1H), 2.5-2.9 (m, 1H), 3.15 (d, 1H, J=5 Hz), 3.6-3.9 (m, 3H).

In the same manner described above, (6R,7S)-2,2-dimethyl-7-(1-hydroxy-1-methylethyl)-7-isocyano-1-aza-3-oxabicyclo[4.2.0]octan-8-one (50 mg) afforded a 2:5 mixture of (6R,7S)-2,2-dimethyl-7-(1-hydroxy-1-methylethyl)-1-aza-3-oxabicyclo[4.2.0]-octan-8-one and its (6R,7R)-isomer (40 mg).

EXAMPLE 111

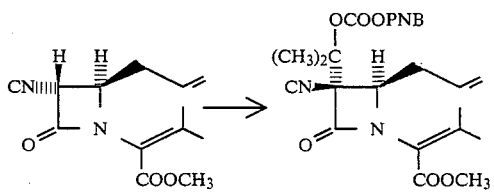

To a solution of methyl 2-[(3R,4R)-3-isocyano-2-oxo-4-allylazetidin-1-yl]-3-methylbut-2-enoate (127.6 mg) in tetrahydrofuran (2.55 ml) was added dropwise a solution of n-butyl lithium (0.409 ml of 1.51M solution in hexane) at −78° C. over a period of 3 minutes. After stirring for 15 minutes at −78° C., the reaction mixture was added dropwise with a solution of acetone (0.0459 ml) in tetrahydrofuran (0.459 ml) at −78° C. over a period of 3 minutes. After stirring for 25 minutes at −78° C., the reaction mixture was added dropwise with a solution of 4-nitrobenzyl chloroformate (124.1 mg) in tetrahydrofuran (1.24 ml) at −78° C. over a period of 3 minutes. The resulting solution was allowed to warm to 0° C. over a period of 40 minutes and added with acetic acid (0.0412 ml) at 0° C. The solvent was distilled off in vacuo at 0° C. and the residue was dissolved in ethyl acetate (30 ml) and washed with brine, aqueous sodium bicarbonate, brine and saturated aqueous sodium chloride. After drying over magnesium sulfate, the ethyl acetate extract was filtered and evaporated in vacuo. The residual oil (285.4 mg) was chromatographed on silica gel (5.7 g) eluting with a mixture of ethyl acetate and hexane (1:5→1:3) to give methyl 2-{(3R,4R)-3-isocyano-3-[1-methyl-1-(4-nitrobenzyloxycarbonyloxy)ethyl]-2-oxo-4-allylazetidin-1-yl}-3-methylbut-2-enoate (211.2 mg) as an oil.

IR (CH$_2$Cl$_2$): 2130, 1775, 1750, 1720, 1520, 1350 cm$^{-1}$.

NMR (CDCl$_3$) δ: 1.74 (s, 3H), 1.83 (s, 3H), 1.97 (s, 3H), 2.22 (s, 3H), 2.53 (t, 2H, J=7 Hz), 3.71 (s, 3H), 4.32 (t, 1H, J=7 Hz), 5.0-5.3 (m, 4H), 5.5-5.9 (m, 1H), 7.84 (A$_2$B$_2$, 4H, J=9 Hz).

EXAMPLE 112

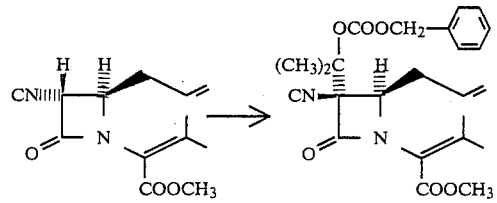

To a solution of methyl 2-[(3R,4R)-3-isocyano-2-oxo-4-allylazetidin-1-yl]-3-methylbut-2-enoate (198.0 mg) in tetrahydrofuran (3.96 ml) was added dropwise a solution of n-butyl lithium (0.634 ml of 1.51M solution in hexane) at −78° C. over a period of 5 minutes. After stirring for 15 minutes at −78° C., the reaction mixture was added with a solution of acetone (0.0713 ml) in tetrahydrofuran (0.642 ml) at −78° C. over a period of 5 minutes. After stirring for 25 minutes at −78° C., the reaction mixture was added dropwise with a solution of benzyl chloroformate (0.1274 ml) in tetrahydrofuran (1.15 ml) at −78° C. over a period of 5 minutes. The resulting solution was allowed to warm to 0° C. over a period of 40 minutes and added with acetic acid (0.0639 ml) at 0° C. The solvent was distilled off in vacuo at 0° C. and the residue was dissolved in ethyl acetate (30 ml) and washed with brine, aqueous sodium bicarbonate, brine, and saturated aqueous sodium chloride. After drying over magnesium sulfate, the ethyl acetate extract was filtered and evaporated in vacuo. The residual oil (381.2 mg) was chromatographed on silica gel (11 g) eluting with a mixture of ethyl acetate and hexane (1:10→1:5) to give methyl 2-[(3R,4R)-3-(1-benzyloxycarbonyloxy-1-methylethyl)-3-isocyano-2-oxo-4-allylazetidin-1-yl]-3-methylbut-2-enoate (221.2 mg) as an oil.

IR (CH$_2$Cl$_2$): 2130, 1770, 1745, 1720 cm$^{-1}$.

NMR (CDCl$_3$) δ: 1.71 (s, 3H), 1.85 (s, 3H), 1.95 (s, 3H), 2.20 (s, 3H), 2.53 (t, 2H, J=7 Hz), 3.63 (s, 3H), 4.35

(t, 1H, J=7 Hz), 5.0–5.35 (m, 4H), 5.5–6.0 (m, 1H), 7.3–7.5 (m, 5H).

EXAMPLE 113

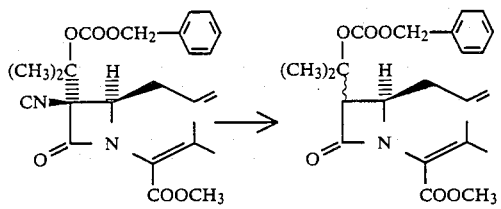

A mixture of methyl 2-[(3R,4R)-3-(1-benzyloxycarbonyloxy-1-methylethyl)-3-isocyano-2-oxo-4-allylazetidin-yl]-3-methylbut-2-enoate (42.7 mg), tri-n-butyltinhydride (0.0308 ml) and azobisisobutyronitrile (0.622 mg) in benzene (2.14 ml) was refluxed for 30 minutes. The resulting solution was chromatographed on silica gel (2.1 g) eluting with a mixture of ethyl acetate and hexane (1:10→1:2) to give a mixture of methyl 2-[(3R,4R)-3-(1-benzyloxycarbonyloxy-1-methylethyl)-2-oxo-4-allylazetidin-1-yl]-3-methylbut-2-enoate and methyl 2-[(3S,4R)-3-(1-benzyloxycarbonyloxy-1-methylethyl)-2-oxo-4-allylazetidin-1-yl]-3-methylbut-2-enoate (39.8 mg; ratio=1:2.3) as an oil.

IR (CH$_2$Cl$_2$): 1750, 1740, 1730 cm$^{-1}$.

NMR (CDCl$_3$) δ: 1.59 (s, 2.1H), 1.61 (s, 0.9H), 1.65 (s, 2.1H), 1.67 (s, 0.9H), 1.75 (s, 0.9H), 1.91 (s, 2.1H), 1.96 (s, 0.9H), 2.18 (s, 2.1H), 2.31 (t, 1.4H, J=7 Hz), 2.61 (t, 0.6H, J=7 Hz), 3.42 (d, 0.7H, J=2 Hz), 3.5–3.8 (m, 3.3H), 3.88–4.22 (m, 1H), 4.8–5.2 (m, 4H), 5.3–5.9 (m, 1H), 7.0–7.5 (m, 5H).

EXAMPLE 114

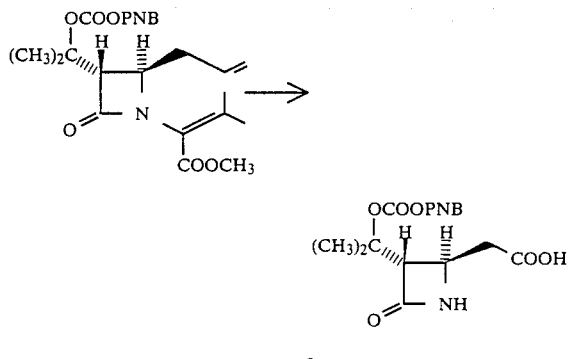

To a solution of methyl 2-{(3S,4R)-3-[1-methyl-1-(4-nitrobenzyloxycarbonyloxy)ethyl]-2-oxo-4-allyl-azetidin-1-yl}-3-methylbut-2-enoate (72.9 mg) in acetone (2.03 ml) was added a 0.7M solution of phosphate butter (pH 6.8, 1.35 ml) at ambient temperature. To the resulting suspension was added dropwise a solution of sodium periodate (86.0 mg) in water (0.594 ml) at ambient temperature. After stirring for 10 minutes, the reaction mixture was added with sodium periodate (117.2 mg) and potassium permanganate (37.5 mg) and stirred at ambient temperature overnight. The resulting mixture was diluted with water-acetone (15 ml–15 ml) and filtered with celite and the filter cake was washed with water-acetone (1:1). The combined filtrates were concentrated in vacuo at 0° C., acidified to pH 1 with 10% aqueous phosphoric acid, and extracted with chloroform. The organic layer was extracted with chilled 10% aqueous sodium bicarbonate (X3). The aqueous extracts were acidified with 3N hydrochloric acid and reextracted with chloroform (X3). The chloroform extracts were washed with saturated aqueous sodium chloride containing a small amount of 3N hydrochloric acid, dried over magnesium sulfate, filtered, and evaporated to give {(2R,3S)-3-[1-methyl-1-(4-nitrobenzyloxycarbonyloxy)ethyl]-4-oxoazetidin-2-yl}acetic acid (36.4 mg) as an amorphous solid.

IR (CH$_2$Cl$_2$): 1740, 1520, 1350 cm$^{-1}$.

EXAMPLE 115

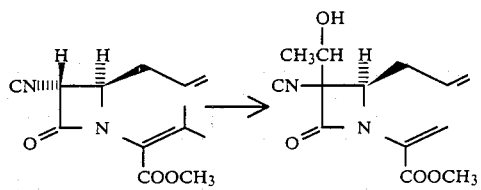

n-Butyllithium (1.51N in hexane, 0.99 ml) was added dropwise to a solution of methyl 2-[(3R,4R)-3-isocyano-2-oxo-4-allylazetidin-1-yl]-3-methylbut-2-enoate (308 mg) in tetrahydrofurane (6 ml) during a three-minutes period at −78° C. under a nitrogen atmosphere. After 15 minutes at −78° C. a solution of acetaldehyde in tetrahydrofuran (2M, 0.93 ml) was added dropwise. The mixture was stirred at −78° C. for 30 minutes and quenched by addition of acetic acid (143 μl). The solution was allowed to warm to 0° C., poured into a mixture of a saturated aqueous solution of sodium bicarbonate and brine, and extracted with ethyl acetate (50 ml). The extract was washed with brine, dried over magnesium sulfate and evaporated to give an oil (274 mg). The residue was chromatographed on silica gel (5 g; eluting with 5–10% acetone in dichloromethane) to give 199 mg (54.9%) of four diastereomeric mixture of methyl 2-[(4R)-3-(1-hydroxyethyl)-3-isocyano-2-oxo-4-allylazetidin-1-yl]-3-methylbut-2-enoate.

IR (CH$_2$Cl$_2$): 3450, 2140, 1770, 1725 cm$^{-1}$.

EXAMPLE 116

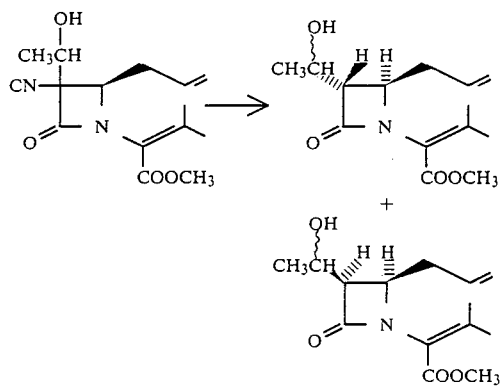

Tri(n-butyl)tin hydride (0.20 ml) and azobisisobutyronitrile (11.5 mg) were added to a solution of the four isomeric mixture of methyl 2-[3-(1-hydroxyethyl)-3-isocyano-2-oxo-4(R)allylazetidin-1-yl]-3-methylbut-2-enoate (195 mg) in anhydrous benzene (4 ml). The stirring mixture was heated to reflux for 15 minutes. The reaction mixture was cooled to ambient temperature and chromatographed on silica gel (6 g; eluting with a mixture of 5-20% acetone in dichloromethane to give 155 mg (87.3%) of the four-isomeric mixture of methyl 2-[(4R)-3-(1-hydroxyethyl)-2-oxo-4-allylazetidin-1-yl]-3-methylbut-2-enoate as a crude oil. This crude oil (118 mg) was chromatographed on silica gel (10 g; eluting with 4-20% acetone in benzene) to give 47 mg of methyl 2-[(3S,4R)-3-((1RS)-1-hydroxyethyl)-2-oxo-4-allylazetidin-1-yl]-3-methylbut-2-enoate and 54 mg of methyl 2-[(3R,4R)-3-((1RS)-1-hydroxyethyl)-2-oxo-4-allylazetidin-1-yl]-3-methylbut-2-enoate.

IR (CH$_2$Cl$_2$) for the mixture of four isomers, 3640, 3550, 3100-3600, 1735, and 1715 cm$^{-1}$.

EXAMPLE 117

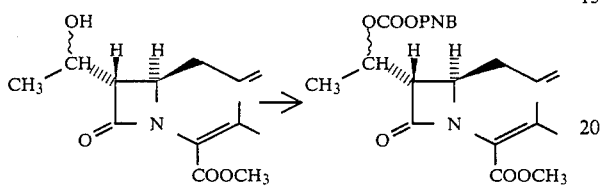

A solution of 4-nitrobenzyl chloroformate (64.7 mg) in dichloromethane (0.65 ml) was added to a solution of methyl 2-[(3S,4R)-3-((1RS)-1-hydroxyethyl)-2-oxo-4-allylazetidin-1-yl]-3-methylbut-2-enoate (54 mg) and dimethylaminopyridine (36.7 mg) in dichloromethane (2.35 ml) at 0° C. under a nitrogen atmosphere. After three minutes the heterogeneous mixture was allowed to warm to ambient temperature (27° C.). After two hours-stirring, additional 4-nitrobenzyl chloroformate (43 mg) and dimethylaminopyridine (25 mg) were added at 0° C. The mixture was stirred at ambient temperature for 15 hours and the resulting solution was evaporated. The residue was taken up into ethyl acetate (20 ml), washed in turn with dilute hydrochloric acid, water, a dilute aqueous solution of sodium bicarbonate, and brine dried over magnesium sulfate, and evaporated. The residue was chromatographed on silica gel (2.5 g; eluting with 2% acetone in dichloromethane) to give 76 mg (84.3%) of a 4:7 mixture of methyl 2-[(3S,4R)-3-[(1RS)-1-(4-nitrobenzyloxycarbonyloxy)ethyl]-2-oxo-4-allylazetidin-1-yl]-3-methylbut-2-enoate.

IR (CH$_2$Cl$_2$): 1750, 1720, 1525, and 1350 cm$^{-1}$.

NMR (CDCl$_3$) δ: 1.46 (d, J=7 Hz, 1.2H), 1.48 (d, J=7 Hz, 1.8H), 1.97 (s, 3H), 2.20 (s, 3H), 2.4 (m, 2H), 3.06 (dd, J=3, 8 Hz, 0.4H), 3.19 (dd, J=3, 5 Hz, 0.6H), 3.76 (s, 3H), 3.92 (m, 1H), 4.9-5.4 (m, 3H), 5.28 (s, 2H), 5.5-6.0 (m, 1H), 7.56 (d, J=9 Hz, 0.8H), 7.58 (d, J=9 Hz, 1.2H), and 8.23 (d, J=9 Hz, 2H).

EXAMPLE 118

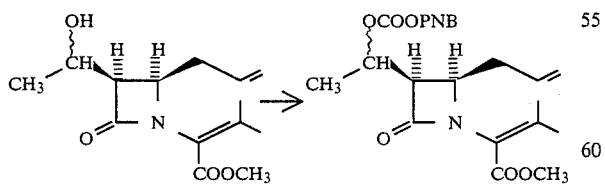

In a manner similar to the Example 117, except using five molar excess of reagents, 47.0 mg of methyl 2-[(3R,4R)-3-((1RS)-1-hydroxyethyl)-2-oxo-4-allylazetidin-1-yl]-3-methylbut-2-enoate afforded 64 mg (81.5%) of a 3:7 mixture of methyl 2-{(3R,4R)-3-[(1RS)-1-(4-nitrobenzyloxycarbonyloxy)ethyl]-2-oxo-4-allylazetidin-1-yl}-3-methylbut-2-enoate and 7 mg (15%) of the starting material.

This mixture (60 mg) was chromatographed on a silica gel plate (20 cm×20 cm×2 mm, three developments with a mixture of 6:4 hexane-ethyl acetate) to give 39 mg of the 1S isomer and 20 mg of the 1R isomer.

Deta for the 1S isomer: IR (CH$_2$Cl$_2$): 1745, 1720, 1525, 1350 cm$^{-1}$. NMR (CDCl$_3$) δ: 1.57 (d, J=6 Hz, 3H), 1.94 (s, 3H), 2.20 (s, 3H), 2.40 (t, J=7 Hz, 2H), 3.51 (dd, J=5.5 and 11 Hz, 1H), 3.74 (s, 3H), 4.14 (dt, J=5.5 and 7 Hz), 4.9-5.3 (m, 3H), 5.27 (s, 2H), 5.4-5.9 (m, 1H), 7.57 (d, J=9 Hz, 2H), and 8.25 (d, J=9 Hz, 2H) ppm.

Deta for the 1R isomer: IR (CH$_2$Cl$_2$): 1745, 1720, 1525, 1350 cm$^{-1}$. NMR (CDCl$_3$) δ: 1.53 (d, J=6 Hz, 3H), 2.03 (s, 3H), 2.22 (s, 3H), 2.40 (t, J=7 Hz, 2H), 3.39 (dd, J=4 and 6 Hz, 1H), 3.76 (s, 3H), 4.13 (dt, J=6 and 7 Hz, 1H), 4.7-5.3 (m, 3H), 5.30 (s, 2H), 5.4-5.9 (m, 1H), 7.56 (d, J=9 Hz, 2H), and 8.25 (d, J=9 Hz, 2H) ppm.

EXAMPLE 119

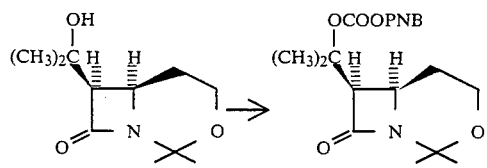

To a solution of (6R,7R)-2,2-dimethyl-7-(1-hydroxy-1-methylethyl)-1-aza-3-oxabicyclo[4.2.0]-octan-8-one (600 mg) in tetrahydrofuran (24 ml) was added a solution of n-butyllithium (2.36 ml of 1.55M solution in hexane) at =70° C. and the mixture was stirred at −70° C. for 15 minutes.

A solution of 4-nitrobenzyl chloroformate (788 mg) in tetrahydrofuran (7 ml) was added to the mixture at −70° C. After stirring at −70° C. for 15 minutes, the reaction mixture was allowed to warm to 0° C. during 50 minutes, stirred at 0° C. for 30 minutes, and evaporated in vacuo. The residue was dissolved in ethyl acetate (100 ml) and the solution was washed with aqueous sodium bicarbonate. The aqueous layer was separated and extracted with ethyl acetate (20 ml). The combined organic layers were washed with aqueous saturated sodium chloride, dried over magnesium sulfate, and evaporated in vacuo. The residue was chromatographed on silica gel (40 g) eluting with a mixture of hexane and ethyl acetate (10:1 to 1:1) to give a crystalline residue. The residue was washed with isopropyl ether and filtered to give (6R,7R)-2,2-dimethyl-7-[1-methyl-1-(4-nitrobenzyloxycarbonyloxy)ethyl]-1-aza-3-oxabicyclo-[4.2.0]octan-8-one (520 mg).

IR (CH$_2$Cl$_2$): 1740, 1520, 1350 cm$^{-1}$.

NMR (CDCl$_3$) δ: 1.41 (s, 3H), 1.62 (s, 3H), 1.77 (s, 6H), 1.5-1.9 (m, 1H), 2.2-2.5 (m, 1H), 3.42 (d, 1H, J=5.5 Hz), 3.6-4.0 (m, 3H), 5.20 (s, 2H), 7.88 (A$_2$B$_2$, 4H, J=9 Hz).

EXAMPLE 120

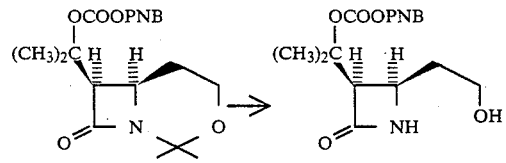

A solution of (6R,7R)-2,2-dimethyl-7-[1-methyl-1-(4-nitrobenzyloxycarbonyloxy)ethyl]-1-aza-3-oxabicyclo[4.2.0]octan-8-one (200 mg) in a mixture of acetic acid (3.2 ml) and water (0.8 ml) was heated at 65° C. for 1 hour. The mixture was cooled to room temperature and evaporated in vacuo. The crystalline residue was washed with ether to give (3R,4R)-4-(2-hydroxyethyl)-3-[1-methyl-1-(4-nitrobenzyloxycarbonyloxy)ethyl]azetidin-2-one (151 mg).

IR (CH$_2$Cl$_2$): 3575, 3375, 1750, 1520, 1350 cm$^{-1}$.

NMR (DMSO-d$_6$) δ: 1.57 (s, 3H), 1.64 (s, 3H), 1.88 (q, 2H, J=7 Hz), 3.1–3.6 (m, 3H), 3.6–3.9 (m, 1H), 4.47 (t, 1H, J=5 Hz), 5.23 (s, 2H), 7.90 (A$_2$B$_2$, 4H, J=9 Hz), 8.08 (s, 1H).

EXAMPLE 121

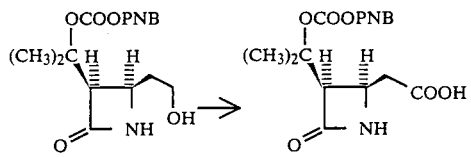

To a solution of (3R,4R)-4-(2-hydroxyethyl)-3-[1-methyl-1-(4-nitrobenzyloxycarbonyloxy)ethyl]-azetidin-2-one (10 mg) in acetone (0.6 ml) was added 2N Jones reagent (50 μl) at 0° C. and the mixture was stirred at 0° C. for 20 minutes. Isopropyl alcohol (100 μl) was added to the mixture at 0° C. and the mixture was evaporated in vacuo. The residue was dissolved in chloroform (10 ml) and the solution was washed with brine. The aqueous layer was separated and extracted with chloroform (5 ml). The conbined organic layers were washed with aqueous saturated sodium chloride, dried over magnesium sulfate, and evaporated in vacuo. The residue was chromatographed on silica gel (0.5 g) eluting with a mixture of methylene chloride and methanol (20:1 to 5:1) to give pure {(2R,3R)-3-[1-methyl-1-(4-nitrobenzyloxycarbonyloxy)ethyl]-4-oxoazetidin-2-yl}acetic acid (3 mg) and impure material (5 mg).

IR (CH$_2$Cl$_2$): 1735, 1520, 1350 cm$^{-1}$.

EXAMPLE 122

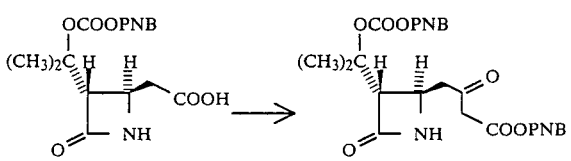

To a solution of [(2R,3S)-3-[1-methyl-1-(4-nitrobenzyloxycarbonyloxy)ethyl]-4-oxoazetidine-2-yl]-acetic acid (56.4 mg) in tetrahydrofuran (1.13 ml) was added N,N-carbonyldiimidazole (27.5 mg) at ambient temperature. After stirring for 6 hours at ambient temperature, the magnesium salts of the mono-p-nitrobenzyl ester of malonic acid (84.8 mg) was added and the resulting mixture was stirred overnight at ambient temperature. The solvent was distilled off and the residue was dissolved in ethyl acetate (30 ml) and filtered with a diatomaceous earth. The filtrate was washed with 1N hydrochloric acid, water, phosphate butter solution (pH 6.8), and saturated aqueous sodium chloride. After drying over magnesium sulfate, the ethyl acetate extract was filtered and evaporated in vacuo. The residual oil (78.8 mg) was chromatographed on silica gel (1.6 g) eluting with a mixture of methylene chloride and ethyl acetate (10:1 to 2:1) to give 4-nitrobenzyl 4-{(2R,3S)-3-[1-methyl-1-(4-nitrobenzyloxycarbonyloxy)ethyl]-4-oxoazetidine-2-yl}-3-oxobutanoate (64.2 mg) as an amorphous solid.

IR (CH$_2$Cl$_2$): 3380, 1760, 1740, 1720, 1520, 1340 cm$^{-1}$.

NMR (CDCl$_3$) δ: 1.62 (s, 3H), 1.66 (s, 3H), 2.86–3.12 (m, 2H), 3.41 (d, 1H, J=2 Hz), 3.65 (s, 2H), 3.94–4.18 (m, 1H), 5.25 (s, 2H), 5.34 (s, 2H), 6.60 (broad s, 1H), 7.63 (d, 4H, J=9 Hz), 8.30 (d, 4H, J=9 Hz).

EXAMPLE 123

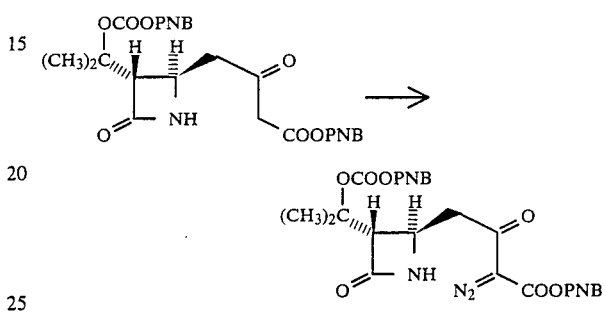

To a solution of 4-nitrobenzyl 4-{(2R,3S)-3-[1-methyl-1-(4-nitrobenzyloxycarbonyloxy)ethyl]-4-oxoazetidine-2-yl}-3-oxobutanoate (58.3 mg) in acetonitrile (1.17 ml) was added a solution of p-toluenesulfonyl azide (25.3 mg) in acetonitrile (0.228 ml) at 0° C. After stirring for 5 minutes at 0° C., a solution of triethylamine (53.7 μl) in acetonitrile (0.483 ml) was added dropwise. The stirring mixture was allowed to warm to ambient temperature during 15 minutes and kept at the same temperature for 20 minutes. The solvent was distilled off and the residue (85.9 mg) was flash chromatographed on silica gel (1 g) eluting with a mixture of methylene chloride and ethyl acetate (50:1 to 3:1) to give 4-nitrobenzyl 2-diazo-4-{(2R,3S)-3-[1-methyl-1-(4-nitrobenzyloxycarbonyloxy)-ethyl]-4-oxoazetidine-2-yl}-3-oxobutanoate (58.4 mg) as an amorphous solid IR (CH$_2$Cl$_2$): 3380, 2140, 1760, 1740, 1715, 1645, 1520, 1345 cm$^{-1}$.

NMR (CDCl$_3$) δ: 1.63 (s, 3H), 1.67 (s, 3H), 2.88–3.34 (m, 2H), 3.46 (d, 1H, J=2 Hz), 3.90–4.20 (m, 1H), 5.26 (s, 2H), 5.45 (s, 2H), 6.48 (broad s, 1H), 7.65 (d, 4H, J=9 Hz), 8.30 (d, 2H, J=9 Hz), 8.34 (d, 2H, J=9 Hz).

EXAMPLE 124

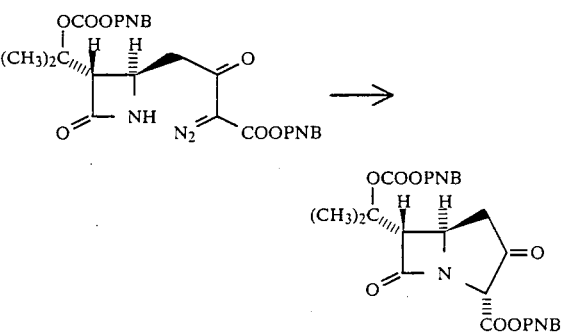

A mixture of 4-nitrobenzyl 2-diazo-4-{(2R,3S)-3-[1-methyl-1-(4-nitrobenzyloxycarbonyloxy)ethyl]-4-oxoazetidine-2-yl}-3-oxobutanoate (58.0 mg) and rhodium (II) acetate (0.1 mg) in benzene (3.4 ml) was refluxed for 30 minutes. After cooling to ambient temperature, the mixture was filtered with a diatomaceous earth and evaporated to give 4-nitrobenzyl(2R,5R,6S)-3,7-dioxo-6-[1-methyl-1-(4-nitrobenzyloxycarbonyloxy)ethyl]-1-azabicyclo[3.2.0]-heptane-2-carboxylate (47.8 mg) as an amorphous solid.

IR (CH₂Cl₂): 1760, 1735, 1730, 1515, 1345 cm⁻¹.

NMR (CDCl₃) δ: 1.70 (s, 3H), 2.49 (AB part of ABX system centered at 2.49, 2H, JAB=18 Hz, JAX=JBX=7 Hz), 3.78 (d, 1H, J=2 Hz), 4.21 (dt, 1H, J=2, 7 Hz), 4.79 (s, 1H), 5.21 (s, 2H), 5.30 (ABq, 1H, J=12 Hz), 7.53 (d, 2H, J=9 Hz), 8.22 (d, 2H, J=9 Hz).

EXAMPLE 125

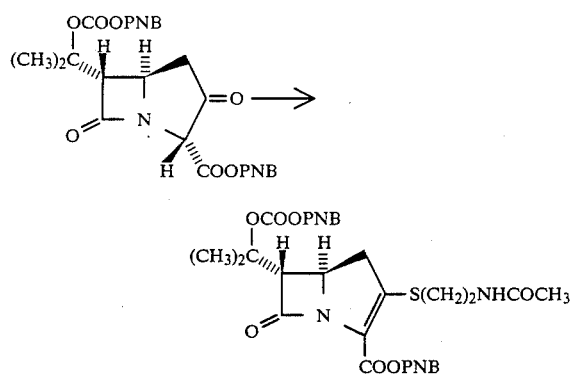

To a solution of 4-nitrobenzyl(2R,5R,6S)-3,7-dioxo-6-[1-methyl-1-(4-nitrobenzyloxycarbonyloxy)-ethyl]-1-azabicyclo[3.2.0]heptane-2-carboxylate (47.8 mg) and 4-(N,N-dimethylamino)pyridine (1.08 mg) in acetonitrile (2.39 ml) was added dropwise a solution of di-isopropylethylamine (18.5 μl) in acetonitrile (166.5 μl) followed by addition of a solution of diphenyl chlorophosphate (19.2 μl) in acetonitrile (172.8 μl) at 0° C. After stirring for an hour at 0° C., a solution of di-isopropylethylamine (61.5 μl) in acetonitrile (553.5 μl) was added followed by addition of a solution of N-(2-mercaptoethyl)-acetamide (11.05 mg) in acetonitrile (99.45 μl) at −15° C. The mixture was allowed to stand overnight at −15° C. The resulting solution was diluted with ethyl acetate (34 ml) and washed with dilute aqueous sodium chloride and saturated aqueous sodium chloride. After drying over magnesium sulfate, the ethyl acetate extract was filtered and evaporated in vacuo. The residual oil (76.4 mg) was chromatographed on silica gel (1.5 g) eluting with a mixture of methylene chloride and acetone (20:1 to 2:1) to give 4-nitrobenzyl(5R,6S)-3-(2-acetamido-ethylthio)-6-[1-methyl-1-(4-nitrobenzyloxycarbonyloxy)ethyl]-7-oxo-1-aza-bicyclo[3.2.0]hept-2-ene-2-carboxylate (54.0 mg) as an amorphous solid.

IR (CH₂Cl₂): 3410, 1775, 1725, 1710, 1685, 1520, 1350 cm⁻¹.

NMR (CDCl₃) δ: 1.65 (s, 6H), 1.98 (s, 3H), 2.7–3.6 (m, 6H), 3.77 (d, 1H, J=3 Hz), 4.27 (dt, 1H, J=3, 8 Hz), 5.18 (s, 2H), 5.33 (ABq centered at 5.33, 2H, J=13 Hz), 6.21 (broad s, 1H), 7.50 (d, 2H, J=9 Hz), 7.58 (d, 2H, J=9 Hz), 8.14 (d, 2H, J=9 Hz), 8.16 (d, 2H, J=9 Hz).

EXAMPLE 126

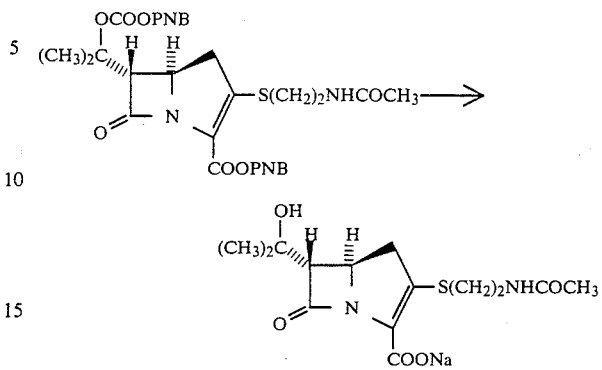

A mixture of 5% palladium-charcoal (40.0 mg), water (0.96 ml) and dioxane (2.24 ml) was shaken for 30 minutes under hydrogen atmosphere (40 psi) at ambient temperature. The mixture was added to a solution of 4-nitrobenzyl(5R,6S)-3-(2-acetamido-ethylthio)-6-[1-methyl-1-(4-nitrobenzyloxycarbonyloxy)-ethyl]-7-oxo-1-azabicyclo[3.2.0]hept-2-ene-2-carboxylate (40.0 mg) in a mixture of water (0.24 ml) and dioxane (0.56 ml), and shaken for 2 hours under hydrogen atmosphere (40 psi) at ambient temperature. The resulting mixture was added with 1% aqueous sodium hydrogen carbonate (0.522 ml) at 0° C. and filtered by using diatomaceous earth. The filtered cake was washed with water (3×5 ml) and the combined filtrates were concentrated, washed with ethyl acetate (3×20 ml) and evaporated in vacuo. The residue was dissolved in water (25 ml) containing sodium chloride (0.7 g) and chromatographed on a non ionic adsorption resin HP-20 (trademark, made by Mitsubishi Chemical Industries) (1.0×20 cm) eluting with a mixture of water and acetone (100:0 to 7:3, 200 ml). The fractions containing the product were combined and lyophilized to give sodium (5R,6S)-3-(2-acetamido-ethylthio)-6-(1-hydroxy-1-methylethyl)-7-oxo-1-azabicyclo[3.2.0]hept-2-ene-2-carboxylate (6.9 mg) as a white solid.

IR (CH₂Cl₂): 3310, 1745, 1655, 1600, 1555, 1400 cm⁻¹. UV (in H₂O): 301 nm.

EXAMPLE 127

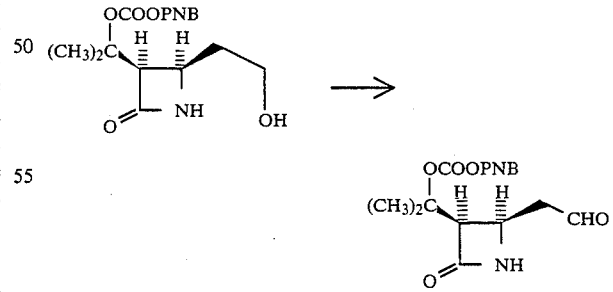

A solution of (3R,4R)-4-(2-hydroxyethyl)-3-[1-methyl-1-(4-nitrobenzyloxycarbonyloxy)ethyl]-azetidin-2-one (10 mg) in dichloromethane (1.5 ml) was added to a suspension of pyridinium chlorochromate (9.2 mg) in dichloromethane at 0° C. The stirring mixture was allowed to warm to ambient temperature and kept at the same temperature for 1.5 hours. The reaction mixture was poured into a mixture of dichloromethane (20 ml)

and dilute hydrochloric acid. The organic layer was separated and washed in turn with brine, dilute aqueous solution of sodium bicarbonate containing sodium thiosulfate, and brine. The organic layer was dried over magnesium sulfate and evaporated to give a crystalline solid (12 mg). A silica gel chromatography (0.5 g) eluting with a mixture of dichloromethane and acetone (10:1 to 5:1) afforded (3R,4R)-3-[1-methyl-1-(4-nitrobenzyloxycarbonyloxy)ethyl]-4-(2-oxoethyl)azetidin-2-one (9.7 mg) as a crystalline solid.

IR (CH$_2$Cl$_2$): 3375, 1760, 1750 (shoulder), 1715, 1520, 1350 cm$^{-1}$.

EXAMPLE 128

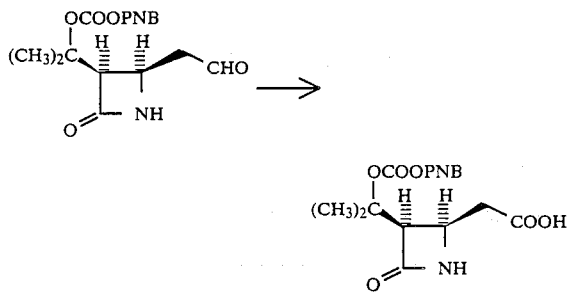

To a solution of (3R,4R)-3-[1-methyl-1-(4-nitrobenzyloxycarbonyloxy)ethyl]-4-(2-oxoethyl)azetidin-2-one (9 mg) in acetone (1 ml) was added 2N Jones reagent (60 μl) at 0° C. and the mixture was stirred at 0° C. for 30 minutes. After addition of isopropyl alcohol (100 μl), the mixture was evaporated in vacuo. The residue was taken up in chloroform (20 ml) and washed with brine. The aqueous layer was extracted with chloroform (5 ml). The combined organic layers were washed with aqueous saturated sodium chloride, dried over magnesium sulfate, and evaporated to give {(2R,3R)-3-[1-methyl-1-(4-nitrobenzyloxycarbonyloxy)ethyl]-4-oxo-azetidin-2-yl}acetic acid (7 mg).

IR (CH$_2$Cl$_2$): 1735, 1520, 1350 cm$^{-1}$.

EXAMPLE 129

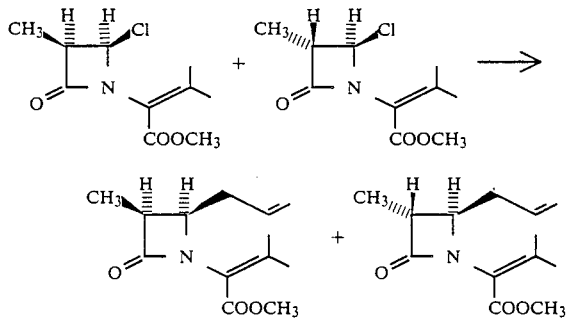

Methyl 3-methyl-2-[(3S,4R)-3-methyl-2-oxo-4-allylazetidin-1-yl]but-2-enoate and its (3S,4R)-isomer were prepared from methyl 3-methyl-2-[(3R,4R)-4-chloro-3-methyl-2-oxo-azetidin-1-yl]but-2-enoate and its (3S,4R)-isomer in a similar manner to that of Example 7.

For the (3R,4R)-isomer:

IR (CH$_2$Cl$_2$): 1740, 1710 cm$^{-1}$. NMR (CDCl$_3$) δ: 1.32 (d, 3H, J=7.5 Hz), 1.93 (s, 1H), 1.19 (s, 1H), 2.36 (q, 2H, J=8 Hz), 2.84 (dq, 1H, J=2.5, 7.5 Hz), 3.56 (dt, 1H, J=2.5, 8 Hz), 3.72 (s, 3H), 4.9–6.3 (m, 2H), 5.5–6.0 (m, 1H).

For the (3S,4R)-isomer:

IR (CH$_2$Cl$_2$): 1740, 1715 cm$^{-1}$. NMR (CDCl$_3$) δ: 1.23 (d, 3H, J=8 Hz), 1.95 (s, 3H), 2.19 (s, 3H), 1.36 (t, 2H, J=7 Hz), 3.36 (dq, 1H, J=6, 8 Hz), 3.75 (s, 3H), 4.04 (dt, 1H, J=6, 7 Hz), 4.9–5.2 (m, 2H), 5.4–5.9 (m, 2H).

EXAMPLE 130

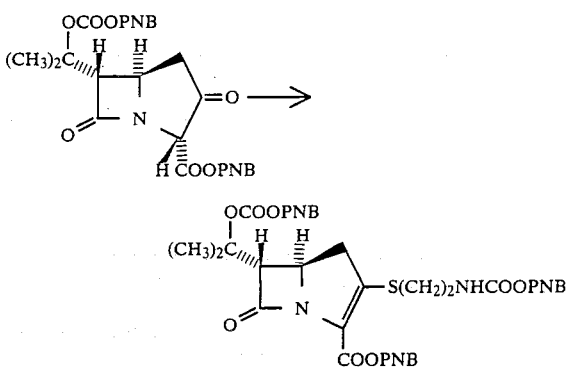

To a solution of 4-nitrobenzyl(2R,5R,6S)-3,7-dioxo-6-[1-methyl-1-(4-nitrobenzyloxycarbonyloxy)ethyl]-1-azabicyclo[3.2.0]heptane-2-carboxylate (148.5 mg) and 4-N,N-dimethylaminopyridine (3.35 mg) in acetonitrile (7.4 ml) was added dropwise a solution of di-isopropylethylamine (57.3 μl) in acetonitrile (0.516 ml). To the mixture was further added a solution of diphenyl chlorophosphate (59.6 μl) in acetonitrile (0.536 ml) at 0° C. After stirring for an hour at 0° C., a solution of diisopropylethylamine (190.9 μl) in acetonitrile (1.72 ml) was added to the mixture. To the mixture was further added a solution of N-(4-nitrobenzyloxycarbonyl)cysteamine (73.8 mg) in acetonitrile (0.664 ml) at −15° C. The mixture was allowed to stand overnight at −15° C. The resulting solution was diluted with ethyl acetate (15 ml) and washed in turn with water and saturated aqueous sodium chloride. After drying over magnesium sulfate, the ethyl acetate extract was filtered and evaporated in vacuo. The residue was chromatographed on silica gel (3 g) eluting with a mixture of methylene chloride and ethyl acetate (50:1 to 5:1) to give 4-nitrobenzyl(5R,6S)-6-[1-methyl-1-(4-nitrobenzyloxycarbonyloxy)ethyl]-3-[2-(4-nitrobenzyloxycarbonylamino)-ethylthio]-7-oxo-1-azabicyclo[3.2.0]hept-2-ene-2-carboxylate (167.8 mg) as an amorphous solid.

IR (CH$_2$Cl$_2$): 3390, 1775, 1730, 1725, 1610, 1520, 1350 cm$^{-1}$.

NMR (CDCl$_3$) δ: 1.62 (6H, s), 2.80–3.60 (6H, m), 3.78 (1H, d, J=3.0 Hz), 4.29 (1H, dt, J=3,8 Hz), 5.17 (2H, s), 5.34 (4H, ABq, J=14 Hz), 7.30–7.80 (6H, m), 8.05–8.30 (6H, m).

EXAMPLE 131

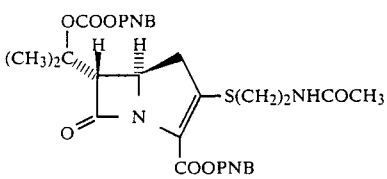

121

-continued

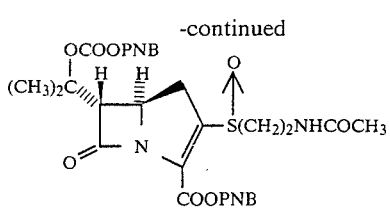

To a solution of 4-nitrobenzyl(5R,6S)-3-(2-acetamidoethylthio)-6-[1-methyl-1-(4-nitrobenzyloxycarbonyloxy)-ethyl]-7-oxo-1-azabicyclo[3.2.0]hept-2-ene-2-carboxylate (17.6 mg) in methylene chloride (0.70 ml) was added dropwise a solution of m-chloroperbenzoic acid (6.50 mg) in methylene chloride (0.319 ml) over a period of 5 minutes at −20° C. After stirring for 30 minutes at −20° C., the reaction mixture was diluted with ethyl acetate (10 ml), washed in turn with chilled 10% aqueous sodium hydrogen carbonate (0.5 ml) and saturated aqueous sodium chloride, filtered and concentrated under reduced pressure to give an oil (20.6 mg). The residual oil was chromatographed on silica gel (400 mg) eluting with a mixture of methylene chloride and acetone (10:1 to 2:1) to give 4-nitrobenzyl(5R,6S)-3-(2-acetamidoethylsulfinyl)-6-[1-methyl-1-(4-nitrobenzyloxycarbonyloxy)ethyl]-7-oxo-1-azabicyclo[3.2.0]-hept-2-ene-2-carboxylate (15.9 mg) as an oil.

IR (CH$_2$Cl$_2$): 1780, 1740, 1705, 1670, 1605, 1530, 1350 cm$^{-1}$.

NMR (CDCl$_3$) δ: 1.27 (3H, s), 1.66 (3H, s), 2.02 (2.1H, s), 2.18 (0.9H, s), 2.50–4.05 (7H, m), 4.10–4.70 (1H, m), 5.18 (2H, s), 5.37 (2H, ABq, J=13 Hz), 6.45 (1H, broad s), 7.30–7.80 (2H, m), 8.00–8.45 (2H, m).

EXAMPLE 132

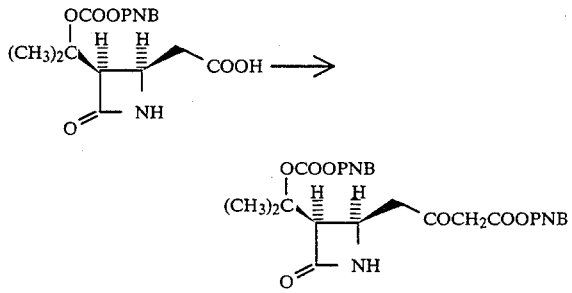

N,N'-Carbonyldiimidazole (540 mg) was added to a solution of [(2R,3R)-3-{1-methyl-1-(4-nitrobenzyloxycarbonyloxy)-ethyl}-4-oxoazetidin-2-yl]acetic acid (1.06 g) in tetrahydrofuran (50 ml) at ambient temperature. After stirring for 7 hours at the same temperature, magnesium salt of mono-p-nitrobenzyl malonate (1.45 g) was added thereto, and the resultant mixture was stirred overnight at ambient temperature. The solvent was distilled off in vacuo. The residue was dissolved in ethyl acetate (100 ml) and filtered. The filtrate was washed in turn with 0.1N hydrochloric acid, water, saturated aqueous sodium chloride, aqueous sodium bicarbonate, water, saturated aqueous sodium chloride, 5% aqueous citric acid, water and saturated aqueous sodium chloride. After drying over magnesium sulfate, the solution was evaporated. The residue was chromatographed on silica gel (30 g) eluting with a mixture of methylene chloride and ethyl acetate (50:1 to 2:1) to give formy substance, which was crystallized from a mixture of chloroform and diisopropyl ether, washed with diisopropyl ether and then dried in vacuo to give 4-nitrobenzyl 4-[(2R,3R)-3-{1-methyl-1-(4-nitrobenzyloxycarbonyloxy)ethyl}-4-oxoazetidin-2-yl]-3-oxobutanoate (1.31 g), mp 123°–125° C. (dec.).

IR (CH$_2$Cl$_2$): 3400, 1760, 1750, 1720, 1525, 1350 cm$^{-1}$. NMR (acetone-d$_6$) δ: 1.64 (3H, s), 1.74 (3H, s), 3.35 (2H, d, J=6.5 Hz), 3.65 (1H, d, J=6 Hz), 3.74 (2H, s), 4.20 (1H, m), 5.28 (2H, s), 5.31 (2H, s), 7.18 (1H, s), 7.93 (8H, A$_2$B$_2$, J=8 Hz).

EXAMPLE 133

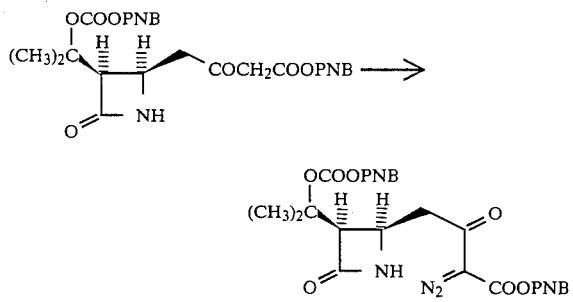

A solution of p-toluenesulfonyl azide (435 mg) in acetonitrile (3.9 ml) was added to a solution of 4-nitrobenzyl 4-[(2R,3R)-3-{1-methyl-1-(4-nitrobenzyloxycarbonyloxy)ethyl}-4-oxoazetidin-2-yl]-3-oxobutanoate (1.00 g) in acetonitrile (20 ml) at 0° C.

After stirring at 0° C. for 5 minutes, triethylamine (0.923 ml) was added dropwise thereto. After stirring at 0° C. for additional 20 minutes, the reaction mixture was evaporated. The residue was chromatographed on silica gel (20 g) eluting with a mixture of n-hexane and ethyl acetate (10:1 to 1:4) to give 4-nitrobenzyl 2-diazo-4-[(2R,3R)-3-{1-methyl-1-(4-nitrobenzyloxycarbonyloxy)-ethyl}-4-oxoazetidin-2-yl]-3-oxobutanoate (1.08 g).

IR (CH$_2$Cl$_2$): 3400, 2150, 1765, 1750, 1720, 1655, 1525, 1350 cm$^{-1}$.

NMR (CDCl$_3$) δ: 1.68 (3H, s), 1.79 (3H, s), 3.4–3.7 (2H, m), 3.46 (2H, d, J=4.5 Hz), 4.0–4.3 (1H, m) 5.20 (2H, s), 5.35 (2H, s), 6.22 (1H, s), 7.80 (4H, A$_2$B$_2$, J=9 Hz), 7.85 (4H, A$_2$B$_2$, J=9 Hz).

EXAMPLE 134

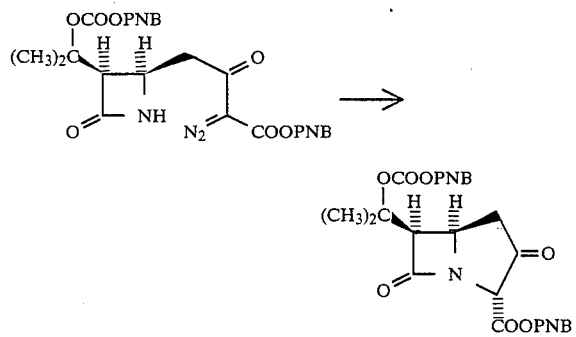

A mixture of 4-nitrobenzyl 2-diazo-4-[(2R,3R)-3-{1-methyl-1-(4-nitrobenzyloxycarbonyloxy)ethyl}-4-oxoazetidin-2-yl]-3-oxobutanoate (1.00 g) and rhodium (II) acetate (5 mg) in benzene (50 ml) was refluxed for 25 minutes. After cooling to ambient temperature, the mixture was filtered through cellulose powder. The filtrate was evaporated to give 4-nitrobenzyl(2R,5R,6R)-3,7-dioxo-6-[1-methyl-1-(4-nitrobenzyloxycarbonyloxy)ethyl]-1-azabicyclo[3.2.0]heptane-2-carboxylate (0.94 g) as an amorphous solid.

IR (CH$_2$Cl$_2$): 1770, 1750, 1525, 1350 cm$^{-1}$.

NMR (CDCl$_3$) δ: 1.64 (3H, s), 1.84 (3H, s), 2.74 (1H, dd, J=19 Hz, 8 Hz), 3.34 (1H, dd, J=19 Hz, 8 Hz), 3.77 (1H, d, J=6 Hz), 4.34 (1H, dt, J=6 Hz, 8 Hz), 4.76 (1H, s), 5.18 (2H, s), 5.32 (2H, ABq, J=16 Hz), 7.88 (4H, A$_2$B$_2$, J=9 Hz), 7.91 (4H, A$_2$B$_2$, J=9 Hz).

EXAMPLE 135

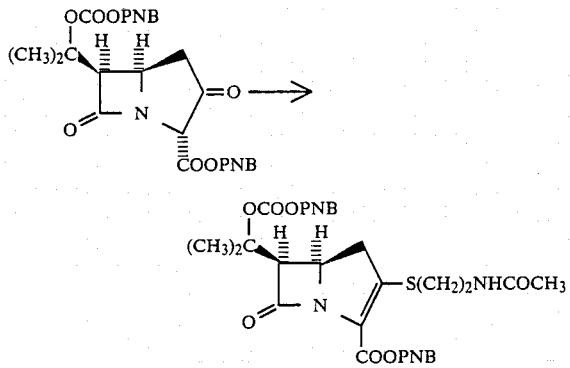

To a solution of 4-nitrobenzyl (2R,5R,6R)-3,7-dioxo-6-[1-methyl-1-(4-nitrobenzyloxycarbonyloxy)ethyl]-1-azabicyclo[3.2.0]heptane-2-carboxylate (58 mg) and 4-(N,N-dimethylamino)pyridine (1.3 mg) in acetonitrile (3 ml) was added a solution of diisopropylethylamine (22.4 μl) in acetonitrile (0.21 ml) at 0° C. To the mixture was added a solution of diphenyl chlorophosphate (23.3 μl) in acetonitrile (0.21 ml) at 0° C. After stirring at 0° C. for 1.5 hours, the reaction mixture was cooled to −15° C., to which a solution of diisopropylethylamine (74.6 μl) in acetonitrile (0.73 ml) was added. To the mixture was added a solution of N-(2-mercaptoethyl)acetamide (13.4 mg) in acetonitrile (0.12 ml). After standing overnight at −15° C., the mixture was diluted with ethyl acetate (50 ml), washed in turn with water and saturated aqueous sodium chloride, and dried over magnesium sulfate. After evaporation of the solvent, the residue was chromatographed on silica gel (2 g) eluting with a mixture of methylene chloride and acetone (20:1 to 2:1) to give 4-nitrobenzyl (5R,6R)-3-(2-acetamidoethylthio)-6-[1-methyl-1-(4-nitrobenzyloxycarbonyloxy)ethyl]-7-oxo-1-azabicyclo[3.2.0]hept-2-ene-2-carboxylate (56 mg) as an amorphous solid.

IR (CH$_2$Cl$_2$): 3400, 1775, 1745, 1695, 1675, 1530, 1350 cm$^{-1}$.

NMR (CDCl$_3$) δ: 1.68 (3H, s), 1.81 (3H, s), 1.96 (3H, s), 2.8–4.0 (6H, m), 3.76 (1H, d, J=6 Hz), 4.2–4.6 (1H, m), 5.18 (2H, s), 5.38 (2H, ABq, J=15 Hz), 6.30 (1H, broad t, J=6 Hz), 7.88 (4H, A$_2$B$_2$, J=9 Hz), 7.95 (4H, A$_2$B$_2$, J=9 Hz).

EXAMPLE 136

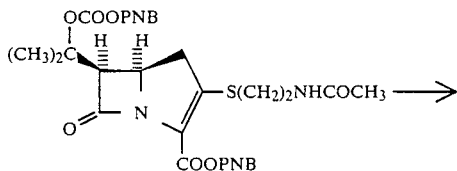

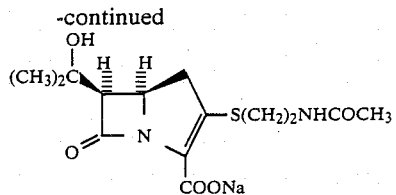

A mixture of 5% palladium on activated carbon (175 mg), dioxane (12.5 ml) and 1/30M sodium phosphate buffer (pH 7.0, 5.5 ml) was shaken for an hour under a hydrogen atmosphere (40 psi) at ambient temperature. A solution of 4-nitrobenzyl (5R,6R)-3-(2-acetamidoethylthio)-6-[1-methyl-1-(4-nitrobenzyloxycarbonyloxy)ethyl]-7-oxo-1-azabicyclo[3.2.0]hept-2-ene-2-carboxylate (175 mg) in a mixture of dioxane (12 ml) and 1/30M sodium phosphate buffer (pH7.0, 5 ml) was added to the mixture at 0° C. and the resulting mixture was shaken under a hydrogen atmosphere (40 psi) for an hour, during which time the reaction temperature rose to ambient temperature. 1% Aqueous solution of sodium bicarbonate (2.29 ml) was added therein at 0° C. and the mixture was filtered through cellulose powder. The filter-cake was washed with water (3×20 ml). The combined filtrates were concentrated to a half volume, washed with ethyl acetate (3×50 ml), and evaporated in vacuo. The residue was dissolved in water (220 ml) containing sodium chloride (6.6 g) and chromatographed on Diaion non-ionic adsorption resin, HP-20 AG (trade mark, made by Mitsubishi Chemical Industries) (150–300μ, φ2.2×36 cm) eluting with water (360 ml) and a mixture of water and acetone (10:0 to 7:3, 600 ml). The fractions, whose UV spectra showed λmax 300 nm, were combined and lyophilized to give sodium (5R,6R)-3-(2-acetamidoethylthio)-6-(1-hydroxy-1-methylethyl)-7-oxo-1-azabicyclo[3.2.0]hept-2-ene-2-carboxylate (46.5 mg) as white powder.

IR (KBr): 1750, 1650, 1590, 1550, 1400 cm$^{-1}$.

NMR (D$_2$O) δ: 1.29 (3H, s), 1.40 (3H, s), 1.97 (3H, s), 2.90 (2H, t, J=8 Hz), 3.04 (1H, dd, J=17 Hz, 10 Hz), 3.36 (2H, t, J=8 Hz), 3.67 (1H, d, J=6 Hz), 3.76 (1H, dd, J=17 Hz, 9 Hz), 4.14 (1H, ddd, J=6 Hz, 9 Hz, 10 Hz).

EXAMPLE 137

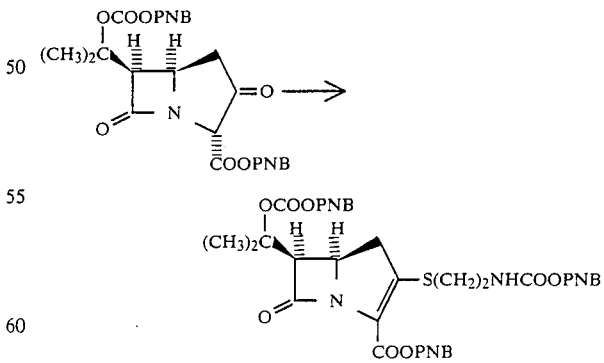

To a solution of 4-nitrobenzyl (2R,5R,6R)-3,7-dioxo-6-[1-methyl-1-(4-nitrobenzyloxycarbonyloxy)ethyl]-1-azabicyclo[3.2.0]heptane-2-carboxylate (602 mg) and 4-(N,N-dimethylamino)pyridine (13.6 ml) in acetonitrile (30 ml) was added a solution of diisopropylethylamine (0.232 ml) in acetonitrile (2.08 ml) at 0° C. To the mixture was further added a solution of diphenyl chlorophosphate (0.242 ml) in acetonitrile (2.18 ml). After stirring at 0° C. for an hour, the mixture was cooled to −15° C. To the mixture was added a solution of diisopropylethylamine (0.775 ml) in acetonitrile (6.97 ml) and N-(4-nitrobenzyloxycarbonyl)cysteamine (299 mg) were added. After standing overnight at −15° C., the mixture was evaporated in vacuo. The residue was dissolved in ethyl acetate (100 ml) and the solution was washed in turn with water and saturated aqueous sodium chloride, dried over magnesium sulfate, and evaporated in vacuo. The residue was chromatographed on silica gel (18 g) eluting with a mixture of benzene and acetone (20:1 to 6:1) to give 4-nitrobenzyl (5R,6R)-6-[1-methyl-1-(4-nitrobenzyloxycarbonyloxy)ethyl]-3-[2-(4-nitrobenzyloxycarbonylamino)ethylthio]-7-oxo-1-azabicyclo[3.2.0]hept-2-ene-2-carboxylate (716 mg) as an amorphous solid.

IR (CH$_2$Cl$_2$): 3430, 1780, 1745, 1730, 1710, 1605, 1520, 1345 cm$^{-1}$.

NMR (CDCl$_3$) δ: 1.64 (3H, s), 1.80 (3H, s), 2.7–3.5 (5H, m), 3.5–4.0 (1H, m), 3.70 (1H, d, J=5 Hz), 4.3 (1H, m), 5.09 (2H, s), 5.13 (2H, s), 5.32 (2H, ABq, J=13 Hz), 7.78 (8H, A$_2$B$_2$, J=8 Hz), 7.85 (4H, A$_2$B$_2$, J=8 Hz).

EXAMPLE 138

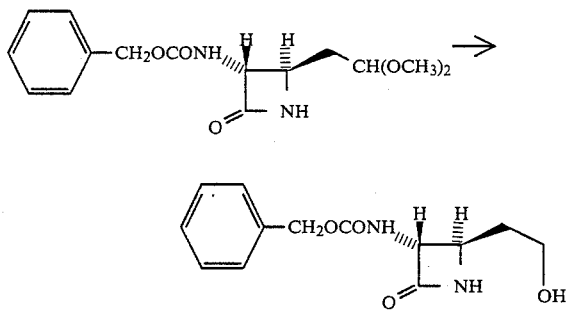

To a solution of (3R,4R)-3-(benzyloxycarbonylamino)-4-(2,2-dimethoxyethyl)azetidin-2-one (1.014 g) in tetrahydrofuran (15 ml) were added portionwise a solution of sodium cyanoborohydride (460 mg) in tetrahydrofuran (2.30 ml) and 2N hydrochloric acid (7.5 ml) at ambient temperature during a period of 90 minutes. The solution was adjusted to pH 7 with saturated aqueous sodium hydrogen carbonate and concentrated in vacuo. The concentrate was acidified to pH 4 with 2N hydrochloric acid, saturated with sodium chloride and extracted four times with chloroform. The combined extracts were dried over magnesium sulfate and evaporated in vacuo. The residue was chromatographed on silica gel (15 g, eluting with 3–10% methanol in dichloromethane) to give a crystalline solid, which was washed with ether and collected by filtration to give 553 mg of (3R,4R)-3-benzyloxycarbonylamino-4-(2-hydroxyethyl)azetidin-2-one.

IR (CH$_2$Cl$_2$): 1770, 1720 cm$^{-1}$.

EXAMPLE 139

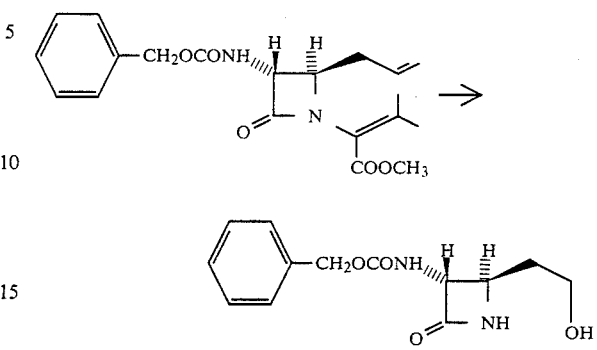

Ozone was bubbled into a solution of methyl 2-[(3R,4R)-3-benzyloxycarbonylamino-2-oxo-4-(prop-2-enyl)-azetidin-1-yl]-3-methylbut-2-enoate (119 mg) in ethyl acetate (6 ml) at −78° C. until a permanent blue color developed. The excess ozone was removed by a stream of nitrogen and dimethyl sulfide (0.3 ml) was added. The mixture was allowed to warm to 4° C., kept in a refrigerator (4° C.) for 7 hours and left at room temperature for 39 hours. The yellow solution was concentrated under reduced pressure and the residue was dissolved in methanol (4 ml). Aqueous potassium hydrogen carbonate (1.0M, 0.4 ml) was added therein and the resulting mixture was stirred at room temperature for 30 minutes. The solution was then cooled to 0° C. and sodium borohydride (22 mg) was added to the solution. After 17 minutes stirring, acetic acid (0.15 ml) was added to the mixture and the mixture was evaporated in vacuo. The residue was dissolved in chloroform and washed with saturated aqueous sodium chloride containing sodium hydrogen carbonate. The aqueous layer was extracted twice with chloroform. The combined extracts were dried over magnesium sulfate and evaporated in vacuo. The residue was chromatographed on silica gel (2 g, eluting with 5–10% methanol in dichloromethane) to give 50 mg of (3R,4R)-3-benzyloxycarbonylamino-4-(2-hydroxyethyl)azetidin-2-one.

IR (CH$_2$Cl$_2$): 1770, 1720 cm$^{-1}$.

EXAMPLE 140

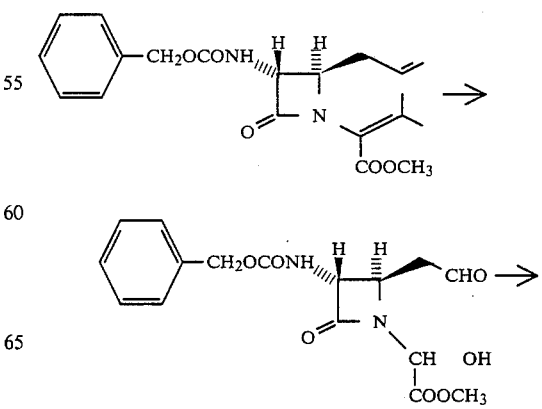

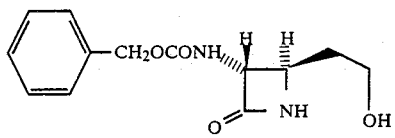

Ozone was bubbled into a solution of methyl 2-[(3R,4R)-3-benzyloxycarbonylamino-2-oxo-4-(prop-2-enyl)-azetidin-1-yl]-3-methylbut-2-enoate (382 mg) in methanol (8 ml) at −78° C. until a permanent blue color developed. After five minutes stirring the excess ozone was removed by a stream of nitrogen. Dimethylsulfide (0.4 ml) was added and the solution was stirred at −78° C. for 35 minutes. Sodium borohydride (80 mg) was then added the solution and the reaction was continued for 40 minutes at the same temperature and quenched by addition of acetic acid (0.15 ml). The resulting mixture was stirred at −78° C. for 30 minutes, allowed to warm to 0° C. during 50 minutes and concentrated in vacuo. The residue was dissolved in a 10:1 mixture of ethyl acetate and chloroform (30 ml) and washed in turn with saturated aqueous sodium chloride (twice), a mixture of saturated aqueous sodium chloride and saturated aqueous sodium hydrogen carbonate, and saturated aqueous sodium chloride. The resultant mixture was dried over magnesium sulfate and concentrated under reduced pressure to give 352 mg of methyl 2-[(3R,4R)-3-benzyloxycarbonylamino-2-oxo-4-(2-oxoethyl)azetidin-1-yl]-2-hydroxyacetate.

IR (CH₂Cl₂): 3300–3700 (br), 3380, 1770, 1740 (sh) 1720 cm⁻¹.

NMR (CDCl₃) δ: 2.0 (1H, br), 2.97 (2H, brd, J=6 Hz), 3.72 (3H, s), 4.16 (1H, dt, J=2,6 Hz), 4.47 (1H, dd, J=2,7 Hz), 5.06 (2H, s), 5.52 (1H, brs), 5.91 (1H, d, J=7 Hz), 7.28 (5H, s), 9.65 (1H, s).

The aldehyde (318 mg) obtained above was dissolved in methanol (5 ml) and the solution was cooled to 0° C. 1N Aqueous potassium hydrogen carbonate (0.5 ml) was added and the mixture was stirred at 0° C. for 5 minutes and at ambient temperature for 30 minutes. Sodium borohydride (38 mg) was then added to the mixture at 0° C. and the mixture was stirred at the same temperature for 15 minutes and quenched by addition of acetic acid (0.15 ml). After concentration in vacuo, the residue was dissolved in chloroform and washed with brine containing sodium hydrogen carbonate. The aqueous layer was extracted three times with chloroform. The combined extracts were dried over magnesium sulfate and evaporated in vacuo to give a crystalline solid, which was chromatographed on silica gel (6 g, eluting with 3–10% methanol in dichloromethane) to give 113 mg of (3R,4R)-3-benzyloxycarbonylamino-4-(2-hydroxyethyl)azetidin-2-one.

IR (CH₂Cl₂): 1770, 1720 cm⁻¹.

EXAMPLE 141

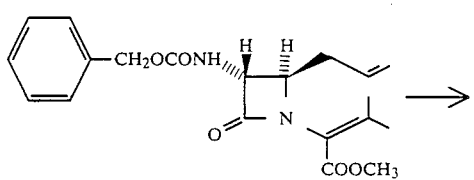

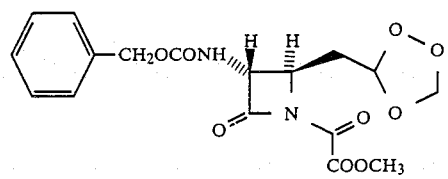

Ozone was bubbled into a solution of methyl 2-[(3R,4R)-3-benzyloxycarbonylamino-2-oxo-4-(prop-2-enyl)azetidin-1-yl]-3-methylbut-2-enoate (255 mg) in ethyl acetate (6.5 ml) at −78° C. until a permanent blue color developed. The excess ozone was removed by a stream of nitrogen. The solution was allowed to warm to 0° C. and washed with dilute aqueous sodium hydrogen sulfite and brine. The resultant mixture was dried over magnesium sulfate and concentrated under reduced pressure to give 251 mg of methyl 2-[(3R,4R)-3-benzyloxycarbonylamino-2-oxo-4-(1,2,4-trioxolan-3-yl)-methylazetidin-1-yl]-2-oxoacetate.

IR (CH₂Cl₂): 3390, 1810, 1745, 1720, 1705 cm⁻¹.

EXAMPLE 142

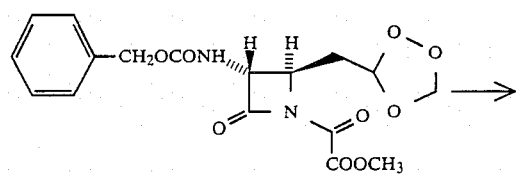

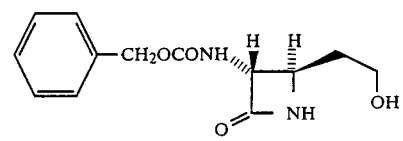

To a solution of methyl 2-[(3R,4R)-3-benzyloxycarbonylamino-2-oxo-4-(1,2,4-trioxolan-3-yl)-methylazetidin-1-yl]-2-oxoacetate (205 mg) in methanol (4 ml) was added 1N aqueous potassium hydrogen carbonate (0.5 ml) at ambient temperature. The mixture was stirred for 25 minutes and cooled to 0° C. Sodium borohydride (40 mg) and 1N aqueous potassium hydrogen carbonate were added to the mixture at 0° C. The reaction mixture was stirred at 0° C. for 30 minutes and at ambient temperature for an additional 30 minutes, and quenched by addition of acetic acid (0.20 ml). The resulting mixture was concentrated under reduced pressure and the residue was dissolved in chloroform and washed with brine containing sodium hydrogen carbonate. The aqueous layer was extracted three times with chloroform. The combined extracts were dried over magnesium sulfate, evaporated in vacuo, and chromatographed on silica gel (3 g, eluting with 10–30% acetone in dichloromethane) to give 66 mg of (3R,4R)-3-benzyloxycarbonylamino-4-(2-hydroxyethyl)azetidin-2-one.

IR (CH₂Cl₂): 1770, 1720 cm⁻¹.

EXAMPLE 143

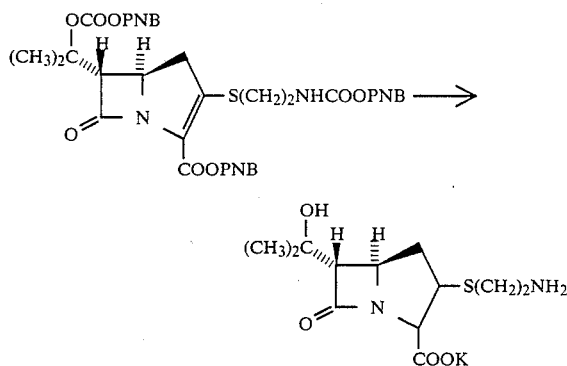

A mixture of platinum oxide (60.0 mg), water (4.2 ml) aqueous dipotassium hydrogen phosphate (1.0M, 0.385 ml) and ethanol (0.6 ml) was shaken for 30 minutes under a hydrogen atmosphere (50 psi) at ambient temperature. The mixture was added to a solution of 4-nitrobenzyl (5R,6S)-6-[1-methyl-1-(4-nitrobenzyloxycarbonyloxy)ethyl]-3-[2-(4-nitrobenzyloxycarbonylamino)ethylthio]-7-oxo-1-azabicyclo[3.2.0]hept-2-ene-2-carboxylate (60.0 mg) in dioxane (7.2 ml) and shaken for 30 minutes under a hydrogen atmosphere (50 psi) at ambient temperature. The reaction mixture was filtered with diatomaceous earth. The filter-cake was washed with water (20 ml) and the combined filtrates (32 ml) were lyophilized over a period of 6 hours. The residue was chromatographed on non-ionic adsorption resin, Diaion HP-20-AG (trade mark, made by Mitsubishi Chemical Industries) (15×260 mm) eluting with water (230 ml) and then a mixture of water and methanol (7:3, 140 ml). The fractions showing UV maxima at 298 nm were collected, concentrated and lyophilized to give potassium (5R,6S)-3-(2-aminoethylthio)-6-(1-hydroxy-1-methylethyl)-7-oxo-1-azabicyclo[3.2.0]hept-2-ene-2-carboxylate (12.1 mg) as pale yellow powder.

IR (Nujol): 3350, 1750, 1575, 1380 cm$^{-1}$.

UV (H$_2$O): 298 nm ($\epsilon$=7970).

NMR (D$_2$O) $\delta$: 1.34 (3H, s), 1.38 (3H, s), 3.00–3.38 (6H, m), 3.47 (1H, d, J=3 Hz), 4.22 (1H, dt, J=3.8 Hz).

EXAMPLE 144

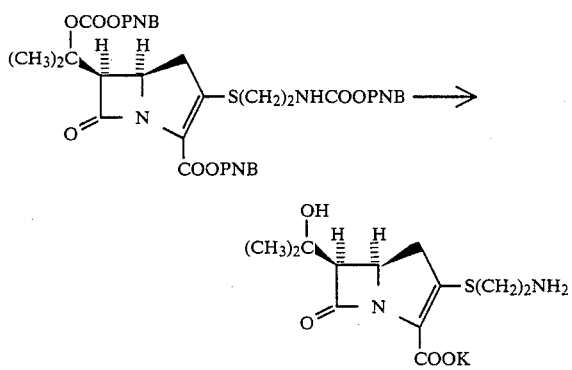

A mixture of platinum oxide (60.0 mg), water (4.2 ml), aqueous dipotassium hydrogen phosphate (1.0M, 0.385 ml) and ethanol (0.6 ml) was shaken for 30 minutes under a hydrogen atmosphere (50 psi) at ambient temperature. The mixture was added to a solution of 4-nitrobenzyl (5R,6R)-6-[1-methyl-1-(4-nitrobenzyloxycarbonyloxy)ethyl]-3-[2-(4-nitrobenzyloxycarbonylamino)-ethylthio]-7-oxo-1-azabicyclo-[3.2.0]hept-2-ene-2-carboxylate (60.0 mg) in dioxane (7.2 ml) and shaken for 2 hours under a hydrogen atmosphere (50 psi) at ambient temperature. The reaction mixture was filtered using diatomaceous earth and the filter-cake was washed with water (20 ml). The combined filtrates (32 ml) were lyophilized over a period of 4 hours. The residue was chromatographed on non-ionic adsorption resin, Diaion HP-20-AG (trade mark, made by Mitsubishi Chemical Industries) (13×230 mm) eluting with water (120 ml) and then a mixture of water and isopropanol (19:1, 60 ml). The fractions showing UV maxima at 296 nm were collected, concentrated and lyophilized to give potassium (5R,6R)-3-(2-aminoethylthio)-6-(1-hydroxy-1-methylethyl)-7-oxo-1-azabicyclo[3.2.0]hept-2-ene-2-carboxylate (10.4 mg) as pale yellow powder.

IR (Nujol): 3350, 1750, 1580, 1375 cm$^{-1}$.

UV (H$_2$O): 296 nm ($\epsilon$=6580).

NMR (D$_2$O) $\delta$: 1.31 (3H, s), 1.43 (3H, s), 2.70–3.38 (6H, m), 3.69 (1H, d, J=5 Hz), 4.25 (1H, dt, J=5,8 Hz).

EXAMPLE 145

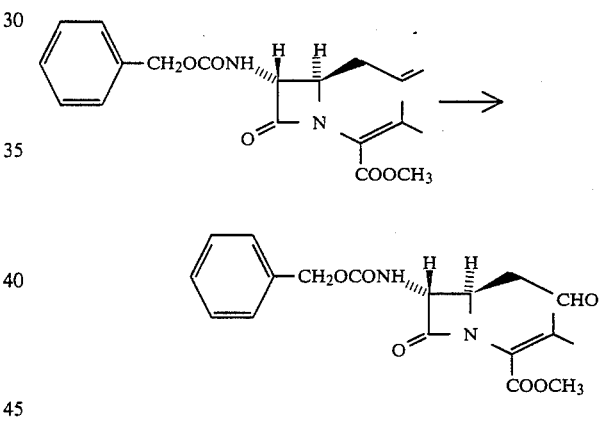

A solution of osmium tetroxide (0.61 mg) in water (0.05 ml) was added to a solution of methyl 2-[(3R,4R)-3-benzyloxycarbonylamino-2-oxo-4-(prop-2-enyl)azetidin-1-yl]-3-methylbut-2-enoate (58 mg) and sodium chlorate (50 mg) in a mixture of tetrahydrofuran (1 ml) and water (1 ml) and the mixture was stirred for 17 hours at ambient temperature. Sodium periodate (60 mg) was then added and stirring was continued for 30 minutes. The resulting mixture was diluted with brine and extracted with ethyl acetate. The extract was washed successively with brine, brine containing sodium bicarbonate, and brine. The mixture was dried over magnesium sulfate and concentrated under reduced pressure to give an oil, which was chromatographed on silica gel (1.5 g, eluting with 2.5% methanol in dichloromethane) to give 49 mg of methyl 2-[(3R,4R)-3-benzyloxycarbonylamino-2-oxo-4-(2-oxoethyl)azetidin-1-yl]-3-methylbut-2-enoate.

IR (CH$_2$Cl$_2$): 3420, 1765, 1725 cm$^{-1}$.

EXAMPLE 146

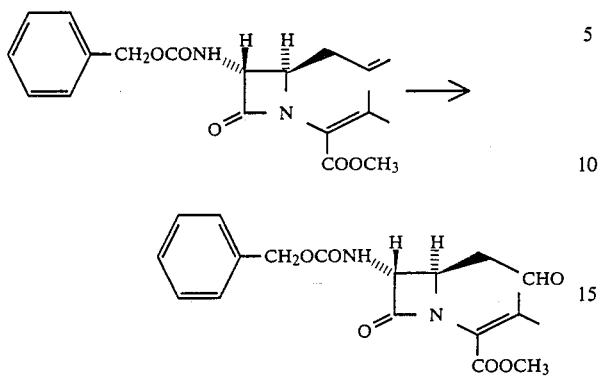

A solution of osmium tetroxide (0.61 mg) in water (0.05 ml) was added to a mixture of methyl 2-[(3R,4R)-3-benzyloxycarbonylamino-2-oxo-4-(prop-2-enyl)acetidin-1-yl]-3-methylbut-2-enoate (106 mg) and sodium periodate (36.5 mg) in a mixture of tetrahydrofuran (1 ml) and water (1 ml). After 25 minutes stirring at ambient temperature, additional sodium periodate (101.2 mg) was added and the mixture was stirred at ambient temperature for 4.5 hours. The resulting mixture was diluted with brine containing sodium bicarbonate and extracted twice with dichloromethane. The combined extracts were dried over magnesium sulfate and evaporated to give 110 mg of methyl 2-[(3R,4R)-3-benzyloxycarbonylamino-2-oxo-4-(2-oxoethyl)azetidin-1-yl]-3-methylbut-2-enoate as an oil.

IR ($CH_2Cl_2$): 3420, 1765, 1725 cm$^{-1}$.

EXAMPLE 147

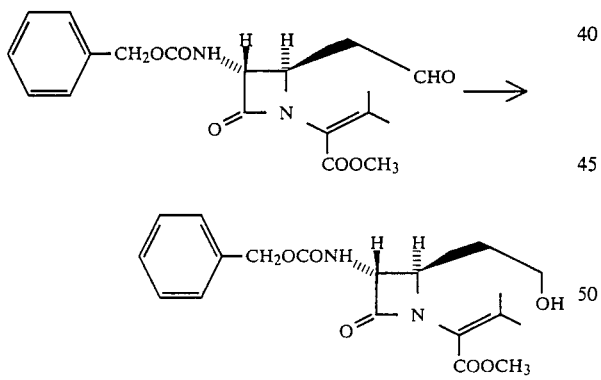

Sodium borohydride (10 mg) was added to a solution of methyl 2-[(3R,4R)-3-benzyloxycarbonylamino-2-oxo-4-(2-oxoethyl)azetidin-1-yl]-3-methylbut-2-enoate (49 mg) in methanol (1 ml) at 0° C. The mixture was stirred at the same temperature for 20 minutes and quenched with acetic acid (~0.05 ml). The resulting solution was evaporated in vacuo. The residue was dissolved in dichloromethane and washed with brine containing sodium bicarbonate. The extract was dried over magnesium sulfate, evaporated, and chromatographed on silica gel (1.5 g, eluting with 5–10% acetone in dichloromethane) to give 39 mg of methyl 2-[(3R,4R)-3-benzyloxycarbonylamino-4-(2-hydroxyethyl)-2-oxoazetidin-1-yl]-3-methylbut-2-enoate.

IR ($CH_2Cl_2$): 1765, 1720 (br) cm$^{-1}$.

NMR ($CDCl_3$): 1.7–2.2 (2H, m), 1.90 (3H, s), 2.17 (3H, s), 3.4–4.0 (4H, m), 3.71 (3H, s), 4.56 (1H, dd, J=2,7 Hz), 5.11 (2H, s), 6.10 (1H, m), 7.33 (5H, s).

EXAMPLE 148

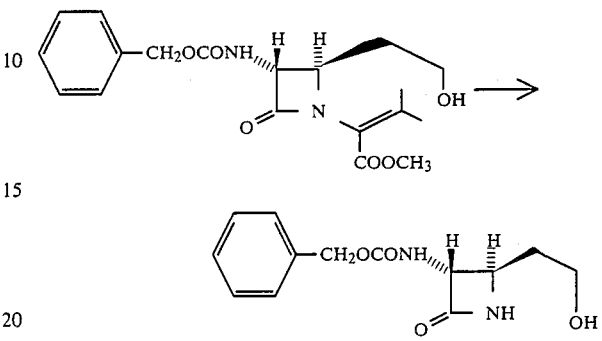

A stream of ozone was bubbled into a solution of methyl 2-[(3R,4R)-3-benzyloxycarbonylamino-4-(2-hydroxyethyl)-2-oxoazetidin-1-yl]-3-methylbut-2-enoate (76 mg) in methanol (6 ml) at −78° C. until the starting material disappeared. The excess ozone was removed by a stream of nitrogen. Dimethyl sulfide (0.3 ml) was added and the resulting solution was allowed to warm to ambient temperature for five hours. The solution was cooled to 0° C., to which a solution of sodium methoxide in methanol (0.1M, 0.25 ml) was added. The mixture was stirred at 0° C. for 30 minutes and quenched by addition of acetic acid (excess). The solution was evaporated in vacuo and the residue was chromatographed on silica gel (1.5 g, eluting with 2.5–10% methanol in dichloromethane) to give 46 mg of a crystalline solid, which was triturated in diethyl ether and filtered to give 40 mg of (3R,4R)-3-benzyloxycarbonylamino-4-(2-hydroxyethyl)azetidin-2-one.

IR ($CH_2Cl_2$): 1770, 1720 cm$^{-1}$.

EXAMPLE 149

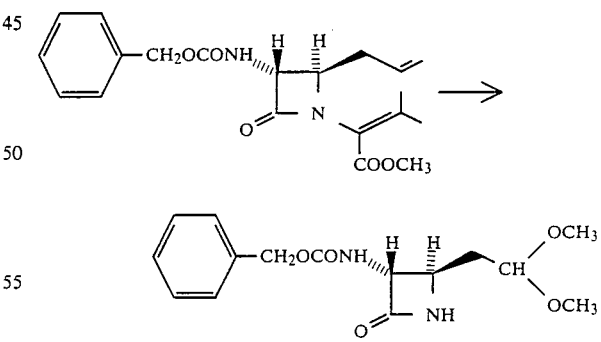

A stream of ozone was bubbled into a solution of methyl 2-[(3R,4R)-3-benzyloxycarbonylamino-2-oxo-4-(prop-2-enyl)azetidin-1-yl]-3-methylbut-2-enoate (85.6 g) in methanol (1.54 l) at −78° C. until a permanent blue color developed. After 30 minutes the excess ozone was removed by purging nitrogen into the solution and dimethyl sulfide (85.6 ml) was then added. The solution was allowed to warm to 4° C., kept at the same temperature for 15 hours and left at ambient temperature for 24 hours. To the resulting solution were added methyl orthoformate (171.2 ml) and p-toluenesulfonic acid monohydrate (1.18 g). The solution was heated at 50° C. for three hours, cooled to ambient temperature, neutralized with pyridine (0.71 ml) and concentrated in vacuo. The residue was dissolved in ethyl acetate (1.5 l) and washed with brine containing 1N hydrochloric acid, and brine. The aqueous layers were combined and extracted with ethyl acetate. The combined organic layers were washed with brine, brine containing sodium bicarbonate, and brine, dried over magnesium sulfate and evaporated in vacuo. The residue was dissolved in methanol (1.54 l) and cooled to 4° C. A 4.9M methanolic sodium methoxide (0.151 ml) was then added and the resultant solution was stirred for 15 minutes, quenched with acetic acid (0.151 ml) and concentrated under reduced pressure. The residue was dissolved in ethyl acetate, washed in turn with brine containing sodium bicarbonate and brine, dried over magnesium sulfate, and evaporated in vacuo. The residue was subjected to column chromatography on silica gel (1 kg, eluting with 10 to 30% acetone in dichloromethane). The eluate was concentrated under reduced pressure to give a residue, which was crystallized from a 1:1 mixture of diethyl ether and diisopropyl ether to give 48.23 g of (3R,4R)-3-benzyloxycarbonylamino-4-(2,2-dimethoxyethyl)azetidin-2-one.

IR (CH$_2$Cl$_2$): 1770, 1720 cm$^{-1}$.

EXAMPLE 150

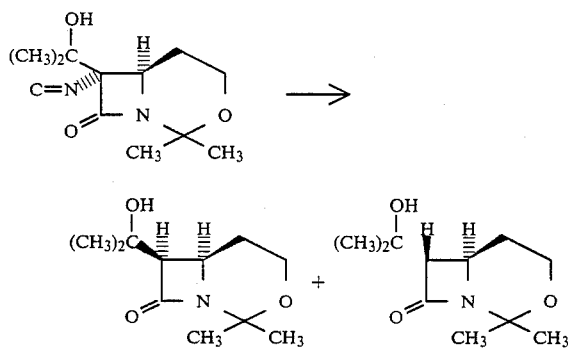

A solution of (6R,7RS)-2,2-dimethyl-7-(1-hydroxy-1-methylethyl)-7-isocyano-1-aza-3-oxabicyclo[4.2.0]-octan-8-one (920 mg), triphenyltin hydride (1.694 g) and azobisisobutyronitrile (63.4 mg) in benzene (46 ml) was heated at 50° C. for thirty minutes under a nitrogen atmosphere. The mixture was cooled to ambient temperature. The precipitates were filtered off and washed with benzene. The filtrate and washings were combined and chromatographed on silica gel (27.6 g, eluting with 10 to 25% acetone in dichloromethane) to give a crude product mixture, which was re-chromatographed on silica gel (46 g; 230–400 mesh, eluting with a 6:1 to 1:2 mixture of hexane and ethyl acetate) to give 513 mg of (6R,7R)-2,2-dimethyl-7-(1-hydroxy-1-methylethyl)-1-aza-3-oxabicyclo[4.2.0]octan-8-one after crystallization from diisopropyl ether and 170 mg of its 7S isomer as a crystalline solid.

EXAMPLE 151

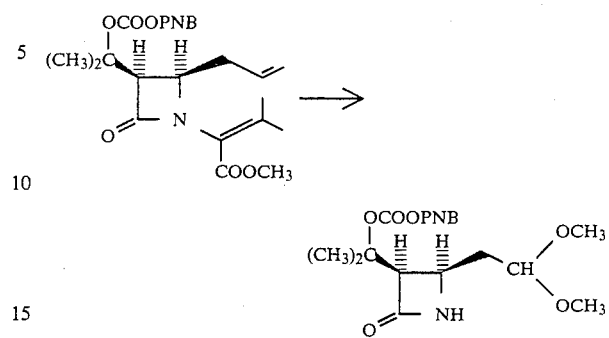

Ozone was bubbled into a solution of methyl 3-methyl-2-{(3R,4R)-3-[1-methyl-1-(4-nitrobenzyloxycarbonyloxy)ethyl]-2-oxo-4-(prop-2-enyl)azetidin-1-yl}but-2-enoate (100 mg) in a mixture of methanol (3 ml) and ethyl acetate (3 ml) at −70° C. until a blue color appeared. After stirring for 20 minutes at −70° C., the excess ozone was removed by a stream of nitrogen at the same temperature and dimethyl sulfide (1 ml) was added to the mixture, which was allowed to warm to ambient temperature over a period of an hour and to stand at 20° C. for 20 hours. After evaporation of the solvent, the residue was dissolved in methanol (5 ml). Trimethyl orthoformate (0.5 ml), dimethyl sulfide (0.3 ml) and p-toluenesulfonic acid monohydrate (4.1 mg) were added to the solution and the mixture was heated at 50° C. for 50 minutes. After cooling, pyridine (3 drops) was added to the mixture. The resulting solution was evaporated in vacuo, dissolved in ethyl acetate (20 ml) and washed in turn with water, 0.1N hydrochloric acid, water, aqueous sodium bicarbonate and brine. The ethyl acetate layer was dried over magnesium sulfate and evaporated in vacuo. The residue was dissolved in methanol (5 ml) and the solution was heated at 50° C. for 5 hours. After evaporation of the solvent, the residue was chromatographed on silica gel (2 g) eluting with a mixture of methylene chloride and ethyl acetate (20:1 to 1:2) to give (3R,4R)-4-(2,2-dimethoxyethyl)-3-[1-methyl-1-(4-nitrobenzyloxycarbonyloxy)ethyl]-azetidin-2-one (75 mg) as an oil.

IR (CH$_2$Cl$_2$): 3400, 1760, 1520, 1350 cm$^{-1}$.

NMR (CDCl$_3$) δ: 1.70 (3H, s), 1.78 (3H, s), 2.0–2.5 (2H, m), 3.42 (6H, s), 3.67 (1H, d, J=5 Hz), 3.8–4.1 (1H, m), 4.55 (1H, t, J=5.5 Hz), 5.31 (2H, s), 6.56 (1H, s), 7.68 (2H, d, J=9 Hz), 8.38 (2H, d, J=9 Hz).

EXAMPLE 152

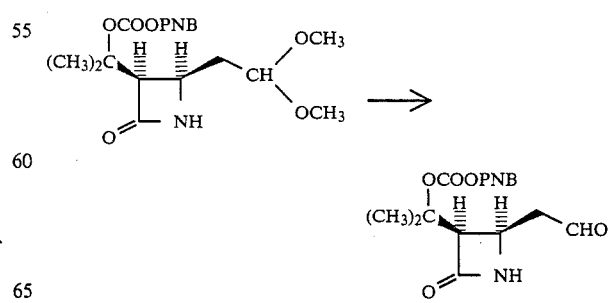

A solution of (3R,4R)-4-(2,2-dimethoxyethyl)-3-[1-methyl-1-(4-nitrobenzyloxycarbonyloxy)ethyl]-azetidin-2-one (64 mg) in 80% aqueous acetic acid (3.0 ml) was heated at 50°–55° C. for 4 hours. After evaporation of the solvent, the residue was dissolved in ethyl acetate (20 ml) and the solution was washed with aqueous sodium bicarbonate. The aqueous layer was extracted with ethyl acetate (10 ml). The organic layers were combined, washed with water and brine, dried over magnesium sulfate and evaporated in vacuo to give (3R,4R)-3-[1-methyl-1-(4-nitrobenzyloxycarbonyloxy)ethyl]-4-(2-oxoethyl)-azetidin-2-one (55 mg) as a solid.

IR (CH$_2$Cl$_2$): 1735, 1520, 1350 cm$^{-1}$.

EXAMPLE 153

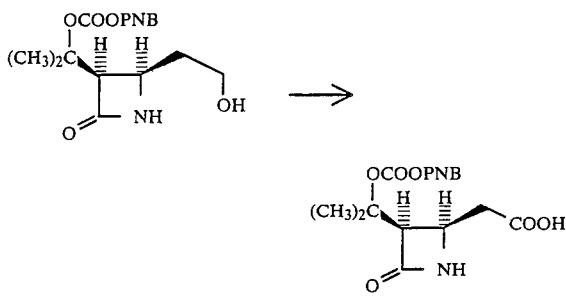

A solution of (3R,4R)-4-(2-hydroxyethyl)-3-[1-methyl-1-(4-nitrobenzyloxycarbonyloxy)ethyl]-azetidin-2-one (50 mg) in acetone (3 ml) was added to a solution of 2N Jones reagent (0.284 ml) in acetone (3 ml) at ambient temperature over a period of 30 minutes and the mixture was stirred for 30 minutes. After addition of an excess of isopropyl alcohol to the mixture, the solvent was evaporated off. The residue was dissolved in chloroform and washed with water. The aqueous layer was extracted twice with chloroform. The organic layers were combined, washed with brine, dried over magnesium sulfate and evaporated in vacuo. The residue was dissolved in chloroform (5 ml) and the solution was extracted with 0.1N aqueous solution of sodium bicarbonate (2 ml), 0.05N aqueous solution of sodium bicarbonate (2 ml) and water. The aqueous extracts were combined, acidified with 1N hydrochloric acid and extracted three times with chloroform. The combined chloroform extracts were washed with brine, dried over magnesium sulfate and evaporated to give {(2R,3R)-3-[1-methyl-1-(4-nitrobenzyloxycarbonyloxy)-ethyl]-4-oxoazetidin-2-yl}acetic acid (56 mg).

IR (CH$_2$Cl$_2$): 1735, 1520, 1350 cm$^{-1}$.

EXAMPLE 154

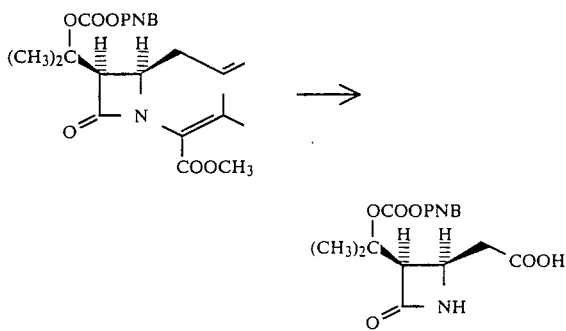

To a solution of methyl 2-{(3R,4R)-3-[1-methyl-1-(4-nitrobenzyloxycarbonyloxy)ethyl]-2-oxo-4-(prop-2-enyl)azetidin-1-yl}-3-methylbut-2-enoate (50 mg) in acetone (2.79 ml) were added water (0.93 ml) and a 0.7M solution of phosphate buffer (pH 6.8, 1.86 ml) at ambient temperature. Sodium periodate (139 mg) was added to the resulting suspension at ambient temperature and the mixture was stirred for 20 minutes. Potassium permanganate (26 mg) was then added and the resulting mixture was stirred for 26 hours at ambient temperature. The mixture was acidified with 2N hydrochloric acid (2 ml) and filtered using diatomaceous earth, and the filter-cake was washed with acetone and water. The filtrates were combined and concentrated under reduced pressure to a half volume. The concentrate was extracted three times with chloroform. The organic layers were combined, washed with brine and extracted with 5% aqueous sodium bicarbonate and water. The combined aqueous extracts were acidified with 2N hydrochloric acid and extracted three times with chloroform. The organic extracts were combined, washed with brine, dried over magnesium sulfate and evaporated in vacuo to give {(2R,3R)-3-[1-methyl-1-(4-nitrobenzyloxycarbonyloxy)ethyl]-4-oxoazetidin-2-yl}acetic acid (16 mg).

IR (CH$_2$Cl$_2$): 1735, 1520, 1350 cm$^{-1}$.

EXAMPLE 155

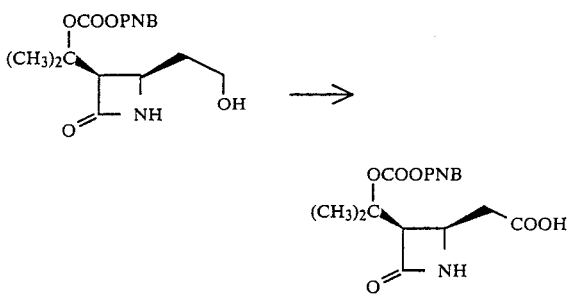

Pyridinium dichromate (3.74 g) was added to a solution of (3R,4R)-4-(2-hydroxyethyl)-3-[1-methyl-1-(4-nitrobenzyloxycarbonyloxy)ethyl]-2-oxo-azetidine (1.00 g) in N,N-dimethylformamide (20 ml) at 0° C., and the stirring mixture was allowed to warm to ambient temperature. After stirring at ambient temperature for 16 hours, the reaction mixture was poured into a mixture of ethyl acetate (150 ml), 10% aqueous sodium bisulfite (40 ml) and 3N hydrochloric acid (15 ml). The organic layer was separated and the remaining aqueous layer was extracted with ethyl acetate (100 ml×2). The organic layers were combined, washed in turn with water and an aqueous sodium chloride, dried over magnesium sulfate, and evaporated in vacuo.

The residue was dissolved in chloroform (30 ml) and the resultant solution was extracted with 5% aqueous sodium bicarbonate (20 ml), 2.5% aqueous sodium bicarbonate (20 ml) and then water (15 ml×2). The aqueous solutions were combined and acidified with 3N hydrochloric acid, followed by re-extraction three times with chloroform (20 ml). The combined extracts were washed with an aqueous sodium chloride, dried over magnesium sulfate, and evaporated to give {(2R,3R)-3-[1-methyl-1-(4-nitrobenzyloxycarbonyloxy)ethyl]-4-oxo-azetidin-2-yl}acetic acid (810 mg).

IR (CH$_2$Cl$_2$): 1735, 1520, 1350 cm$^{-1}$.

EXAMPLE 156

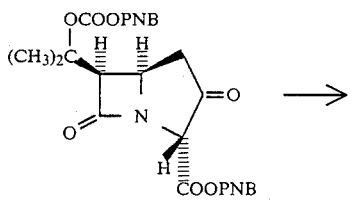

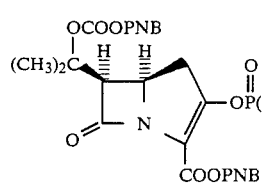

A solution of diisopropylethylamine (0.386 ml) in acetonitrile (0.34 ml) was added to a solution of 4-nitrobenzyl (2R, 5R, 6R)-3, 7-dioxo-6-[1-methyl-1-(4-nitrobenzyloxycarbonyloxy)ethyl]-1-azabicyclo [3.2.0] heptane-2-carboxylate (100 mg) and 4-(N, N-dimethylamino)-pyridine (2.3 mg) in acetonitrile (5 ml) at 0° C.

A solution of diphenyl chlorophosphate (0.0402 ml) in acetonitrile (0.36 ml) was then added at 0° C.

After stirring at 0° C. for 30 minutes, the mixture was evaporated in vacuo and the residue was dissolved in ethyl acetate. The organic solution was washed in turn with water and brine, dried over magnesium sulfate, and evaporated to give 4-nitrobenzyl (5R,6R)-3-(diphenoxyphosphoryloxy)-6-[1-methyl-1-(4-nitrobenzyloxycarbonyloxy)ethyl]-7-oxo-1-azabicyclo [3.2.0] hept-2-ene-2-carboxylate (148 mg).

IR (CH$_2$Cl$_2$): 1780, 1745, 1725, 1640, 1520, 1485, 1345 cm$^{-1}$.

NMR (CDCl$_3$): 1.61(s, 3H), 1.80(s, 3H), 3.14(dd, 1H, J=9.16 Hz), 3.73(d, 1H, J=6 Hz) 3.5–4.0(m, 1H), 4.0–4.3(m, 1H), 5.00 (s, 2H), 5.18(ABq, 2H, J=14 Hz), 7.0–7.7(m, 14H), 7.8–8.2(m, 4H).

EXAMPLE 157

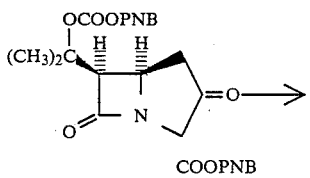

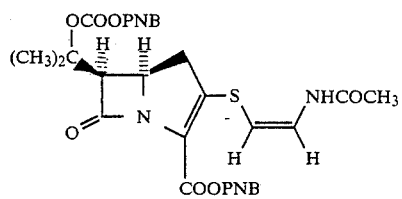

A solution of diisopropylethylamine (0.0579 ml) in acetonitrile (0.5 ml) was added to a solution of 4-nitrobenzyl (2R,5R,6R)-3, 7-dioxo-6-[1-methyl-1-(4-nitrobenzyloxycarbonyloxy)ethyl]-1-azabicyclo [3.2.0] heptane-2-carboxylate (150 mg) and 4-(N, N-dimethylamino)pyridine (3.38 mg) in acetonitrile (20 ml) at 0° C. A solution of diphenylchlorophosphate (78 mg) in acetonitrile (0.54 ml) was added to the mixture, which was stirred at 0° C. for 15 minutes. Sodium iodide (415 mg) and silver (Z)-2-acetamidoethylenethiolate (93 mg) were added at 0° C. and the mixture was stirred at 0° C. for 2.5 hours.

After the precipitate was filtered off, the filtrate was evaporated in vacuo and the residue was dissolved in ethylacetate (50 ml). The organic solution was washed in turn with water and brine, dried over magnesium sulfate and evaporated in vacuo. The residue was chromatographed on silica gel (4 g) eluting with a mixture of benzene and acetone (20:1–8:1) to give 4-nitrobenzyl (5R,6R)-3-[(Z)-2-acetamidovinyl-thio]-6-[1-methyl-1-(4-nitrobenzyloxycarbonyloxy)ethyl]-7-oxo-1-azabicyclo [3.2.0] hept-2-ene-2-carboxylate (155 mg) as an oil.

IR (CH$_2$Cl$_2$): 1785, 1750, 1710, 1630, 1515, 1350 cm$^{-1}$.

NMR (CDCl$_3$) δ: 1.62(s, 3H), 1.78(s, 3H), 2.06(s, 3H), 2.96(dd, 1H, J=11, 18 Hz), 3.66 (dd, 1H, J=8, 18 Hz), 3.76(d, 1H, J=5 Hz), 4.0–4.5(m, 1H), 5.14(s, 2H), 5.28(d, 1H, J=7 Hz), 5.37(ABq 2H, J=13 Hz), 7.3–7.8(m, 6H), 8.22 (d, 4H, J=8 Hz).

EXAMPLE 158

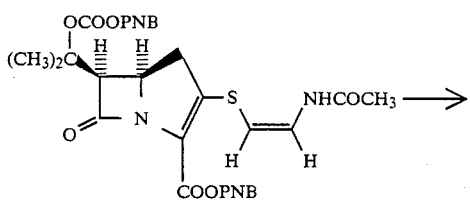

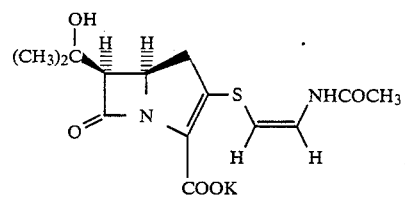

A mixture of 4-nitrobenzyl (5R,6R)-3-[(Z)-2-acetamidovinylthio]-6-[1-methyl-1-(4-nitrobenzyloxy carbonyloxy)ethyl]-7-oxo-1-azabicyclo [3.2.0] hept-2-ene-2-carboxylate (100 mg), platinum (IV) oxide monohydrate (50 mg), ethanol (1 ml) and 0.1 M aqueous solution of dipotassium hydrogen phosphate (4.68 ml) in a mixture of water (5 ml) and dioxane (12 ml) was shaken under a hydrogen atmosphere (40 psi) at ambient temperature for an hour. After the catalyst was filtered off, the filtrate was evaporated to the half volumn.

The aqueous solution was washed three times with ether and evaporated. The residue was dissolved in water (50 ml) and potassium chloride (2.5 g) was added. The aqueous solution was chromatographed on a column of non-ionic adsorption resin Diaion HP-20 AG (trade mark, Mitsubishi Chemical Industries) eluting with water (200 ml) and 10% aqueous isopropyl alcohol (200 ml). The fractions, whose UV spectra showed λ max 308 nm, were combined and lyophilized to give potassium (5R,6R)-3-[(Z)-2-acetamido-vinylthio]-6-(1-hydroxy-1-methylethyl)-7-oxo-1-azabicyclo [3.2.0] hept-2-ene-2-carboxylate (30 mg) as powder.

IR (nujol): 1750, 1670 1620, 1585 cm$^{-1}$.

UV (H$_2$O): λmax 234 nm (ε=11460), 308 nm (11650).

What we claim is:

1. A carbapenam compound of the formula:

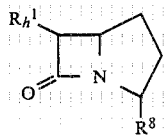

wherein $R_h^1$ is 1-hydroxy-1-methylethyl or 1-hydroxy-1-methylethyl protected by a removable hydroxy protecting group and $R^8$ is carboxy or carboxy protected by a removable carboxy protecting group and a pharmaceutically acceptable salt thereof.

2. A compound according to claim 1, in which $R_h^1$ is 1-hydroxy-1-methylethyl protected by a removable hydroxy protecting group and $R^8$ is carboxy protected by a removable carboxy protecting group.

3. A compound according to claim 2, in which
$R_h^1$ is 1-[mono(or di or tri)phenyl(lower)alkoxycarbonyl]-1-methylethyl optionally substituted by nitro and
$R^8$ is mono(or di or tri)phenyl(lower)alkoxycarbonyl optionally substituted by nitro.

4. A compound according to claim 3, in which
$R_h^1$ is 1-(4-nitrobenzyloxycarbonyloxy)-1-methylethyl and
$R^8$ is 4-nitrobenzyloxycarbonyl.

* * * * *